(12) United States Patent
Bruce et al.

(10) Patent No.: US 10,724,018 B2
(45) Date of Patent: *Jul. 28, 2020

(54) MODIFIED HELICASES

(71) Applicant: Oxford Nanopore Technologies Ltd., Oxford (GB)

(72) Inventors: Mark John Bruce, Oxford (GB); Andrew John Heron, Oxford (GB); Ruth Moysey, Oxford (GB); Szabolcs Soeroes, Oxford (GB); Elizabeth Jayne Wallace, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 629 days.

This patent is subject to a terminal disclaimer.

(21) Appl. No.: 15/028,651

(22) PCT Filed: Sep. 10, 2014

(86) PCT No.: PCT/GB2014/052736
§ 371 (c)(1),
(2) Date: Apr. 11, 2016

(87) PCT Pub. No.: WO2015/055981
PCT Pub. Date: Apr. 23, 2015

(65) Prior Publication Data
US 2016/0257942 A1    Sep. 8, 2016
US 2018/0037874 A9    Feb. 8, 2018

Related U.S. Application Data

(63) Continuation-in-part of application No. PCT/GB2014/050175, filed on Jan. 22, 2014.

(30) Foreign Application Priority Data

Oct. 18, 2013  (GB) .................................. 1318464.3
Mar. 17, 2014  (GB) .................................. 1404718.7
Apr. 4, 2014   (GB) .................................. 1406151.9

(51) Int. Cl.
*C12N 9/14* (2006.01)
*C12N 9/90* (2006.01)
*C12Q 1/6869* (2018.01)

(52) U.S. Cl.
CPC .................. *C12N 9/14* (2013.01); *C12N 9/90* (2013.01); *C12Q 1/6869* (2013.01); *C12Q 2565/631* (2013.01); *C12Y 306/04012* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 | 12/2009 | Akeson et al. | |
| 7,745,116 B2 | 6/2010 | Williams | |
| 7,851,203 B2 | 12/2010 | Letant et al. | |
| 7,947,454 B2 | 5/2011 | Akeson et al. | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 9,617,591 B2 | 4/2017 | Moysey et al. | |
| 9,758,823 B2 | 9/2017 | Moysey et al. | |
| 9,797,009 B2 | 10/2017 | Heron et al. | |
| 10,221,450 B2 | 3/2019 | Heron et al. | |
| 10,322,150 B2 | 6/2019 | Honda et al. | |
| 10,385,382 B2 | 8/2019 | Heron et al. | |
| 10,392,658 B2 | 8/2019 | Heron et al. | |
| 2003/0010638 A1 | 1/2003 | Hansford et al. | |
| 2004/0058378 A1 | 3/2004 | Kong et al. | |
| 2004/0248114 A1 | 12/2004 | Taira et al. | |
| 2006/0063171 A1 | 3/2006 | Akeson et al. | |
| 2008/0293045 A1* | 11/2008 | Piepenburg .......... | C12Q 1/6844 435/6.12 |
| 2009/0256116 A1 | 10/2009 | Shumaker-Parry et al. | |
| 2010/0035260 A1 | 2/2010 | Olasagasti et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2011/0177498 A1 | 7/2011 | Clarke et al. | |

(Continued)

FOREIGN PATENT DOCUMENTS

| | | |
|---|---|---|
| CA | 2927728 | 4/2015 |
| CA | 2937411 | 7/2015 |

(Continued)

OTHER PUBLICATIONS

Ra Petrov et al. (Uniprot: Q7Y5C3, Oct. 1, 2003, Retrieved from the Internet: http://www.uniprot.org/ [retrieved on Jul. 17, 2018]).*

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to a new method of characterising a target polynucleotide. The method uses a pore and a Dda helicase. The helicase controls the movement of the target polynucleotide through the pore. The invention also relates to modified Dda helicases which can be used to control the movement of polynucleotides and are particularly useful for sequencing polynucleotides.

5 Claims, 34 Drawing Sheets

Specification includes a Sequence Listing.

(56) References Cited

U.S. PATENT DOCUMENTS

| | | |
|---|---|---|
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0107802 A1 | 5/2012 | Stoddart et al. |
| 2013/0048499 A1 | 2/2013 | Mayer et al. |
| 2013/0149769 A1 | 6/2013 | Kizaki et al. |
| 2013/0225421 A1 | 8/2013 | Li et al. |
| 2014/0051069 A1 | 2/2014 | Jayasinghe et al. |
| 2014/0186823 A1 | 7/2014 | Clarke et al. |
| 2014/0255921 A1 | 9/2014 | Moysey et al. |
| 2014/0262784 A1 | 9/2014 | Clarke et al. |
| 2014/0335512 A1 | 11/2014 | Moysey et al. |
| 2015/0008126 A1 | 1/2015 | Maglia et al. |
| 2015/0031020 A1 | 1/2015 | Jayasinghe et al. |
| 2015/0065354 A1 | 3/2015 | Moysey et al. |
| 2015/0152492 A1 | 6/2015 | Brown et al. |
| 2015/0191709 A1 | 7/2015 | Heron et al. |
| 2015/0197796 A1 | 7/2015 | White et al. |
| 2015/0218629 A1 | 8/2015 | Heron et al. |
| 2017/0002406 A1 | 1/2017 | Bowen et al. |
| 2018/0030530 A1 | 2/2018 | Moysey et al. |
| 2018/0179500 A1 | 6/2018 | Heron et al. |
| 2018/0230526 A1 | 8/2018 | Heron et al. |
| 2019/0203288 A1 | 7/2019 | Gutierrez et al. |
| 2019/0345550 A1 | 11/2019 | Bowen et al. |

FOREIGN PATENT DOCUMENTS

| | | |
|---|---|---|
| JP | 2006-500028 A | 1/2006 |
| WO | WO 2000/28312 A1 | 5/2000 |
| WO | WO 2002/092821 A1 | 11/2002 |
| WO | WO 2004/027025 A2 | 4/2004 |
| WO | WO 2005/124888 A1 | 12/2005 |
| WO | WO 2006/028508 A2 | 3/2006 |
| WO | WO 2006/100484 A2 | 9/2006 |
| WO | WO 2007/057668 A1 | 5/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/044170 A1 | 4/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/109197 A2 | 9/2010 |
| WO | WO 2010/117470 A2 | 10/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2014/158665 A1 | 10/2014 |
| WO | WO 2015/022544 A1 | 2/2015 |
| WO | WO 2015/055981 A2 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2016/034591 A2 | 3/2016 |
| WO | WO 2016/055777 A2 | 4/2016 |
| WO | WO 2016/059363 A1 | 4/2016 |

OTHER PUBLICATIONS

Eoff et al. (Biochemistry. Jun. 1, 2010; 49(21): 4543-4553).*
Sequence ID No. 2 Search Results. US-14-351-038-2. Sep. 16, 2015. 69 pages.
Data sheet SEQ ID No. 10 search results from STIC, printed on Oct. 29, 2019, pp. 1-38 (Year: 2018).
Data sheet SEQ ID No. 2 search results from STIC, printed on Oct. 29, 2018, pp. 1-24 (Year: 2018).
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2009;128(5):1705-10.
Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bessler et al., The amino terminus of the *Saccharomyces cerevisiae* DNA helicase Rrm3p modulates protein function ltering replication and checkpoint activity. Genetics. Nov. 2004;168(3):1205-18.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan. 14, 2015.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi:10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dou et al., The DNA binding properties of the *Escherichia coli* RecQ helicase. J Biol Chem. Feb. 20, 2004;279(8):6354-63. Epub Dec. 9, 2003.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Garalde et al., Highly parallel direct RNA sequencing on an array of nanopores. bioRxiv. 2016. doi: http://dx.doi.org/10.1101/068809.
Garcillán-Barcia et al., The diversity of conjugative relaxases and its application in plasmid classification. FEMS Microbiol Rev. May 2009;33(3):657-87.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
Guo et al., The linker region between the helicase and primase domains of the bacteriophage T7 gene 4 protein is critical for hexamer formation. J Biol Chem. Oct. 15, 1999;274(42):30303-9.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.

(56) References Cited

OTHER PUBLICATIONS

He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.

Holden et al., Direct introduction of single protein channels and pores into lipid bilayers. J Am Chem Soc. May 11, 2005;127(18):6502-3.

Hopfner et al., Mechanisms of nucleic acid translocases: lessons from structural biology and single-molecule biophysics. Curr Opin Struct Biol. Feb. 2007;17(1):87-95. Epub Dec. 6, 2006.

Hornblower et al., Single-molecule analysis of DNA-protein complexes using nanopores. Nat Methods. Apr. 2007;4(4):315-7. Epub Mar. 4, 2007.

Howorka et al., Nanopore analytics: sensing of single molecules. Chem Soc Rev. Aug. 2009;38(8):2360-84. doi: 10.1039/b813796j. Epub Jun. 15, 2009.

Ivanov et al., DNA tunneling detector embedded in a nanopore. Nano Lett. Jan. 12, 2011;11(1):279-85. doi: 10.1021/nl103873a. Epub Dec. 6, 2010.

Jezewska et al., Interactions of *Escherichia coli* replicative helicase PriA protein with single-stranded DNA. Biochemistry. Aug. 29, 2000;39(34):10454-67. Abstract only.

Kafri et al., Dynamics of molecular motors and polymer translocation with sequence heterogeneity. Biophys J. Jun. 2004;86(6):3373-91.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.

Kar et al., Defining the structure-function relationships of bluetongue virus helicase protein VP6. J Virol. Nov. 2003;77(21):11347-56.

Keyser, Controlling molecular transport through nanopores. J R Soc Interface. Oct. 7, 2011;8(63):1369-78. doi: 10.1098/rsif.2011.0222. Epub Jun. 29, 2011.

Khafizov, Single Molecule Force Spectroscopy of Single Stranded Dna Binding Protein and Rep Helicase. University of Illinois at Urbana-Champaign Dissertation. 2012.

Korolev et al., Major domain swiveling revealed by the crystal structures of complexes of *E. coli* Rep helicase bound to single-stranded DNA and ADP. Cell. Aug. 22, 1997;90(4):635-47.

Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.

Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.

Langecker et al., Synthetic lipid membrane channels formed by designed DNA nanostructures. Science. Nov. 16, 2012;338(6109):932-6. doi: 10.1126/science.1225624.

Lee et al., Direct imaging of single UvrD helicase dynamics on long single-stranded DNA. Nat Commun. 2013;4:1878. doi:10.1038/ncomms2882.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Lohman et al., Mechanisms of helicase-catalyzed DNA unwinding. Annu Rev Biochem. 1996;65:169-214.

Lohman et al., Non-hexameric DNA helicases and translocases:mechanisms and regulation. Nat Rev Mol Cell Biol. May 2008;9(5):391-401. doi:10.1038/nrm2394.

Ma et al., Bright functional rotaxanes. Chem Soc Rev. Jan. 2010;39(1):70-80. doi: 10.1039/b901710k. Epub Jul. 21, 2009.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Marini et al., A human DNA helicase homologous to the DNA cross-link sensitivity protein Mus308. J Biol Chem. Mar. 8, 2002;277(10):8716-23. Epub Dec. 18, 2001

Mechanic et al., *Escherichia coli* DNA helicase II is active as a monomer. J Biol Chem. Apr. 30, 1999;274(18):12488-98.

Miles et al., Properties of Bacillus cereus hemolysin II: a heptameric transmembrane pore. Protein Sci. Jul. 2002;11(7):1813-24.

Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.

Press release: Oxford Nanopore introduces DNA 'strand sequencing' on the high-throughput GridlON platform and presents MinlON, a sequencer the size of a USB; memory stick, Feb. 2012.

Raney et al., Structure and Mechanisms of SF1 DNA Helicases. Adv Exp Med Biol. 2013;767:17-46. doi: 10.1007/978-1-4614-5037-5_2.

Richards et al., Structure of the DNA repair helicase hel308 reveals DNA binding and autoinhibitory domains. J Biol Chem. Feb. 22, 2008;283(8):5118-26. Epub Dec. 4, 2007.

Rudolf et al., The DNA repair helicases XPD and FancJ have essential iron-sulfur domains. Mol Cell. Sep. 15, 2006;23(6):801-8.

Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.

Saariaho et al., Characteristics of MuA transposase-catalyzed processing of model transposon end DNA hairpin substrates. Nucleic Acids Res. Jun. 6, 2006;34(10):3139-49. Print 2006.

Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.

Schneider et al., DNA sequencing with nanopores. Nat Biotechnol. Apr. 10, 2012;30(4):326-8. doi: 10.1038/nbt.2181.

Singleton et al., Structure and mechanism of helicases and nucleic acid translocases. Annu Rev Biochem. 2007;76:23-50.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.

Venkatesan et al., Nanopore sensors for nucleic acid analysis. Nat Nanotechnol. Sep. 18, 2011;6(10):615-24. doi: 10.1038/nnano.2011.129.

Wang et al., DNA helicase activity of the RecD protein from Deinococcus radiodurans. J Biol Chem. Dec. 10, 2004;279(50):52024-32.

White, Structure, function and evolution of the XPD family of iron—sulfur-containing 5'→3' DNA helicases. Biochem Soc Trans. 2009;37:547-551.

Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.

Woodman et al., Molecular biology of Hel308 helicase in archaea. Biochem Soc Trans. Feb. 2009;37(Pt 1):74-8. doi: 10.1042/BST0370074.

Woodman et al., Winged helix domains with unknown function in Hel308 and related helicases. Biochem Soc Trans. Jan. 2011;39(1):140-4. doi:10.1042/BST0390140.

Zhang et al., Structural evidence for consecutive Hel308-like modules in the spliceosomal ATPase Brr2. Nat Struct Mol Biol. Jul. 2009;16(7):731-9. doi: 10.1038/nsmb.1625.

UniProt Database Accession No. K7NRI8 sequence. Feb. 6, 2013.
UniProt Database accession No. I7J3V8 sequence. Oct. 3, 2012.

(56) References Cited

OTHER PUBLICATIONS

Farah et al., The RecBCD enzyme initiation complex for DNA unwinding:enzyme positioning and DNA opening. J Mol Biol. Oct. 10, 1997;272(5):699-715.

Jankowsky, RNA helicases at work: binding and rearranging. Trends Biochem Sci. Jan. 2011;36(1):19-29. doi: 10.1016/j.tibs.2010.07.008.

Lee et al., Cooperative translocation enhances the unwinding of duplex DNA by SARS coronavirus helicase nsP13. Nucleic Acids Res. Nov. 2010;38(21):7626-36. doi: 10.1093/nar/gkq647. Epub Jul. 29, 2010.

Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.

U.S. Appl. No. 16/506,407, filed Jul. 9, 2019, Bowen et al.

[No Author Listed] Antibodies bind specific molecules through their hypervariable loops. 33.3 Antibody Binding. 6th edition. 2007;953-954.

Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Arslan et al., Protein structure. Engineering of a superhelicase through conformational control. Science. Apr. 17, 2015;348(6232):344-7. doi: 10.1126/science.aaa0445.

Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.

Bennett et al., Association of yeast DNA topoisomerase III and Sgs1 DNA helicase: studies of fusion proteins. Proc Natl Acad Sci U S A. Sep. 25, 2010;98(20):11108-13. Epub Sep. 11, 2001.

Berger, SnapShot: nucleic acid helicases and translocases. Cell. Sep. 5, 2008;134(5):888-888.e1. doi: 10.1016/j.cell.2008.08.027.

Blast® NCBI. Sequence ID No. 10; ZSYBNHWV114. Sep. 18, 2015.

Blast® NCBI. Sequence ID No. 52; ZT1133A811N. Sep. 18, 2015.

Braha et al., Designed protein pores as components for biosensors. Chem Biol. Jul. 1997;4(7):497-505.

Buttner et al., Structural basis for DNA duplex separation by a superfamily-2 helicase. Nat Struct Mol Biol. Jul. 2007;14(7):647-52.

Byrd et al., Superfamily 2 helicases. Front Biosci (Landmark Ed). Jun. 1, 2012;17:2070-88.

Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.

Colas et al., Microscopical investigations of nisin-loaded nanoliposomes prepared by Mozafari method and their bacterial targeting. Micron. 2007;38(8):841-7.

Devereux et al., A comprehensive set of sequence analysis programs for the VAX. Nucleic Acids Res. Jan. 11, 1984;12(1 Pt 1):387-95.

Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.

Durrieu et al., Interactions between neuronal fusion proteins explored by molecular dynamics. Biophys J. May 1, 2008;94(9):3436-46. doi:10.1529/biophysj.107.123117. Epub Jan. 22, 2008.

Eliseev et al., Molecular Recognition of Nucleotides, Nucleosides, and Sugars by Aminocyclodextrins. J. Am. Chem. Soc., 1994;116:6081-88.

Genbank accession No. AEA72977 sequence. Apr. 6, 2011.

Genbank Submission. NCBI; Accession No. AM778123. Richards et al.; Sep. 18, 2008.

GenPept Accession No. XP 003728286. Jun. 7, 2012.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. Epub May 21, 2007.

Green et al., Quantitative evaluation of the lengths of homobifunctional protein cross-linking reagents used as molecular rulers. Protein Sci. Jul. 2001;10(7):1293-304.

Heron et al., Simultaneous measurement of ionic current and fluorescence from single protein pores. J Am Chem Soc. Feb. 11, 2009;131(5):1652-3. doi: 10.1021/ja808128s.

Holden et al., Functional bionetworks from nanoliter water droplets. J Am Chem Soc. Jul. 11, 2007;129(27):8650-5. Epub Jun. 16, 2007.

James, Aptamers. Encyclopedia of Analytical Chemistry. R.A. Meyers (Ed.). 4848-4871. John Wiley & Sons Ltd, Chichester, 2000.

Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.

Kankia et al., Folding of the thrombin aptamer into a G-quadruplex with Sr(2+): stability, heat, and hydration. J Am Chem Soc. Nov. 7, 2001;123(44):10799-804.

Kutyavin et al., Oligonucleotides containing 2-aminoadenine and 2-thiothymine act as selectively binding complementary agents. Biochemistry. Aug. 27, 1996;35(34):11170-6.

Levin et al., Helicase from hepatitis C virus, energetics of DNA binding. J Biol Chem. Aug. 16, 2002;277(33):29377-85. Epub May 28, 2002.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Maddox et al., Elevated serum levels in human pregnancy of a molecule immunochemically similar to eosinophil granule major basic protein. J Exp Med. Oct. 1, 1983;158(4):1211-26.

Marathias et al., Structures of the potassium-saturated, 2:1, and intermediate, 1:1, forms of a quadruplex DNA. Nucleic Acids Res. May 1, 2000;28(9):1969-77.

Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.

Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.

Montal et al., Formation of bimolecular membranes from lipid monolayers and a study of their electrical properties. Proc Natl Acad Sci U S A. Dec. 1972;69(12):3561-6.

Nikolov et al., Behavior of giant vesicles with anchored DNA molecules. Biophys J. Jun. 15, 2007;92(12):4356-68. Epub Mar. 23, 2007.

Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.

O'Shea et al., X-ray structure of the GCN4 leucine zipper, a two-stranded, parallel coiled coil. Science. Oct. 25, 1991;254(5031):539-44.

Pfeiffer et al., Bivalent cholesterol-based coupling of oligonucletides to lipid membrane assemblies. J Am Chem Soc. Aug. 25, 2004;126(33):10224-5.

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Remaut et al., Protein-protein interaction through beta-strand addition. Trends Biochem Sci. Aug. 2006;31(8):436-44. Epub Jul. 7, 2006.

(56) References Cited

OTHER PUBLICATIONS

Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.
Stelter et al., Structural and mechanistic insight into DNA unwinding by Deinococcus radiodurans UvrD. PLoS One. Oct. 15, 2013;8(10):e77364. doi: 10.1371/journal.pone.0077364.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
UniProt Database accession No. a4s1e1 sequence. May 15, 2007.
UniProt Database accession No. b4kac8 sequence. Sep. 23, 2008.
UniProt Database accession No. D0KN27. Dec. 15, 2009.
UniProt Database accession No. D7RM26 sequence. Aug. 10, 2010.
UniProt Database accession No. e1qus6 sequence. Nov. 30, 2010.
UniProt Database accession No. i3d0e7 sequence. Jul. 11, 2012.
UniProt Database accession No. I6ZR75 sequence. Oct. 3, 2012.
UniProt Database accession No. k0im99 sequence. Nov. 28, 2012.
UniProt Database accession No. Q12WZ6 sequence. Apr. 12, 2017.
Van Heel et al., Single-particle electron cryo-microscopy:towards atomic resolution. Q Rev Biophys. Nov. 200;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Vinson, Proteins in motion. Introduction. Science. Apr. 10, 2009;324(5924):197. doi: 10.1126/science.324.5924.197.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.

* cited by examiner

Figure 2
A
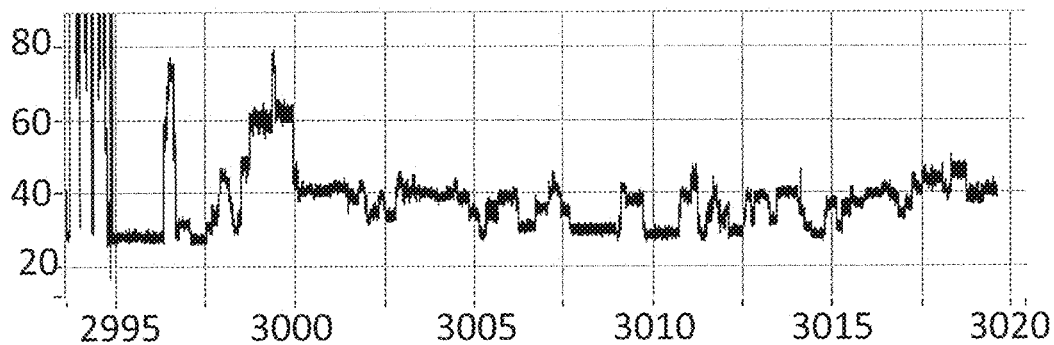
B
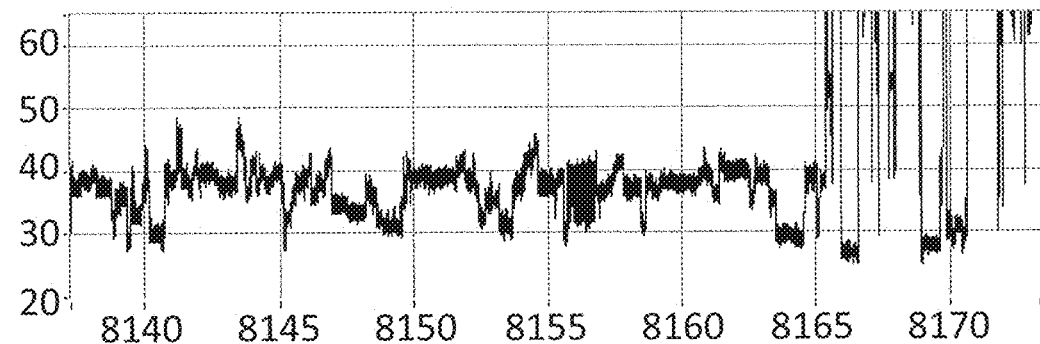

Figure 9
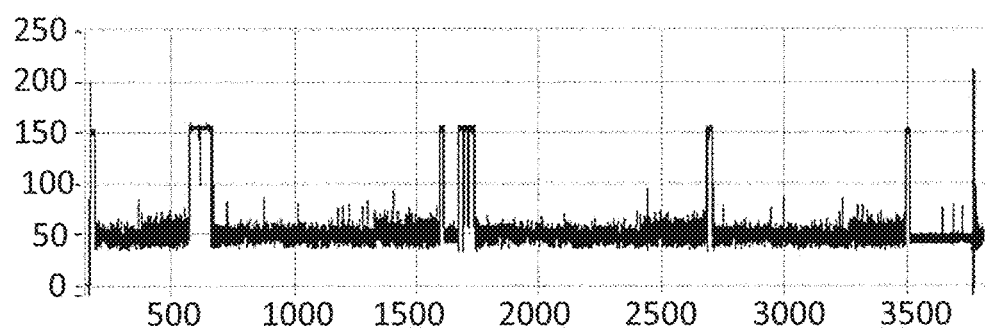
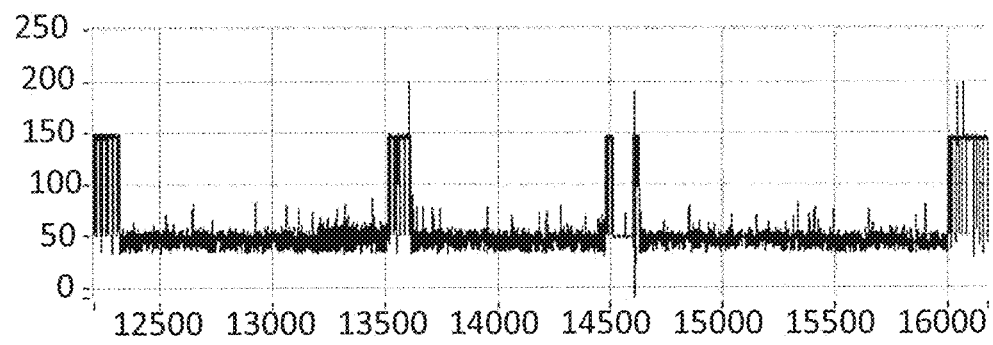

Figure 10
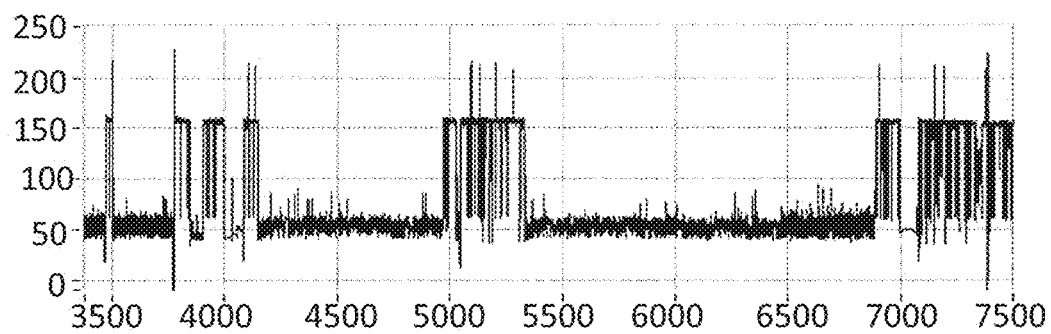
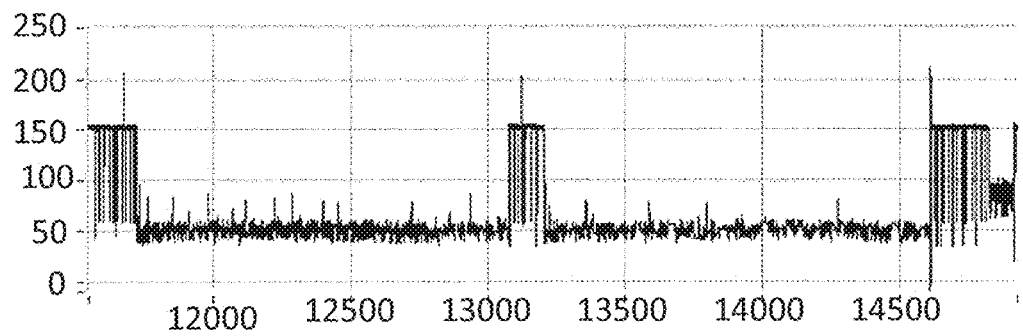

Figure 18
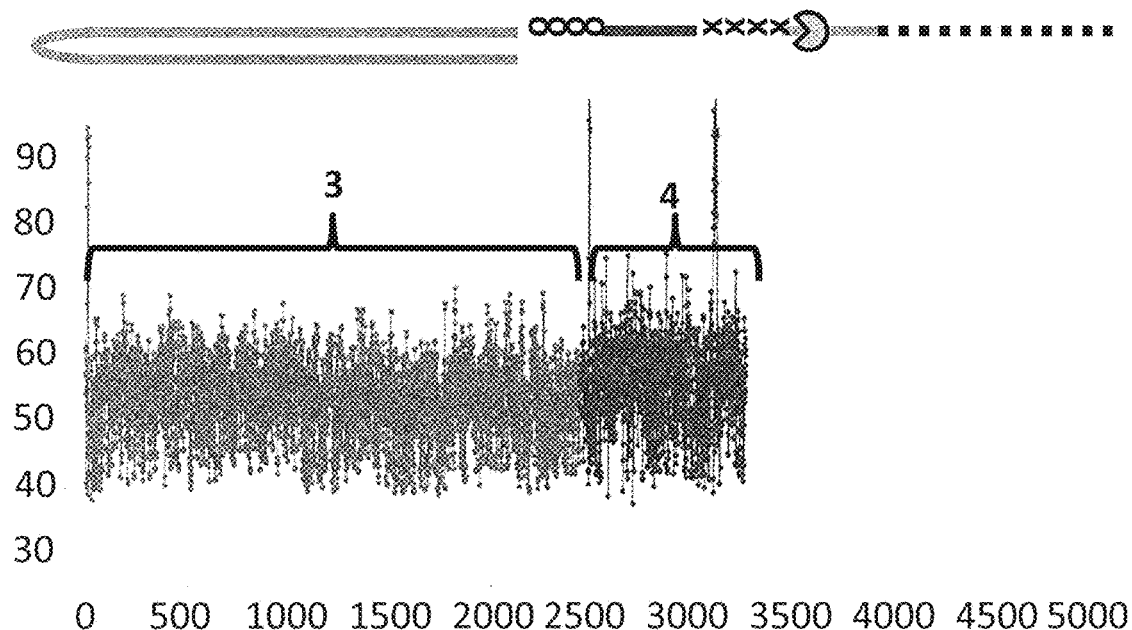
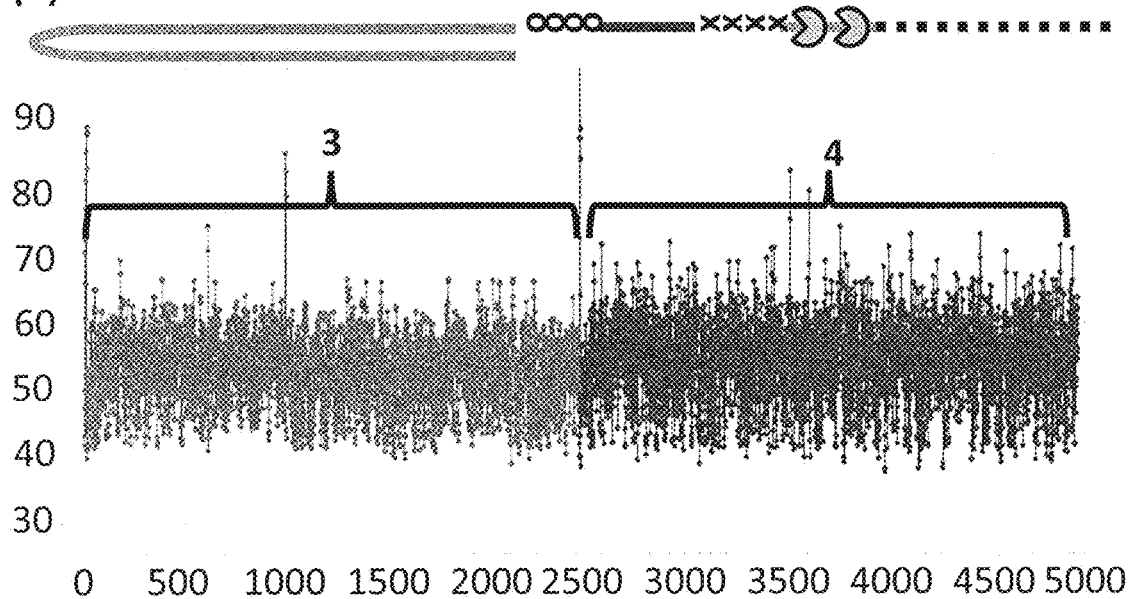

Figure 19
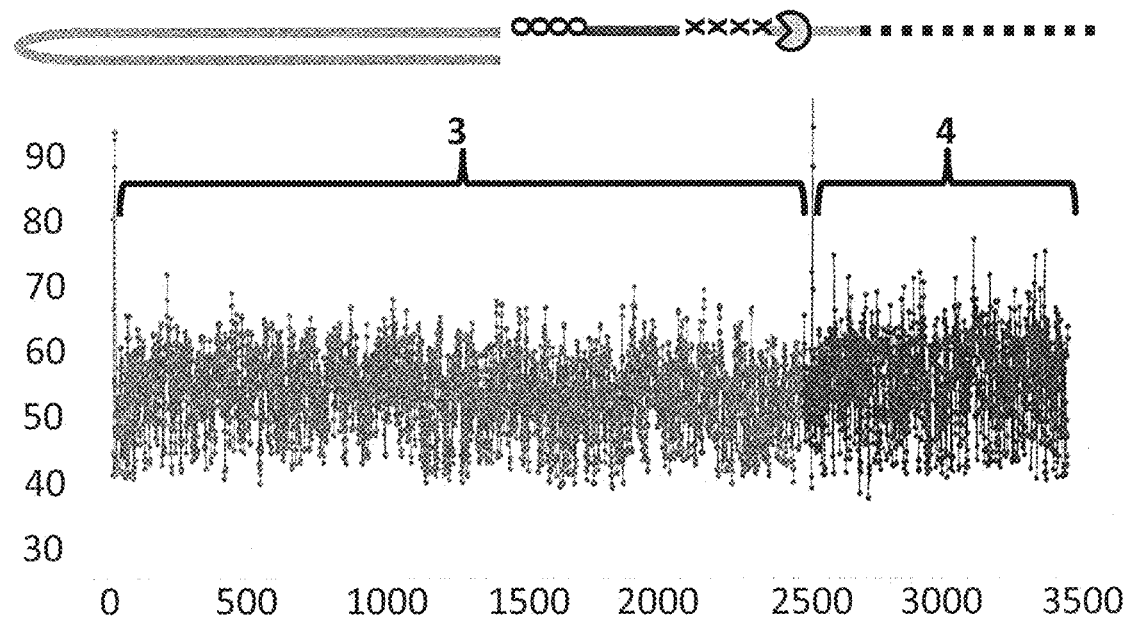
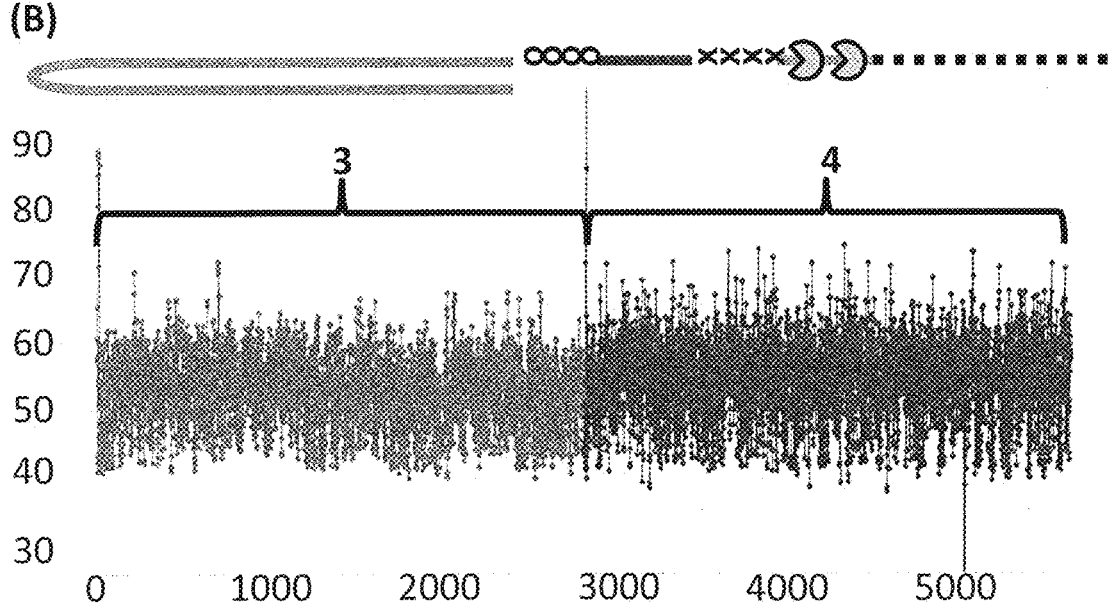

Figure 21
(A)
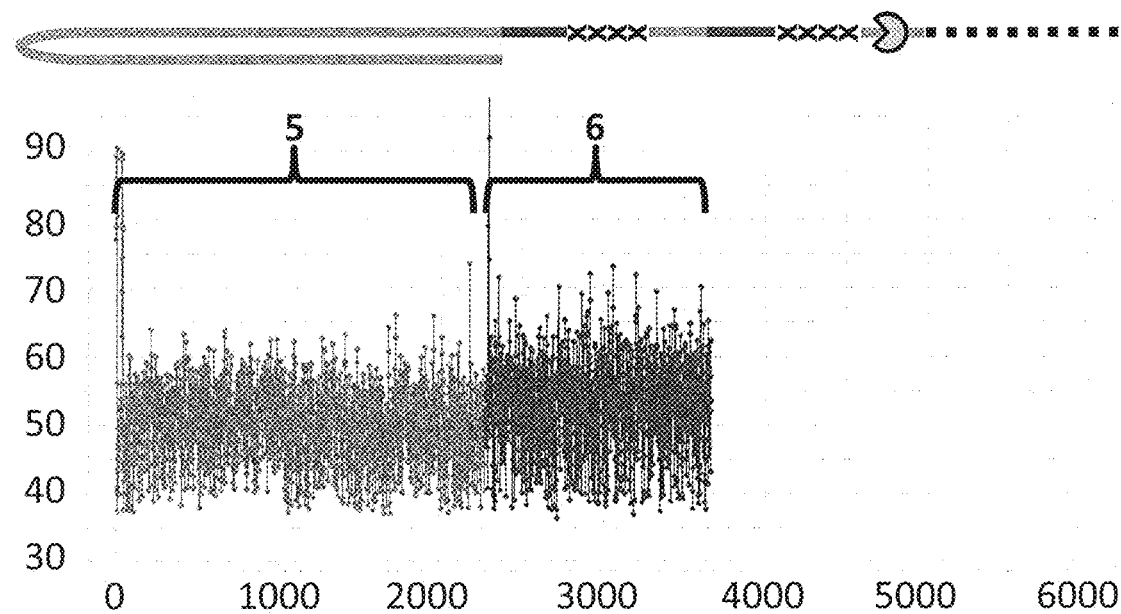
(B)
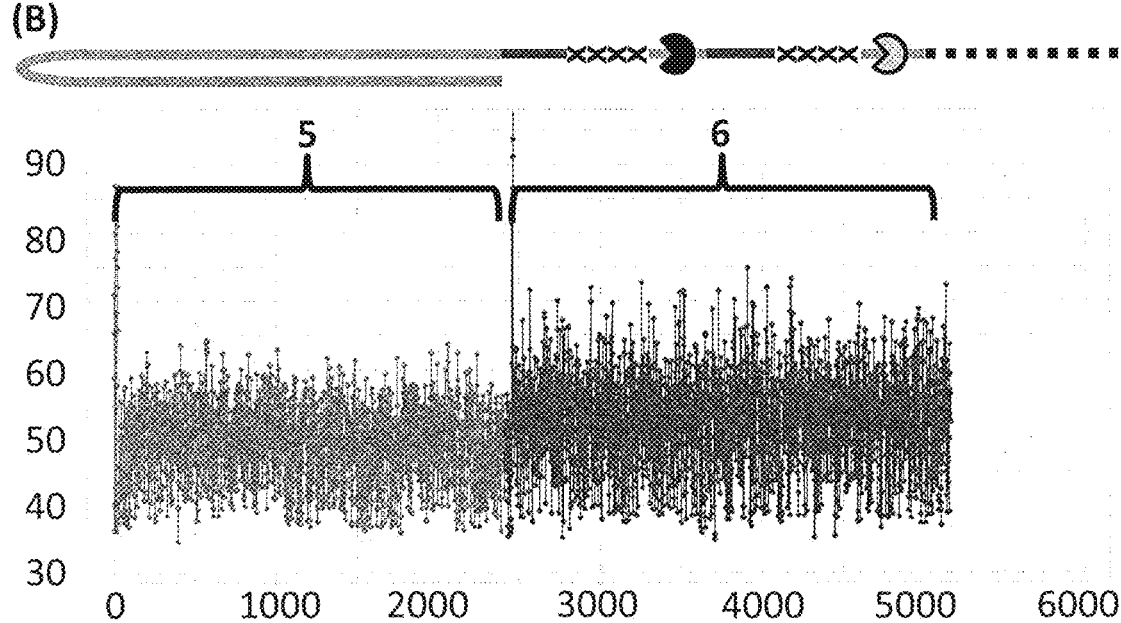

Figure 22
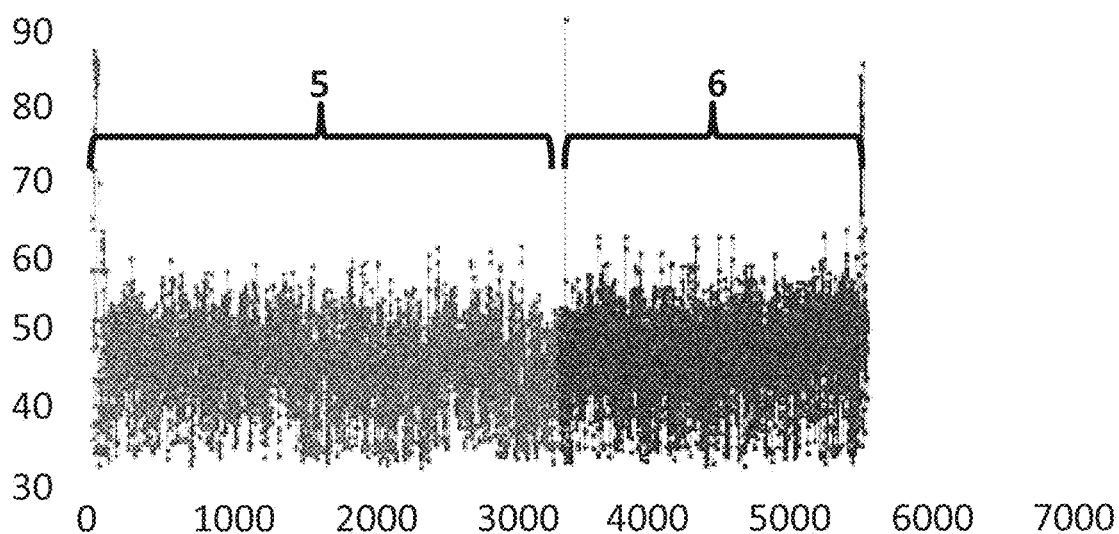
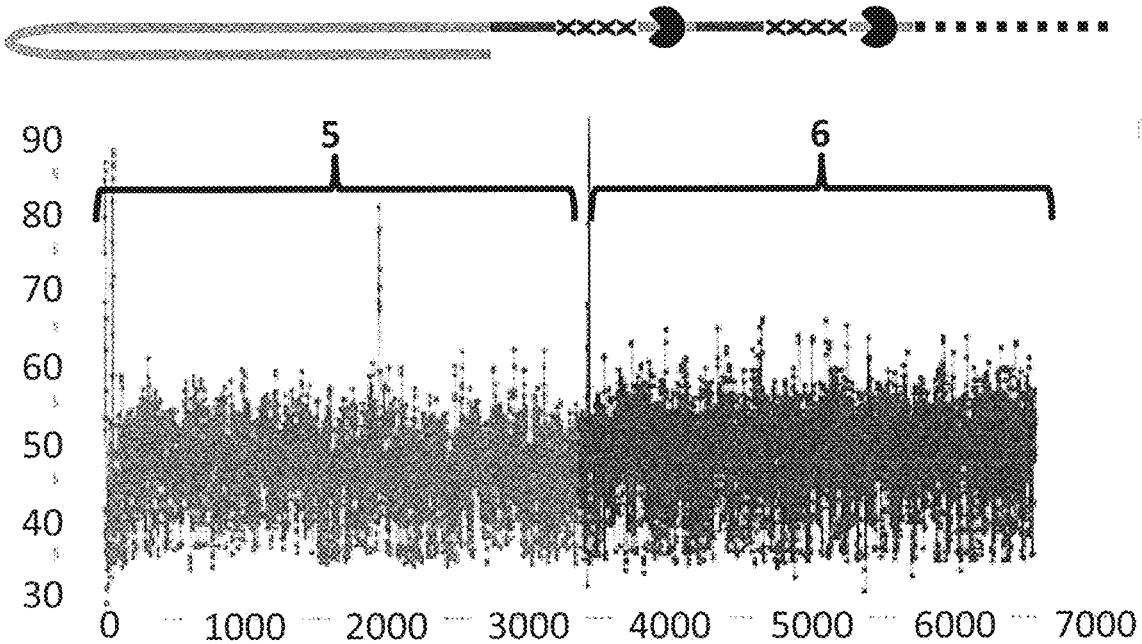

Figure 23A

```
Dda-Rma-DSM    1 ........................................
Dda-Csp        1 M S Q S V V V P D E L G E I I T A V I E F Y Q D A V D K I E P
Dda-Sru        1 ........................................
Dda-Sgo        1 ........................................
Dda-Vph12B8    1 ........................................
Dda-Vph        1 ........................................
Dda-Aph65      1 ........................................
Dda-AphCC2     1 ........................................
Dda-Cph        1 ........................................
Dda-Kph        1 ........................................
Dda-SphIME13   1 ........................................
Dda-AphAc42    1 ........................................
Dda-SphSP18    1 ........................................
Dda-Yph        1 ........................................
Dda-SphS16     1 ........................................
Dda-1993       1 ........................................    TO
                                                             Figure
                                                             23B
Dda-Rma-DSM   59 A A P T G R A A R I L S E R T - - - - - - G D H A R T L H S
Dda-Csp      117 A A P T N K A A K N L T Q I A R S Q G I - - K I E A T T V A K
Dda-Sru       62 C A P T H K A V Q V L S D E L G D A - - - - P V Q M Q T L F S
Dda-Sgo       85 T A P T H K A V G V L S K L L R E N N I - - Q S S C K T I H S
Dda-Vph12B8   64 C S P T H K S V K V I R R M A R E A G I S H R V D I R T I H S
Dda-Vph       52 V T P T H Q A K N V L H K A T G Q - - - - - - - E V S T I H S
Dda-Aph65     56 A A P T H Q A K I V L T E M S G I - - - - - - - E A C T I H S
Dda-AphCC2    43 A A P T H Q A K I V L T E M S G I - - - - - - - E A C T I H S
Dda-Cph       62 T A P T H Q A K N V L A A A T G M - - - - - - - D A T T I H S
Dda-Kph       62 T A P T H Q A K N V L S E A V G M - - - - - - - D A T T I H S
Dda-SphIME13  60 T A P T H Q A K K E L S K H A L R - - - - - - - K S Y T I Q S
Dda-AphAc42   66 A A P T H Q A K K V L S Q H A G M - - - - - - - E A S T I H S
Dda-SphSP18   62 A A P T H Q A K K V L S K L S G Q - - - - - - - T A N T I H S
Dda-Yph       61 C A P T H Q A K K V L S K L S G M - - - - - - - D A S T I H S
Dda-SphS16    61 T A P T H A A K K V L T K L S G M - - - - - - - E A N T I H K
Dda-1993      60 A A P T H A A K K I L S K L S G K - - - - - - - E A S T I H S
```

FROM                                                                                              TO
Figure                                                                                            Figure
23A  L I Y T F D R Y Q L V E E A D R Q T D E P L S L Q L H F A L R S A E H - - - D   23C
     L L K L Q P T I D V D T - - - - - - - - - G Q Q S F E F N S E K E L E L K D
     F L G L R L Q P K - Q D - - - - - - - - - G E Y E L V A E E E R N F - - - A
     F L G L K P F I D Y T T G E - - - - - - - E K F V V D K T N K R K D - - - R
     A L G L V M K P V - R G - - - - - - - - - D E V L V K E P F A E R - - - I
     L L K H P D T Y E D Q K H - - - - - - - F T Q S - - G E V E G L D - - - E
     L M K H P E T L E D I Q I - - - - - - - F D Q - - - S K L P D L S - - - N
     L M K H P E T L E D I Q I - - - - - - - F D - Q - - S K M P D L S - - - T
     A L K S P V T N E E L R V - - - - - - - F E Q Q K G K K A P D L S - - - T
     A L K S P V T N E E L R V - - - - - - - F E Q Q K G K K A A D L S - - - E
     V L K N P S T L E E N Q I - - - - - - - F E Q - - - K G T P D F S - - - K
     L L K N P T T Y E D S T T - - - - - - - F E Q - - - K D V P D M S - - - E
     I L K N P T T Y E D Q N I - - - - - - - F E Q - - - R E M P D M S - - - K
     V L K N P T T Y E E N Q I - - - - - - - F E Q - - - R E V P D L A - - - A
     I L K N P T T Y E E S M L - - - - - - - F E Q - - - K E V P D L A - - - S
     I L K N B V T Y E E N V L - - - - - - - F E Q - - - K E V P D L A - - - K
```

Figure 23C

```
       L D H V L A W L E R N D A . . . . P P I F I L T G S A G T G K T L L I R H L V
       Y K E M I N F I E N S S E . . . . . Q Y F R L S G V A G T G K S F L M A K V I
       Y D H V Y D R L A Q . G E . . . . . R F T G L R G Y A G T G K T Y L V S R L V
       L D T K V S S I L K S T N I . . E D Y L L S L T G P A G T G K T F L T T Q I A
       L G E V I S T I L K P V N L N D T S R F H T M H G P A G S G K T T V L Q R I I
       M D A F L E S D . . . G . . . . . . . H M T I S G P A G S G K T F L M K S I L
       V N E V K N G T . . . G . . . . . . . H I T I S G P P G S G K T F L V K Y L I
       V D A V Q S G T . . . G . . . . . . . H I T I S G P P G S G K T F L V K Y I I
       H D R V I H N I Q N A I . . . . . . . H T T I T G G P G V G K T T L V K F V F
       H D R V I K N I R N K I . . . . . . . H T T I T G G P G V G K T T L V K F V F
       I E K A L Q A M R T K R . . . . . . . H I T I R G P A G S G K T T M T R F L L
       Y T A A I K A I E T V P S S S A E K R H L T I N G P A G T G K T T L T K F L I
       F D Y I T E A I Q R R S . . . . . G E C I T L N G P A G T G K T T L T K F V I
       F D N T M E A I K N K K . . . . . . G H I T I N G P A G T G K T T L T K F I I
       F D E T I R A I K E . K . . . . . K N H V T I N G P A G T G K T T L T K F I M
FROM   F N I V M K A I K E K K . . . . . . H H V T I N G P A G T G K T T L T K F L I   TO
Figure                                                                                 Figure
23B    A R L I I V D E A S M V S D T A G E E E L Y R F G S G R L L N D L L T F A R L   23D
       Y D V I I I D E Y S M L N K D N F R D L Q Q A V K G G E S . . . . . . . . . .
       E G V V I V D E A S M I G R E E W S H I Q D A P F . . W V . . . . . . . . . .
       T S I L I V D E S S M I G N T L Y E Y I L E A I E D K R V . . . . . . . . . .
       Y D V L I I D E A G I L N D E I I M Y I L E S Q . . . S S . . . . . . . . . .
       I D V L V V E E A S M V D E E L F Q I T G R T M P R K C . . . . . . . . . . .
       I R Y L I V E E A S M H S K T L F K I T M K S I P P T C . . . . . . . . . . .
       V R Y L I I E E A S M H S K A L F N I T M K S I P P T C . . . . . . . . . . .
       C R V F V V E E V S M V D M D L F R I I R R S I P S N A . . . . . . . . . . .
       C R V F V V E E V S M V D K E L F R I I K R T I P S C A . . . . . . . . . . .
       T R V L I C D E V S M F Y T R K L F D I L M R N V P S H C . . . . . . . . . .
       C R V L I C D E A S M Y D L K L F Q I L M S S I P L C C . . . . . . . . . . .
       C N V L V C D E A S M Y D G S L F K I C N S V P E W C . . . . . . . . . . . .
       C R V L I C D E A S F Y D R K L F G I I L A T V P S W C . . . . . . . . . . .
       C R V L I C D E A S M W D R K L F K I L M A S I P K W C . . . . . . . . . . .
       C R V L I C D E V S M Y D R K L F K I L L S T I P P W C . . . . . . . . . . .
```

Figure 23D

```
                RA L Q D R R - - - - - - - - - - - I H Y A L  58
                E W L K Q E D - - - - - - - - - - - Y K Y S V 116
                E Q L L D E D - - - - - - - - - - - C T V T V  61
                K Y L V E K R K E S E Y P M S S D F D F I I    84
                S Q I P A Y K - - - - - - - - - - - T I G F   63
                E A L E S K G - - - - - - - - - - - K N V T M 51
                K M L G D E - - - - - - - - - - - - L G T V L 55
                K M L G D E - - - - - - - - - - - - L G T V L 42
                N T L K G L G I - - - - - - - - - - S G I W L 61
                E T L K K L G I - - - - - - - - - - S G I W L 61
                E R L F Q T G Q - - - - - - - - - - Q G I V L 59
                A E L I R R G E - - - - - - - - - - R G V Y L 65
                D H L V R N G V - - - - - - - - - - M G I V L 61
                D H L I K T G E - - - - - - - - - - A G I I L 60
                E H L V S T G E - - - - - - - - - - T G I I L 60
FROM            E A L I S T G E - - - - - - - - - - T G I I L 59              TO
Figure                                                                        Figure
23C   I P K R D R P P T T R L L F V G D P A Q L - 178                         23E
                              K F I F V G D S S Q L - 214
                              Q W L F V G D P A Q L - 151
                            N V V L F I G D P Y Q L - 182
                              K V I F V G D M C Q I - 156
                              R I L A V G D K Y Q L - 140
                              R I I A I G D K D Q I Q 144
                              R I I A I G D K D Q I - 130
                              V I L G L G D K D Q I - 152
                              V I L G L G D K D Q I - 152
                              V V I G I G D K A Q I - 147
                              T V I A L G D I A Q I - 153
                              T I L G I G D M H Q L - 149
                              T V I A L G D K D Q L - 148
                              T I V A I G D V A Q I - 148
                              T I I G I G D N K Q I - 147
```

Figure 23E

```
Dda-Rma-DSM  179 P P V G Q S V S P A L S A Q Y L R D T F G L S A E - - - - - -
Dda-Csp      215 P P V - - - - - - - K E K E P I V A N H P D I R - - - - - - -
Dda-Sru      152 P P V - - - - - - - N E D P S P A L D V P - - - - - - - - - -
Dda-Sgo      183 L P I E - - - - - - N S K N E I Y D L P N - - - - - - - - - -
Dda-Vph12B8  157 G P I - - - - - - - Q S N L P E E D G Y T P T S T D D V S K V
Dda-Vph      141 Q P V K H - - - D - P - - G V I S P F F T K - F T - - - - - -
Dda-Aph65    145 P E E H A - - - Q - G - - E L S P Y F T D P R F S - - - - - -
Dda-AphCC2   131 Q P V D H - - - A - P G - E L S P Y F T D S R F T - - - - - -
Dda-Cph      153 R P V N A - - - D - G R V E L S P F F D E E I F D - - - - - -
Dda-Kph      153 R P V N T - - - E - G I T E L S P F F D E E I F D - - - - - -
Dda-SphME13  148 R G V S E - - - D - D T H E L S P F F T D N R F E - - - - - -
Dda-AphAc42  154 R P V E P - - - G A F E G Q V S P F F T Y E K F E - - - - - -
Dda-SphSP18  150 Q P V D P - - - G S T Q Q K I S P F F T H P K F K - - - - - -
Dda-Yph      149 R P V T P - - - G E S E Q Q L S P F F S H A K F K - - - - - -
Dda-SphS16   149 R P V D P - - - G E T E A H I S P F F I H K D F K - - - - - -
Dda-1993     148 R P V D P - - - G E N T A Y I S P F F T H K D F Y - - - - - -

Dda-Rma-DSM  288 A R L W G R E G L P P Q P G D L L L V N R N A - - - - - - - - -
Dda-Csp      321 E A L Y G E N V E Q L V V G D R L I A L K P V F R S L P G G K
Dda-Sru      254 A E R Y G A D A D R F V E G E W L V G T E T W Y Y D - - - - - -
Dda-Sgo      287 N K F W E Q K G N T T - P S T L L A G D M I R - - - - - - - - -
Dda-Vph12B8  281 K R L F G A D V P E W L E D E I L V A Q E - - - - - - - - - - -
Dda-Vph      244 E H V Y - N T S E P F I P G E Y L V T Q M P V M V - S N - - - -
Dda-Aph65    249 E H V Y - K T K L P F I E G E K I V L Q E P V M V - - - E H E
Dda-AphCC2   236 K H V Y - K T D L P F I E G E K L V L Q E P V M V E Y D - - -
Dda-Cph      257 K H L Y - K T T E P F I L D E V I V M Q E P L V Q E M R L N G
Dda-Kph      257 K H L Y - K T D Q P F I V G E V V V M Q E P L V T E G R V N G
Dda-SphME13  251 K Q L Y G A N A A P F L P D E I L V M Q E P L M F D I D I G G
Dda-AphAc42  260 K K I Y - N T L E P F I D G E V L V M Q E P L I K S Y T Y E G
Dda-SphSP18  256 R K L Y - E T D K A F L P Y E V L V M Q E P H M K E L E F E G
Dda-Yph      255 R K L Y - E T D K P F I N G E V L V M Q E P L M K E L E F D G
Dda-SphS16   255 R R L Y - Q T E E A F V V G E V I V M Q E P L M R E L V F E G
Dda-1993     254 K K I F - E T D K D F I V G E I I V M Q E P L F K T Y K I D G
```

FROM Figure 23D

```
                  T A H L R S V Y R Q R K G H P I L E T A T A L R N A L E K G H Y H
              K S A N L T Q I V R Y D G E I V K V A E S I R R N P R W N H Q T Y P
                G P T L E T I H R Q A A D N P I L E L A T K I R T G A D G R F G S
                R F F L S E V V R Q A E N S Y I I R V A T K L R E R I K N Q D F I
        F T E V E M M S A L T E V V R Q A E G S P I I Q L A T E F R L A Q D D I Y A D
                T F E M N E V V R Q A K D N P L I Q V A T E V R N G Q W L R T N W
                Q I R L T D I M R Q S L D N P I I Q V A T K I R E G G W I E P N W
                Q I R M T D I M R Q S L D N P I I Q V A T T I R E G G W I Y Q N W
                V I R M D K I M R Q A E G N P I I Q V S R A V R D G K M L K P M -
                V I R M D K I M R Q A E G N P I I Q V S R A I R D G K P L M P L -
                Q V E L T E V K R H Q . . G P I I E V A T D I R N G K W I Y E K -
                Q V S L T E V M R S N . . A P I I D V A T S I R T G N W I Y E N V
                Q I H L T E V M R S N . . A P I I E V A T E I R N G G W F R D C M
                Q V H L T E I K R S N . . G P I I Q V A T D I R N G G W L S E N I
                Q L N L T E V M R S N . . A P I I D V A T D I R N G S W I Y E K T
FROM            Q C E L T E V K R S N . . A P I I D V A T D V R N G K W I Y D K V  TO
Figure                                                                              Figure
23E       P L H G L F N G D . . L V L V E T V G P L E H R R V G R R G R P P V D L   23G
      K K E K K I I L N S E . . E C K V I E T P K I N Y N E K Y K W E F Y Q . . .
          G V Q R L T N S E . . E V R V K K A Q V E T F E A D D Q S E W T V W E L
          F L D A Y T V G D . . I T I Y H N G Q E L Q L G S T E V K Y H D S L H .
          M G S T W N N A D . . E L R I V S I D D H F D Q Q Y E V P C W R M . . .
      G K Y P V C V I E N G E . . V V K I L D V R Q K T I D G M . L P K V D N E A F
      D D T I E T L F T N G E V V T I N E I E V F D R T I R I D G S P E F K V N A A
      D D T I E T L F T N G E . . V V T V D E I E V S D M N I R . I D G S P A F S I
      Q I F T E I V Y N N N E . . K I R V L E I I P R R E V I K A E K C D E K I E I
      V S F V E V I Y N N N E . . Q I K I L E I I P R S D T I K A D R C D . P V Q I
      Q T L K E V I F N N G Q . . N V R V I N V . K P S R K T L K A K G V G E I E V
      K K V S E I V F N N G E . . M V K V L C C S Q T S D E I S V R G C S T K Y M V
      K K F S E T I F N N G Q . . L V R I K D C K Y T S T I L R C K G E S H Q L V I
      K K F H E I V F N N G Q . . L V K I L Y A S E T S T F I S A R N V P G E Y M I
      K K F H E T L F T N G Q . . Y V R I L S A D Y T S S F L G A K G V S G E H L I
      K P V S E I L F N N G Q . . L V R I I E A E Y T S T F V A A R G V P G E Y L I
```

Figure 23G

```
         TFRLPE..........QPPDLRPVGLEEAIETTATDFRR
         FETVADGT.......IIKLNTEDWLQQALSHFEKEDWLSN
         TFEDGKGV.......AVTRNREEFLDSILRAFDADAFAED
         SLQQFFQEN.....MEDEITFFHNKEAFLEDFYKEEEWY
         LPRIVTNTTPDGNGIITMPNGNWVDSAVARFQSDQFKED
         SKE-RR.........QGVLHVPNVNKMLDTYLSKVNSPED
         NRD-TK.........TGVYKVSGITDLVNSYLRAVKTPED
         NKE-KK.........SGVYKVKSITDLINSYLRVVKTPED
         -SV-GD.........LGVFQHANAVDFLRQYFRRVKTPDD
         -MN-GE.........LGVMKHENASDFLRRYFSRVKTPDD
         LDD-SG.........NGVKQFHTVKDFLSKYFERTKTPND
         IDGAGV.........HNLTSERSVKSFMEKYFSIVKTPED
         YDGHGV.........QGFTSQTALKDFMVNYFGIVKDADM
         VDGEGV.........HAFNSNTALKDFMIRYFDVVKTSDD
         VDGHGV.........HGFTSTTALKDFMMQYFSIVKSPED
FROM     VDGHGV.........RGFTGDTALRDFMVNYFSIVKSLDD    TO
Figure                                                Figure
23F      YFRDVELLYPHEKPRNRIRCKLLENLLESPDGQLSPDII    23H
         .............VKVRTDEGGMIELRILTSESEEKRQKKLK
         .............KIRTPGRGLTRTIHVLHEEERERYE....
         ........IEYWECKSIYALEQQVFRVVNPDSEAVFNQKLQ
         ............QLESVEDHKLHNALVVKGDYIEDFKFR...
         DVAVLTVE-KEDGN....VYEFTVLWDDLQKERFARYLS
         KLSVSSD....YSGI...EHDFCVLYGSESRLEFEYQLS
         SVAKLKVT-SDFSGV...THDIMSVYGEDSKAEFNYQLS
         EFYLLKTV-SLEEET...EAQIQVVVDPVMKDRLGNYLA
         DYFLMKTE-SMFEDT...KADIQVIADPVMQERLGDYLN
         ECTMLECE-SYEEDE...DDYRRAWFTVVHDQNTQYAIN
         RYWQLDLQ-SLDDPDL..TGSINVIVDEAEINKLNLVLG
         NYWDLEVE-SIDEDEEY-QVDRIKVLPEDQQPKFQAYLA
         RYWNLEVE-TADSDDDYATSQIQVICDPAEMTKFQMFLA
         RHWVLDVE-TYDDEEYA-REKINVISDEQEMNKFQFFLA
         RHWDLTVE-TYGDDEYY-REKIKIISSDEELYKFNLFLG
```

FROM Figure 23G

```
Dda-Rma-DSM  406 L M L A N D A Y F N A L H V R Y G Y A M T V H K A D G E W K
Dda-Csp      433 M A I Y Y E L D E L F D N M A Y A Y A L T C H K A D G S S I D
Dda-Sru      355 M D R F F E L R E R H A R V D Y A Y A T T V H R A D G S T Y D
Dda-Sgo      392 M K L Y Y E T R N M F A N V Q Y I H A S T I H K L Q G S T Y D
Dda-Vph12B8  378 M K E F N G M R K K F N T F K N V Y A G T A H K S D G S T F D
Dda-Vph      356 M R A F N G L K E Q M I E T K S L G A S T V H K S D G T T V K
Dda-Aph65    365 M K S F N A A K K M F I E T K S L G A S T I H K S D G S T V K
Dda-AphCC2   351 M A S F N D A K K T F T E T K S L G A C T I H K S D G S T V K
Dda-Cph      377 M H S F N A I K N K F Q D V K P L P V C T Y H K S D G S T Y D
Dda-Kph      376 M Y S F N Q I K N K F Q T V K A L P V C T Y H K G D G S T Y D
Dda-SphME13  371 M K D F N A I R N T F V K V R P L G A M T F H K S D G S T F D
Dda-AphAc42  377 M A D W N K L K R N F H K V K A L P C S T I H K S D G T S V D
Dda-SphSP18  377 M K D F N K A R R T F L K V R A L P V S T I H K A D G V S V D
Dda-Yph      374 M K D F N S V K N K F K K V K A L P V S T I H K S D G C T V N
Dda-SphS16   375 M S E F N D A K R K F H K V K A L P C S T F H K A D G I S V D
Dda-1993     374 M S D F N D A K S Q F S K V K A L P A S T F H K A D G M S V D
```

FROM Figure 23H

```
         RATVVFNDWRHF---RHAEFFRWAMTAITRAREELLTIG
         NVFLLVS-DMHY----CRDKTKMIHTGLTRAKKCCYVG-
         TVFVDHR-DLRV--CRGEERGALLLYVAVTRPSRRLALLV
         VSYIDIFSLVHNHYMSDEEKYRLLLYVAITRASKDIKIFM
         YTYVFTPDFYKF--GATMTIKRLLYTAITRSRYTTYFAM
         GVCLYTQDMGYA---EPEILQQLVYVGLTRPTDWALYN-
         GVWLALHDIHYA---DEELKQQLVYVGVTRPTDFCLYFD
FROM     GVWLGLHDISYA---DTDLQQQLVYVGVTRPTDFCLYFD     TO
Figure   HAYMYTRDAYAF--ADYDLCKQLIYVGVTRARYTVDYV-     Figure
23I      HSYMYTRDAYAY--ADYELCKQLLYVGTTRARFTVDYV-     23K
         NAYLFTPCLHQY-CRDPDVQELIYVGNTRARKNVCFV-
         NVFLYTPCIHKA---DSQLAQQLLYVGATRARHNVYYI-
         KAFIYTPCIHMA---EASLASQLAYVGITRARYDAYYV-
         NTFLYTPCIHMA---DAQLAKQLLYVGATRARTNLYYI-
         SSFIYTPCIHVS--SDNKFKLELLYVGATRGRHDVFFV-
         RAFIYTPCIHYA---DVELAQQLLYVGVTRGRYDVFYV-
```

FROM Figure 23J

```
             E T Y H Q R L S E A L T A A G I E T T G V E 530
             . . . . . . . . . . . . . . . . . . . . . . 496
             . . . . . . . . . . . . . . . . . . . . . . 421
             H D I D I I L K D L D L - - - - - - - - - - 500
             . . . . . . . . . . . . . . . . . . . . . . 450
             . . . . . . . . . . . . . . . . . . . . . . 421
             . . . . . . . . . . . . . . . . . . . . . . 434
FROM         . . . . . . . . . . . . . . . . . . . . . . 420
Figure       . . . . . . . . . . . . . . . . . . . . . . 443
23K          . . . . . . . . . . . . . . . . . . . . . . 442
             . . . . . . . . . . . . . . . . . . . . . . 438
             . . . . . . . . . . . . . . . . . . . . . . 442
             . . . . . . . . . . . . . . . . . . . . . . 442
             . . . . . . . . . . . . . . . . . . . . . . 439
             . . . . . . . . . . . . . . . . . . . . . . 441
             . . . . . . . . . . . . . . . . . . . . . . 439
```

… # MODIFIED HELICASES

RELATED APPLICATIONS

This application is a national stage filing under U.S.C. § 371 of PCT International Application PCT/GB2014/052736, which has an international filing date of Sep. 10, 2014; is a continuation-in-part of PCT International Application PCT/GB2014/050175, which has an international filing date of Jan. 22, 2014; and claims foreign priority benefits under 35 U.S.C. § 119(a)-(d) or 35 U.S.C. § 365(b) of British application number 1406151.9, filed Apr. 4, 2014, British application number 1404718.7, filed Mar. 17, 2014, and British application number 1318464.3, filed Oct. 18, 2013, the contents of which are herein incorporated by reference in their entireties.

FIELD OF THE INVENTION

The invention relates to a new method of characterising a target polynucleotide. The method uses a pore and a DNA-dependent ATPase (Dda) helicase. The helicase controls the movement of the target polynucleotide through the pore. The invention also relates to modified Dda helicases which can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing" method, a single polynucleotide strand is passed through the pore and the identity of the nucleotides are derived. Strand sequencing can involve the use of a nucleotide handling protein, such as a helicase, to control the movement of the polynucleotide through the pore.

SUMMARY OF THE INVENTION

The inventors have demonstrated that a Dda helicase can control the movement of a polynucleotide through a pore especially when a potential, such as a voltage, is applied. The helicase is capable of moving a target polynucleotide in a controlled and stepwise fashion against or with the field resulting from the applied voltage.

The inventors have also surprisingly identified specific Dda mutants which have an improved ability to control the movement of a polynucleotide through a pore. Such mutants typically comprise one or more modifications in (i) the tower domain and/or (ii) the pin domain and/or (iii) the 1A (RecA-like motor) domain.

Accordingly, the invention provides a Dda helicase in which at least one cysteine residue and/or at least one non-natural amino acid have been introduced into (i) the tower domain and/or (ii) the pin domain and/or (iii) the 1A (RecA-like motor) domain, wherein the helicase retains its ability to control the movement of a polynucleotide.

The invention also provides:

a Dda helicase in which at least one cysteine residue and/or at least one non-natural amino acid have been introduced into the hook domain and/or the 2A (RecA-like motor) domain, wherein the helicase retains its ability to control the movement of a polynucleotide;

a Dda helicase which is modified to reduce its surface negative charge, wherein the helicase retains its ability to control the movement of a polynucleotide;

a first polypeptide comprising the pin domain and the 1A (RecA-like motor) domain from a Dda helicase and not comprising any other domains from a Dda helicase, wherein at least one cysteine residue and/or at least one non-natural amino acid have been introduced into the pin domain and/or the 1A (RecA-like motor) domain;

a second polypeptide comprising the 2A (RecA-like motor) domain, tower domain and hook domain from a Dda helicase and not comprising any other domains from a Dda helicase, wherein at least one cysteine residue and/or at least one non-natural amino acid have been introduced into the tower domain;

a helicase comprising a first polypeptide of the invention covalently attached to a second polypeptide of the invention, wherein the helicase has the ability to control the movement of a polynucleotide;

a construct comprising a Dda helicase or a helicase of the invention and an additional polynucleotide binding moiety, wherein the helicase is attached to the polynucleotide binding moiety and the construct has the ability to control the movement of a polynucleotide;

a polynucleotide comprising a sequence which encodes a helicase of the invention, a polypeptide of the invention or a construct of the invention;

a vector which comprises a polynucleotide of the invention operably linked to a promoter;

a host cell comprising a vector of the invention;

a method of making a helicase of the invention, a polypeptide of the invention or a construct of the invention, which comprises expressing a polynucleotide of the invention, transfecting a cell with a vector of the invention or culturing a host cell of the invention; a method of controlling the movement of a polynucleotide, comprising contacting the polynucleotide with a Dda helicase or a construct of the invention and thereby controlling the movement of the polynucleotide;

a method of characterising a target polynucleotide, comprising (a) contacting the target polynucleotide with a transmembrane pore and a Dda helicase or a construct of the invention such that the helicase controls the movement of the target polynucleotide through the pore and (b) taking one or more measurements as the polynucleotide moves with respect to the pore wherein the measurements are indicative of one or more characteristics of the target polynucleotide and thereby characterising the target polynucleotide;

method of forming a sensor for characterising a target polynucleotide, comprising forming a complex between (a) a pore and (b) a Dda helicase or a construct of the invention and thereby forming a sensor for characterising the target polynucleotide;

sensor for characterising a target polynucleotide, comprising a complex between (a) a pore and (b) a Dda helicase or a construct of the invention;

use of a Dda helicase or a construct of the invention to control the movement of a target polynucleotide through a pore;

a kit for characterising a target polynucleotide comprising (a) a pore and (b) a Dda helicase or a construct of the invention;

an apparatus for characterising target polynucleotides in a sample, comprising (a) a plurality of pores and (b) a plurality of Dda helicases or a plurality of constructs of the invention; and a series of two or more helicases attached to a polynucleotide, wherein at least one of the two or more helicases is a Dda helicase of the invention.

DESCRIPTION OF THE FIGURES

FIG. 2 shows zoomed in regions of the helicase-controlled DNA movement shown in the current trace in FIG. 1 (y-axis label=Current (pA, upper trace 20 to 80, lower trace 20 to 60), x-axis label=Time (s, upper trace 2995 to 3020, lower trace 8140 to 8170) upper and lower trace). A) shows the beginning of the helicase-controlled DNA movement and B) shows the end of the helicase controlled DNA movement.

FIG. 9 shows example current traces (both traces have the following axes labels y-axis label=Current (pA), x-axis label=Time (s)) of when a helicase (T4 Dda-E94C/A360C/C109A/C136A (SEQ ID NO: 8 with mutations E94C/A360C/C109A/C136A and then (ΔM1)G1G2)) controlled the translocation of DNA (0.1 nM, SEQ ID NO: 67 attached by its 3' end to four iSpC3 spacers which are attached to the 5' end of SEQ ID NO: 61 which is attached at its 3' end to four four 5-nitroindoles spacers which are attached to the 5' end of SEQ ID NO: 69, the SEQ ID NO: 61 region of this construct is hybridised to SEQ ID NO: 63 (which has a 3' cholesterol tether)) through an MspA nanopore. Both traces showed multiple helicase controlled DNA movements.

FIG. 10 shows example current traces (both traces have the following axes labels y-axis label=Current (pA), x-axis label=Time (s)) of when a helicase (T4 Dda-E94C/A360C/C114A/C171A/C421D (SEQ ID NO: 8 with mutations E94C/A360C/C114A/C171A/C421D and then (ΔM1)G1G2)) controlled the translocation of DNA (0.1 nM, SEQ ID NO: 67 attached by its 3' end to four iSpC3 spacers which are attached to the 5' end of SEQ ID NO: 61 which is attached at its 3' end to four 5-nitroindoles spacers which are attached to the 5' end of SEQ ID NO: 69, the SEQ ID NO: 61 region of this construct is hybridised to SEQ ID NO: 63 (which has a 3' cholesterol tether)) through an MspA nanopore. Both traces showed multiple helicase controlled DNA movements.

FIG. 18 shows example plots of when the helicase T4 Dda-E94C/A360C (SEQ ID NO: 24 with mutations E94C/A360C) controlled the translocation of DNA construct X (see FIG. 17 for details) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots A and B each showed a single DNA strand moving through the nanopore under the control of helicases, the labelled regions 3 and 4 corresponded to the translocation of region 3 and 4 of DNA construct X (see FIG. 17). Trace A shows the movement index observed when construct X was translocated through the pore under the control of a single T4 Dda-E94C/A360C helicase. Trace B shows the movement index observed when construct X was translocated through the pore under the control of two T4 Dda-E94C/A360C helicases. As region 3 and region 4 were approximately the same length, the movement index observed for each region would have been expected to have had approximately the same number of points in the movement index. Plot A shows a significantly reduced number of points in the movement index for region 4 when compared to region 3, therefore, less information was derived from region 4 than region 3. However, plot B (where the movement of construct X was controlled by two T4 Dda-E94C/A360C helicases) showed many more points in the movement index of region 4, which indicated that approximately the same amount of information was derived from region 4 as region 3. Using two helicases to control the movement of construct X provided improved movement as more information was derived from region 4 than when a single helicase controlled the movement.

FIG. 19 shows example plots of when the helicase T4 Dda-E94C/C109A/C136A/A360C (SEQ ID NO: 24 with mutations E94C/C109A/C136A/A360C) controlled the translocation of DNA construct X (see FIG. 17 for details) through an MspA nanopore. The x-axis corresponds to the movement index (see FIG. 18's figure legend for description of movement index) and the y-axis corresponds to the current (pA). Plots A and B each showed a single DNA strand moving through the nanopore under the control of helicases, the labelled regions 3 and 4 corresponded to the translocation of region 3 and 4 of DNA construct X (see FIG. 17). Trace A shows the movement index observed when construct X was translocated through the pore under the control of a single T4 Dda-E94C/C109A/C136A/A360C. Trace B shows the movement index observed when construct X was translocated through the pore under the control of two T4 Dda-E94C/C109A/C136A/A360C helicases. As region 3 and region 4 were approximately the same length, the movement index observed for each region would have been expected to have had approximately the same number of points in the movement index. Plot A shows a significantly reduced number of points in the movement index for region 4 when compared to region 3, therefore, less information was derived from region 4 than region 3. However, plot B (where the movement of construct X was controlled by two T4 Dda-E94C/C109A/C136A/A360C helicases) showed approximately the same number of points in both sections of the movement index, and therefore approximately the same amount of information was derived from region 4 as region 3. Using two helicases to control the movement of construct X provided improved movement as more information was derived from region 4 than when a single helicase controlled the movement.

FIG. 21 shows example plots of when either the helicase T4 Dda-E94C/C109A/C136A/A360C (section (A), SEQ ID NO: 24 with mutations E94C/C109A/C136A/A360C) or the helicases T4 Dda-E94C/C109A/C136A/A360C and T4 Dda-E94C/C109A/C136A/A360C/W378A (section (B)) controlled the translocation of DNA construct Z (FIG. 20) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots A and B each showed a single DNA strand moving through the nanopore under the control of helicases, the labelled regions 5 and 6 corresponded to the translocation of region 5 and 6 of DNA construct Z (see FIG. 20). Trace A shows the movement index observed when construct Z was translocated through the pore under the control of a single T4 Dda-E94C/C109A/C136A/A360C helicase. Trace B shows the movement index observed when construct Z was translocated through the pore under the control of both T4 Dda-E94C/C109A/C136A/A360C and T4 Dda-E94C/C109A/C136A/A360C/W378A. As region 5 and region 6 were approximately the same length, the movement index observed for each region would have been expected to have had approximately the same number of points in the movement index. Plot A shows a significantly reduced number of points in the movement index for region 6 when compared to region 5, therefore, less information was derived from region 6 than region 5. However, plot B (where the movement of construct Z was controlled by both T4 Dda-E94C/C109A/C136A/A360C and T4 Dda-E94C/C109A/C136A/A360C/W378A) showed many more points in the movement index of region 6, which indicated that approximately the same amount of information was derived from region 6 as region 5. Using two different helicases to control the movement of construct Z provided improved movement as more information was derived from region 6 than when a single helicase controlled the movement.

FIG. 22 shows example plots of when either the single helicase T4 Dda-E94C/C109A/C136A/A360C/W378A (section (a), SEQ ID NO: 24 with mutations E94C/C109A/C136A/A360C/W378A) or two T4 Dda-E94C/C109A/C136A/A360C/W378A helicases (section (b)) were used to controlled the translocation of DNA construct Z (FIG. 20) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step, and assigned an incrementing movement index point. The mean current against movement index therefore closely approximated the original current signal, and was used to characterise the translocated DNA. Plots (A) and (B) showed a single DNA strand moving through the nanopore under the control of either one or two a helicases, the labelled regions 5 and 6 corresponded to the translocation of region 5 and 6 of DNA construct Z (see FIG. 20). Trace A shows the movement index observed when construct Z was translocated through the pore under the control of a single T4 Dda-E94C/C109A/C136A/A360C/W378A helicase. Trace B shows the movement index observed when construct Z was translocated through the pore under the control of two T4 Dda-E94C/C109A/C136A/A360C/W378A helicases. As region 5 and 6 were approximately the same length, the movement index observed for each region would have been expected to have had approximately the same number of points in the movement index. Plot A shows a significantly reduced number of points in the movement index for region 6 when compared to region 5, therefore, less information was derived from region 6 than region 5. However, plot B (where the movement of construct Z was controlled by two T4 Dda-E94C/C109A/C136A/A360C/W378A helicases) showed many more points in the movement index of region 6, which indicated that approximately the same amount of information was derived from region 6 as region 5. Therefore, using two helicases to control the movement of construct Z provided improved movement as more information was derived from region 6 than when a single helicase controlled the movement.

FIGS. 23A-23L show an alignment of the preferred Dda helicases of the invention. The sequences in the figures correspond to SEQ ID NOs: 8-23.

DESCRIPTION OF THE SEQUENCE LISTING

Figure 1:
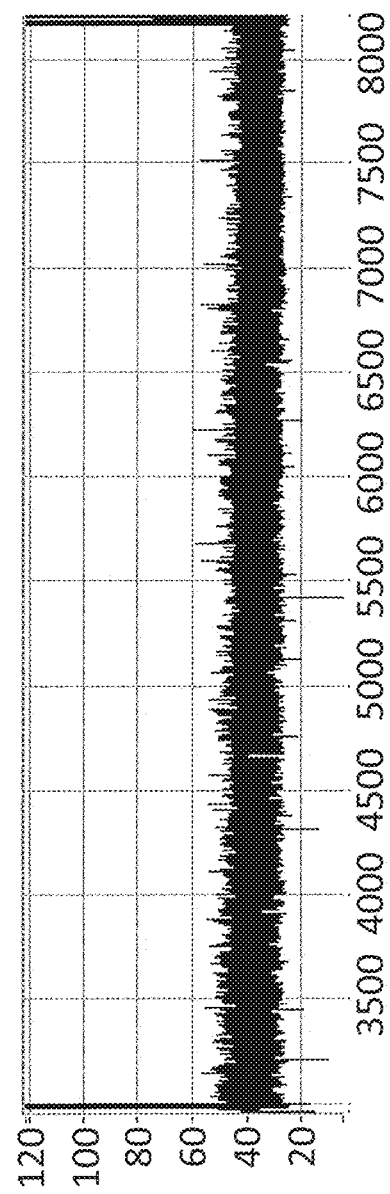
FIG. 1 shows an example current trace (y-axis label=Current (pA, 20 to 120), x-axis label=Time (s, 3500 to 8000)) of when a helicase (T4 Dda-E94C/A360C (SEQ ID NO: 8 with mutations E94C/A360C)) controlled the translocation of the Lambda DNA construct (0.2 nM, SEQ ID NO: 60 attached by its 3' end to four iSpC3 spacers which are attached to the 5' end of SEQ ID NO: 61 which is attached at its 3' end to SEQ ID NO: 62, the SEQ ID NO: 61 region of this construct is hybridised to SEQ ID NO: 63 (which has a 3' cholesterol tether)) through a nanopore (MS(B1-G75S/G77S/L88N/Q126R)8 MspA (SEQ ID NO: 2 with mutations G75S/G77S/L88N/Q126R)).

SEQ ID NO: 1 shows the codon optimised polynucleotide sequence encoding the MS-B 1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B 1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NOs: 8 to 23 show the amino acid sequences of the Dda helicases shown in Tables 1 and 2.

SEQ ID NO: 24 shows the amino acid sequence of a preferred HhH domain.

SEQ ID NO: 25 shows the amino acid sequence of the ssb from the bacteriophage RB69, which is encoded by the gp32 gene.

SEQ ID NO: 26 shows the amino acid sequence of the ssb from the bacteriophage T7, which is encoded by the gp2.5 gene.

SEQ ID NO: 27 shows the amino acid sequence of the UL42 processivity factor from Herpes virus 1.

SEQ ID NO: 28 shows the amino acid sequence of subunit 1 of PCNA.

SEQ ID NO: 29 shows the amino acid sequence of subunit 2 of PCNA.

SEQ ID NO: 30 shows the amino acid sequence of subunit 3 of PCNA.

SEQ ID NO: 31 shows the amino acid sequence of Phi29 DNA polymerase.

SEQ ID NO: 32 shows the amino acid sequence (from 1 to 319) of the UL42 processivity factor from the Herpes virus 1.

SEQ ID NO: 33 shows the amino acid sequence of the ssb from the bacteriophage RB69, i.e. SEQ ID NO: 25, with its C terminus deleted (gp32RB69CD).

SEQ ID NO: 34 shows the amino acid sequence (from 1 to 210) of the ssb from the bacteriophage T7 (gp2.5T7-R211Del). The full length protein is shown in SEQ ID NO: 96.

SEQ ID NO: 35 shows the amino acid sequence of the $5^{th}$ domain of Hel308 Hla.

SEQ ID NO: 36 shows the amino acid sequence of the $5^{th}$ domain of Hel308 Hvo.

SEQ ID NO: 37 shows the amino acid sequence of the (HhH)2 domain.

SEQ ID NO: 38 shows the amino acid sequence of the (HhH)2-(HhH)2 domain.

SEQ ID NO: 39 shows the amino acid sequence of the human mitochondrial SSB (HsmtSSB).

SEQ ID NO: 40 shows the amino acid sequence of the p5 protein from Phi29 DNA polymerase.

SEQ ID NO: 41 shows the amino acid sequence of the wild-type SSB from E. coli.

SEQ ID NO: 42 shows the amino acid sequence of the ssb from the bacteriophage T4, which is encoded by the gp32 gene.

SEQ ID NO: 43 shows the amino acid sequence of EcoSSB-CterAla.

SEQ ID NO: 44 shows the amino acid sequence of EcoSSB-CterNGGN.

SEQ ID NO: 45 shows the amino acid sequence of EcoSSB-Q152del.

SEQ ID NO: 46 shows the amino acid sequence of EcoSSB-G117del.

SEQ ID NO: 47 shows the amino acid sequence of Topoisomerase V Mka (*Methanopyrus Kandleri*).

SEQ ID NO: 48 shows the amino acid sequence of domains H-L of Topoisomerase V Mka (*Methanopyrus Kandleri*).

SEQ ID NO: 49 shows the amino acid sequence of Mutant S (*Escherichia coli*).

SEQ ID NO: 50 shows the amino acid sequence of Sso7d (*Sulfolobus solfataricus*).

SEQ ID NO: 51 shows the amino acid sequence of Sso10b1 (*Sulfolobus solfataricus* P2).

SEQ ID NO: 52 shows the amino acid sequence of Sso10b2 (*Sulfolobus solfataricus* P2).

SEQ ID NO: 53 shows the amino acid sequence of Tryptophan repressor (*Escherichia coli*).

SEQ ID NO: 54 shows the amino acid sequence of Lambda repressor (Enterobacteria phage lambda).

SEQ ID NO: 55 shows the amino acid sequence of Cren7 (Histone crenarchaea Cren7 Sso).

SEQ ID NO: 56 shows the amino acid sequence of human histone (*Homo sapiens*).

SEQ ID NO: 57 shows the amino acid sequence of dsbA (Enterobacteria phage T4).

SEQ ID NO: 58 shows the amino acid sequence of Rad51 (*Homo sapiens*).

SEQ ID NO: 59 shows the amino acid sequence of PCNA sliding clamp (*Citromicrobium bathyomarinum* JL354).

SEQ ID NO: 60 shows a polynucleotide sequence used in Example 1. SEQ ID NO: 60 is attached by its 3' end to four iSpC3 spacers which are attached to the 5' end of SEQ ID NO: 61.

SEQ ID NO: 61 shows a polynucleotide sequence used in Example 1, 3, 4 and 6.

SEQ ID NO: 62 shows a polynucleotide sequence used in Example 1. SEQ ID NO: 62 is attached by its 5' end to three iSpC3 spacers which are attached to the 3' end of SEQ D NO: 61.

SEQ ID NO: 63 shows a polynucleotide sequence used in Example 1 which at the 3' end of the sequence has six iSp18 spacers attached to two thymine residues and a 3' cholesterol TEG.

SEQ ID NO: 64 shows a polynucleotide sequence used in Example 2. The sequence has a carboxyfluorescein (FAM) attached to the thymine at position 37 in the sequence.

SEQ ID NO: 65 shows a circular polynucleotide sequence used in Example 2. The sequence has a carboxyfluorescein (FAM) attached to one thymine in the sequence.

SEQ ID NO: 66 shows the amino acid sequence for the Trwc Cba helicase.

SEQ ID NO: 67 shows a polynucleotide sequence used in Example 3 and 4.

SEQ ID NO: 68 shows a polynucleotide sequence used in Example 3. SEQ ID NO: 68 is attached by its 5' end to four 5-nitroindoles which are attached to the 3' end of SEQ ID NO: 61.

SEQ ID NO: 69 shows a polynucleotide sequence used in Example 4.

SEQ ID NO: 70 shows a polynucleotide sequence used in Example 5 and 6.

SEQ ID NO: 71 shows a polynucleotide sequence used in Example 5.

SEQ ID NO: 72 shows a polynucleotide sequence used in Example 6.

SEQ ID NO: 73 shows a polynucleotide sequence used in Example 6.

SEQ ID NO: 74 shows a polynucleotide sequence used in Example 6, 7 and 8.

SEQ ID NO: 75 shows a polynucleotide sequence used in Example 6, 7 and 8.

SEQ ID NO: 76 shows a polynucleotide sequence used in Example 7 and 8.

SEQ ID NO: 77 shows a polynucleotide sequence used in Example 7 and 8.

SEQ ID NO: 78 shows a polynucleotide sequence used in Example 7 and 8.

SEQ ID NO: 79 shows a polynucleotide sequence used in Example 7 and 8.

SEQ ID NO: 80 shows a polynucleotide sequence used in Example 7 and 8.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a helicase" includes "helicases", reference to "a modification" includes two or more such modifications, reference to "a transmembrane protein pore" includes two or more such pores, and the like.

All publications, patents and patent applications cited herein, whether supra or infra, are hereby incorporated by reference in their entirety.

Modified Dda Helicases

The present invention provides a modified Dda helicase. The one or more specific modifications are discussed in more detail below. The modification(s) allows the modified helicase to remain bound to the polynucleotide for longer. The modified helicase retains its ability to control the movement of a polynucleotide. In other words, the modified helicase is still capable of controlling the movement of a polynucleotide. The extent to which the helicase can control the movement of a polynucleotide is typically altered by the modifications as discussed in more detail below.

The Dda helicase of the invention is modified. The modified helicase is typically modified compared with the corresponding wild-type helicase or natural helicase. The helicase of the invention is artificial or non-natural.

The ability of a helicase to bind to and unbind from a polynucleotide can be determined using any method known in the art. Suitable binding/unbinding assays include, but are not limited to, native polyacrylamide gel electrophoresis (PAGE), fluorescence anisotropy, calorimetry and Surface plasmon resonance (SPR, such as Biacore™). The ability of a helicase to unbind from a polynucleotide can of course be determined by measuring the time for which the helicase can control the movement of a polynucleotide. This may also be determined using any method known in the art. The ability of a helicase to control the movement of a polynucleotide is typically assayed in a nanopore system, such as the ones described below. The ability of a helicase to control the movement of a polynucleotide can be determined as described in the Examples.

A modified helicase of the invention is a useful tool for controlling the movement of a polynucleotide during Strand Sequencing. The Dda helicase can control the movement of DNA in at least two active modes of operation (when the helicase is provided with all the necessary components to facilitate movement e.g. ATP and Mg$^{2+}$) and one inactive mode of operation (when the helicase is not provided with the necessary components to facilitate movement). When provided with all the necessary components to facilitate movement the Dda helicase moves along the DNA in the 5'-3' direction, but the orientation of the DNA in the nanopore (dependent on which end of the DNA is captured) means that the enzyme can be used to either move the DNA out of the nanopore against the applied field, or move the DNA into the nanopore with the applied field. When the 3' end of the DNA is captured the helicase works against the direction of the field applied by the voltage, pulling the threaded DNA out of the nanopore and into the cis chamber. However, when the DNA is captured 5'-down in the nanopore, the helicase works with the direction of the field applied by the voltage, pushing the threaded DNA into the nanopore and into the trans chamber. When the Dda helicase is not provided with the necessary components to facilitate movement it can bind to the DNA and act as a brake slowing the movement of the DNA when it is pulled into the pore by the applied field. In the inactive mode it does not matter whether the DNA is captured either 3' or 5' down, it is the applied field which pulls the DNA into the nanopore towards the trans side with the enzyme acting as a brake. When in the inactive mode the movement control of the DNA by the helicase can be described in a number of ways including ratcheting, sliding and braking.

A problem which occurs in sequencing polynucleotides, particularly those of 500 nucleotides or more, is that the molecular motor which is controlling the movement of the polynucleotide may disengage from the polynucleotide. This allows the polynucleotide to be pulled through the pore rapidly and in an uncontrolled manner in the direction of the applied field. A modified helicase of the invention is less likely to unbind or disengage from the polynucleotide being sequenced. The modified helicase can provide increased read lengths of the polynucleotide as they control the movement of the polynucleotide through a nanopore. The ability to move an entire polynucleotide through a nanopore under the control of a modified helicase of the invention allows characteristics of the polynucleotide, such as its sequence, to be estimated with improved accuracy and speed over known methods. This becomes more important as strand lengths increase and molecular motors are required with improved processivity. A modified helicase of the invention is particularly effective in controlling the movement of target polynucleotides of 500 nucleotides or more, for example 1000 nucleotides, 5000, 10000, 20000, 50000, 100000 or more.

In addition, using a modified helicase in accordance with the invention means that a lower concentration of helicase may be used. For instance, in Example 3, 1 nM of a modified helicase of the invention is used. In contrast, in Example 3, 1 μM of TrwC Cba, which is not a modified Dda helicase of the invention, is used.

A modified helicase of the invention is also a useful tool for isothermal polymerase chain reaction (PCR). In such methods, the strands of double stranded DNA are typically first separated by a helicase of the invention and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesized DNA products may then be used as substrates by the helicases of the invention, entering the next round of the reaction. Thus, a simultaneous chain reaction develops, resulting in exponential amplification of the selected target sequence.

The modified helicase has the ability to control the movement of a polynucleotide. The ability of a helicase to control the movement of a polynucleotide can be assayed using any method known in the art. For instance, the helicase may be contacted with a polynucleotide and the position of the polynucleotide may be determined using standard methods. The ability of a modified helicase to control the movement of a polynucleotide is typically assayed in a nanopore system, such as the ones described below and, in particular, as described in the Examples.

A modified helicase of the invention may be isolated, substantially isolated, purified or substantially purified. A helicase is isolated or purified if it is completely free of any other components, such as lipids, polynucleotides, pore monomers or other proteins. A helicase is substantially isolated if it is mixed with carriers or diluents which will not interfere with its intended use. For instance, a helicase is substantially isolated or substantially purified if it is present in a form that comprises less than 10%, less than 5%, less than 2% or less than 1% of other components, such as lipids, polynucleotides, pore monomers or other proteins.

Any Dda helicase may be modified in accordance with the invention. Preferred Dda helicases are discussed below.

Dda helicases typically comprises the following five domains: 1A (RecA-like motor) domain, 2A (RecA-like motor) domain, tower domain, pin domain and hook domain (Xiaoping He et al., 2012, Structure; 20: 1189-1200). The domains may be identified using protein modelling, x-ray diffraction measurement of the protein in a crystalline state (Rupp B (2009). Biomolecular Crystallography: Principles, Practice and Application to Structural Biology. New York: Garland Science), nuclear magnetic resonance (NMR) spectroscopy of the protein in solution (Mark Rance; Cavanagh, John; Wayne J. Fairbrother; Arthur W. Hunt III; Skelton, Nicholas J. (2007). Protein NMR spectroscopy: principles and practice (2nd ed.). Boston: Academic Press) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69). Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

Modifications in the Tower Domain and/or Pin Domain and/or 1A Domain

In one embodiment, the Dda helicase of the invention is one in which at least one cysteine residue (i.e. one or more cysteine residues) and/or at least one non-natural amino acid (i.e. one or more non-natural amino acids) have been introduced into (i) the tower domain and/or (ii) the pin domain and/or the (iii) 1A (RecA-like motor) domain, wherein the helicase retains its ability to control the movement of a polynucleotide. At least one cysteine residue and/or at least one non-natural amino acid may be introduced into the tower domain, the pin domain, the 1A domain, the tower domain and the pin domain, the tower domain and the 1A domain or the tower domain, the pin domain and the 1A domain.

The Dda helicase of the invention is preferably one in which at least one cysteine residue and/or at least one non-natural amino acid have been introduced into each of (i) the tower domain and (ii) the pin domain and/or the 1A (RecA-like motor) domain, i.e. into the tower domain and the pin domain, the tower domain and the 1A domain or the tower domain, the pin domain and the 1A domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are/is preferably introduced by substitution. Methods for doing this are known in the art.

These modifications do not prevent the helicase from binding to a polynucleotide. These modifications decrease the ability of the polynucleotide to unbind or disengage from the helicase. In other words, the one or more modifications increase the processivity of the Dda helicase by preventing dissociation from the polynucleotide strand. The thermal stability of the enzyme is typically also increased by the one or more modifications giving it an improved structural stability that is beneficial in Strand Sequencing.

A non-natural amino acid is an amino that is not naturally found in a Dda helicase. The non-natural amino acid is preferably not histidine, alanine, isoleucine, arginine, leucine, asparagine, lysine, aspartic acid, methionine, cysteine, phenylalanine, glutamic acid, threonine, glutamine, tryptophan, glycine, valine, proline, serine or tyrosine. The non-natural amino acid is more preferably not any of the twenty amino acids in the previous sentence or selenocysteine Preferred non-natural amino acids for use in the invention include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl) carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino] phenyl}propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl) norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, O-(4,5-Dimethoxy-2-nitrobenzyl)-L-serine, (2S)-2-amino-6-([[(2-nitrobenzyl)oxy]carbonyl]amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino] hexanoic acid, $N^6$-[(Cyclopentyloxy)carbonyl]-L-lysine, (2S)-2-amino-6-{[(2R)-tetrahydrofuran-2-ylcarbonyl] amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy) carbonyl]amino}hexanoic acid and $N^6$-[(2-Azidoethoxy) carbonyl]-L-lysine. The most preferred non-natural amino acid is 4-azido-L-phenylalanine (Faz).

Table 1 below summarises the preferred Dda helicases which may be modified in accordance with the invention.

| Dda Homologue (SEQ ID NO:) | | Habitat | Uniprot | Length | Sequence Identity to 1993/% | Number of D/E vs. K/R amino acids | # C |
|---|---|---|---|---|---|---|---|
| Rma-DSM (SEQ ID NO: 9) | *Rhodothermus marinus* | Mild halophile, moderate thermophile >65° C. | D0MKQ2 | 678 | 21 | −84/+85 | 2 |
| Csp (SEQ ID NO: 10) | *Cyanothece* sp. (strain ATCC 51142) | Marine bacterium | B1X365 | 496 | 24 | −76/+76 | 5 |
| Sru | *Salinibacter ruber* | Extremely | Q2S429 | 421 | 26 | −78/+54 | 3 |

-continued

| Dda Homologue (SEQ ID NO:) | Habitat | Uniprot | Length | Sequence Identity to 1993/% | Number of D/E vs. K/R amino acids | # C |
|---|---|---|---|---|---|---|
| (SEQ ID NO: 11) | halophilic, 35-45° C. | | | | | |
| Sgo (SEQ ID NO: 12) | *Sulfurimonas gotlandica* GD1 | Habitat: hydrothermal vents, coastal sediments | B6BJ43 | 500 | 27 | −72/+64 | 2 |
| Vph12B8 (SEQ ID NO: 13) | *Vibrio phage henriette* 12B8 | Host found in saltwater, stomach bug | M4MBC3 | 450 | 27 | −62/+47 | 6 |
| Vph (SEQ ID NO: 14) | *Vibrio phage phi-pp2* | Host found in saltwater, stomach bug | I6XGX8 | 421 | 39 | −55/+45 | 5 |
| Aph65 (SEQ ID NO: 15) | *Aeromonas phage* 65 | Host found in fresh/brackish water, stomach bug | E5DRP6 | 434 | 40 | −57/+48 | 4 |
| AphCC2 (SEQ ID NO: 16) | *Aeromonas phage* CC2 | Host found in fresh/brackish water, stomach bug | I6XH64 | 420 | 41 | −53/+44 | 4 |
| Cph (SEQ ID NO: 17) | *Cronobacter phage* vB CsaM GAP161 | Host member of enterobacteriaceae | K4FBD0 | 443 | 42 | −59/+57 | 4 |
| Kph (SEQ ID NO: 18) | *Klebsiella phage* KP15 | Host member of enterobacteriaceae | D5JF67 | 442 | 44 | −59/+58 | 5 |
| SphIME13 (SEQ ID NO: 19) | *Stenotrophomonas phage* IME13 | Host found in soil | J7HXT5 | 438 | 51 | −58/+59 | 7 |
| AphAc42 (SEQ ID NO: 20) | *Acinetobacter phage* Ac42 | Host found in soil | E5EYE6 | 442 | 59 | −53/+49 | 9 |
| SphSP18 (SEQ ID NO: 21) | *Shigella phage* SP18 | Host member of enterobacteriaceae | E3SFA5 | 442 | 59 | −55/+55 | 9 |
| Yph (SEQ ID NO: 22) | *Yersinia phage* phiR1-RT | Host member of enterobacteriaceae | I7J3V8 | 439 | 64 | −52/+52 | 7 |
| SphS16 (SEQ ID NO: 23) | *Salmonella phage* S16 | Host member of enterobacteriaceae | M1EA88 | 441 | 72 | −56/+55 | 5 |
| 1993 (SEQ ID NO: 8) | *Enterobateria phage* T4 | Host member of enterobacteriaceae | P32270 | 439 | 100 | −57/+58 | 5 |

Table 2 below (which is separated in two parts) identifies the residues making up each domain in each Dda homologue (SEQ ID NOs: 8 to 23).

| Homologue | SEQ ID NO | 1A | 2A |
|---|---|---|---|
| Dda-Rma-DSM | 9 | M1-I84 + R113-Y211 | R212-E294 + G422-S678 |
| Dda-Csp | 10 | M1-L147 + S166-V240 | R241-N327 + A449-G496 |
| Dda-Sru | 11 | M1-L90 + E108-H173 | R174-D260 + A371-V421 |
| Dda-Sgo | 12 | M1-L115 + N136-V205 | R206-K293 + I408-L500 |
| Dda-Vph12B8 | 13 | M1-L96 + F114-V194 | R195-D287 + V394-Q450 |
| Dda-Vph | 14 | M1-L77 + V96-V166 | R167-T249 + L372-N421 |
| Dda-Aph65 | 15 | M1-M81 + L99-M171 | R172-T254 + L381-K434 |
| Dda-AphCC2 | 16 | M1-M68 + M86-M158 | R159-T241 + L367-K420 |
| Dda-Cph | 17 | M1-L87 + A108-M181 | R182-T262 + L393-V443 |
| Dda-Kph | 18 | M1-L87 + A108-M181 | R182-T262 + L392-V442 |
| Dda-SphIME13 | 19 | M1-L85 + T103-K176 | R177-N257 + L387-V438 |
| Dda-AphAc42 | 20 | M1-L91 + V109-M183 | R184-T265 + L393-I442 |
| Dda-SphSP18 | 21 | M1-L87 + M105-M179 | R180-T261 + L393-V442 |
| Dda-Yph | 22 | M1-L86 + V104-K178 | R179-T260 + L390-I439 |
| Dda-SphS16 | 23 | M1-L86 + V104-M178 | R179-T260 + L391-V441 |
| Dda-1993 | 8 | M1-L85 + V103-K177 | R178-T259 + L390-V439 |

-continued

| Homologue | SEQ ID | tower | pin | hook |
| --- | --- | --- | --- | --- |
| Dda-Rma-DSM | 9 | G295-N309 + F316-Y421 | Y85-L112 | A310-L315 |
| Dda-Csp | 10 | V328-P342 + N360-Y448 | K148-N165 | V343-L359 |
| Dda-Sru | 11 | A261-T275 + T285-Y370 | G91-E107 | W276-L284 |
| Dda-Sgo | 12 | G294-I307 + T314-Y407 | G116-T135 | R308-Y313 |
| Dda-Vph12B8 | 13 | V288-E301 + N307-N393 | G97-P113 | M302-W306 |
| Dda-Vph | 14 | S250-P264 + E278-S371 | K78-E95 | V265-I277 |
| Dda-Aph65 | 15 | K255-P269 + T284-S380 | K82-K98 | V270-F283 |
| Dda-AphCC2 | 16 | D242-P256 + T271-S366 | K69-K85 | V257-F270 |
| Dda-Cph | 17 | T263-P277 + N295-P392 | K88-K107 | L278-Y294 |
| Dda-Kph | 18 | D263-P277 + N295-A391 | K88-K107 | L278-Y294 |
| Dda-SphIME13 | 19 | A258-P272 + N290-P386 | K86-G102 | L273-F289 |
| Dda-AphAc42 | 20 | L266-P280 + N298-A392 | K92-D108 | L281-F297 |
| Dda-SphSP18 | 21 | D262-P276 + N294-A392 | K88-E104 | H277-F293 |
| Dda-Yph | 22 | D261-P275 + N293-A389 | K87-E103 | L276-F292 |
| Dda-SphS16 | 23 | E261-P275 + T293-A390 | K87-E103 | L276-F292 |
| Dda-1993 | 8 | D260-P274 + N292-A389 | K86-E102 | L275-F291 |

The helicase of the invention preferably comprises a variant of SEQ ID NO: 8 in which at least one cysteine residue and/or at least one non-natural amino acid have been introduced into (i) the tower domain (residues D260-P274 and N292-A389) and/or (ii) the pin domain (residues K86-E102) and/or the (iii) 1A domain (residues M1-L85 and V103-K177). The at least one cysteine residue and/or at least one non-natural amino acid are preferably introduced into residues N292-A389 of the tower domain.

The helicase of the invention preferably comprises a variant of SEQ ID NO: 9 in which at least one cysteine residue and/or at least one non-natural amino acid have been introduced into (i) the tower domain (residues G295-N309 and F316-Y421) and/or (ii) the pin domain (residues Y85-L112) and/or the (iii) 1A domain (residues M1484 and R113-Y211). The at least one cysteine residue and/or at least one non-natural amino acid are preferably introduced into residues F316-Y421 of the tower domain.

The helicase of the invention preferably comprises a variant of SEQ ID NO: 10 in which at least one cysteine residue and/or at least one non-natural amino acid have been introduced into (i) the tower domain (residues V328-P342 and N360-Y448) and/or (ii) the pin domain (residues K148-N165) and/or the (iii) 1A domain (residues M1-L147 and 5166-V240). The at least one cysteine residue and/or at least one non-natural amino acid are preferably introduced into residues N360-Y448 of the tower domain.

The helicase of the invention preferably comprises a variant of SEQ ID NO: 11 in which at least one cysteine residue and/or at least one non-natural amino acid have been introduced into (i) the tower domain (residues A261-T275 and T285-Y370) and/or (ii) the pin domain (residues G91-E107) and/or the (iii) 1A domain (residues M1-L90 and E108-H173). The at least one cysteine residue and/or at least one non-natural amino acid are preferably introduced into residues T285-Y370 of the tower domain.

The helicase of the invention preferably comprises a variant of SEQ ID NO: 12 in which at least one cysteine residue and/or at least one non-natural amino acid have been introduced into (i) the tower domain (residues G294-I307 and T314-Y407) and/or (ii) the pin domain (residues G116-T135) and/or the (iii) 1A domain (residues M1-L115 and N136-V205). The at least one cysteine residue and/or at least one non-natural amino acid are preferably introduced into residues T314-Y407 of the tower domain.

The helicase of the invention preferably comprises a variant of SEQ ID NO: 13 in which at least one cysteine residue and/or at least one non-natural amino acid have been introduced into (i) the tower domain (residues V288-E301 and N307-N393) and/or (ii) the pin domain (residues G97-P113) and/or the (iii) 1A domain (residues M1-L96 and F114-V194). The at least one cysteine residue and/or at least one non-natural amino acid are preferably introduced into residues N307-N393 of the tower domain.

The helicase of the invention preferably comprises a variant of SEQ ID NO: 14 in which at least one cysteine residue and/or at least one non-natural amino acid have been introduced into (i) the tower domain (residues S250-P264 and E278-S371) and/or (ii) the pin domain (residues K78-E95) and/or the (iii) 1A domain (residues M1-L77 and V96-V166). The at least one cysteine residue and/or at least one non-natural amino acid are preferably introduced into residues E278-S371 of the tower domain.

The helicase of the invention preferably comprises a variant of SEQ ID NO: 15 in which at least one cysteine residue and/or at least one non-natural amino acid have been introduced into (i) the tower domain (residues K255-P269 and T284-S380) and/or (ii) the pin domain (residues K82-K98) and/or the (iii) 1A domain (residues M1-M81 and L99-M171). The at least one cysteine residue and/or at least one non-natural amino acid are preferably introduced into residues T284-S380 of the tower domain.

The helicase of the invention preferably comprises a variant of SEQ ID NO: 16 in which at least one cysteine residue and/or at least one non-natural amino acid have been introduced into (i) the tower domain (residues D242-P256 and T271-S366) and/or (ii) the pin domain (residues K69-K85) and/or the (iii) 1A domain (residues M1-M68 and M86-M158). The at least one cysteine residue and/or at least one non-natural amino acid are preferably introduced into residues T271-S366 of the tower domain.

The helicase of the invention preferably comprises a variant of SEQ ID NO: 17 in which at least one cysteine residue and/or at least one non-natural amino acid have been introduced into (i) the tower domain (residues T263-P277 and N295-P392) and/or (ii) the pin domain (residues K88-K107) and/or the (iii) 1A domain (residues M1-L87 and A108-M181). The at least one cysteine residue and/or at least one non-natural amino acid are preferably introduced into residues N295-P392 of the tower domain.

The helicase of the invention preferably comprises a variant of SEQ ID NO: 18 in which at least one cysteine residue and/or at least one non-natural amino acid have been introduced into (i) the tower domain (residues D263-P277 and N295-A391) and/or (ii) the pin domain (residues K88-K107) and/or the (iii) 1A domain (residues M1-L87 and A108-M181). The at least one cysteine residue and/or at least one non-natural amino acid are preferably introduced into residues N295-A391 of the tower domain.

The helicase of the invention preferably comprises a variant of SEQ ID NO: 19 in which at least one cysteine residue and/or at least one non-natural amino acid have been introduced into (i) the tower domain (residues A258-P272 and N290-P386) and/or (ii) the pin domain (residues K86-G102) and/or the (iii) 1A domain (residues M1-L85 and T103-K176). The at least one cysteine residue and/or at least one non-natural amino acid are preferably introduced into residues N290-P386 of the tower domain.

The helicase of the invention preferably comprises a variant of SEQ ID NO: 20 in which at least one cysteine residue and/or at least one non-natural amino acid have been introduced into (i) the tower domain (residues L266-P280 and N298-A392) and/or (ii) the pin domain (residues K92-D108) and/or the (iii) 1A domain (residues M1-L91 and V109-M183). The at least one cysteine residue and/or at least one non-natural amino acid are preferably introduced into residues N298-A392 of the tower domain.

The helicase of the invention preferably comprises a variant of SEQ ID NO: 21 in which at least one cysteine residue and/or at least one non-natural amino acid have been introduced into (i) the tower domain (residues D262-P276 and N294-A392) and/or (ii) the pin domain (residues K88-E104) and/or the (iii) 1A domain (residues M1-L87 and M105-M179). The at least one cysteine residue and/or at least one non-natural amino acid are preferably introduced into residues N294-A392 of the tower domain.

The helicase of the invention preferably comprises a variant of SEQ ID NO: 22 in which at least one cysteine residue and/or at least one non-natural amino acid have been introduced into (i) the tower domain (residues D261-P275 and N293-A389) and/or (ii) the pin domain (residues K87-E103) and/or the (iii) 1A domain (residues M1-L86 and V104-K178). The at least one cysteine residue and/or at least one non-natural amino acid are preferably introduced into residues N293-A389 of the tower domain.

The helicase of the invention preferably comprises a variant of SEQ ID NO: 23 in which at least one cysteine residue and/or at least one non-natural amino acid have been introduced into (i) the tower domain (residues E261-P275 and T293-A390) and/or (ii) the pin domain (residues K87-E103) and/or the (iii) 1A domain (residues M1-L86 and V104-M178). The at least one cysteine residue and/or at least one non-natural amino acid are preferably introduced into residues T293-A390 of the tower domain.

The helicase of the invention preferably comprises a variant of any one of SEQ ID NOs: 8 to 23 in which at least one cysteine residue and/or at least one non-natural amino acid have been introduced into each of (i) the tower domain and (ii) the pin domain and/or the 1A domain. The helicase of the invention more preferably comprises a variant of any one of SEQ ID NOs: 8 to 23 in which at least one cysteine residue and/or at least one non-natural amino acid have been introduced into each of (i) the tower domain, (ii) the pin domain and (iii) the 1A domain. Any number and combination of cysteine residues and non-natural amino acids may be introduced as discussed above.

The helicase of the invention preferably comprises a variant of SEQ ID NO: 8 which comprises (or only comprises) (i) E94C and/or A360C; (ii) E93C and/or K358C; (iii) E93C and/or A360C; (iv) E93C and/or E361C; (v) E93C and/or K364C; (vi) E94C and/or L354C; (vii) E94C and/or K358C; (viii) E93C and/or L354C; (ix) E94C and/or E361C; (x) E94C and/or K364C; (xi) L97C and/or L354C; (xii) L97C and/or K358C; (xiii) L97C and/or A360C; (xiv) L97C and/or E361C; (xv) L97C and/or K364C; (xvi) K123C and/or L354C; (xvii) K123C and/or K358C; (xviii) K123C and/or A360C; (xix) K123C and/or E361C; (xx) K123C and/or K364C; (xxi) N155C and/or L354C; (xxii) N155C and/or K358C; (xxiii) N155C and/or A360C; (xxiv) N155C and/or E361C; (xxv) N155C and/or K364C; (xxvi) any of (i) to (xxv) and G357C; (xxvii) any of (i) to (xxv) and Q100C; (xxviii) any of (i) to (xxv) and I127C; (xxix) any of (i) to (xxv) and Q100C and I127C; (xxx) E94C and/or F377C; (xxxi) N95C; (xxxii) T91C; (xxxiii) Y92L, E94Y, Y350N, A360C and Y363N; (xxxiv) E94Y and A360C; (xxxv) A360C; (xxxvi) Y92L, E94C, Y350N, A360Y and Y363N; (xxxvii) Y92L, E94C and A360Y; (xxxviii) E94C and/or A360C and F276A; (xxxix) E94C and/or L356C; (xl) E93C and/or E356C; (xli) E93C and/or G357C; (xlii) E93C and/or A360C; (xliii) N95C and/or W378C; (xliv) T91C and/or S382C; (xlv) T91C and/or W378C; (xlvi) E93C and/or N353C; (xlvii) E93C and/or S382C; (xlviii) E93C and/or K381C; (xlix) E93C and/or D379C; (l) E93C and/or S375C; (li) E93C and/or W378C; (lii) E93C and/or W374C; (liii) E94C and/or N353C; (liv) E94C and/or S382C; (lv) E94C and/or K381C; (lvi) E94C and/or D379C; (lvii) E94C and/or S375C; (lviii) E94C and/or W378C; (lix) E94C and/or W374C; (lx) E94C and A360Y; (lxi) E94C, G357C and A360C or (lxii) T2C, E94C and A360C. In any one of (i) to (lxii), and/or is preferably and.

The helicase of the invention preferably comprises a variant of any one of SEQ ID NOs: 9 to 23 which comprises a cysteine residue at the positions which correspond to those in SEQ ID NO: 8 as defined in any of (i) to (lxii). Positions in any one of SEQ ID NOs: 9 to 23 which correspond to those in SEQ ID NO: 8 can be identified using the alignment of SEQ ID NOs: 8 to 23 below. The helicase of the invention preferably comprises a variant of SEQ ID NO: 11 which comprises (or only comprises) (a) D99C and/or L341C, (b) Q98C and/or L341C or (d) Q98C and/or A340C. The helicase of the invention preferably comprises a variant of SEQ ID NO: 15 which comprises (or only comprises) D90C and/or A349C. The helicase of the invention preferably comprises a variant of SEQ ID NO: 21 which comprises (or only comprises) D96C and/or A362C.

The helicase of the invention preferably comprises a variant of any one of SEQ ID NOs: 8 to 23 as defined in any one of (i) to (lxii) in which Faz is introduced at one or more of the specific positions instead of cysteine. Faz may be introduced at each specific position instead of cysteine. The helicase of the invention preferably comprises a variant of SEQ ID NO: 8 which comprises (or only comprises) (i) E94Faz and/or A360C; (ii) E94C and/or A360Faz; (iii) E94Faz and/or A360Faz; (iv) Y92L, E94Y, Y350N, A360Faz and Y363N; (v) A360Faz; (vi) E94Y and A360Faz; (vii) Y92L, E94Faz, Y350N, A360Y and Y363N; (viii) Y92L, E94Faz and A360Y; (ix) E94Faz and A360Y; and (x) E94C, G357Faz and A360C.

The helicase of the invention preferably further comprises one or more single amino acid deletions from the pin domain. Any number of single amino acid deletions may be made, such as 1, 2, 3, 4, 5, 6, 7, 8, 9, 10 or more. The helicase more preferably comprises a variant of SEQ ID NO: 8 which comprises deletion of E93, deletion of E95 or deletion of E93 and E95. The helicase more preferably comprises a variant of SEQ ID NO: 8 which comprises (or only comprises) (a) E94C, deletion of N95 and A360C; (b) deletion of E93, deletion of E94, deletion of N95 and A360C; (c)

deletion of E93, E94C, deletion of N95 and A360C or (d) E93C, deletion of N95 and A360C. The helicase of the invention preferably comprises a variant of any one of SEQ ID NOs: 9 to 23 which comprises deletion of the position corresponding to E93 in SEQ ID NO: 8, deletion of the position corresponding to E95 in SEQ ID NO: 8 or deletion of the positions corresponding to E93 and E95 in SEQ ID NO: 8.

The helicase of the invention preferably further comprises one or more single amino acid deletions from the hook domain. Any number of single amino acid deletions may be made, such as 1, 2, 3, 4, 5, 6, 7, 8, 9, 10 or more. The helicase more preferably comprises a variant of SEQ ID NO: 8 which comprises deletion of any number of positions T278 to 5287. The helicase more preferably comprises a variant of SEQ ID NO: 8 which comprises (a) E94C, deletion of Y279 to K284 and A360C, (b) E94C, deletion of T278, Y279, V286 and S287 and A360C, (c) E94C, deletion of 1281 and K284 and replacement with a single G and A360C, (d) E94C, deletion of K280 and P2845 and replacement with a single G and A360C, or (e) deletion of Y279 to K284, E94C, F276A and A230C. The helicase of the invention preferably comprises a variant of any one of SEQ ID NOs: 9 to 23 which comprises deletion of any number of the positions corresponding to 278 to 287 in SEQ ID NO: 8.

The helicase of the invention preferably further comprises one or more single amino acid deletions from the pin domain and one or more single amino acid deletions from the hook domain.

The helicase of the invention is preferably one in which at least one cysteine residue and/or at least one non-natural amino acid have been further introduced into the hook domain and/or the 2A (RecA-like) domain. Any number and combination of cysteine residues and non-natural amino acids may be introduced as discussed above for the tower, pin and 1A domains.

The helicase of the invention preferably comprises a variant of SEQ ID NO: 8 in which at least one cysteine residue and/or at least one non-natural amino acid have further been introduced into the hook domain (residues L275-F291) and/or the 2A (RecA-like) domain (residues R178-T259 and L390-V439).

The helicase of the invention preferably comprises a variant of SEQ ID NO: 9 in which at least one cysteine residue and/or at least one non-natural amino acid have further been introduced into the hook domain (residues A310-L315) and/or the 2A (RecA-like) domain (residues R212-E294 and G422-S678).

The helicase of the invention preferably comprises a variant of SEQ ID NO: 10 in which at least one cysteine residue and/or at least one non-natural amino acid have further been introduced into the hook domain (residues V343-L359) and/or the 2A (RecA-like) domain (residues R241-N327 and A449-G496).

The helicase of the invention preferably comprises a variant of SEQ ID NO: 11 in which at least one cysteine residue and/or at least one non-natural amino acid have further been introduced into the hook domain (residues W276-L284) and/or the 2A (RecA-like) domain (residues R174-D260 and A371-V421).

The helicase of the invention preferably comprises a variant of SEQ ID NO: 12 in which at least one cysteine residue and/or at least one non-natural amino acid have further been introduced into the hook domain (residues R308-Y313) and/or the 2A (RecA-like) domain (residues R206-K293 and I408-L500).

The helicase of the invention preferably comprises a variant of SEQ ID NO: 13 in which at least one cysteine residue and/or at least one non-natural amino acid have further been introduced into the hook domain (residues M302-W306) and/or the 2A (RecA-like) domain (residues R195-D287 and V394-Q450).

The helicase of the invention preferably comprises a variant of SEQ ID NO: 14 in which at least one cysteine residue and/or at least one non-natural amino acid have further been introduced into the hook domain (residues V265-I277) and/or the 2A (RecA-like) domain (residues R167-T249 and L372-N421).

The helicase of the invention preferably comprises a variant of SEQ ID NO: 15 in which at least one cysteine residue and/or at least one non-natural amino acid have further been introduced into the hook domain (residues V270-F283) and/or the 2A (RecA-like) domain (residues R172-T254 and L381-K434).

The helicase of the invention preferably comprises a variant of SEQ ID NO: 16 in which at least one cysteine residue and/or at least one non-natural amino acid have further been introduced into the hook domain (residues V257-F270) and/or the 2A (RecA-like) domain (residues R159-T241 and L367-K420).

The helicase of the invention preferably comprises a variant of SEQ ID NO: 17 in which at least one cysteine residue and/or at least one non-natural amino acid have further been introduced into the hook domain (residues L278-Y294) and/or the 2A (RecA-like) domain (residues R182-T262 and L393-V443).

The helicase of the invention preferably comprises a variant of SEQ ID NO: 18 in which at least one cysteine residue and/or at least one non-natural amino acid have further been introduced into the hook domain (residues L278-Y294) and/or the 2A (RecA-like) domain (residues R182-T262 and L392-V442).

The helicase of the invention preferably comprises a variant of SEQ ID NO: 19 in which at least one cysteine residue and/or at least one non-natural amino acid have further been introduced into the hook domain (residues L273-F289) and/or the 2A (RecA-like) domain (residues R177-N257 and L387-V438).

The helicase of the invention preferably comprises a variant of SEQ ID NO: 20 in which at least one cysteine residue and/or at least one non-natural amino acid have further been introduced into the hook domain (residues L281-F297) and/or the 2A (RecA-like) domain (residues R184-T265 and L393-I442).

The helicase of the invention preferably comprises a variant of SEQ ID NO: 21 in which at least one cysteine residue and/or at least one non-natural amino acid have further been introduced into the hook domain (residues H277-F293) and/or the 2A (RecA-like) domain (residues R180-T261 and L393-V442).

The helicase of the invention preferably comprises a variant of SEQ ID NO: 22 in which at least one cysteine residue and/or at least one non-natural amino acid have further been introduced into the hook domain (residues L276-F292) and/or the 2A (RecA-like) domain (residues R179-T260 and L390-I439).

The helicase of the invention preferably comprises a variant of SEQ ID NO: 23 in which at least one cysteine residue and/or at least one non-natural amino acid have further been introduced into the hook domain (residues L276-F292) and/or the 2A (RecA-like) domain (residues R179-T260 and L391-V441).

The helicase of the invention preferably comprises a variant of SEQ ID NO: 8 which comprises one or more of (i) I181C; (ii) Y279C; (iii) I281C; and (iv) E288C. The helicase may comprise any combination of (i) to (iv), such as (i); (ii); (iii); (iv); (i) and (ii); (i) and (iii); (i) and (iv); (ii) and (iii); (ii) and (iv); (iii) and (iv); or (i), (ii), (iii) and (iv). The helicase more preferably comprises a variant of SEQ ID NO: 8 which comprises (or only comprises) (a) E94C, I281C and A360C or (b) E94C, I281C, G357C and A360C. The helicase of the invention preferably comprises a variant of any one of SEQ ID NOs: 9 to 23 which comprises a cysteine residue at one or more of the position(s) which correspond to those in SEQ ID NO: 8 as defined in (i) to (iv), (a) and (b). The helicase may comprise any of these variants in which Faz is introduced at one or more of the specific positions (or each specific position) instead of cysteine.

The helicase of the invention is further modified to reduce its surface negative charge. Surface residues can be identified in the same way as the Dda domains disclosed above. Surface negative charges are typically surface negatively-charged amino acids, such as aspartic acid (D) and glutamic acid (E).

The helicase is preferably modified to neutralise one or more surface negative charges by substituting one or more negatively charged amino acids with one or more positively charged amino acids, uncharged amino acids, non-polar amino acids and/or aromatic amino acids or by introducing one or more positively charged amino acids, preferably adjacent to one or more negatively charged amino acids. Suitable positively charged amino acids include, but are not limited to, histidine (H), lysine (K) and arginine (R). Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y).

Preferred substitutions include, but are not limited to, substitution of E with R, substitution of E with K, substitution of E with N, substitution of D with K and substitution of D with R.

The helicase of the invention preferably comprises a variant of SEQ ID NO: 8 and the one or more negatively charged amino acids are one or more of D5, E8, E23, E47, D167, E172, D202, D212 and E273. Any number of these amino acids may be neutralised, such as 1, 2, 3, 4, 5, 6, 7 or 8 of them. Any combination may be neutralised. The helicase of the invention preferably comprises a variant of any one of SEQ ID NOs: 9 to 23 and the one or more negatively charged amino acids correspond to one or more of D5, E8, E23, E47, D167, E172, D202, D212 and E273 in SEQ ID NO: 8. Amino acids in SEQ ID NOs: 9 to 23 which correspond to D5, E8, E23, E47, D167, E172, D202, D212 and E273 in SEQ ID NO: 8 can be determined using the alignment below. The helicase of the invention preferably comprises a variant of SEQ ID NO: 8 which comprises (or only comprises) (a) E94C, E273G and A360C or (b) E94C, E273G, N292G and A360C.

The helicase of the invention is preferably further modified by the removal of one or more native cysteine residues. Any number of native cysteine residues may be removed. The number of cysteine residues in each of SEQ ID NOs: 9 to 23 is shown in Table 1 (as # C). The one or more cysteine residues are preferably removed by substitution. The one or more cysteine residues are preferably substituted with alanine (A), serine (S) or valine (V). The helicase of the invention preferably comprises a variant of SEQ ID NO: 8 and the one or more native cysteine residues are one or more of C109, C114, C136, C171 and C412. Any number and combination of these cysteine residues may be removed. For instance, the variant of SEQ ID NO: 8 may comprise {C109}; {C114}; {C136}; {C171}; {C412}; {C109 and C114}; {C109 and C136}; {C109 and C171}; {C109 and C412}; {C114 and C136}; {C114 and C171}; {C114 and C412}; {C136 and C171}; {C136 and C412}; {C171 and C412}; {C109, C114 and C136}; {C109, C114 and C171}; {C109, C114 and C412}; {C109, C136 and C171}; {C109, C136 and C412}; {C109, C171 and C412}; {C114, C136 and C171}; {C114, C136 and C412}; {C114, C171 and C412}; {C136, C171 and C412}; {C109, C114, C136 and C171}; {C109, C114, C136 and C412}; {C109, C114, C171 and C412}; {C109, C136, C171 and C412}; {C114, C136, C171 and C412}; or {C109, C114, C136, C171 and C412}.

The helicase of the invention is preferably one in which at least one cysteine residue (i.e. one or more cysteine residues) and/or at least one non-natural amino acid (i.e. one or more non-natural amino acids) have been introduced into the tower domain only. Suitable modifications are discussed above.

The helicase of the invention preferably comprises a variant of SEQ ID NO: 8 comprising (or comprising only) the following mutations:

E93C and K364C;
E94C and K364C;
E94C and A360C;
L97C and E361C;
L97C and E361C and C412A;
K123C and E361C;
K123C, E361C and C412A;
N155C and K358C;
N155C, K358C and C412A;
N155C and L354C;
N155C, L354C and C412A;
deltaE93, E94C, deltaN95 and A360C;
E94C, deltaN95 and A360C;
E94C, Q100C, I127C and A360C;
L354C;
G357C;
E94C, G357C and A360C;
E94C, Y279C and A360C;
E94C, I281C and A360C;
E94C, Y279Faz and A360C;
Y279C and G357C;
I281C and G357C;
E94C, Y279C, G357C and A360C;
E94C, I281C, G357C and A360C;
E8R, E47K, E94C, D202K and A360C;
D5K, E23N, E94C, D167K, E172R, D212R and A360C;
D5K, E8R, E23N, E47K, E94C, D167K, E172R, D202K, D212R and A360C;
E94C, C114A, C171A, A360C and C412D;
E94C, C114A, C171A, A360C and C412S;
E94C, C109A, C136A and A360C;
E94C, C109A, C114A, C136A, C171A, A360C and C412S;
E94C, C109V, C114V, C171A, A360C and C412S;
C109A, C114A, C136A, G153C, C171A, E361C and C412A;

C109A, C114A, C136A, G153C, C171A, E361C and C412D;
C109A, C114A, C136A, G153C, C171A, E361C and C412S;
C109A, C114A, C136A, G153C, C171A, K358C and C412A;
C109A, C114A, C136A, G153C, C171A, K358C and C412D
C109A, C114A, C136A, G153C, C171A, K358C and C412S;
C109A, C114A, C136A, N155C, C171A, K358C and C412A;
C109A, C114A, C136A, N155C, C171A, K358C and C412D;
C109A, C114A, C136A, N155C, C171A, K358C and C412S;
C109A, C114A, C136A, N155C, C171A, L354C and C412A;
C109A, C114A, C136A, N155C, C171A, L354C and C412D;
C109A, C114A, C136A, N155C, C171A, L354C and C412S;
C109A, C114A, K123C, C136A, C171A, E361C and C412A;
C109A, C114A, K123C, C136A, C171A, E361C and C412D;
C109A, C114A, K123C, C136A, C171A, E361C and C412S;
C109A, C114A, K123C, C136A, C171A, K358C and C412A;
C109A, C114A, K123C, C136A, C171A, K358C and C412D;
C109A, C114A, K123C, C136A, C171A, K358C and C412S;
C109A, C114A, C136A, G153C, C171A, E361C and C412A;
E94C, C109A, C114A, C136A, C171A, A360C and C412D;
E94C, C109A, C114V, C136A, C171A, A360C and C412D;
E94C, C109V, C114A, C136A, C171A, A360C and C412D;
L97C, C109A, C114A, C136A, C171A, E361C and C412A;
L97C, C109A, C114A, C136A, C171A, E361C and C412D; or
L97C, C109A, C114A, C136A, C171A, E361C and C412S.

Modifications in the hook domain and/or 2A domain

In one embodiment, the Dda helicase of the invention is one in which at least one cysteine residue and/or at least one non-natural amino acid have been introduced into the hook domain and/or the 2A (RecA-like motor) domain, wherein the helicase retains its ability to control the movement of a polynucleotide. At least one cysteine residue and/or at least one non-natural amino acid is preferably introduced into the hook domain and the 2A (RecA-like motor) domain.

Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced.

The at least one cysteine residue and/or at least one non-natural amino acid are preferably introduced by substitution. Methods for doing this are known in the art. Suitable modifications of the hook domain and/or the 2A (RecA-like motor) domain are discussed above.

The helicase of the invention is preferably a variant of SEQ ID NO: 8 comprising (or comprising only) (a) Y279C, I181C, E288C, Y279C and I181C, (b) Y279C and E288C, (c) I181C and E288C or (d) Y279C, I181C and E288C. The helicase of the invention preferably comprises a variant of any one of SEQ ID NOs: 9 to 23 which comprises a mutation at one or more of the position(s) which correspond to those in SEQ ID NO: 8 as defined in (a) to (d).

Surface Modification In one embodiment, the Dda helicase is modified to reduce its surface negative charge, wherein the helicase retains its ability to control the movement of a polynucleotide. Suitable modifications are discussed above. Any number of surface negative charges may be neutralised.

The helicase of the invention preferably comprises a variant of SEQ ID NO: 8 comprising (or comprising only) the following mutations:
E273G;
E8R, E47K and D202K;
D5K, E23N, D167K, E172R and D212R;
D5K, E8R, E23N, E47K, D167K, E172R, D202K and D212R.

Other Modified Helicases

In one embodiment, the Dda helicase of the invention comprises a variant of SEQ ID NO: 8 comprising (or comprising only):
A360K;
Y92L and/or A360Y;
Y92L, Y350N and Y363N;
Y92L and/or Y363N; or
Y92L.

Other Modifications

In addition to the specific mutations disclosed above, a variant of SEQ ID NO: 8 may comprise (or may only comprise) one or more of the following mutations:

| | | |
|---|---|---|
| K38A; | | |
| H64N; | | |
| H64K; | H82A; | S83K; |
| H64Q; | H82F; | S83N; |
| H64S; | H82Q; | S83T; |
| H64W; | H82R; | N88H; |
| T80K; | H82W; | N88Q; |
| T80N; | H82Y; | P89A; |
| P89F; | V150I; | F291G; |
| P89S; | V150K; | N292F; |
| P89T; | V150L; | N292G; |
| P89W; | V150S; | N292P; |
| P89Y; | V150T; | N292Y; |
| T91F; | V150W; | N293F; |
| T91N; | V150Y; | N293K; |
| T91Q; | F240W; | N293Q; |
| T91W; | F240Y; | N293Y; |
| V96E; | N242K; | G294Y; |
| V96F; | P274G; | G294F; |
| V96L; | F276A; | K364A; |
| V96Q; | F276I; | W378A; |
| V96R; | F276M; | T394K; |
| V96W; | F276V; | T394N; |
| V96Y; | F276W; | H396Q; |
| F98A; | F276Y; | H396S; |
| F98L; | V286F; | H396W; |
| F98V; | V286W; | Y415F; |
| F98W; | V286Y; | Y415K; |
| F98Y; | S287F; | Y415M; or |
| V150A; | S287W; | Y415W. |
| V150F; | S287Y; | |

The helicase of the invention preferably comprises a variant of SEQ ID NO: 8 which comprises (or only comprises):

K38A, E94C and A360C;
H64K; E94C and A360C;
H64N; E94C and A360C;
H64Q; E94C and A360C;
H64S; E94C and A360C;
H64W, E94C and A360C;
T80K, E94C and A360C;
T80K, S83K, E94C, N242K, N293K and A360C;
T80K, S83K, E94C, N242K, N293K, A360C and T394K;
T80K, E94C, N242K, N293K and A360C;
T80K, E94C, N293K and A360C;
T80N, E94C and A360C;
H82A, E94C and A360C;
H82A, P89A, E94C, F98A and A360C;
H82F, E94C and A360C;
H82Q, E94C, A360C;
H82R, E94C and A360C;
H82W, E94C and A360C;
H82W, P89W, E94C, F98W and A360C;
H82Y, E94C and A360C;
S83K, E94C and A360C;
S83K, T80K, E94C, A360C and T394K;
S83N, E94C and A360C;
S83T, E94C and A360C;
N88H, E94C and A360C;
N88Q, E94C and A360C;
P89A, E94C and A360C;
P89A, F98W, E94C and A360C;
P89A, E94C, F98Y and A360C;
P89A, E94C, F98A and A360C;
P89F, E94C and A360C;
P89S, E94C and A360C;
P89T, E94C and A360C;
P89W, E94C, F98W and A360C;
P89Y, E94C and A360C;
T91F, E94C and A360C;
T91N, E94C and A360C;
T91Q, E94C and A360C;
E94C, F276Y and A360C;
E94C, V286F and A360C;
E94C, V286W and A360C;
E94C, V286Y and A360C;
E94C, S287F and A360C;
E94C, S287W and A360C;
E94C, S287Y and A360C;
E94C, F291G and A360C;
E94C, N292F and A360C;
E94C, N292G and A360C;
E94C, N292P and A360C;
E94C, N292Y and A360C;
E94C, N293F and A360C;
E94C, N293K and A360C;
T80K, S83K, E94C, N293K and A360C;
T80K, S83K, E94C, A360C and T394K;
T80K, S83K, E94C, A360C and T394N;
T80K, E94C, N242K and A360C;
T91W, E94C and A360C;
E94C, V96E and A360C;
E94C, V96F and A360C;
E94C, V96L and A360C;
E94C, V96Q and A360C;
E94C, V96R and A360C;
E94C, V96W and A360C;
E94C, V96Y and A360C;
E94C, F98A and A360C;
E94C, F98L and A360C;
E94C, F98V and A360C;
E94C, F98Y and A360C;
E94C; F98W and A360C;
E94C, V150A and A360C;
E94C, V150F and A360C;
E94C, V150I and A360C;
E94C, V150K and A360C;
E94C, V150L and A360C;
E94C, V150S and A360C;
E94C, V150T and A360C;
E94C, V150W and A360C;
E94C, V150Y and A360C;
E94C, F240Y and A360C;
E94C, F240W and A360C;
E94C, N242K and A360C;
E94C, N242K, N293K and A360C;
E94C, P274G and A360C;
E94C, L275G and A360C
E94C, F276A and A360C;
E94C, F276I and A360C;
E94C, F276M and A360C;
E94C, F276V and A360C;
E94C, F276W and A360C;
E94C, N293Q and A360C;
E94C, N293Y and A360C;
E94C, G294F and A360C;
E94C, G294Y and A360C;
E94C, A36C and K364A;
E94C, A360C, W378A;
E94C, A360C and T394K;
E94C, A360C and H396Q;
E94C, A360C and H396S;
E94C, A360C and H396W;
E94C, A360C and Y415F;
E94C, A360C and Y415K;
E94C, A360C and Y415M; or
E94C, A360C and Y415W.

The helicase of the invention preferably comprises a variant of SEQ ID NO: 8 which comprises (or only comprises) (a) E94C/A360C/W378A, (b) E94C/A360C/W378A W378A and then (ΔM1)G1G2 (i.e. deletion of M1 and then addition G1 and G2), (c) E94C/A360C/C109A/C136A/W378A or (d) E94C/A360C/C109A/C136A/W378A and then (ΔM1)G1G2 (i.e. deletion of M1 and then addition G1 and G2).

Variants

A variant of a Dda helicase is an enzyme that has an amino acid sequence which varies from that of the wild-type helicase and which retains polynucleotide binding activity. In particular, a variant of any one of SEQ ID NOs: 8 to 23 is an enzyme that has an amino acid sequence which varies from that of any one of SEQ ID NOs: 8 to 23 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature.

Over the entire length of the amino acid sequence of any one of SEQ ID NOs: 8 to 23, a variant will preferably be at least 20% homologous to that sequence based on amino acid identity. More preferably, the variant polypeptide may be at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 8 to 23 over the entire sequence. There may be at least 70%, for example at least 80%, at least 85%, at least 90% or at least 95%, amino acid identity over a stretch of 100 or more, for example 150, 200, 300, 400 or 500 or more, contiguous amino acids ("hard homology"). Homology is determined as described below. The variant may differ from the wild-type sequence in any of the ways discussed below with reference to SEQ ID NOs: 2 and 4. In particular, in addition to the specific modifications discussed above, the variant of any one of SEQ ID NOs: 8 to 23 may comprise one or more substitutions, one or more deletions and/or one or more additions as discussed below.

Preferred variants of any one of SEQ ID NOs: 8 to 23 have a non-natural amino acid, such as Faz, at the amino-(N-) terminus and/or carboxy (C-) terminus. Preferred variants of any one of SEQ ID NOs: 8 to 23 have a cysteine residue at the amino-(N-) terminus and/or carboxy (C-) terminus. Preferred variants of any one of SEQ ID NOs: 8 to 23 have a cysteine residue at the amino-(N-) terminus and a non-natural amino acid, such as Faz, at the carboxy (C-) terminus or vice versa.

Preferred variants of SEQ ID NO: 8 contain one or more of, such as all of, the following modifications E54G, D151E, I196N and G357A.

The most preferred variants of any one of SEQ ID NOs: 8 to 23 have (in addition to the modifications of the invention) the N-terminal methionine (M) deleted and replaced with two glycine residues (GG). In the examples this is shown as (ΔM1)G1G2. For instance, preferred variants of SEQ ID NO: 8 comprise (or only comprise):
E94C, A360C and then (ΔM1)G1G2; and
E94C, C109A, C136A, A360C and then (ΔM1)G1G2.

Dda Helicase Fragments

The invention also provides fragments of Dda helicases which may be used to produce a helicase of the invention. In a first embodiment, the polypeptide comprises the pin domain and the 1A (RecA-like motor) domain from a Dda helicase and does not comprise any other domains from a Dda helicase, wherein at least one cysteine residue and/or at least one non-natural amino acid have been introduced into the pin domain and/or the 1A (RecA-like motor) domain.

Preferred helicases from which the domains may be derived include any of SEQ ID NOs: 8 to 23. The relevant domains of these helicases are defined in Table 2 above. The pin domain and/or the 1A domain may be modified in any of the ways discussed above for the helicases of the invention. In particular, the polypeptide may comprise any of the variants of the pin domains and the 1A domains defined above and any of the pin domain and/or 1A domain mutations defined above.

In a second embodiment, the polypeptide comprises the 2A (RecA-like motor) domain, tower domain and hook domain from a Dda helicase and does not comprise any other domains from a Dda helicase, wherein at least one cysteine residue and/or at least one non-natural amino acid have been introduced into the tower domain. Preferred helicases from which the domains may be derived include any of SEQ ID NOs: 8 to 23. The relevant domains of these helicases are defined in Table 2 above. The tower domain may be modified in any of the ways discussed above for the helicases of the invention. In particular, the polypeptide may comprise any of the variants of the tower defined above and any of the tower mutations defined above.

In addition to the specific modifications discussed above, a polypeptide of the invention may comprise one or more substitutions, one or more deletions and/or one or more additions as discussed below with reference to SEQ ID NOs: 2 and 4.

The invention also provides a helicase comprising a polypeptide of the first embodiment covalently attached to a polypeptide of the second embodiment, wherein the helicase has the ability to control the movement of a polynucleotide. The ability of the helicase to control the movement of a polynucleotide may be determined as discussed above.

No Connection

In one preferred embodiment, none of the introduced cysteines and/or non-natural amino acids in a modified Dda helicase of the invention are connected to one another.

Connecting Two More of the Introduced Cysteines and/or Non-Natural Amino Acids

In another preferred embodiment, two more of the introduced cysteines and/or non-natural amino acids in a modified Dda helicase of the invention are connected to one another. This typically reduces the ability of the helicase of the invention to unbind from a polynucleotide.

Any number and combination of two more of the introduced cysteines and/or non-natural amino acids may be connected to one another. For instance, 3, 4, 5, 6, 7, 8 or more cysteines and/or non-natural amino acids may be connected to one another. One or more cysteines may be connected to one or more cysteines. One or more cysteines may be connected to one or more non-natural amino acids, such as Faz. One or more non-natural amino acids, such as Faz, may be connected to one or more non-natural amino acids, such as Faz.

The two or more cysteines and/or non-natural amino acids may be connected in any way. The connection can be transient, for example non-covalent. Even transient connection will reduce unbinding of the polynucleotide from the helicase.

The two or more cysteines and/or non-natural amino acids are preferably connected by affinity molecules. Suitable affinity molecules are known in the art. The affinity molecules are preferably (a) complementary polynucleotides (International Application No. PCT/GB10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by β-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848-4871 John Wiley & Sons Ltd, Chichester, 2000) or (h) half-chelators (Hammerstein et al. J Biol Chem. 2011 Apr. 22; 286(16): 14324-14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e. g. between aspartate and arginine.

The two or more parts may be transiently connected by a hexa-his tag or Ni-NTA.

The two or more cysteines and/or non-natural amino acids are preferably permanently connected. In the context of the invention, a connection is permanent if is not broken while the helicase is used or cannot be broken without intervention on the part of the user, such as using reduction to open —S—S— bonds.

The two or more cysteines and/or non-natural amino acids are preferably covalently-attached. The two or more cysteines and/or non-natural amino acids may be covalently attached using any method known in the art.

The two or more cysteines and/or non-natural amino acids may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more cysteines and/or non-natural amino acids may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more cysteines and/or non-natural amino acids are connected using linkers. Linker molecules are discussed in more detail below. One suitable method of connection is cysteine linkage. This is discussed in more detail below. The two or more cysteines and/or non-natural amino acids are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more cysteines and/or non-natural amino acids as discussed above. If both or all ends are covalently attached, the one or more linkers permanently connect the two or more cysteines and/or non-natural amino acids.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S—S-PEG3-biotin, DBCO-S-S-PEG3-biotin, DBCO-S-S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY(ETHYLENE GLYCOL)). The most preferred crosslinker is maleimide-propyl-SRDFWRS-(1,2-diaminoethane)-propyl-maleimide.

The one or more linkers may be cleavable. This is discussed in more detail below.

The two or more cysteines and/or non-natural amino acids may be connected using two different linkers that are specific for each other. One of the linkers is attached to one part and the other is attached to another part. The linkers should react to form a modified helicase of the invention. The two or more cysteines and/or non-natural amino acids may be connected using the hybridization linkers described in International Application No. PCT/GB10/000132 (published as WO 2010/086602). In particular, the two or more cysteines and/or non-natural amino acids may be connected using two or more linkers each comprising a hybridizable region and a group capable of forming a covalent bond. The hybridizable regions in the linkers hybridize and link the two or more cysteines and/or non-natural amino acids. The linked cysteines and/or non-natural amino acids are then coupled via the formation of covalent bonds between the groups. Any of the specific linkers disclosed in International Application No. PCT/GB10/000132 (published as WO 2010/086602) may be used in accordance with the invention.

The two or more cysteines and/or non-natural amino acids may be modified and then attached using a chemical crosslinker that is specific for the two modifications. Any of the crosslinkers discussed above may be used.

The linkers may be labeled. Suitable labels include, but are not limited to, fluorescent molecules (such as Cy3 or AlexaFluor®555), radioisotopes, e.g. $^{125}$I, $^{35}$S, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting two or more cysteines is via cysteine linkage. This can be mediated by a bi-functional chemical crosslinker or by an amino acid linker with a terminal presented cysteine residue.

The length, reactivity, specificity, rigidity and solubility of any bi-functional linker may be designed to ensure that the size of the opening is reduced sufficiently and the function of the helicase is retained. Suitable linkers include bismaleimide crosslinkers, such as 1,4-bis(maleimido)butane (BMB) or bis(maleimido)hexane. One drawback of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S⁻ group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage is discussed in more detail below.

Another preferred method of attachment via Faz linkage. This can be mediated by a bi-functional chemical linker or by a polypeptide linker with a terminal presented Faz residue.

Other Modified Helicases of the Invention

The invention also provides a Dda helicase which has been modified to increase the attraction between (i) the tower domain and (ii) the pin domain and/or the 1A domain. Any known chemical modifications can be made in accordance with the invention.

In particular, the invention provides a Dda helicase in which at least one charged amino acid has been introduced into (i) the tower domain and/or (ii) the pin domain and/or (iii) the 1A (RecA-like motor) domain, wherein the helicase retains its ability to control the movement of a polynucleotide. The ability of the helicase to control the movement of a polynucleotide may be measured as discussed above. The invention preferably provides a Dda helicase in which at least one charged amino acid has been introduced into (i) the tower domain and (ii) the pin domain and/or the 1A domain.

The at least one charged amino acid may be negatively charged or positively charged. The at least one charged amino acid is preferably oppositely charged to any amino acid(s) with which it interacts in the helicase. For instance, at least one positively charged amino acid may be introduced into the tower domain at a position which interacts with a negatively charged amino acid in the pin domain. The at least one charged amino acid is typically introduced at a position which is not charged in the wild-type (i.e. unmodified) helicase. The at least one charged amino acid may be used to replace at least one oppositely charged amino acid in the helicase. For instance, a positively charged amino acid may be used to replace a negatively charged amino acid.

Suitable charged amino acids are discussed above. The at least one charged amino acid may be natural, such as arginine (R), histidine (H), lysine (K), aspartic acid (D) or glutamic acid (D). Alternatively, the at least one charged amino acid may be artificial or non-natural. Any number of charged amino acids may be introduced into each domain. For instance, 1, 2, 3, 4, 5, 6, 7, 8, 9, 10 or more charged amino acids may be introduced into each domain.

The helicase preferably comprises a variant of SEQ ID NO: 8 which comprises a positively charged amino acid at one or more of the following positions: (i) 93; (ii) 354; (iii) 360; (iv) 361; (v) 94; (vi) 97; (vii) 155; (viii) 357; (ix) 100; and (x) 127. The helicase preferably comprises a variant of SEQ ID NO: 8 which comprises a negatively charged amino acid at one or more of the following positions: (i) 354; (ii) 358; (iii) 360; (iv) 364; (v) 97; (vi) 123; (vii) 155; (viii); 357; (ix) 100; and (x) 127. The helicase preferably comprises a variant of any one of SEQ ID NOs: 9 to 23 which comprises a positively charged amino acid or negatively charged amino acid at the positions which correspond to those in SEQ ID NO: 8 as defined in any of (i) to (x). Positions in any one of SEQ ID NOs: 9 to 23 which correspond to those in SEQ ID NO: 8 can be identified using the alignment of SEQ ID NOs: 8 to 23 below.

The helicase preferably comprises a variant of SEQ ID NO: 8 which is modified by the introduction of at least one charged amino acid such that it comprises oppositely charged amino acid at the following positions: (i) 93 and 354; (ii) 93 and 358; (iii) 93 and 360; (iv) 93 and 361; (v) 93 and 364; (vi) 94 and 354; (vii) 94 and 358; (viii) 94 and 360; (ix) 94 and 361; (x) 94 and 364; (xi) 97 and 354; (xii) 97 and 358; (xiii) 97 and 360; (xiv) 97 and 361; (xv) 97 and 364; (xvi) 123 and 354; (xvii) 123 and 358; (xviii) 123 and 360; (xix) 123 and 361; (xx) 123 and 364; (xxi) 155 and 354; (xxii) 155 and 358; (xxiii) 155 and 360; (xxiv) 155 and 361; (xxv) 155 and 364. The helicase of the invention preferably comprises a variant of any one of SEQ ID NOs: 9 to 23 which comprises oppositely charged amino acids at the positions which correspond to those in SEQ ID NO: 8 as defined in any of (i) to (xxv).

The invention also provides a Dda helicase in which (i) at least one charged amino acid has been introduced into the tower domain and (ii) at least one oppositely charged amino acid has been introduced into the pin domain and/or the 1A (RecA-like motor) domain, wherein the helicase retains its ability to control the movement of a polynucleotide. The at least one charged amino acid may be negatively charged and the at least one oppositely charged amino acid may be positively charged or vice versa. Suitable charged amino acids are discussed above. Any number of charged amino acids and any number of oppositely charged amino acids may be introduced. For instance, 1, 2, 3, 4, 5, 6, 7, 8, 9, 10 or more charged amino acids may be introduced and/or 1, 2, 3, 4, 5, 6, 7, 8, 9, 10 or more oppositely charged amino acids may be introduced.

The charged amino acids are typically introduced at positions which are not charged in the wild-type helicase. One or both of the charged amino acids may be used to replace charged amino acids in the helicase. For instance, a positively charged amino acid may be used to replace a negatively charged amino acid. The charged amino acids may be introduced at any of the positions in the (i) tower domain and (ii) pin domain and/or 1A domain discussed above. The oppositely charged amino acids are typically introduced such that they will interact in the resulting helicase. The helicase preferably comprises a variant of SEQ ID NO: 8 in which oppositely charged amino acids have been introduced at the following positions: (i) 97 and 354; (ii) 97 and 360; (iii) 155 and 354; or (iv) 155 and 360. The helicase of the invention preferably comprises a variant of any one of SEQ ID NOs: 9 to 23 which comprises oppositely charged amino acids at the positions which correspond to those in SEQ ID NO: 8 as defined in any of (i) to (iv).

Construct

The invention also provides a construct comprising a Dda helicase or a modified Dda helicase of the invention and an additional polynucleotide binding moiety, wherein the helicase is attached to the polynucleotide binding moiety and the construct has the ability to control the movement of a polynucleotide. The construct is artificial or non-natural.

A construct of the invention is a useful tool for controlling the movement of a polynucleotide during Strand Sequencing. A construct of the invention is even less likely than a modified helicase of the invention to disengage from the polynucleotide being sequenced. The construct can provide even greater read lengths of the polynucleotide as it controls the translocation of the polynucleotide through a nanopore.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The construct has the ability to control the movement of a polynucleotide. This can be determined as discussed above.

A construct of the invention may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

The Dda helicase may be any Dda helicase. Preferred Dda helicases include, but are not limited to, any one of SEQ ID NOs: 8 to 23 and variants thereof. Variants are defined above. Variants are preferably at least 20% homologous to any one of SEQ ID NOs: 8 to 23 based on amino acid identity. The Dda helicase in the construct does not have to comprise the specific modification(s) discussed above with reference to the modified Dda helicases of the invention (i.e. does not have to be modified in accordance with the invention). For instance, the construct may comprise a Dda helicase which comprises the sequence shown in any one of SEQ ID NOs: 8 to 23 or a variant thereof, wherein:

no cysteine residues and no non-natural amino acids have been introduced into the tower domain, the pin domain and the 1A (RecA-like motor) domain of the variant;

the variant does not comprise one or more single amino acid deletions from the pin domain;

no cysteine residues and no non-natural amino acids have been introduced into the hook domain and the 2A (RecA-like) domain;

the variant is not modified to reduce its surface negative charge;

the variant is not modified by the removal of one or more native cysteine residues;

no cysteine residues and no non-natural amino acids have been introduced into the tower domain only; or no charged amino acids have introduced into the tower domain, the pin domain and the 1A domain of the variant.

The helicase is preferably a modified Dda helicase of the invention. Any of the helicases of the invention may be present in a construct of the invention.

The helicase is preferably covalently attached to the additional polynucleotide binding moiety. The helicase may be attached to the moiety at more than one, such as two or three, points.

The helicase can be covalently attached to the moiety using any method known in the art. Suitable methods are discussed above with reference to connecting the two or more parts.

The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase.

In a preferred embodiment, the helicase is chemically attached to the moiety, for instance via one or more linker molecules as discussed above. In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The helicase may be attached directly to the moiety. The helicase is preferably attached to the moiety using one or more, such as two or three, linkers as discussed above. The one or more linkers may be designed to constrain the mobility of the moiety. The helicase and/or the moiety may be modified to facilitate attachment of the one or more linker as discussed above.

Cleavable linkers can be used as an aid to separation of constructs from non-attached components and can be used to further control the synthesis reaction. For example, a heterobifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

Preferred methods of attaching the helicase to the moiety are cysteine linkage and Faz linkage as described above. In a preferred embodiment, a reactive cysteine is presented on a peptide linker that is genetically attached to the moiety. This means that additional modifications will not necessarily be needed to remove other accessible cysteine residues from the moiety.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used are shown below.

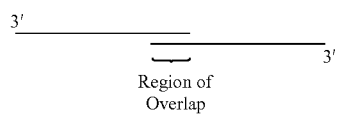
Region of Overlap

For helicase-Phi29 constructs the DNA below could be used.

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-Tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs of the invention can also be purified from unreacted proteins on the basis of a different DNA processivity property. In particular, a construct of the invention can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

Polynucleotide Binding Moiety

The constructs of the invention comprise a polynucleotide binding moiety. A polynucleotide binding moiety is a polypeptide that is capable of binding to a polynucleotide. The moiety is preferably capable of specific binding to a defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct of the invention.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs of the invention are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M.

The moiety is more preferably modified to increase its activity at high salt concentrations. The moiety may also be modified to improve its processivity, stability and shelf life.

Suitable modifications can be determined from the characterisation of polynucleotide binding moieties from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 47). As discussed below, the polynucleotide binding moiety may be domains H-L of SEQ ID NO: 47 as shown in SEQ ID NO: 48. Topoisomerase V from *Methanopyrus kandleri* is an example of a double-stranded binding protein as discussed below.

The HhH domain preferably comprises the sequence shown in SEQ ID NO: 24 or 37 or 38 or a variant thereof. This domain increases the processivity and the salt tolerance of a helicase when used in a construct of the invention. A variant of SEQ ID NO: 24 or 37 or 38 is a protein that has an amino acid sequence which varies from that of SEQ ID NO: 24 or 37 or 38 and which retains polynucleotide binding activity. This can be measured as described above. A variant typically has at least 50% homology to SEQ ID NO: 24 or 37 or 38 based on amino acid identity over its entire sequence (or any of the % homologies discussed above in relation to helicases) and retains polynucleotide binding activity. A variant may differ from SEQ ID NO: 24 or 37 or 38 in any of the ways discussed above in relation to helicases or below in relation to pores. A variant preferably comprises one or more substituted cysteine residues and/or one or more substituted Faz residues to facilitate attachment to the helicase as discussed above.

SSBs bind single stranded DNA with high affinity in a sequence non-specific manner. They exist in all domains of life in a variety of forms and bind DNA either as monomers or multimers. Using amino acid sequence alignment and logarithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukariotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Ther-* motoga maritima). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 39, the human replication protein A 70 kDa subunit, the human replication protein A 14 kDa subunit, the telomere end binding protein alpha subunit from *Oxytricha nova*, the core domain of telomere end binding protein beta subunit from *Oxytricha nova*, the protection of telomeres protein 1 (Pot1) from *Schizosaccharomyces pombe*, the human Pot1, the OB-fold domains of BRCA2 from mouse or rat, the p5 protein from phi29 (SEQ ID NO: 40) or a variant of any of those proteins. A variant is a protein that has an amino acid sequence which varies from that of the wild-type protein and which retains single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO: 39 or 40 typically has at least 50% homology to SEQ ID NO: 39 or 40 based on amino acid identity over its entire sequence (or any of the % homologies discussed above in relation to helicases) and retains single stranded polynucleotide binding activity. A variant may differ from SEQ ID NO: 39 or 40 in any of the ways discussed above in relation to helicases. In particular, a variant may have one or more conservative substitutions as shown in Tables 5 and 6.

Examples of SSBs which require one or more modifications in their C-terminal region to decrease the net negative charge include, but are not limited to, the SSB of *E. coli* (EcoSSB; SEQ ID NO: 41, the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDCl3 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 42), the SSB from RB69 (gp32; SEQ ID NO: 25), the SSB from T7 (gp2.5; SEQ ID NO: 26) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity. Polynucleotide binding activity can be determined as discussed above.

The SSB used in the invention may be derived from a variant of SEQ ID NO: 25, 26, 41 or 42. In other words, a variant of SEQ ID NO: 25, 26, 41 or 42 may be used as the starting point for the SSB used in the invention, but the SSB actually used further includes one or more modifications in its C-terminal region which decreases the net negative charge of the C-terminal region. A variant of SEQ ID NO: 25, 26, 41 or 42 typically has at least 50% homology to SEQ ID NO: 25, 26, 41 or 42 based on amino acid identity over its entire sequence (or any of the % homologies discussed above in relation to helicases) and retains single stranded polynucleotide binding activity. A variant may differ from SEQ ID NO: 25, 26, 41 or 42 in any of the ways discussed above in relation to helicases. In particular, a variant may have one or more conservative substitutions as shown in Tables 5 and 6.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Suitable modifications for decreasing the net negative charge are disclosed in International Application No. PCT/GB2013/051924 (published as WO 2014/013259). The SSB may be any of the SSBs disclosed in this International application.

The modified SSB most preferably comprises a sequence selected from those shown in SEQ ID NOs: 33, 34, 43 to 46.

Double-stranded binding proteins bind double stranded DNA with high affinity. Suitable double-stranded binding proteins include, but are not limited to Mutator S (MutS; NCBI Reference Sequence: NP_417213.1; SEQ ID NO: 49), Sso7d (*Sufolobus solfataricus* P2; NCBI Reference Sequence: NP_343889.1; SEQ ID NO: 50; Nucleic Acids Research, 2004, Vol 32, No. 3, 1197-1207), Sso10b1 (NCBI Reference Sequence: NP_342446.1; SEQ ID NO: 51), Sso10b2 (NCBI Reference Sequence: NP_342448.1; SEQ ID NO: 52), Tryptophan repressor (Trp repressor; NCBI Reference Sequence: NP_291006.1; SEQ ID NO: 53), Lambda repressor (NCBI Reference Sequence: NP_040628.1; SEQ ID NO: 54), Cren7 (NCBI Reference Sequence: NP_342459.1; SEQ ID NO: 55), major histone classes HI/H5, H2A, H2B, H3 and H4 (NCBI Reference Sequence: NP_066403.2, SEQ ID NO: 56), dsbA (NCBI Reference Sequence: NP_049858.1; SEQ ID NO: 57), Rad51 (NCBI Reference Sequence: NP_002866.2; SEQ ID NO: 58), sliding clamps and Topoisomerase V Mka (SEQ ID NO: 47) or a variant of any of these proteins. A variant of SEQ ID NO: 47, 49, 50, 51, 52, 53, 54, 55, 56, 57 or 58 typically has at least 50% homology to SEQ ID NO: 47, 49, 50, 51, 52, 53, 54, 55, 56, 57 or 58 based on amino acid identity over its entire sequence (or any of the % homologies discussed above in relation to helicases) and retains single stranded polynucleotide binding activity. A variant may differ from SEQ ID NO: 47, 49, 50, 51, 52, 53, 54, 55, 56, 57 or 58 in any of the ways discussed above in relation to helicases. In particular, a variant may have one or more conservative substitutions as shown in Tables 5 and 6. Most polymerases achieve processivity by interacting with sliding clamps. In general, these are multimeric proteins (homo-dimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids).

Related to DNA sliding clamps, processivity factors are viral proteins that anchor their cognate polymerases to DNA, leading to a dramatic increase in the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 27 or SEQ ID NO: 32 or a variant thereof. A variant of SEQ ID NO: 27 or 32 is a protein that has an amino acid sequence which varies from that of SEQ ID NO: 27 or 32 and which retains polynucleotide binding activity. This can be measured as described above. A variant typically has at least 50% homology to SEQ ID NO: 27 or 32 based on amino acid identity over its entire sequence (or any of the % homologies discussed above in relation to helicases) and retains polynucleotide binding activity. A variant may differ from SEQ ID NO: 27 or SEQ ID NO: 32 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage Φx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from crenarchaeota is unique in being a hetero-trimer so it is possible to functionalise one subunit and retain activity. Its subunits are shown in SEQ ID NOs: 28, 29 and 30. The PCNA is preferably a trimer comprising the sequences shown in SEQ ID NOs: 28, 29 and 30 or variants thereof. PCNA sliding clamp (NCBI Reference Sequence: ZP_06863050.1; SEQ ID NO: 59) forms a dimer. The PCNA is preferably a dimer comprising SEQ ID NO: 59 or a variant thereof. A variant is a protein that has an amino acid sequence which varies from that of SEQ ID NO: 28, 29, 30 or 59 and which retains polynucleotide binding activity. This can be measured as described above. A variant is typically a trimer comprising sequences that have at least 50% homology to SEQ ID NOs: 28, 29 and 30 or a dimer comprising sequences that have at least 50% homology to SEQ ID NO: 59 based on amino acid identity over each entire sequence (or any of the % homologies discussed above in relation to helicases) and which retains polynucleotide binding activity. A variant may comprise sequences which differ from SEQ ID NO: 28, 29, 30 or 59 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 of the PCNA from crenarchaeota (i.e. SEQ ID NOs: 28 and 29 or variants thereof) are attached, such as genetically fused, and the resulting protein is attached to a helicase to form a construct of the invention. During use of the construct, subunit 3 (i.e. SEQ ID NO: 30 or a variant thereof) may be added to complete the PCNA clamp (or doughnut) once the construct has bound the polynucleotide. In a preferred embodiment, one monomer of the PCNA sliding clamp (i.e. SEQ ID NO: 59 or a variant thereof) is attached, such as genetically fused, to a helicase to form a construct of the invention. During use of the construct, the second monomer (i.e. SEQ ID NO: 59 or a variant thereof) may be added to complete the PCNA clamp (or doughnut) once the construct has bound the polynucleotide.

The polynucleotide binding motif may be selected from any of those shown in Table 3 below.

TABLE 3

Suitable polynucleotide binding motifs

| No. | Name | Class | Organism | Structure | Sequence | Functional form | MW (Da) | Notes |
|---|---|---|---|---|---|---|---|---|
| 1 | SSBEco | ssb | Escherichia coli | 1QVC, 1EYG | P0AGE0 | homo-tetramer | 18975 | |
| 2 | SSBBhe | ssb | Bartonella henselae | 3LGJ, 3PGZ | Q6G302 | homo-tetramer | 16737 | structure only |
| 3 | SSBCbu | ssb | Coxiella burnetii | 3TQY | Q83EP4 | homo-tetramer | 17437 | structure only |
| 4 | SSBTma | ssb | Thermathoga maritima | 1Z9F | Q9WZ73 | homo-dimer | 16298 | small, thermostable, salt independent DNA binding |
| 5 | SSBHpy | ssb | Helicobacter pylori | 2VW9 | O25841 | homo-tetramer | 20143 | |
| 6 | SSBDra | ssb | Deinococcus radiodurans | 1SE8 | Q9RY51 | homo-dimer | 32722 | |
| 7 | SSBTaq | ssb | Thermus aquaticus | 2FXQ | Q9KH06 | homo-dimer | 30026 | |
| 8 | SSBMsm | ssb | Mycobacterium smegmatis | 3A5U, 1X3E | Q9AFI5 | homo-tetramer | 17401 | tetramer more stable than E.coli, binding less salt dependent |
| 9 | SSBSso | ssb/RPA | Sulfolobus solfataricus | 1O7I | Q97W73 | homo-tetramer | 16138 | similarities with RPA |
| 10 | SSBMHsmt | ssb | Homo sapiens | 3ULL | Q04837 | homo-tetramer | 17260 | |
| 11 | SSBMle | ssb | Mycobacterium leprae | 3AFP | P46390 | homo-tetramer | 17701 | |
| 12 | gp32T4 | ssb | Bacteriophage T4 | 1GPC | P03695 | monomer | 33506 | Homo-dimer in the absence of DNA, monomer when binding DNA. |
| 13 | gp32RB69 | ssb | Bacteriophage RB69 | 2A1K | Q7Y265 | monomer | 33118 | |
| 14 | gp2.5T7 | ssb | Bacteriophage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |
| 18 | RPAMja | RPA | Methanococcus jannaschii | 3DM3 | Q58559 | monomer | 73842 | contains 4 OB folds. Structure of fragment |
| 19 | RPAMma | RPA | Methanococcus maripaludis | 3E0E, 2K5V | Q6LYF9 | monomer | 71388 | Core domain structure |
| 20 | RPAMth | RPA | Methanothermobacter thermoautotrophicus | | | monomer | 120000 | Shown to interact directly with Hel308. Sequence from paper. |
| 21 | RPA70Sce | RPA | Saccharomyces cerevisiae | 1YNX | P22336 | hetero-trimer | 70348 | unit has two OB folds and binds DNA |
| 22 | RPAMbu1 | RPA | Methanococcoides burtonii | | Q12V72 | ? | 41227 | three OB folds identified |
| 23 | RPAMbu2 | RPA | Methanococcoides burtonii | | Q12W96 | ? | 47082 | two OB folds identified |
| 24 | RPA70Hsa | RPA | Homo sapiens | 1JMC | P27694 | homo-trimer | 68138 | |
| 25 | RPA14Hsa | RPA | Homo sapiens | 3KDF | P35244 | homo-trimer | 13569 | in complex with RPA32 |

TABLE 3-continued

Suitable polynucleotide binding motifs

| No. | Name | Class | Organism | Structure | Sequence | Functional form | MW (Da) | Notes |
|---|---|---|---|---|---|---|---|---|
| 26 | gp45T4 | sliding clamp | Bacteriophage T4 | 1CZD | P04525 | homo-trimer | 24858 | ring shape threads DNA |
| 27 | BetaEco | sliding clamp | E.coli | 3BEP | P0A988 | homo-dimer | 40587 | ring shape threads DNA, may bind ssDNA in poket |
| 28 | PCNASce | sliding clamp | Saccharomyces cerevisiae | 1PLQ, 3K4X | P15873 | homo-dimer | 28916 | ring shape threads DNA |
| 29 | PCNATko | sliding clamp | Thermococcus kodakaraensis | 3LX1 | Q5JF32 | homo-dimer | 28239 | |
| 30 | PCNAHvo | sliding clamp | Haloferax volcanii | 3IFV | D0VWY8 | homo-dimer | 26672 | |
| 31 | PCNAPfu | sliding clamp | Pyrococcus furiosus | 1GE8 | O73947 | homo-dimer | 28005 | |
| 32 | PCNAMbu | sliding clamp | Methanococcoides burtonii | | Q12U18 | homo-dimer | 27121 | Inferred from homology |
| 33 | BetaMtu | sliding clamp | Mycobacterium tuberculosis | 3P16 | Q50790 | homo-dimer | 42113 | |
| 34 | BetaTma | sliding clamp | Thermotoga maritima | 1VPK | Q9WYA0 | homo-dimer | 40948 | |
| 35 | BetaSpy | sliding clamp | Streptococcus pyrogenes | 2AVT | Q9EVR1 | homo-dimer | 41867 | |
| 36 | gp45RB69 | sliding clamp | Bacteriophage RB69 | 1B77 | O80164 | homo-trimer | 25111 | Structure shows interaction with polypeptide fom polymerase |
| 37 | p55Hsa | DNA binding protein | Homo sapiens (mitochondrial) | 2G4C, 3IKL, 3IKM | Q9UHN | monomer | 54911 | interacts with specific polymerase domain |
| 38 | p55Dme | DNA binding protein | Drosophylla melanogaster | | Q9VJV8 | monomer | 41027 | associates with polymerase Gamma conferring salt tolerance, processivity and increased activity |
| 39 | p55Xla | DNA binding protein | Xenopus laevis | | Q9W6G7 | monomer | 52283 | |
| 40 | RepDSau | DNA replication initiation protein | Staphylococcus aureus | | P08115 | homo-dimer | 37874 | increases processivity of PcrA, covalently and specifically links DNA |
| 41 | G2P | replication initiation protein | Enterobacteria phage 1 | | P69546 | monomer | 46168 | increases processivity of Rep, covalently and specifically links DNA |
| 42 | MutLEco | mismatch repair protein | Escherichia coli | 1BKN, 1B62, 1B63 | P23367 | homo-dimer | 67924 | increases processivity of UvrD (and Rep) |
| 43 | KuMtu | DNA repair protein | Mycobacterium tuberculosis | | O05866 | homo-dimer | 30904 | increases processivity of UvrD1. Structure available for human Ku |
| 44 | OnTEBP | telomere binding protein | Oxytricha nova-Alpha | 1OTC | P29549 | hetero-dimer | 56082 | Specific biding to 3' end T4G4T4G4. Alpha subunit may be enough |
| | | | Oxytricha nova-Beta | | P16458 | | 41446 | |
| 45 | EcrTEBP | telomere binding protein | Euplotes crassus | | Q06183 | monomer | 53360 | Homolog to OnTEBP with no Beta subunit in genome |
| 46 | TteTEBP | telomere binding protein | Tetrachymena termophila Alpha | | Q23FB9 | hetero-dimer | 53073 | Homolog to OnTEBP-Alpha |
| | | | Tetrachymena termophila Beta | | Q23FH0 | | 54757 | May be homolog to OnTEBP Beta |
| 47 | pot1Spo | telomere binding protein | Schizosaccharom yces pombe | | O13988 | monomer | 64111 | related to TEBP |
| 48 | Cdc13pSce | telomere binding protein | Saccharomyces cerevisiae | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |

TABLE 3-continued

Suitable polynucleotide binding motifs

| No. | Name | Class | Organism | Structure | Sequence | Functional form | MW (Da) | Notes |
|---|---|---|---|---|---|---|---|---|
| 50 | LexA | repressor | *Escherichia coli* | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from *E. coli*, exonuclease III enzyme from *E. coli*, RecJ from *T. thermophilus* and bacteriophage lambda exonuclease, TatD exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polymerase may be PyroPhage® 3173 DNA Polymerase (which is commercially available from Lucigen® Corporation), SD Polymerase (commercially available from Bioron®) or variants thereof. The polynucleotide binding moiety is preferably derived from Phi29 DNA polymerase (SEQ ID NO: 31). The moiety may comprise the sequence shown in SEQ ID NO: 101 or a variant thereof. A variant of SEQ ID NO: 31 is an enzyme that has an amino acid sequence which varies from that of SEQ ID NO: 31 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 31, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 31 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NOs: 35 or 36 or a variant thereof. A variant of SEQ ID NOs: 35 or 36 is a protein that has an amino acid sequence which varies from that of SEQ ID NOs: 35 or 36 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NOs: 35 or 36, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOs: 35 or 36 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described below. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above.

The moiety may be labelled with a revealing label. The label may be any of those described above.

The moiety may be isolated from any moiety-producing organism, such as *E. coli*, *T. thermophilus* or bacteriophage, or made synthetically or by recombinant means. For example, the moiety may be synthesized by in vitro translation and transcription as described below. The moiety may be produced in large scale following purification as described below.

Helicase Oligomers

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above with reference to the constructs of the invention, including the helicases of the invention and helicases which are not modified in accordance with the invention. In such embodiments, the constructs of the invention of course comprise two or more helicases attached together. At least one of the helicases is preferably modified in accordance with the invention. The constructs may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid position or spatially proximate amino acid positions in each helicase. This is termed the "head-to-head" formation. Alternatively, identical or similar helicases may be attached via positions on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or -pentamer etc.). For instance, the constructs of the invention may comprise (a) one or more helicases of the invention and one or more helicases which are not modified in accordance with the invention; (b) two or more different helicases of the invention; or (c) two or more helicases which are not modified in accordance with the invention. The construct may comprise two different variants of the same Dda helicase. For instance, the construct may comprise two variants of one of the helicases discussed above with one or more cysteine residues or Faz residues introduced at different positions in each variant. In this instance, the helicases can be in a head-to-tail formation.

Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

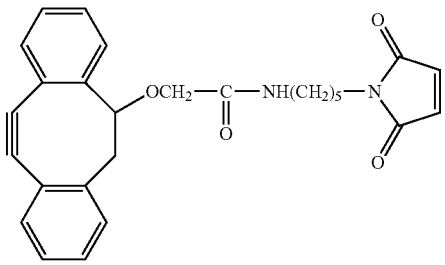

The second helicase variant can be modified with a second PEG linker containing maleimide or iodoacetamide functional group at one end and an azide functional group at the other end. An example is show below:

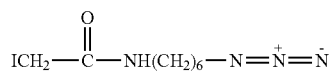

The two helicase variants with two different linkers can then be purified and clicked together (using copper free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant can be modified with a large excess of linker in such a way that one linker is attached to one molecule of the protein. This linker modified Faz variant can then be purified away from unmodified proteins, possible homo-dimers and unreacted linkers to react with the second Faz variant. The resulting dimer can then be purified away from other species.

Hetero-dimers can also be made by linking cysteine variants and Faz variants of the same helicase or different helicases. Hetero-bifunctional PEG linkers with maleimide or iodoacetamide functionalities at one end and DBCO functionality at the other end can be used in this combination of mutants. An example of such a linker is shown below (DBCO-PEG4-maleimide):

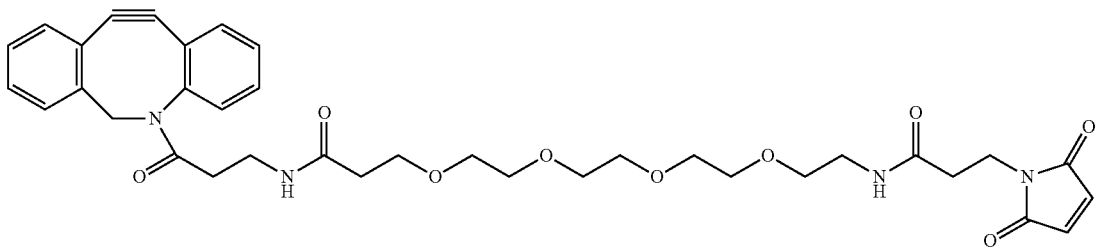 [SMILES: O=C(CCOCCOCCOCCOCCNC(=O)CCN1C(=O)C=CC1=O)NCCC(=O)N1Cc2ccccc2C#Cc2ccccc21]

The length of the linker can be varied by changing the number of PEG units between the two functional groups.

Helicase hetero-trimers can comprise three different types of helicases. The same is true for oligomers comprising more than three helicases. The two or more helicases within a construct may be different variants of the same helicase, such as different variants of any one of SEQ ID NOs: 8 to 23. The different variants may be modified at different positions to facilitate attachment via the different positions. The hetero-trimers may therefore be in a head-to-tail and head-to-head formation.

The two or more helicases in the constructs of the invention may be the same as one another (i.e. the construct is a homo-dimer, -trimer, -tetramer or -pentamer etc.) In such embodiments, the helicases are preferably attached using the same position in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

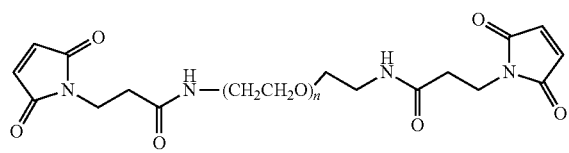

The length of the linker can be varied to suit the required applications. For example, n can be 2, 3, 4, 8, 11, 12, 16 or more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

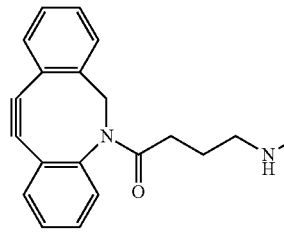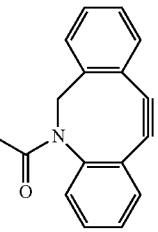

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

Homo-dimers or longer homo-oligomers may also be prepared in the head-to-tail formation if two or more cysteine residues or non-natural amino acids are introduced in the helicase in accordance with the invention and different cysteines or non-natural amino acids in the different helicase monomers are attached together. For instance, homo-oligomers may be formed from variants of SEQ ID NO: 8 comprising Y279C and G357C and the C at 279 in one monomer may be attached to the C at 357 in another monomer. Similarly, homo-oligomers may be formed from variants of SEQ ID NO: 8 comprising I281C and G357C and the C at 281 in one monomer may be attached to the C at 357 in another monomer. The same is true when Faz is introduced at these positions instead of C. Such C and Faz mutants allow series or trains of helicases to be created.

Polynucleotide Sequences

The invention provides a polynucleotide comprising a sequence which encodes a helicase of the invention, a polypeptide of the invention or a construct of the invention. The polynucleotide may consist of such a sequence. The polynucleotide may be any of those discussed above.

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably E. coli. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Series

The invention also provides a series of two or more helicases attached (or bound) to a polynucleotide, wherein at least one of the two or more helicases is a Dda helicase of the invention. The series may comprise any number of helicases such as 2, 3, 4, 5, 6, 7, 8, 9, 10 or more helicases. Any number of the helicases may be Dda helicases of the invention. All of the two or more helicases are preferably Dda helicases of the invention. The one or more Dda helicases of the invention may be any of those discussed above.

The two or more helicases may be the same helicase or may be different helicases. For instance, if the series comprises two or more Dda helicases of the invention, the Dda helicases of the invention may be the same or may be different.

The series may comprise any number and any combination of Dda helicases of the invention. The series of two or more helicases preferably comprises at least two Dda helicases of the invention. The series may comprise two or more Dda helicases each of which comprises a variant of SEQ ID NO: 8 comprising (or comprising only) (i) E94C/A360C, (ii) E94C/A360C and then (ΔM1)G1G2 (i.e. deletion of M1 and then addition G1 and G2), (iii) E94C/A360C/C109A/C136A, (iv) E94C/A360C/C109A/C136A and then (ΔM1) G1G2 (i.e. deletion of M1 and then addition G1 and G2), (v) E94C/A360C/W378A, (vi) E94C/A360C/W378A and then (ΔM1)G1G2 (i.e. deletion of M1 and then addition G1 and G2), (vii) E94C/A360C/C109A/C136A/W378A or (viii) E94C/A360C/C109A/C136A/W378A and then (ΔM1) G1G2 (i.e. deletion of M1 and then addition G1 and G2). One Dda helicase of the invention in the series preferably comprises a variant of SEQ ID NO: 8 comprising (or comprising only) one of (i) to (iv) and another Dda helicase of the invention in the series preferably comprises a variant of SEQ ID NO: 8 comprising (or comprising only) one of (v) to (viii).

In addition to one or more Dda helicases of the invention, the series may comprise one or more helicases which are not part of the invention. The one or more helicases may be or be derived from a Hel308 helicase, a RecD helicase, such as TraI helicase or a TrwC helicase, a XPD helicase or a Dda helicase. The one or more helicases may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013/098561); PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013. In particular, the one or more helicases are preferably modified to reduce the size of an opening in the polynucleotide binding domain through which in at least one conformational state the polynucleotide can unbind from the helicase. This is disclosed in WO 2014/013260.

The two or more helicases in the series may be separate from one another. The two or more helicases in the series may be brought together by a transmembrane pore as the polynucleotide moves through the pore. The two or more helicases in the series may contact one another.

The two or more helicases are preferably not attached to one another except via the polynucleotide. The two or more helicases are preferably not covalently attached to one another.

The two or more helicases may be attached or covalently attached to one another. The helicases may be attached in any order and using any method. A series of attached helicases may be called a train.

Polynucleotides to which the series of the invention may be attached/bound are discussed in more detail below.

Methods of the Invention

The invention provides a method of controlling the movement of a target polynucleotide. The method comprises contacting the target polynucleotide with a Dda helicase, a modified helicase of the invention or a construct of the invention and thereby controlling the movement of the polynucleotide. The method is preferably carried out with a potential applied across the pore. As discussed in more detail below, the applied potential typically results in the formation of a complex between the pore and the helicase or construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a Dda helicase, a modified helicase of the invention or a construct of the invention such that the helicase or construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

In all of the methods of the invention, the helicase may be any of those discussed above with reference to the constructs of the invention, including the modified Dda helicases of the invention and Dda helicases which are not modified in accordance with the invention.

Any number of Dda helicases of the invention may be used in these methods. For instance, 1, 2, 3, 4, 5, 6, 7, 8, 9, 10 or more helicases may be used. If two or more Dda helicases of the invention are used, they may be the same or different. Suitable numbers and combinations are discussed above with reference to the series of the invention. These equally apply to the methods of the invention.

If two or more helicases are used, they may be attached to one another. The two or more helicases may be covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

If two or more helicases are used, they are preferably not attached to one another except via the polynucleotide. The two or more helicases are more preferably not covalently attached to one another.

Steps (a) and (b) are preferably carried out with a potential applied across' the pore as discussed above. In some instances, the current passing through the pore as the polynucleotide moves with respect to the pore is used to determine the sequence of the target polynucleotide. This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is typically attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the membrane and the helicase's active site. If the coupling is transient, then when the coupled end randomly becomes free of the membrane, then the polynucleotide can be processed to completion. Chemical groups that form stable or transient links with the membrane are discussed in more detail below.

The polynucleotide may be transiently coupled to an amphiphilic layer, such as a lipid bilayer using cholesterol or a fatty acyl chain. Any fatty acyl chain having a length of from κ to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 4 below.

TABLE 4

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *JAmChemSoc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *JAmChem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the membrane. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the membrane, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8 or at least 9 subunits. The pore is preferably made up of 6, 7, 8 or 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane 13 barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (www.ncbi.nlm.nih.gov).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 5 below. Where amino acids have similar polarity, this can also be determined by reference to the hydropathy scale for amino acid side chains in Table 6.

TABLE 5

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 6

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |

TABLE 6-continued

Hydropathy scale

| Side Chain | Hydropathy |
|---|---|
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (ABC, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase or construct may be covalently attached to the pore. The helicase or construct is preferably not covalently attached to the pore. The application of a voltage to the pore and helicase or construct typically results in the formation of a sensor that is capable of sequencing target polynucleotides. This is discussed in more detail below.

Any of the proteins described herein, i.e. the helicases, the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The helicase, pore or construct may be labelled with a revealing label. The revealing label may be any suitable label which allows the pore to be detected. Suitable labels include, but are not limited to, fluorescent molecules, radio-isotopes, e.g. $^{125}I$, $^{35}S$, enzymes, antibodies, antigens, polynucleotides and ligands such as biotin.

Proteins may be made synthetically or by recombinant means. For example, the helicase, pore or construct may be synthesized by in vitro translation and transcription (IVTT). The amino acid sequence of the helicase, pore or construct may be modified to include non-naturally occurring amino acids or to increase the stability of the protein. When a protein is produced by synthetic means, such amino acids may be introduced during production. The helicase, pore or construct may also be altered following either synthetic or recombinant production.

The helicase, pore or construct may also be produced using D-amino acids. For instance, the pore or construct may comprise a mixture of L-amino acids and D-amino acids. This is conventional in the art for producing such proteins or peptides.

The helicase, pore or construct may also contain other non-specific modifications as long as they do not interfere with pore formation or helicase or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The helicase, pore and construct can be produced using standard methods known in the art. Polynucleotide sequences encoding a helicase, pore or construct may be derived and replicated using standard methods in the art. Polynucleotide sequences encoding a helicase, pore or construct may be expressed in a bacterial host cell using standard techniques in the art. The helicase, pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The helicase, pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below, For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a transmembrane pore and a helicase of the invention or a construct of the invention such that the target polynucleotide moves through the pore and the helicase or construct controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffer include, but are not limited to, HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the helicase or construct and the pore in any order. In is preferred that, when the target polynucleotide is contacted with the helicase or construct and the pore, the target polynucleotide firstly forms a complex with the helicase or construct. When the voltage is applied across the pore, the target polynucleotide/helicase or construct complex then forms a complex with the pore and controls the movement of the polynucleotide through the pore.

Other Methods

The invention also provides a method of forming a sensor for characterising a target polynucleotide. The method comprises forming a complex between a pore and a Dda helicase, a helicase of the invention or a construct of the invention. The helicase may be any of those discussed above with reference to the constructs of the invention, including the helicases of the invention and helicases which are not modified in accordance with the invention. Any number and combination of Dda helicases of the invention discussed above with reference to the series and methods of the invention may be used.

The complex may be formed by contacting the pore and the helicase or construct in the presence of the target polynucleotide and then applying a potential across the pore. The applied potential may be a chemical potential or a voltage potential as described above. Alternatively, the complex may be formed by covalently attaching the pore to the helicase or construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a helicase of the invention or a construct of the invention. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a Dda helicase, a helicase of the invention of the invention or a construct of the invention. Any of the embodiments discussed above with reference to the method of the invention equally apply to the kits. The helicase may be any of those discussed above with reference to the constructs of the invention, including the helicases of the invention and helicases which are not modified in accordance with the invention. The kit may comprise any number and combination of Dda helicases of the invention discussed above with reference to the series and methods of the invention.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of Dda helicases, a plurality of helicases of the invention or a plurality of constructs of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention. The helicase may be any of those discussed above with reference to the constructs of the invention, including the helicases of the invention and helicases which are not modified in accordance with the invention. The apparatus may comprise any number and combination of Dda helicases of the invention discussed above with reference to the series and methods of the invention.

The apparatus is preferably set up to carry out the method of the invention.

The apparatus preferably comprises:
a sensor device that is capable of supporting the plurality of pores and being operable to perform polynucleotide characterisation using the pores and helicases or constructs; and
at least one port for delivery of the material for performing the characterisation.

Alternatively, the apparatus preferably comprises:
a sensor device that is capable of supporting the plurality of pores and being operable to perform polynucleotide characterisation using the pores and helicases or constructs; and
at least one reservoir for holding material for performing the characterisation.

The apparatus more preferably comprises:
a sensor device that is capable of supporting the membrane and plurality of pores and being operable to perform polynucleotide characterising using the pores and helicases or constructs;
at least one reservoir for holding material for performing the characterising;
a fluidics system configured to controllably supply material from the at least one reservoir to the sensor device; and
one or more containers for receiving respective samples, the fluidics system being configured to supply the samples selectively from one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

Methods of Producing Helicases of the Invention

The invention also provides methods of producing a modified helicase of the invention. The method comprises providing a Dda helicase and modifying the helicase to form a modified helicase of the invention.

The method preferably further comprises determining whether or not the helicase is capable of controlling the movement of a polynucleotide. Assays for doing this are described above. If the movement of a polynucleotide can be controlled, the helicase has been modified correctly and a helicase of the invention has been produced. If the movement of a polynucleotide cannot be controlled, a helicase of the invention has not been produced.

Methods of Producing Constructs of the Invention

The invention also provides a method of producing a construct of the invention. The method comprises attaching, preferably covalently attaching, a Dda helicase or a helicase of the invention to an additional polynucleotide binding moiety. Any of the helicases and moieties discussed above can be used in the methods. The site of and method of covalent attachment are selected as discussed above.

The method preferably further comprises determining whether or not the construct is capable of controlling the movement of a polynucleotide. Assays for doing this are described above. If the movement of a polynucleotide can be controlled, the helicase and moiety have been attached correctly and a construct of the invention has been produced. If the movement of a polynucleotide cannot be controlled, a construct of the invention has not been produced.

The following Examples illustrate the invention.

EXAMPLES

Example 1

This example describes how a T4 Dda-E94C/A360C (SEQ ID NO: 8 with mutations E94C/A360C and then (ΔM1)G1G2) controlled the movement of intact DNA strands through a single MspA nanopore (MS(B1-G75S/G77S/L88N/Q126R)$_8$ MspA (MspA-B2C) (SEQ ID NO: 2 with mutations G75S/G77S/L88N/Q126R).

Materials and Methods

Figure 8:
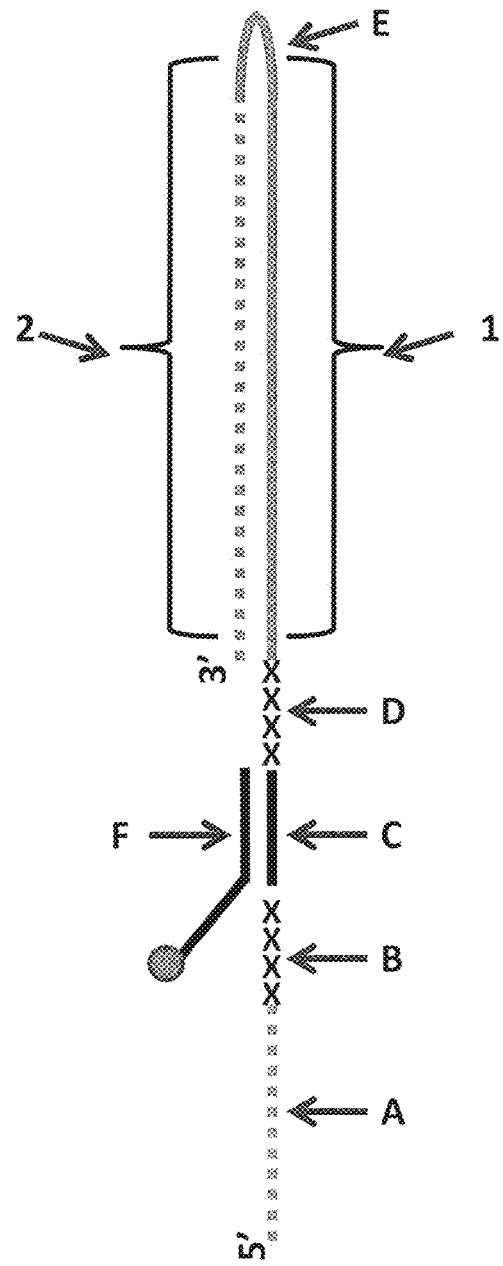
FIG. 8 shows a diagram of the lambda DNA construct used in Examples 1 and 4. SEQ ID NO: 60 (labelled A) is attached at its 3' end to four iSpC3 spacers (labelled B). The four iSpC3 spacers are attached to the 5' end of SEQ ID NO: 61 (labelled C). SEQ ID NO: 61 is attached to four iSpC3 spacers (labelled D) which are attached to SEQ ID NO: 62 (labelled E) at its 5' end. SEQ ID NO: 61 is hybridised to SEQ ID NO: 63 (labelled F, which has a 3' cholesterol tether). Two separate sections of labelled region E are highlighted as region 1 (shown as a solid grey line) and region 2 (shown as a dotted grey line) in the figure and are referred to in Example 4.

Prior to setting up the experiment, the Lambda DNA construct (SEQ ID NO: 60 attached by its 3' end to four iSpC3 spacers which are attached to the 5' end of SEQ ID NO: 61 which is attached at its 3' end to four iSPC3 spacers which are attached to the 5' end of SEQ ID NO: 62, the SEQ ID NO: 61 region of this construct is hybridised to SEQ ID NO: 63 (which has a 3' cholesterol tether) see FIG. 8 for a diagram of the construct) and T4 Dda-E94C/A360C were pre-incubated together for 15 minutes at 23° C. in buffer (20 mM CAPS, pH 10.0, 500 mM NaCl, 5% Glycerol, 2 mM DTT).

Electrical measurements were acquired at 20° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MspA-B2C) and finally experimental buffer was flowed into the system (2 mL 960 mM KCl, 25 mM potassium phosphate, 3 mM Potassium Ferrocyanide (II), 1 mM Potassium ferricyanide (III), pH 8). MgCl$_2$ (10 mM final concentration) and ATP (1 mM final concentration) were mixed together with buffer (960 mM KCl, 25 mM potassium phosphate, 3 mM Potassium Ferrocyanide (II), 1 mM Potassium ferricyanide (III), pH 8) and then added to the Lambda DNA construct (0.2 nM final concentration), T4 Dda-E94C/A360C (10 nM final concentration) buffer (20 mM CAPS, pH 10.0, 500 mM NaCl, 5% Glycerol, 2 mM DTT) pre-mix. The pre-mix was then added to the single nanopore experimental system. Experiments were carried out for four hours following a potential flip process (+100 mV for 2 s, then 0 V for 2 s, then −120 mV for 14500s applied at the cis side) and helicase-controlled DNA movement was monitored.

Results and Discussion

Helicase controlled DNA movement was observed for the Lambda DNA construct, an example of a helicase-controlled DNA movement is shown in FIG. 1. The helicase-controlled DNA movement was 5170 seconds long and corresponded to the translocation of approximately 30 kB of the lambda construct through the nanopore. FIG. 2 shows zoomed in regions of the beginning (a) and end (b) of the helicase-controlled DNA movement.

Example 2

This example describes how a T4 Dda-E94C/A360C exhibited tight binding to both linear (SEQ ID NO: 64) and circular (SEQ ID NO: 65) single-stranded DNA. The tight binding of the enzyme was measured using a fluorescence anisotropy-based assay.

Materials and Methods

Figure 3:
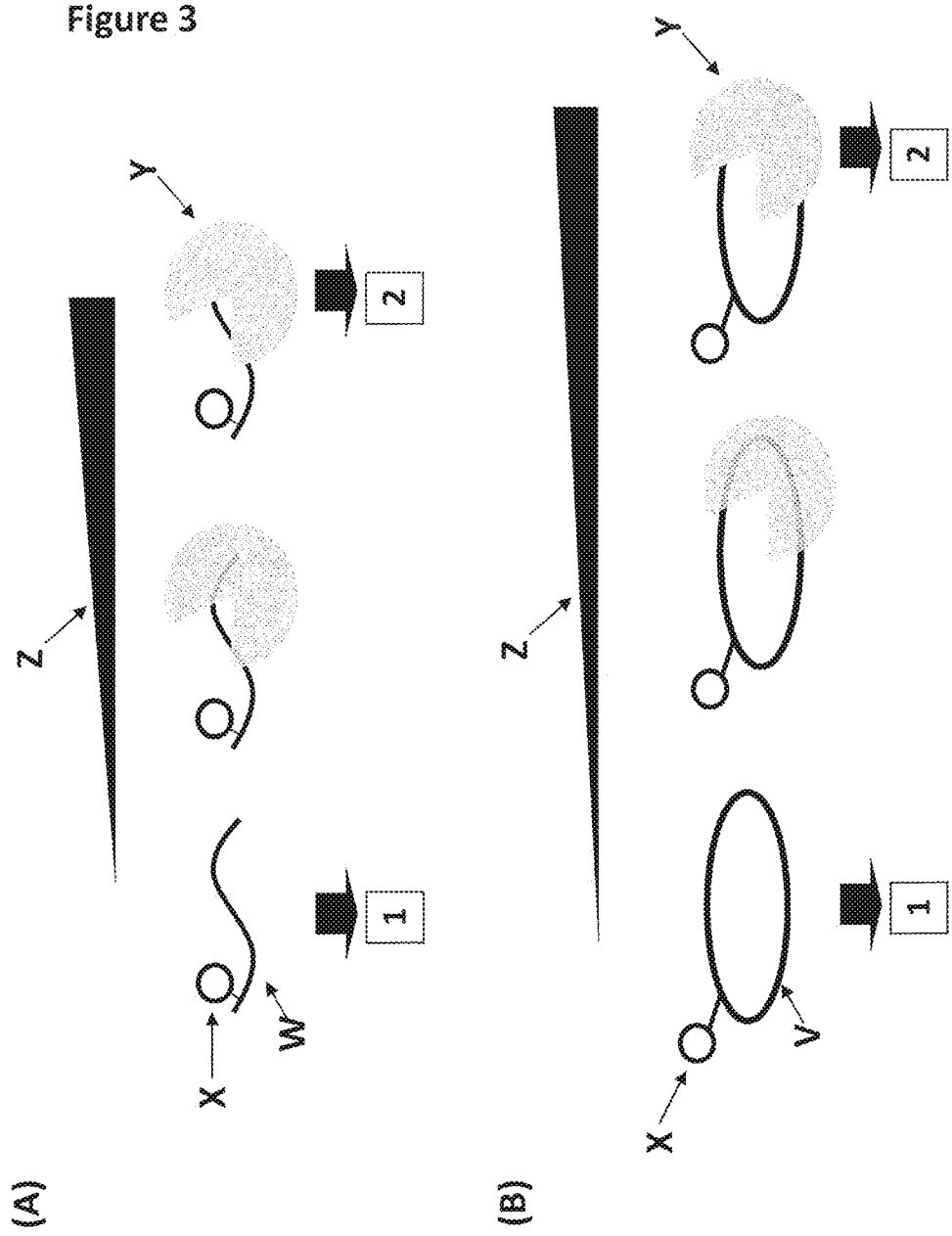
FIG. 3 shows a fluorescence assay for testing helicase binding to linear (A) or circular (B) single-stranded DNA. (A) shows a custom fluorescent substrate used to assay the ability of T4 Dda-E94C/A360C (SEQ ID NO: 8 with mutations E94C/A360C) helicase to bind to linear single-stranded DNA. The 44 nt single-stranded DNA substrate (1 nM final, SEQ ID NO: 64, labelled W) has a carboxyfluorescein (FAM) attached to the thymine base at position 37 in SEQ ID NO: 64 (circle labelled X). As the helicase (labelled Y) bound to the DNA substrate in buffered solution (25 mM potassium phosphate, 151.5 mM KCl, pH8.0, 10 mM MgCl$_2$), the fluorescence anisotropy (a property relating to the speed of tumbling of the DNA substrate in solution) increased. The lower the amount of helicase needed to affect an increase in anisotropy, the tighter the binding affinity between the DNA and helicase. In situation 1 with no enzyme bound the DNA substrate exhibited faster tumbling and low anisotropy, whereas, in situation 2 with enzyme bound to the DNA substrate it exhibited slower tumbling and high anisotropy (this was attributed to the mass increase upon binding of a large protein molecule to the DNA). The black bar labelled Z corresponds to increasing helicase concentration (the thicker the bar the higher the helicase concentration). (B) shows a custom fluorescent substrate used to assay the ability of T4 Dda-E94C/A360C (SEQ ID NO: 8 with mutations E94C/A360C) helicase to bind to circular single-stranded DNA. The 75 nt circular single-stranded DNA substrate (1 nM final, SEQ ID NO: 65, labelled V) had a carboxyfluorescein (FAM) attached to one of the thymine bases in SEQ ID NO: 65 (circle labelled X). As the helicase (labelled Y) bound to the oligonucleotide in buffered solution (25 mM potassium phosphate, 151.5 mM KCl, pH8.0, 10 mM MgCl$_2$), the fluorescence anisotropy (a property relating to the rate of tumbling of the oligonucleotide in solution) increased. The lower the amount of helicase needed to affect an increase in anisotropy, the tighter the binding affinity between the DNA and helicase. In situation 1 with no enzyme bound the DNA substrate exhibited faster tumbling and low anisotropy, whereas, in situation 2 with enzyme bound to the DNA substrate it exhibited slower tumbling and high anisotropy (this was attributed to the mass increase upon binding of a large protein molecule to the DNA). The black bar labelled Z corresponds to increasing helicase concentration (the thicker the bar the higher the helicase concentration).

Two custom fluorescent substrates were used to assess the ability of T4 Dda-E94C/A360C helicase to bind to linear (SEQ ID NO: 64) and circular (SEQ ID NO: 65) single-stranded DNA. The 44 nt linear single-stranded DNA substrate (1 nM final, SEQ ID NO: 64) had a carboxyfluorescein (FAM) attached to the thymine base at position 37 in SEQ ID NO: 64. The 75 nt circular single-stranded DNA substrate (1 nM final, SEQ ID NO: 65) had a carboxyfluorescein (FAM) attached to a thymine base in SEQ ID NO: 65. As the helicase bound to either fluorescent substrate in a buffered solution (25 mM potassium phosphate, 151.5 mM KCl, pH8.0, 10 mM $MgCl_2$), the fluorescence anisotropy (a property relating to the speed of tumbling of the DNA substrate in solution) increased. The lower the amount of helicase needed to effect an increase in anisotropy, the tighter the binding affinity between the DNA and helicase (FIG. 3).

T4 Dda-E94C/A360C was buffer exchanged into the binding buffer (25 mM potassium phosphate, 151.5 mM KCl, pH8.0, 10 mM $MgCl_2$) and then serially diluted over a concentration range of 0.02 nM to 750 nM. Each sample concentration was then mixed with linear or circular single-stranded DNA (1 nM of SEQ ID NO: 64 or 65) giving a final concentration range of T4 Dda-E94C/A360C of 0.01 nM to 375 nM and the fluorescence anisotropy assessed over the course of 60 min at 25° C.

Results and Discussion

Figure 4:
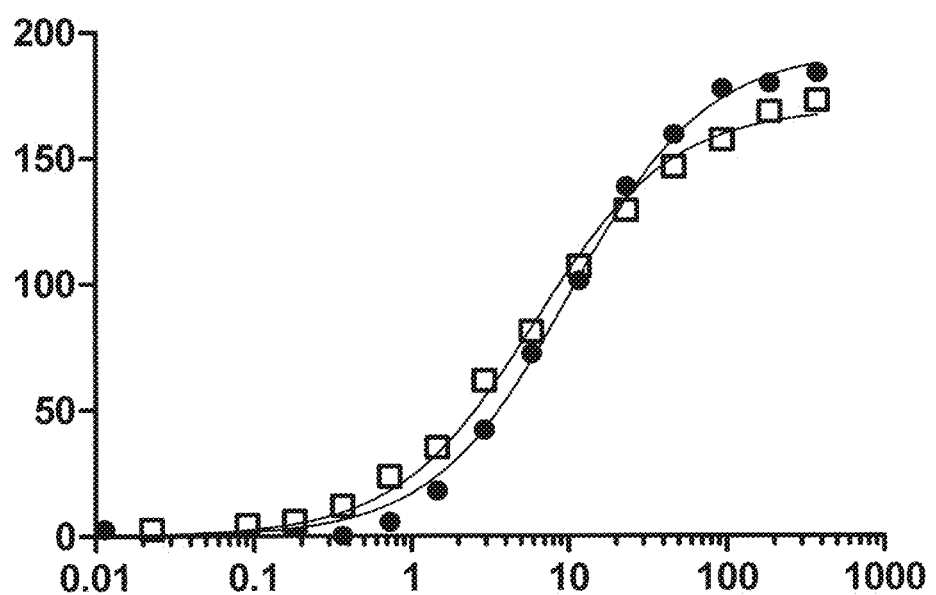
FIG. 4 shows the change in anisotropy of the linear and circular single-stranded DNA oligonucleotides (SEQ ID NO: 64 or 65) with increasing amounts of T4 Dda-E94C/A360C (SEQ ID NO: 8 with mutations E94C/A360C) (y-axis label=Anisotropy (blank subtracted, 50 to 200), x-axis label=Concentration T4 Dda (nM, 0.01 to 1000)) at the end of a 60 min incubation period. The data with black circles corresponded to the linear ssDNA construct. The data with the empty squares corresponded to the circular ssDNA construct.
Figure 5:
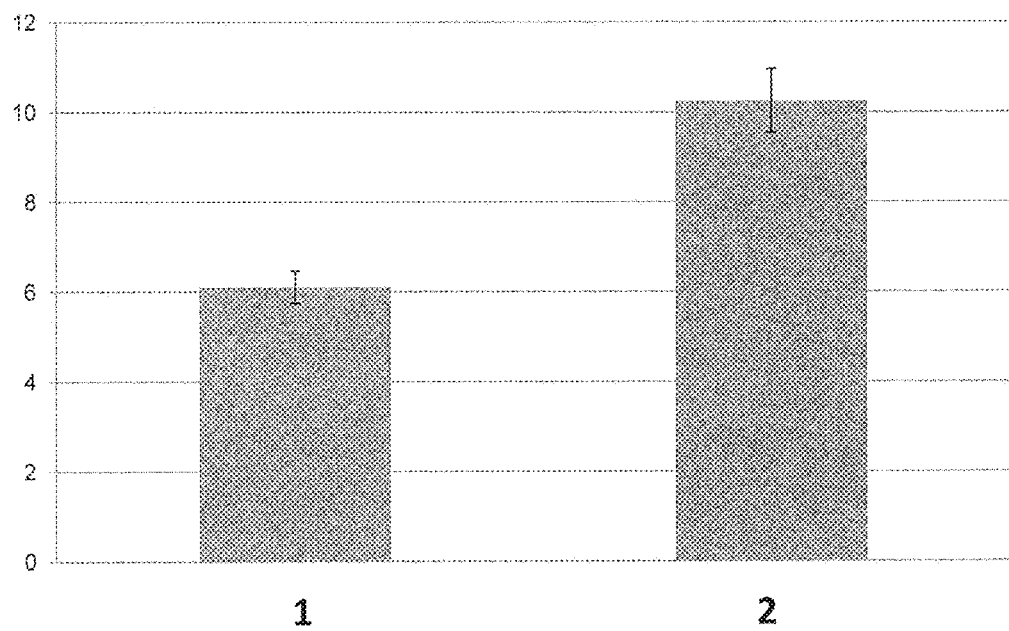
FIG. 5 shows the equilibrium dissociation constants ($K_d$) for T4 Dda-E94C/A360C (SEQ ID NO: 8 with mutations E94C/A360C) binding to linear or circular single-stranded DNA after a 60 minute incubation. The graph was obtained through fitting one phase dissociation binding curves through the data shown in FIG. 4 using Graphpad Prism software (y-axis label=dissociation constant Kd (nM, 0 to 12), x-axis label=Ref. Number, where Ref. Number 1 corresponded to the linear single-stranded DNA oligonucleotide and Ref. Number 2 corresponded to the circular single-stranded DNA oligonucleotide).

FIGS. 4 and 5 show the fluorescence binding assay data collected for the linear and circular single-stranded DNA binding experiments. FIG. 4 shows the change in anisotropy of the linear and circular single-stranded DNA oligonucleotides (SEQ ID NO: 64 or 65) with increasing amounts of T4 Dda-E94C/A360C at the end of a 60 minute incubation period. FIG. 5 shows the equilibrium dissociation constants ($K_d$) for T4 Dda-E94C/A360C binding to linear or circular single-stranded DNA after a 60 minute incubation, obtained through fitting one phase dissociation binding curves through the data shown in FIG. 4 using Graphpad Prism software (y-axis label=dissociation constant Kd (nM), x-axis label=Ref. Number, where Ref. Number 1 corresponded to the linear single-stranded DNA oligonucleotide and Ref. Number 2 corresponded to the circular single-stranded DNA oligonucleotide).

The T4 Dda-E94C/A360C helicase was found to exhibit tight binding affinity (sub 15 nM binding affinity) to both circular and linear single-stranded DNA (see FIGS. 4 and 5).

Example 3

This example compared the helicase-controlled DNA movement of T4 Dda-E94C/A360C with that of TrwC Cba (SEQ ID NO: 66). Both helicases move along the polynucleotide in a 5' to 3' direction. When the 5'end of the polynucleotide (the end away from which the helicases move) is captured by the pore, the helicases work with the direction of the field resulting from the applied potential and move the threaded polynucleotide into the pore and into the trans chamber. T4 Dda was observed to control the translocation of DNA through the nanopore smoothly without the DNA stepping back (i.e. towards its 3'end relative to the pore), whereas TrwC Cba resulted in stepping back of the DNA between states as it controlled translocation of the DNA. In this Example, stepping back involves the DNA moving backwards relative to the pore (i.e. towards its 5' and away from it 3' end in this Example). This phenomenon was called slipping in UK Application Nos. 1318464.3 and 1404718.7.

Materials and Methods

Prior to setting up the experiments, the DNA strand (3 uL of 20 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) and TrwC Cba (SEQ ID NO: 66, 22.5 uL of 13.3 µM) were pre-incubated together for over an hour at room temperature in buffer (50 mM CAPS, pH 10.0, 100 mM NaCl). In a separate tube, 3 uL of MgCl2 (1 M) and 3 uL of dTTP (100 mM) were mixed with 260 uL of buffer (960 mM KCl, 3 mM potassium ferrocyanide (II), 1 mM potassium ferricyanide (III) and 25 mM potassium phosphate pH 8.0). After the hour pre-incubation, the DNA enzyme mix was added to MgCl2/dTTP mix giving final concentrations of reagents as follows—DNA strand (0.2 nM), TrwC Cba (SEQ ID NO: 66, 1 µM), MgCl2 (10 mM), dTTP (1 mM) in buffer (960 mM KCl, 3 mM potassium ferrocyanide (II), 1 mM potassium ferricyanide (III) and 25 mM potassium phosphate pH 8.0).

Prior to setting up the experiments, the DNA strand (0.2 uL of 300 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) and T4 Dda-E94C/A360C (0.1 uL of 3300 nM) were pre-incubated together for 15 minutes at room temperature. In a separate tube, MgCl2 (3 uL of 1M) and ATP (3 uL of 100 mM) were mixed with 294 uL of buffer (960 mM KCl, 3 mM potassium ferrocyanide (II), 1 mM potassium ferricyanide (III) and 25 mM potassium phosphate, pH 8.0). After the 15 minute pre-incubation, the DNA enzyme mix was added to MgCl2/ATP mix giving final concentrations of reagents as follows—DNA strand (0.2 nM), T4 Dda-E94C/A360C (1 nM), MgCl2 (10 mM), ATP (1 mM) in buffer (960 mM KCl, 3 mM potassium ferrocyanide (II), 1 mM potassium ferricyanide (III) and 25 mM potassium phosphate pH 8.0).

Electrical measurements were acquired at 20° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (3 mL, 960 mM KCl, 25 mM potassium phosphate, 3 mM Potassium Ferrocyanide (II), 1 mM Potassium ferricyanide (III), pH 8) was flowed through the system to remove any excess MspA nanopores (MspA-B2C). Either the TrwC Cba (SEQ ID NO: 66) or the T4 Dda E94C/A360C pre-mix was then added to the single nanopore experimental system. Each experiment was carried out for 6 hours at a holding potential of −120 mV) and helicase-controlled DNA movement was monitored.

Results and Discussion

Figure 6:
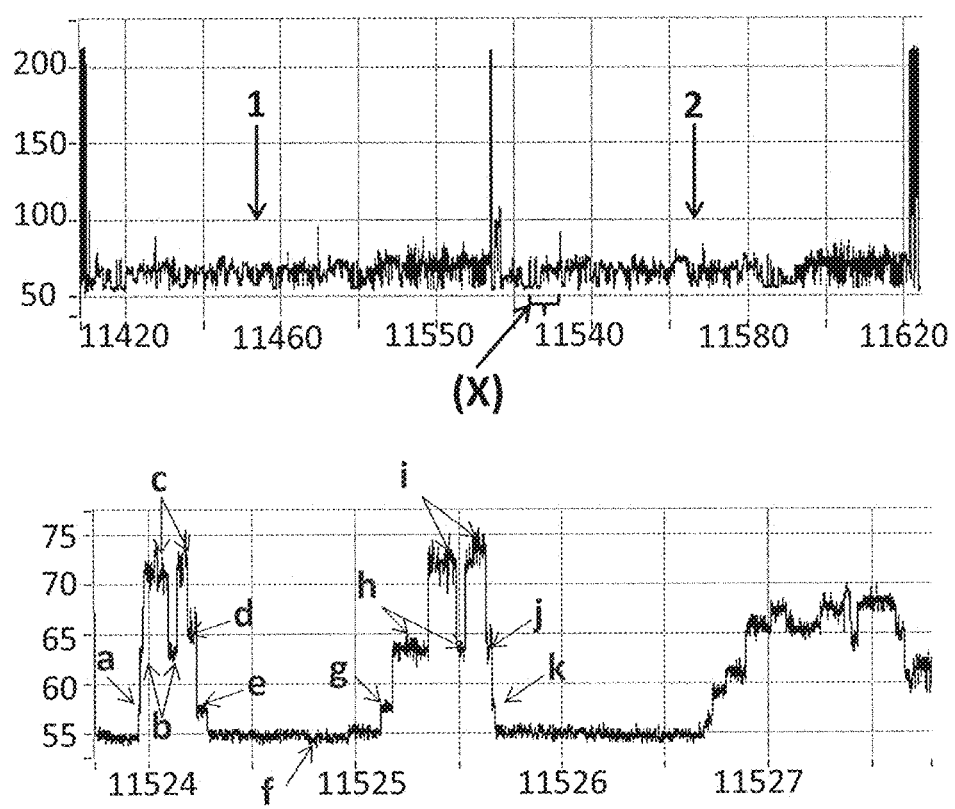
FIG. 6 shows an example current trace (y-axis label=Current (pA, upper trace 50 to 200, lower trace 55 to 75), x-axis label=Time (s, upper trace 11420 to 11620, lower trace 11524 to 11527)) of when a helicase (TrwC Cba (SEQ ID NO: 66)) controlled the translocation of DNA (0.2 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) through a nanopore (MS(B1-G75S/G77S/L88N/Q126R)8 MspA (SEQ ID NO: 2 with mutations G75S/G77S/L88N/Q126R)). The upper trace shows two helicase controlled DNA movements and the lower trace shows a zoomed in region labelled X in the upper level. As the helicase moved the DNA through the nanopore the current levels detected have been labelled a to k. When TrwC Cba controlled translocation through the nanopore, the DNA stepped back and therefore levels corresponding to b, c, h and i were observed several times.
Figure 7:
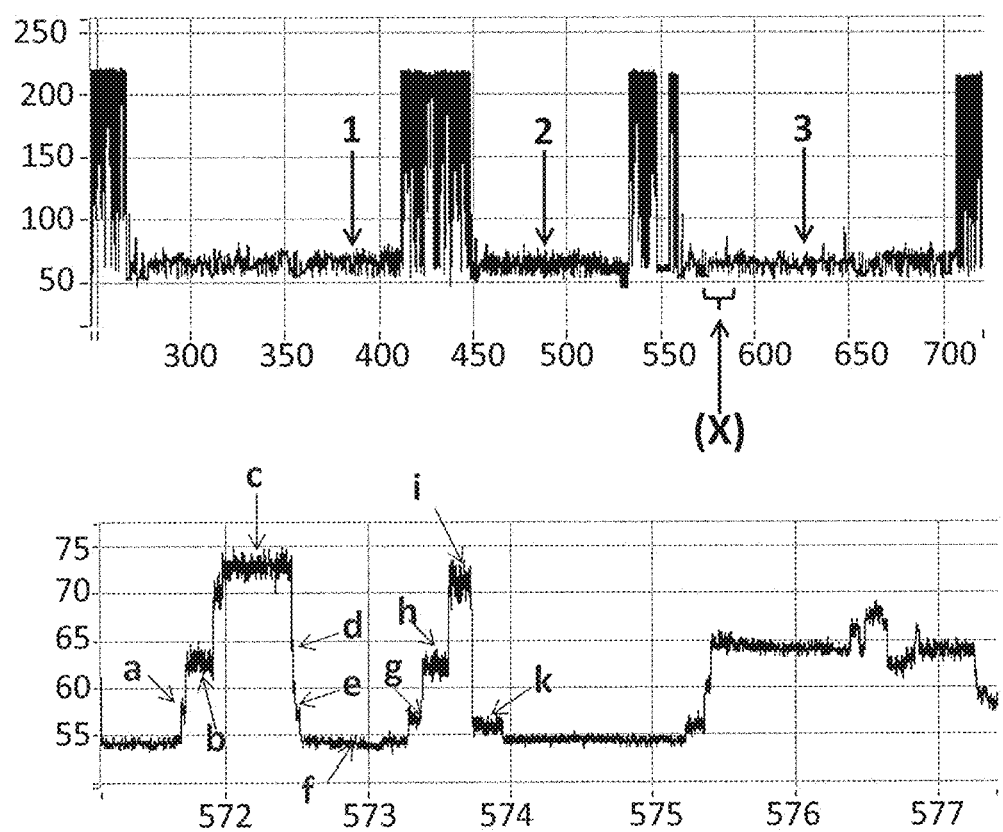
FIG. 7 shows an example current trace (y-axis label=Current (pA, upper trace 50 to 250, lower trace 55 to 75), x-axis label=Time (s, upper trace 300 to 700, lower trace 572 to 577)) of when a helicase (T4 Dda E94C/A360C (SEQ ID NO: 8 with mutations E94C/A360C)) controlled the translocation of DNA (0.2 nM, SEQ ID NO: 67 attached by its 3' end to four iSpC3 spacers which are attached to the 5' end of SEQ ID NO: 61 which is attached at its 3' end to four 5-nitroindoles the last of which is attached to the 5' end of SEQ ID NO: 68, in addition SEQ ID NO: 63 is hybridised to SEQ ID NO: 61) through a nanopore (MS(B1-G75S/G77S/L88N/Q126R)8 MspA (SEQ ID NO: 2 with mutations G75S/G77S/L88N/Q126R)). The upper trace shows three helicase controlled DNA movements and the lower trace shows a zoomed in region labelled X in the upper level. As the helicase moved the DNA through the nanopore the current levels detected have been labelled a to k. When T4 Dda E94C/A360C (SEQ ID NO: 8 with mutations E94C/A360C) controlled translocation through the nanopore, the DNA did not step back and therefore single current levels corresponding to levels a to i were observed.

FIGS. 6 and 7 show helicase controlled DNA movements for the TrwC Cba (SEQ ID NO: 66) and T4 Dda E94C/A360C respectively. The upper trace of FIG. 6 shows two TrwC Cba (SEQ ID NO: 66) helicase controlled DNA movements (labelled 1 and 2) and the lower section shows zoomed in region X. The upper trace of FIG. 7 shows three T4 Dda E94C/A360C helicase controlled DNA movements (labelled 1, 2 and 3) and the lower section shows zoomed in region X. The Trwc Cba helicase controlled the movement of the DNA strand through the nanopore and the current changed as the DNA translocated. In the lower trace a number of current levels were labelled a to k which corresponded to consecutive current levels produced when the section of the DNA strand translocated through the pore. It was clear from zoomed in region X in FIG. 6 that the DNA stepped back so that levels corresponding to b, c, h and i were observed several times. Whereas, FIG. 7 lower trace shows that the T4 Dda E94C/A360C helicase controlled the movement of DNA through a nanopore such that stepping back was not observed and a single current level which corresponded to consecutive current levels a to k was observed. It was advantageous to have an enzyme which did not allow stepping back of the DNA strand as this meant it was much easier to map the changes in current to the sequence of the DNA strand when the enzyme moved in one direction along the strand. This made T4 Dda E94C/A360C an improved enzyme for DNA translocation when compared to TrwC Cba (SEQ ID NO: 66).

Example 4

This example describes how T4 Dda-E94C/A360C, T4 Dda-E94C/A360C/C109A/C136A (SEQ ID NO: 8 with mutations E94C/A360C/C109A/C136A and then (ΔM1) G1G2) and T4 Dda-E94C/A360C/C114A/C171A/C421D (SEQ ID NO: 8 with mutations E94C/A360C/C114A/C171A/C421D and then (ΔM1)G1G2) controlled the movement of intact DNA strands through a single MspA nanopore. The helicase controlled movement speed of both region 1 and region 2 of the lambda DNA construct (shown in FIG. 8) was observed to decrease overtime for T4 Dda-E94C/A360C and T4 Dda-E94C/A360C/C114A/C171A/C421D. However, T4 Dda-E94C/A360C/C109A/C136A exhibited improved helicase controlled DNA movement in comparison as the speed of movement remained high and fairly constant during the entire experimental run.
Materials and Methods Prior to setting up the experiment, the DNA construct X (5.2 μL, 25 nM, SEQ ID NO: 67 attached by its 3' end to four iSpC3 spacers which are attached to the 5' end of SEQ ID NO: 61 which is attached at its 3' end to four 5-nitroindoles spacers which are attached to the 5' end of SEQ ID NO: 69, the SEQ ID NO: 61 region of this construct is hybridised to SEQ ID NO: 63 (which has a 3' cholesterol tether) this is a similar construct as shown in FIG. 8 except the region labelled A corresponds to SEQ ID NO: 67 and the region labelled E corresponds to SEQ ID NO: 69) in buffer (in 50 mM NaCl, 10 mM Tris pH7.5) was pre-incubated for 5 minutes at ambient temperature with either T4 Dda-E94C/A360C, T4 Dda-E94C/A360C/C109A/C136A or T4 Dda-E94C/A360C/C114A/C171A/C421D in buffer (5.2 μL, 250 nM in 253 mM KCl, 50 mM potassium phosphate pH 8.0 2 mM EDTA). TMAD (2.6 μL, 500 μM) was then added to the DNA/enzyme pre-mix and incubated for a further 5 minutes. Finally, buffer (1241.5 μL, 25 mM potassium phosphate, 150 mM potassium ferrocyanide (II) and 150 mM potassium ferricyanide (III), pH 8.0) MgCl2 (13 μL, 1M) and ATP (32.5 μL, 100 mM) were added to the pre-mix.

Electrical measurements were acquired from single MspA nanopores inserted in block co-polymer in buffer (25 mM potassium phosphate, 150 mM potassium ferrocyanide (II), 150 mM potassium ferricyanide (III)) at a peltier temperature of 28° C. After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (either T4 Dda-E94C/A360C, T4 Dda-E94C/A360C/C109A/C136A or T4 Dda-E94C/A360C/C114A/C171A/C421D (1 nM final concentration)), DNA (0.1 nM final concentration), fuel (MgCl2 10 nM final concentration, ATP 2.5 mM final concentration) pre-mix was then added to the single nanopore experimental system. Each experiment was carried out for 6 hours at a holding potential of 120 mV with potential flicks every hour with an applied potential of −120 mV and helicase-controlled DNA movement was monitored.
Results and Discussion Helicase controlled DNA movement was observed for DNA construct X, with all mutant helicases investigated (T4 Dda-E94C/A360C, T4 Dda-E94C/A360C/C109A/C136A or T4 Dda-E94C/A360C/C114A/C171A/C421D). Examples of T4 Dda-E94C/A360C/C109A/C136A and T4 Dda-E94C/A360C/C114A/C171A/C421D helicase-controlled DNA movements are shown in FIGS. 9 and 10 respectively.

Figure 11:
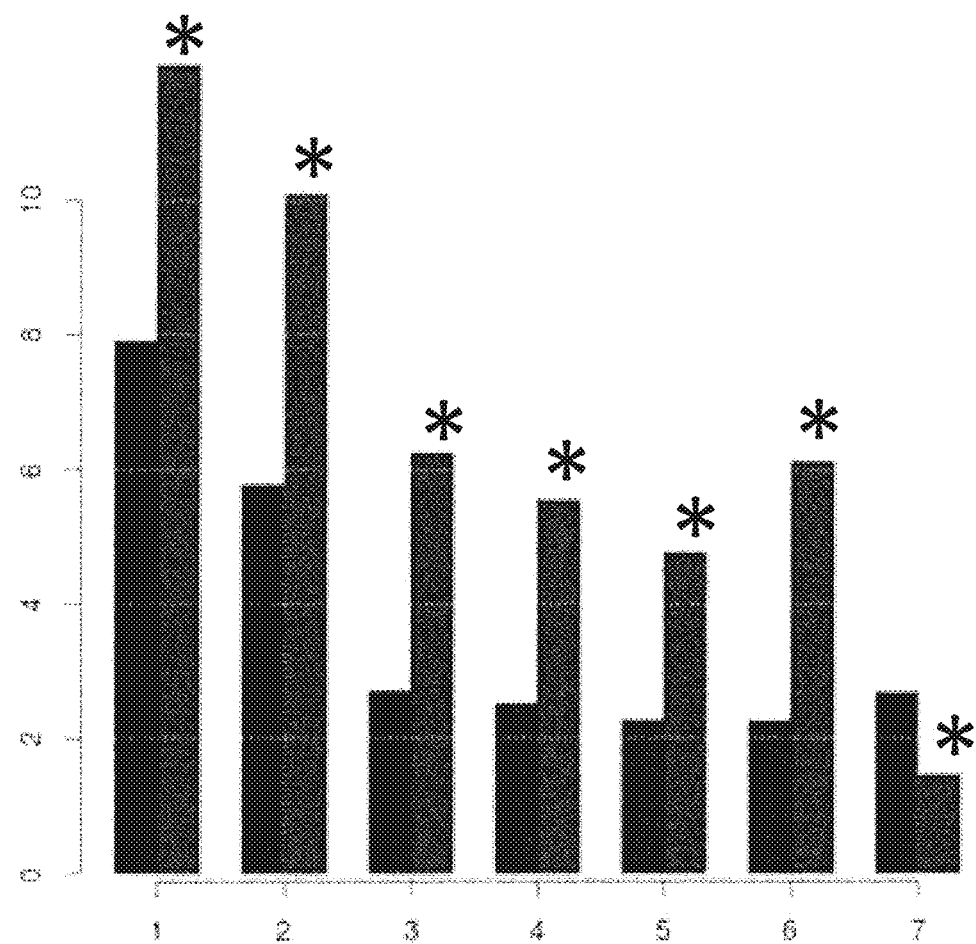
FIG. 11 shows how the helicase controlled DNA movement speed for the mutant T4 Dda-E94C/A360C varied during the course of a 6 hour 5 minute experimental run (y-axis label=events per second, x-axis label=time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of of region 1 of the lambda DNA construct (shown in FIG. 8) passing through the nanopore. Events per second was used in the examples as a measure of the speed of translocation of DNA movement through the nanopore.
Figure 12:
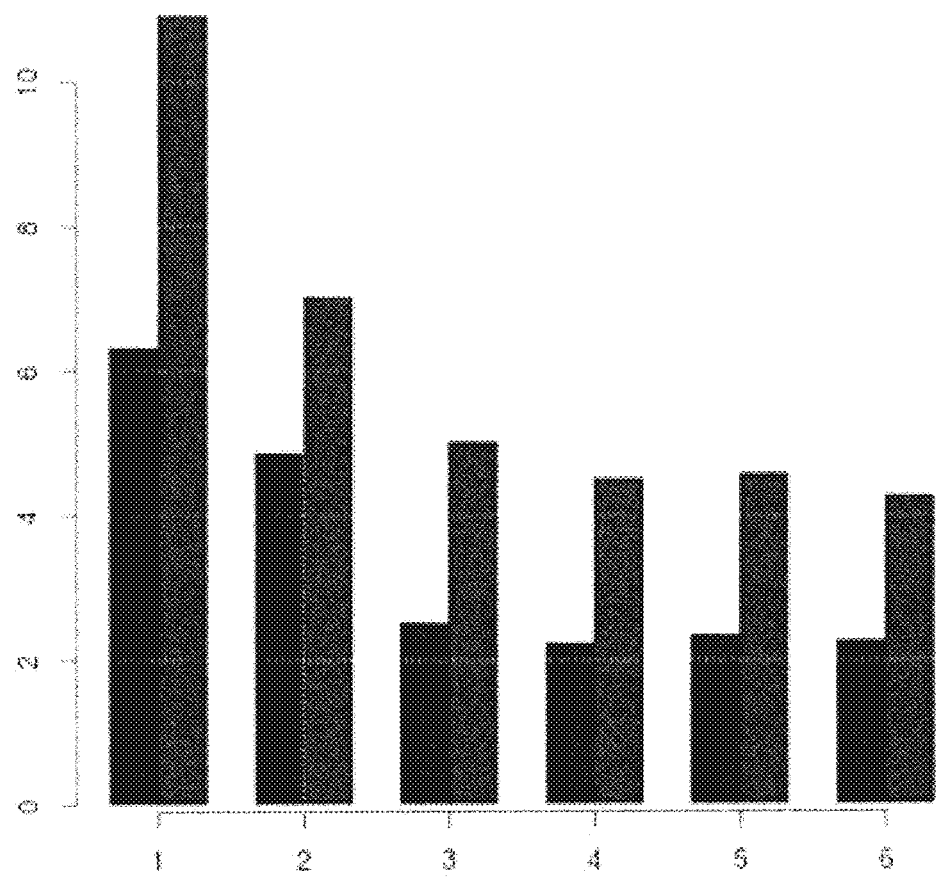
FIG. 12 shows how the helicase controlled DNA movement speed for the mutant T4 Dda-E94C/A360C/C114A/C171A/C421D varied during the course of a six hour five minute experimental run (y-axis label=events per second, x-axis label=time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of region 1 of the lambda DNA construct (shown in FIG. 8) passing through the nanopore. Events per second was used in the examples as a measure of the speed of translocation of DNA movement through the nanopore.
Figure 13:
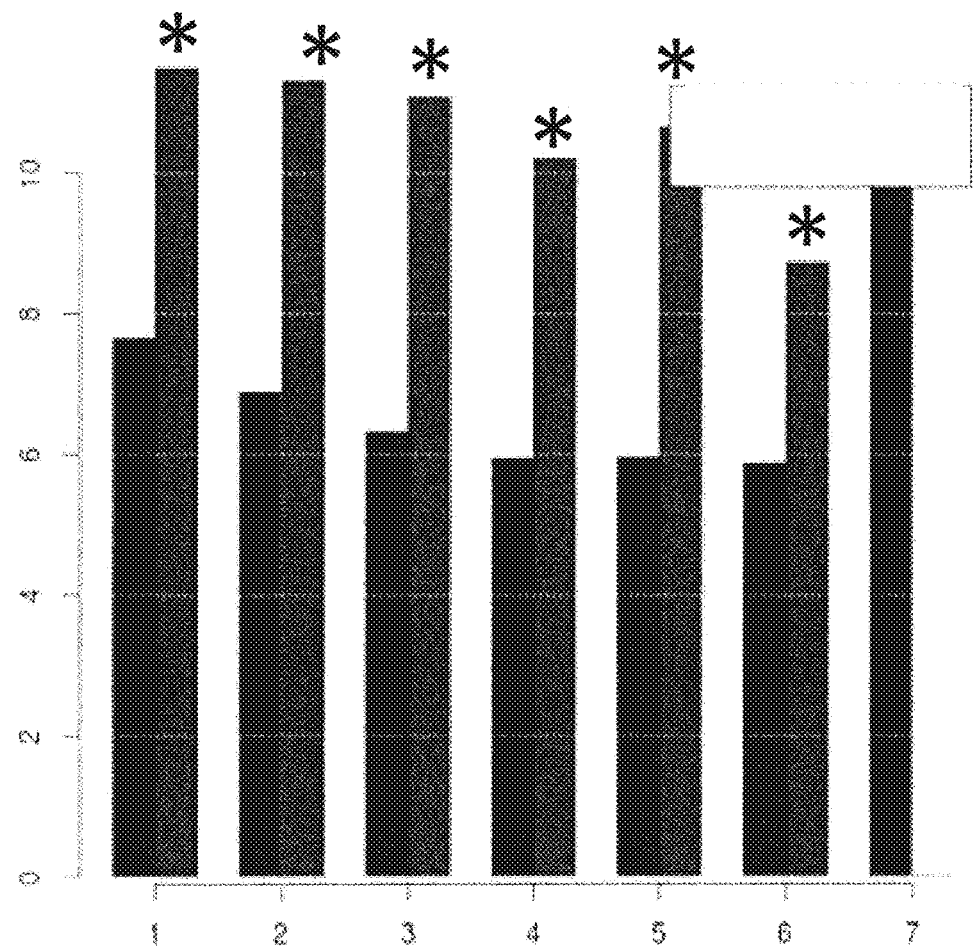
FIG. 13 shows how the helicase controlled DNA movement speed for the mutant T4 Dda-E94C/A360C/C109A/C136A varied during the course of a six hour five minute experimental run (y-axis label=events per second, x-axis label=time (hours)). The bars in the graph labelled with a star (*) corresponded to helicase controlled movement speed of region 2 of the lambda DNA construct (shown in FIG. 8) passing through the nanopore and those without a star corresponded to the helicase controlled movement speed of of region 1 of the lambda DNA construct (shown in FIG. 8) passing through the nanopore. Events per second was used in the examples as a measure of the speed of translocation of DNA movement through the nanopore.

The helicase controlled DNA movement speed was monitored through both region 1 and the region 2 of the lambda DNA construct X. For T4 Dda-E94C/A360C and T4 Dda-E94C/A360C/C114A/C171A/C421D the number of helicase controlled DNA movements per second was found to gradually decrease over the seven hour run time for both region 1 and 2 (See FIG. 11 for T4 Dda-E94C/A360C and FIG. 12 for T4 Dda-E94C/A360C/C114A/C171A/C421D). However, the T4 Dda-E94C/A360C/C109A/C136A mutant helicase observed only a slight decrease in the number of helicase controlled DNA movements per second over the 7 hour experimental run for both region 1 and region 2 (see FIG. 13). The T4 Dda-E94C/A360C/C109A/C136A mutant therefore showed improved helicase controlled DNA movement as the speed of movement remained high and fairly constant during the entire experimental run. This allowed increased throughput in comparison to the T4 Dda-E94C/A360C which exhibited a gradual reduction in speed over time.

Example 5

Figure 14:
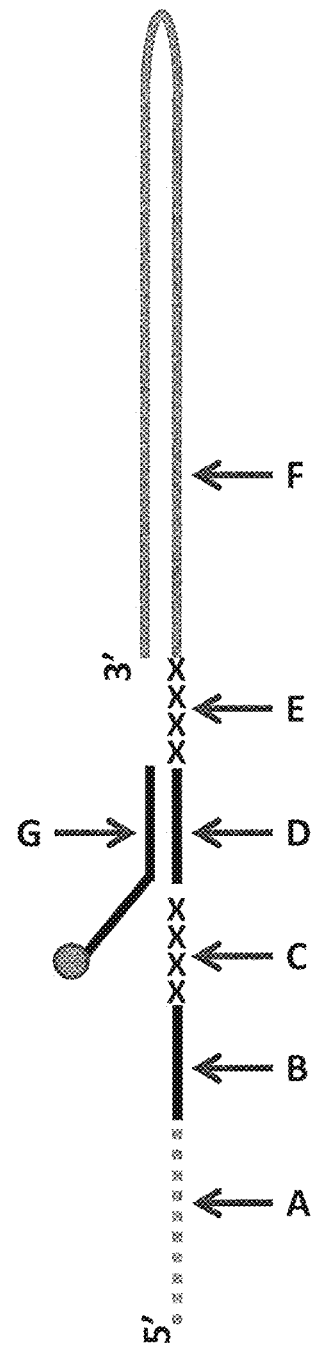
FIG. 14 shows a diagram of the DNA construct used in Example 5. Label A corresponds to 25iSpC3 spacers which are attached at its 3' end to SEQ ID NO: 70 (labelled B). Label B is attached at its 3' end to four iSp18 spacers (labelled C). The four iSp18 spacers are attached to the 5' end of SEQ ID NO: 61 (labelled D). SEQ ID NO: 61 is attached to four 5-nitroindoles (labelled E) which are attached to SEQ ID NO: 71 (labelled F) at its 5' end. SEQ ID NO: 61 is hybridised to SEQ ID NO: 63 (labelled•G). SEQ ID NO: 63 has six iSp18 spacers, two thymines and a 3' cholesterol TEG attached at its 3' end.

This example describes how a T4 Dda-E94C/C109A/C136A/A360C/W378A (SEQ ID NO: 8 with mutations E94C/C109A/C136A/A360C/W378A and then (ΔM1) G1G2) helicase can control the movement of intact DNA construct Z strands (shown in FIG. 14) through a single MspA nanopore.
Materials and Methods Prior to setting up the experiment, the DNA construct Z (see FIG. 8 for a diagram of the construct and sequences, 1.2 μL) and T4 Dda-E94C/C109A/C136A/A360C/W378A (2.84 μL) were pre-incubated together for 5 minutes at 23° C. in buffer (151 mM KCl, 25 mM potassium phosphate pH 8, 1 mM EDTA, 5% Glycerol). TMAD (500 μM, 0.92 μL) was added to the DNA enzyme mix and incubated at 23° C. for a further five minutes. Finally, buffer (282 μL of 500 mM KCl, 25 mM potassium phosphate pH 8), ATP (final concentration of 2 mM) and MgCL2 (final concentration 2 mM) were added to the mixture.

Electrical measurements were acquired as described in Example 1 using MspA nanopores inserted in block co-polymer in buffer (500 mM KCl, 25 mM potassium phosphate, pH 8). The pre-mix was added to the single nanopore experimental system and the experiment run at a holding potential of −120 mV for 6 hours (with potential flips to +60 mV for 2 seconds) and helicase-controlled DNA movement monitored.

Results and Discussion

Figure 15:
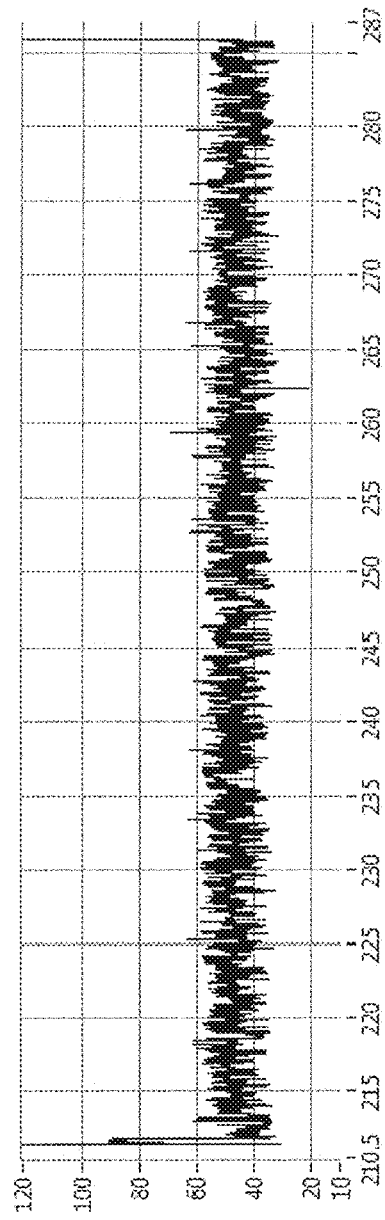
FIG. 15 shows an example current trace (y-axis label=Current (pA, 10 to 120), x-axis label=Time (s, 210.5 to 287)) of when a helicase (T4 Dda-E94C/C109A/C136A/A360C/W378A (SEQ ID NO: 8 with mutations E94C/C109A/C136A/A360C/W378A)) controlled the translocation of DNA construct Z (shown in FIG. 8) through an MspA nanopore.
Figure 16:
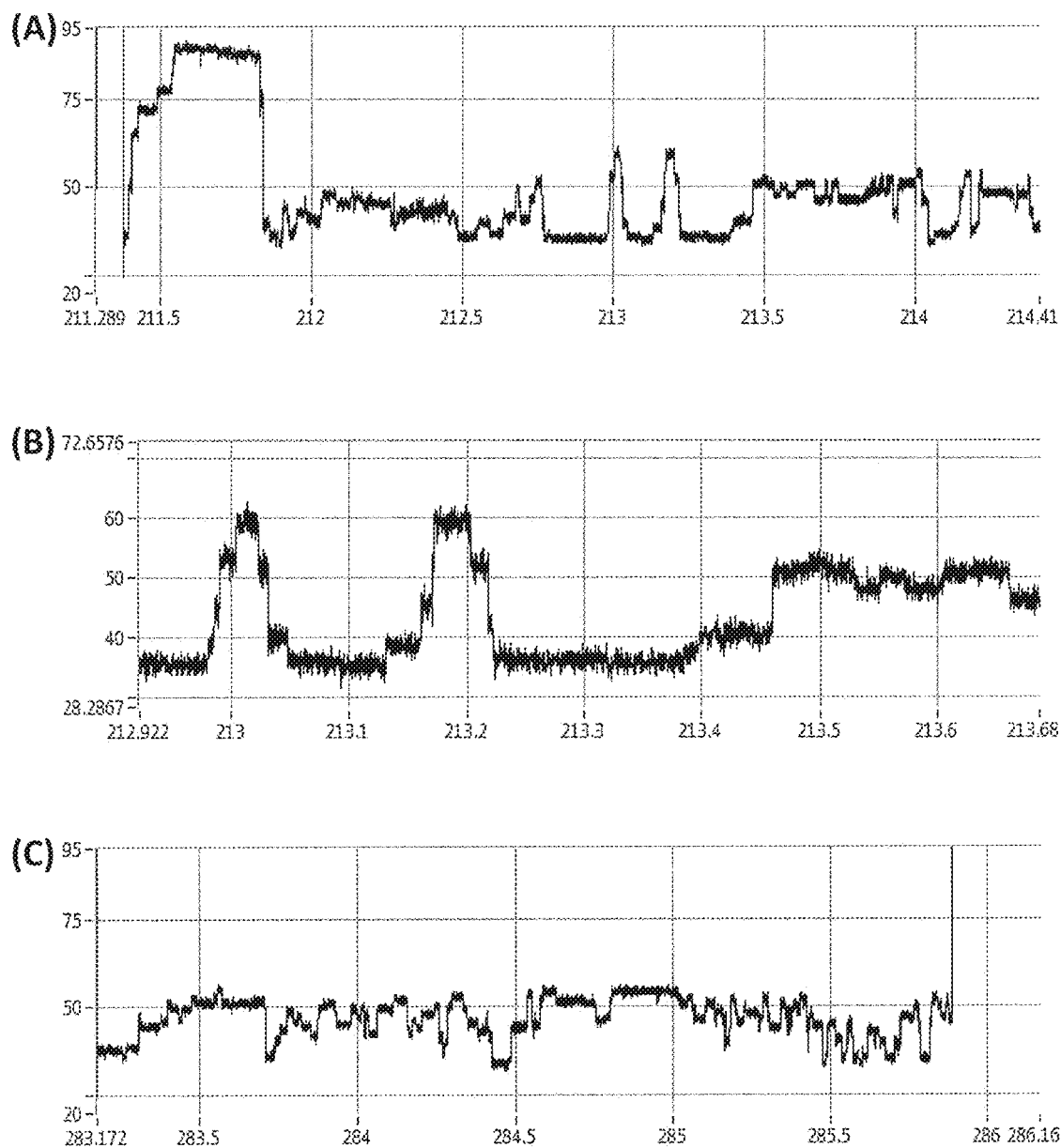
FIG. 16 shows zoomed in regions of the helicase-controlled DNA movement shown in the current trace in FIG. 15 (y-axis label=Current (pA, upper trace 20 to 95, middle trace 28.3 to 72.7 and lower trace 20 to 95), x-axis label=Time (s, upper trace 211.3 to 214.4, middle trace 212.9 to 213.7 and lower trace 283.2 to 286.2). A) shows the beginning of the helicase-controlled DNA movement B) shows a zoomed in region of trace A and C) shows the end of the helicase controlled DNA movement.

Helicase controlled DNA movement was observed for DNA construct Z, an example of a helicase-controlled DNA movement is shown in FIG. 15. FIG. 16 shows the beginning of the helicase-controlled DNA movement in trace (A), shows a zoomed in region of trace A in trace (B) and shows the end of the helicase controlled DNA movement in trace (C).

Example 6

This example compared the use of a single T4 Dda-E94C/A360C or Ta Dda-E94C/C109A/C136A/A360C to two T4 Dda-E94C/A360C (SEQ ID NO: 24 with mutations E94C/A360C) or two T4 Dda-E94C/C109A/C136A/A360C (SEQ ID NO: 24 with mutations E94C/C109A/C136A/A360C) helicases in order to control the movement of DNA construct X (shown in FIG. 17) through an MspA nanopore. When two helicases were used to control the movement of the construct through the nanopore then improved movement was observed in comparison to when the movement was controlled by a single helicase.

Materials and Methods

Prior to setting up the experiment, DNA construct X (see FIG. 17 for diagram and sequences used in construct X, final concentration added to the nanopore system 0.1 nM) was pre-incubated at room temperature for five minutes with T4 Dda-E94C/A360C (final concentration added to the nanopore system 1 nM, SEQ ID NO: 24 with mutations E94C/A360C) or T4 Dda-E94C/C109A/C136A/A360C (final concentration added to the nanopore system 1 nM, SEQ ID NO: 24 with mutations E94C/C109A/C136A/A360C, which was provided in buffer (253 mM KCl, 50 mM potassium phosphate, pH 8.0, 2 mM EDTA)). After five minutes, TMAD (1 µM final concentration added to the nanopore system) was added to the pre-mix and the mixture incubated for a further 5 minutes. Finally, MgCl2 (2 mM final premix concentration), ATP (2 mM final premix concentration) and buffer (25 mM potassium phosphate and 500 mM KCl pH 8.0) were added to the pre-mix.

Electrical measurements were acquired from single MspA nanopores inserted in block co-polymer in buffer (25 mM potassium phosphate, 150 mM potassium ferrocyanide (II), 150 mM potassium ferricyanide (III), pH 8.0). After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (T4 Dda-E94C/A360C or T4 Dda-E94C/C109A/C136A/A360C, 1 nM final concentration), DNA construct X (0.1 nM final concentration), fuel (MgCl2 2 mM final concentration, ATP 2 mM final concentration) pre-mix (300 µL total) was then flowed into the single nanopore experimental system and the experiment run at a holding potential of 120 mV for 6 hours and helicase-controlled DNA movement monitored.

Results

Helicase controlled DNA movement was observed for DNA construct X (FIG. 17) using T4 Dda-E94C/A360C and T4 Dda-E94C/C109A/C136A/A360C (see FIGS. 18A and 18B respectively). When a single enzyme was bound to DNA construct X (movement index shown in FIG. 18A), then helicase controlled DNA movement through the nanopore was observed for regions 3 and 4 (see FIG. 18). Region 3 moved through the pore in a controlled manner in which it was possible to observe a movement index (see FIG. 18's figure legend for description of movement index) for the region which was plotted in FIG. 18A. However, when region 4 translocated through the nanopore, the movement index plotted in FIG. 18A showed many less points than that produced for region 3. As region 3 and 4 were approximately the same length, the movement index observed for each region would have been expected to have had approximately the same number of points. This meant that the movement control of region 4 provided by a single enzyme (T4 Dda-E94C/A360C) resulted in less points and therefore less information was obtained for region 4 in comparison to region 3. Less information was obtained owing to the enzyme movement not being as consistent when region 4 was translocated through the nanopore (e.g. the DNA slipped forward along sections of region 4) that meant sections of DNA sequence were missed.

In this Example, the helicases move along the polynucleotide in a 5' to 3' direction. When the 5'end of the polynucleotide (the end away from which the helicases move) is captured by the pore, the helicases work with the direction of the field resulting from the applied potential and move the threaded polynucleotide into the pore and into the trans chamber. In this Example, slipping forward involves the DNA moving forwards relative to the the pore (i.e. towards its 3' and away from it 5' end in this Example) at least 4 consecutive nucleotides and typically more than 10 consecutive nucleotides. Slipping forward may involve movement forward of 100 consecutive nucleotides or more and this may happen more than once in each strand. This phenomenon was called skipping and slipping in UK Application Nos. 1406151.9.

FIG. 18B shows the movement index produced when the movement of DNA construct X (regions 3 and 4) was controlled using a "series" of enzymes, in this case two T4 Dda-E94C/A360C enzymes. The movement index of region 3 of DNA construct X was similar to that observed for the single enzyme. However, when region 4 translocated through the nanopore under the control of two enzymes then the DNA movement index was significantly different from that observed when a single T4 Dda-E94C/A360C helicase controlled the movement. A similar movement index was observed for region 4 as for region 3 when the movement was controlled using two T4 Dda-E94C/A360C enzymes, with both regions having approximately the same number of points. This illustrated that improved helicase-controlled DNA movement was observed when two T4 Dda-E94C/A360C enzymes in a "series" were used to control movement. This was because a similar amount of information was obtained for region 4 as region 3, whereas movement controlled using a single enzyme resulted in less information for region 4 than region 3. More information was obtained because the series of helicases resulted in more consistent movement of the DNA (e.g. slower movement or less slipping forward of the DNA region labelled 4). This meant that a series of T4 Dda-E94C/A360C enzymes could be used to improve sequencing of a strand of DNA.

The same experiment was carried out using the helicase T4 Dda-E94C/C109A/C136A/A360C to control the movement of DNA construct X through the nanopore. FIG. 19A shows the movement index for construct X when movement was controlled by a single T4 Dda-E94C/C109A/C136A/A360C enzyme and FIG. 19B shows the movement index when the movement was controlled by two T4 Dda-E94C/C109A/C136A/A360C helicases. As was observed for T4 Dda-E94C/A360C, a series of two T4 Dda-E94C/C109A/

C136A/A360C helicases resulted in more points being observed in the movement index when the movement of region 2 of the DNA was controlled by two enzymes, which indicated improved movement of this region (slower movement or less slipping forward). This meant that a series of T4 Dda-E94C/C109A/C136A/A360C enzymes could be used to improve sequencing of a strand of DNA.

Figure 17:
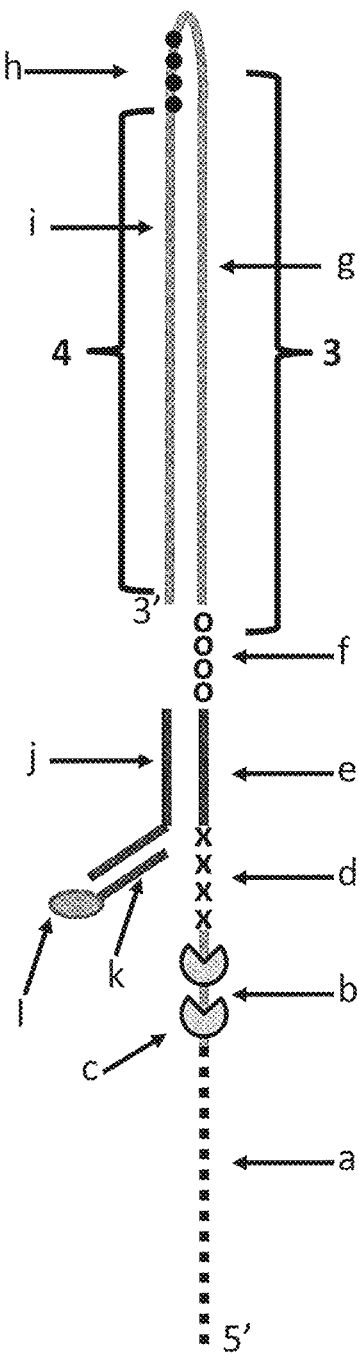
FIG. 17 shows DNA construct X which was used in Example 6. Section a of DNA construct X corresponds to 25 iSpC3 spacers, which are attached to the 5' end of SEQ ID NO: 70 (labelled b). Section b is the region of construct X to which the helicase enzymes T4 Dda-E94C/A360C or T4 Dda-E94C/C109A/C136A/A360C (depending on the experiment) bound (labelled c). The length of section b corresponded to the footprint (binding region) of two enzymes e.g. it was long enough to allow two enzymes to bind to this region. Section d corresponds to four iSp18 spacers. Section e corresponds to SEQ ID NO: 61. Section f corresponds to four 5'-nitroindoles. Section g corresponds to SEQ ID NO: 72 (this section of the strand was referred to as region 3 of DNA construct X). Section h (shown by black dots) corresponds to four iSpC3 spacers, which are attached to the 5' end of SEQ ID NO: 73 (labelled i which was referred to as region 4 of DNA construct X). Section j corresponds to SEQ ID NO: 74 and section k corresponds to SEQ ID NO: 75 which is attached to a 5' cholesterol TEG. It was possible to distinguish between regions 3 and 4 as they translocated through a nanopore as they produced different characteristics. Furthermore, the section h spacers (four iSpC3 spacers) produced a current spike in the current trace which aided identification of the transition from region 3 to region 4.

DNA construct X, shown and described in FIG. 17, has a section labelled b onto which two enzymes could bind. Control experiments where the length of section b was only sufficient to allow one enzyme to bind (10-12 T binding sites) were carried out for both T4 Dda-E94C/106 A360C and T4 Dda-E94C/C109A/C136A/A360C. In the control experiments, when region 4 translocated through the nanopore no strands with improved movement were detected when only a single enzyme bound to the construct and controlled the movement of the strand through the nanopore. In comparison, in the experiments above where two enzymes could have bound to the DNA, although we observed some strands with poor movement because only a single enzyme bound, it was also possible to identify strands with improved movement indexes which corresponded to DNA translocation controlled by two enzymes, rather than just one.

Example 7

Figure 20:
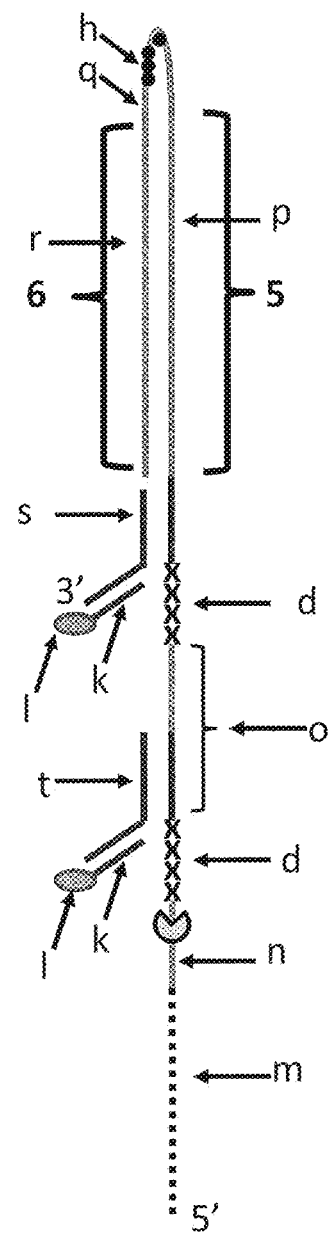
FIG. 20 shows DNA construct Z which was used in Example 7 and 8. Section m of DNA construct Z corresponds to 40 iSpC3 spacers, which are attached to the 5' end of SEQ ID NO: 76 (labelled n). Section n is a region of construct Z to which the helicase enzyme T4 Dda-E94C/C109A/C136A/A360C or T4 Dda-E94C/C109A/C136A/A360C/W378A bound. The length of section n corresponded to the footprint (binding region) of one enzyme e.g. it was long enough to allow one enzyme to bind to this region. The sections labelled d correspond to four iSp18 spacers. Section o corresponds to SEQ ID NO: 77, part of this section was a region of construct Z to which the helicase enzyme T4 Dda-E94C/C109A/C136A/A360C/W378A bound. Section p corresponds to SEQ ID NO: 78 (part of this section of the strand was referred to as region 5 of DNA construct Z). Section h (shown by black dots) corresponds to four iSpC3 spacers, which are attached to the 5' end of SEQ ID NO: 79 (labelled q). Section r corresponds to the complementary sequence of SEQ ID NO: 78 (labelled r, which was referred to as region 6 of DNA construct Z). Section s corresponds to SEQ ID NO: 74. Section k corresponds to SEQ ID NO: 75 which is attached to a 5' cholesterol TEG (labelled l). Section t corresponds to SEQ ID NO: 80. It was possible to distinguish between regions 5 and 6 as they translocated through a nanopore as they produced different characteristics. Furthermore, the section h spacers (four iSpC3 spacers) produced a current spike in the current trace which aided identification of the transition from region 5 to region 6.

This example compared the use of a single T4 Dda-E94C/C109A/C136A/A360C or both T4 Dda-E94C/C109A/C136A/A360C and T4 Dda-E94C/C109A/C136A/A360C/W378A (SEQ ID NO: 24 with mutations E94C/C109A/C136A/A360C/W378A) in order to control the movement of DNA construct Z (shown in FIG. 20) through an MspA nanopore. T4 Dda-E94C/C109A/C136A/A360C and T4 Dda-E94C/C109A/C136A/A360C/W378A are both active helicases which moved along the DNA when provided with appropriate fuel. When these two different helicases were used to control the movement of the construct through the nanopore then improved movement was observed in comparison to when the movement was controlled by a single helicase (T4 Dda-E94C/C109A/C136A/A360C).

Materials and Methods

The DNA construct Z (final concentration added to the nanopore system 0.1 nM) which either had both enzymes pre-bound (see FIG. 21B data) or only T4 Dda-E94C/C109A/C136A/A360C pre-bound (control experiment, see FIG. 21A data) was added to buffer (final concentrations added to the nanopore system were 500 mM KCl, 25 mM potassium phosphate pH 8.0), ATP (final concentration added to the nanopore system 2 mM) and MgCL2 (final concentration added to the nanopore system 2 mM). This was the pre-mix which was then added to the nanopore system (total volume 150 μL).

Electrical measurements were acquired from single MspA nanopores inserted in block co-polymer in buffer (25 mM potassium phosphate, 75 mM potassium ferrocyanide 25 mM potassium ferricyanide (III), 600 mM KCl, pH 8.0). After achieving a single pore inserted in the block co-polymer, then buffer (2 mL, 25 mM potassium phosphate, 75 mM potassium ferrocyanide (II), 25 mM potassium ferricyanide (III), 600 mM KCl, pH 8.0) was flowed through the system to remove any excess MspA nanopores. The enzyme pre-bound to construct Z (either a single T4 Dda-E94C/C109A/C136A/A360C (control) or T4 Dda-E94C/C109A/C136A/A360C and T4 Dda-E94C/C109A/C136A/A360C/W378A), fuel (MgCl2 and ATP) pre-mix (150 μL total) was then flowed into the single nanopore experimental system and the experiment run at a holding potential of −120 mV for 6 hours (with potential flips to +60 mV for 2 seconds) and helicase-controlled DNA movement monitored.

Results

Helicase controlled DNA movements corresponding to controlled translocation by T4 Dda-E94C/C109A/C136A/A360C only (control experiment, FIG. 21A) or both T4 Dda-E94C/C109A/C136A/A360C and T4 Dda-E94C/C109A/C136A/A360C/W378A (FIG. 22B) were observed. The trace shown in FIG. 21 section A showed an example movement index plot when only the helicase T4 Dda-E94C/C109A/C136A/A360C controlled the translocation of DNA construct Z (see FIG. 20) through an MspA nanopore. When region 5 translocated through the nanopore, it was possible to observe the movement index for region 5. However, this figure showed that the movement index for region 6 had less points than for region 5 which indicated that less information was obtained for this region of DNA construct Y when it translocated through the nanopore. This resulted in DNA movement that was less consistent (e.g. more slipping forward of the DNA region labelled 6) and sections of DNA sequence were missed.

FIG. 21B shows the movement index when T4 Dda-E94C/C109A/C136A/A360C and T4 Dda-E94C/C109A/C136A/A360C/W378A controlled the translocation of DNA construct Z (see FIG. 20) through an MspA nanopore. When region 5 translocated through the nanopore under the control of T4 Dda-E94C/C109A/C136A/A360C and T4 Dda-E94C/C109A/C136A/A360C/W378A, it was possible to observe a movement index. Moreover, when region 6 translocated through the nanopore, the movement was again controlled by both T4 Dda-E94C/C109A/C136A/A360C and T4 Dda-E94C/C109A/C136A/A360C/W378A. When region 6 translocated through the nanopore under the control of the two enzymes (T4 Dda-E94C/C109A/C136A/A360C and T4 Dda-E94C/C109A/C136A/A360C/W378A) then the DNA movement was significantly different from that observed when a single T4 Dda-E94C/C109A/C136A/A360C helicase controlled the movement of this region (see FIG. 21A section 6). This figure showed that the movement index for region 6, when the helicase movement was controlled using T4 Dda-E94C/C109A/C136A/A360C and T4 Dda-E94C/C109A/C136A/A360C/W378A, had many more points than for region 6 when the helicase movement was controlled by the single enzyme T4 Dda-E94C/C109A/C136A/A360C which indicated that more information was obtained for this region of DNA construct Z when it translocated through the nanopore under the control of two different enzymes and that the DNA movement was more consistent (e.g. slower movement or less slipping forward of the DNA region labelled 6). This meant that the combination of T4 Dda-E94C/C109A/C136A/A360C and T4 Dda-E94C/C109A/C136A/A360C/W378A enzymes were used to improve sequencing of a strand of DNA.

Example 8

This example compared the use of either a single T4 Dda-E94C/C109A/C136A/A360C/W378A or two T4 Dda-E94C/C109A/C136A/A360C/W378A helicases (SEQ ID NO: 24 with mutations E94C/C109A/C136A/A360C/W378A) in order to control the movement of DNA construct Z (shown in FIG. 20) through an MspA nanopore. T4 Dda-E94C/C109A/C136A/A360C/W378A is an active helicase which moved along the DNA when provided with appropriate fuel. When two helicases (T4 Dda-E94C/C109A/C136A/A360C/W378A) were used to control the movement of the construct through the nanopore then improved movement was observed in comparison to when the movement was controlled by a single helicase (T4 Dda-E94C/C109A/C136AJA360C/W378A).

Materials and Methods

The DNA construct Z (final concentration added to the nanopore system 0.1 nM) which either had two T4 Dda-E94C/C109A/C136A/A360C/W378A helicases pre-bound (see FIG. 21B data) or a single T4 Dda-E94C/C109A/C136A/A360C/W378A pre-bound (control experiment, see FIG. 21A data) was added to buffer (final concentrations added to the nanopore system were 500 mM KCl, 25 mM potassium phosphate pH 8.0), ATP (final concentration added to the nanopore system 2 mM) and MgCL2 (final concentration added to the nanopore system 2 mM). This was the pre-mix which was then added to the nanopore system (total volume 150 µL).

Electrical measurements were acquired from single MspA nanopores as described in Example 7 above, except either the DNA construct Z with a single T4 Dda-E94C/C109A/C136A/A360C/W378A pre-bound (as a control experiment) or two T4 Dda-E94C/C109A/C136A/A360C/W378A helicases pre-bound were added to the nanopore system.

Results

Helicase controlled DNA movements corresponding to controlled translocation by T4 Dda-E94C/C109A/C136A/A360C/W378A only (control experiment, FIG. 22A) or two T4 Dda-E94C/C109A/C136A/A360C/W378A helicases (FIG. 22B) were observed. The trace shown in FIG. 22 section A showed an example movement index plot when only a single helicase T4 Dda-E94C/C109A/C136A/A360C/W378A controlled the translocation of DNA construct Z (see FIG. 20) through an MspA nanopore. When region 5 translocated through the nanopore, it was possible to observe the movement index for region 5. However, this figure showed that the movement index for region 6 had less points than for region 5 which indicated that less information was obtained for this region of DNA construct Z when it translocated through the nanopore. This resulted in DNA movement that was less consistent (e.g. more slipping forward of the DNA region labelled 6) and sections of DNA sequence were missed.

FIG. 22B shows the movement index when two T4 Dda-E94C/C109A/C136A/A360C/W378A helicases controlled the translocation of DNA construct Z (see FIG. 20) through an MspA nanopore. When region 5 translocated through the nanopore under the control of two T4 Dda-E94C/C109A/C136A/A360C/W378A helicases, it was possible to observe a movement index. Moreover, when region 6 translocated through the nanopore, the movement was again controlled by twoT4 Dda-E94C/C109A/C136A/A360C/W378A helicases. When region 6 translocated through the nanopore under the control of the two enzymes (two T4 Dda-E94C/C109A/C136A/A360C/W378A helicases) then the DNA movement was significantly different from that observed when a single T4 Dda-E94C/C109A/C136A/A360C/W378A helicase controlled the movement of region 6 (see FIG. 22A section 6). This figure showed that the movement index for region 6, when the helicase movement was controlled using two T4 Dda E94C/C109A/C136A/A360C/W378A helicases, had many more points than when the helicase movement was controlled by the single enzyme T4 Dda-E94C/C109A/C136A/A360C/W378A which indicated that more information was obtained for this region of DNA construct Z when it translocated through the nanopore under the control of two enzymes than was observed for the region 6 of construct Z under the control of a single T4 Dda-E94C/C109A/C136A/A360C/W378A helicase. Furthermore, the DNA movement which was observed when DNA translocation was controlled by two T4 Dda-E94C/C109A/C136A/A360C/W378A helicases was also more consistent (e.g. slower movement or less slipping forward of the DNA region labelled 8). This meant that the use of two T4 Dda-E94C/C109A/C136A/A360C/W378A enzymes resulted in improved sequencing of a strand of DNA.

SEQUENCE LISTING

```
<160> NUMBER OF SEQ ID NOS: 80

<210> SEQ ID NO 1
<211> LENGTH: 558
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 1
atgggtctgg ataatgaact gagcctggtg gacggtcaag atcgtaccct gacggtgcaa      60
caatgggata ccttttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
```

```
ccgtggaata tgaactaa                                                  558
```

```
<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 2
```

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

```
<210> SEQ ID NO 3
<211> LENGTH: 885
<212> TYPE: DNA
<213> ORGANISM: Artificial Sequence
<220> FEATURE:
<223> OTHER INFORMATION: alpha-hemolysin mutant E111N/K147N

<400> SEQUENCE: 3
```

```
atggcagatt ctgatattaa tattaaaacc ggtactacag atattggaag caatactaca   60
gtaaaaacag gtgatttagt cacttatgat aaagaaaatg gcatgcacaa aaaagtattt  120
tatagtttta tcgatgataa aaatcacaat aaaaaactgc tagttattag aacaaaaggt  180
accattgctg tcaatatag agtttatagc gaagaaggtg ctaacaaaag tggtttagcc   240
tggcccttcag cctttaaggt acagttgcaa ctacctgata tgaagtagc tcaaatatct  300
gattactatc caagaaattc gattgataca aaaaactata tgagtacttt aacttatgga  360
ttcaacggta atgttactgg tgatgataca ggaaaaattg gcggcctta tggtgcaaat  420
gtttcgattg gtcatacact gaactatgtt caacctgatt tcaaaacaat tttagagagc  480
ccaactgata aaaagtagg ctggaaagtg atatttaaca atatggtgaa tcaaaattgg  540
ggaccatacg atcgagattc ttggaacccg gtatatggca atcaactttt catgaaaact  600
```

```
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial Sequence
<220> FEATURE:
<223> OTHER INFORMATION: alpha-hemolysin mutant E111N/K147N

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5

```
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160
```

-continued

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 439
<212> TYPE: PRT
<213> ORGANISM: Enterobacteria phage T4

<400> SEQUENCE: 8

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435

<210> SEQ ID NO 9
<211> LENGTH: 678
<212> TYPE: PRT
<213> ORGANISM: Rhodothermus marinus

<400> SEQUENCE: 9

Met Glu Glu Leu Ser Asn Glu Gln Gln Arg Val Leu Asp His Val Leu
1               5                   10                  15

Ala Trp Leu Glu Arg Asn Asp Ala Pro Pro Ile Phe Ile Leu Thr Gly
            20                  25                  30

Ser Ala Gly Thr Gly Lys Thr Leu Leu Ile Arg His Leu Val Arg Ala

```
                35                  40                  45
Leu Gln Asp Arg Arg Ile His Tyr Ala Leu Ala Ala Pro Thr Gly Arg
 50                  55                  60
Ala Ala Arg Ile Leu Ser Glu Arg Thr Gly Asp His Ala Arg Thr Leu
 65                  70                  75                  80
His Ser Leu Ile Tyr Ile Phe Asp Arg Tyr Gln Leu Val Glu Glu Ala
                 85                  90                  95
Asp Arg Gln Thr Asp Glu Pro Leu Ser Leu Gln Leu His Phe Ala Leu
                100                 105                 110
Arg Ser Ala Glu His Asp Ala Arg Leu Ile Ile Val Asp Glu Ala Ser
                115                 120                 125
Met Val Ser Asp Thr Ala Gly Glu Glu Leu Tyr Arg Phe Gly Ser
                130                 135                 140
Gly Arg Leu Leu Asn Asp Leu Leu Thr Phe Ala Arg Leu Ile Pro Lys
145                 150                 155                 160
Arg Asp Arg Pro Pro Thr Thr Arg Leu Leu Phe Val Gly Asp Pro Ala
                165                 170                 175
Gln Leu Pro Pro Val Gly Gln Ser Val Ser Pro Ala Leu Ser Ala Gln
                180                 185                 190
Tyr Leu Arg Asp Thr Phe Gly Leu Ser Ala Glu Thr Ala His Leu Arg
                195                 200                 205
Ser Val Tyr Arg Gln Arg Lys Gly His Pro Ile Leu Glu Thr Ala Thr
210                 215                 220
Ala Leu Arg Asn Ala Leu Glu Lys Gly His Tyr His Thr Phe Arg Leu
225                 230                 235                 240
Pro Glu Gln Pro Pro Asp Leu Arg Pro Val Gly Leu Glu Glu Ala Ile
                245                 250                 255
Glu Thr Thr Ala Thr Asp Phe Arg Arg Gln Asn Pro Ser Val Leu Leu
                260                 265                 270
Cys Arg Thr Asn Ala Leu Ala Arg Lys Leu Asn Ala Ala Val Arg Ala
                275                 280                 285
Arg Leu Trp Gly Arg Glu Gly Leu Pro Pro Gln Pro Gly Asp Leu Leu
290                 295                 300
Leu Val Asn Arg Asn Ala Pro Leu His Gly Leu Phe Asn Gly Asp Leu
305                 310                 315                 320
Val Leu Val Glu Thr Val Gly Pro Leu Glu His Arg Arg Val Gly Arg
                325                 330                 335
Arg Gly Arg Pro Pro Val Asp Leu Tyr Phe Arg Asp Val Glu Leu Leu
                340                 345                 350
Tyr Pro His Glu Lys Pro Arg Asn Arg Ile Arg Cys Lys Leu Leu Glu
                355                 360                 365
Asn Leu Leu Glu Ser Pro Asp Gly Gln Leu Ser Pro Asp Ile Ile Gln
                370                 375                 380
Ala Leu Leu Ile Asp Phe Tyr Arg Arg His Pro Ser Leu Lys His Gly
385                 390                 395                 400
Ser Ser Glu Phe Arg Leu Met Leu Ala Asn Asp Ala Tyr Phe Asn Ala
                405                 410                 415
Leu His Val Arg Tyr Gly Tyr Ala Met Thr Val His Lys Ala Gln Gly
                420                 425                 430
Gly Glu Trp Lys Arg Ala Thr Val Val Phe Asn Asp Trp Arg His Phe
                435                 440                 445
Arg His Ala Glu Phe Phe Arg Trp Ala Tyr Thr Ala Ile Thr Arg Ala
                450                 455                 460
```

Arg Glu Glu Leu Leu Thr Ile Gly Ala Pro Ser Phe Glu Ala Leu Ser
465                 470                 475                 480

Asp Met Arg Trp Gln Pro Ala Pro Ser Val Pro Ala Pro Glu Gln Ala
                485                 490                 495

Ala Glu Asn Ala Thr Arg Phe Pro Leu Lys Ala Leu Thr Tyr His
                500                 505                 510

Gln Arg Leu Ser Glu Ala Leu Thr Ala Ala Gly Ile Glu Thr Thr Gly
            515                 520                 525

Val Glu Leu Leu Gln Tyr Ala Val Arg Tyr His Leu Ala Arg Ala Asp
        530                 535                 540

Arg Thr Thr Arg Ile Gln Tyr Tyr Tyr Arg Gly Asp Gly Gln Ile Ser
545                 550                 555                 560

Arg Ile Val Thr Leu Gly Gly Ala Asp Asp Pro Glu Leu Thr Gln Gln
                565                 570                 575

Ala Tyr Ala Leu Phe Glu Arg Ile Leu Ser Glu Pro Pro Ala Asp Ser
                580                 585                 590

Gly Glu Leu Pro Glu Asn Pro Leu Leu Arg Glu Phe Leu Glu Arg Ala
            595                 600                 605

His Leu Arg Leu Glu Gly Ser Gly Ile Arg Ile Val His Trp Lys Glu
    610                 615                 620

Met Pro Tyr Ala Leu Arg Leu Tyr Phe Ser Ala Asp Gly Glu Asn Val
625                 630                 635                 640

Thr Ile Asp Phe Tyr Tyr Asn Arg Arg Gly Val Trp Thr His Ala Gln
                645                 650                 655

Glu Val Gly Arg Ser Ser Ser Gly Ala Leu Phe Ala Arg Ile Gln Ser
                660                 665                 670

Leu Leu Gln Ala Asp Ser
            675

<210> SEQ ID NO 10
<211> LENGTH: 496
<212> TYPE: PRT
<213> ORGANISM: Cyanothece ATCC51142

<400> SEQUENCE: 10

Met Ser Gln Ser Val Val Pro Asp Glu Leu Gly Glu Ile Ile Thr
1               5                   10                  15

Ala Val Ile Glu Phe Tyr Gln Asp Ala Val Asp Lys Ile Glu Pro Lys
                20                  25                  30

Ile Val Phe Leu Glu Leu Arg Lys Asn Val Val Asp Trp Val Ser Arg
            35                  40                  45

Thr Gln Leu Lys Ile Glu Glu Lys Glu Ile Gln Ala Thr Gly Leu Thr
    50                  55                  60

Arg Gln Gln Gln Thr Ala Tyr Lys Glu Met Ile Asn Phe Ile Glu Asn
65                  70                  75                  80

Ser Ser Glu Gln Tyr Phe Arg Leu Ser Gly Tyr Ala Gly Thr Gly Lys
                85                  90                  95

Ser Phe Leu Met Ala Lys Val Ile Glu Trp Leu Lys Gln Glu Asp Tyr
                100                 105                 110

Lys Tyr Ser Val Ala Ala Pro Thr Asn Lys Ala Ala Lys Asn Leu Thr
            115                 120                 125

Gln Ile Ala Arg Ser Gln Gly Ile Lys Ile Glu Ala Thr Thr Val Ala
    130                 135                 140

Lys Leu Leu Lys Leu Gln Pro Thr Ile Asp Val Asp Thr Gly Gln Gln

-continued

Ser Phe Glu Phe Asn Ser Glu Lys Glu Leu Glu Leu Lys Asp Tyr Asp
145                 150                 155                 160

Val Ile Ile Ile Asp Glu Tyr Ser Met Leu Asn Lys Asp Asn Phe Arg
            165                 170                 175

Asp Leu Gln Gln Ala Val Lys Gly Gly Glu Ser Lys Phe Ile Phe Val
                180                 185                 190

Gly Asp Ser Ser Gln Leu Pro Pro Val Lys Lys Glu Pro Ile Val
        195                 200                 205

Ala Asn His Pro Asp Ile Arg Lys Ser Ala Asn Leu Thr Gln Ile Val
210                 215                 220

Arg Tyr Asp Gly Glu Ile Val Lys Val Ala Glu Ser Ile Arg Arg Asn
225                 230                 235                 240

Pro Arg Trp Asn His Gln Thr Tyr Pro Phe Glu Thr Val Ala Asp Gly
                245                 250                 255

Thr Ile Ile Lys Leu Asn Thr Glu Asp Trp Leu Gln Gln Ala Leu Ser
            260                 265                 270

His Phe Glu Lys Glu Asp Trp Leu Ser Asn Pro Asp Tyr Val Arg Met
        275                 280                 285

Ile Thr Trp Arg Asn Lys Thr Ala Asp Lys Tyr Asn Gln Ala Ile Arg
290                 295                 300

Glu Ala Leu Tyr Gly Glu Asn Val Glu Gln Leu Val Val Gly Asp Arg
305                 310                 315                 320

Leu Ile Ala Lys Lys Pro Val Phe Arg Ser Leu Pro Gly Gly Lys Lys
                325                 330                 335

Lys Glu Lys Lys Ile Ile Leu Asn Asn Ser Glu Glu Cys Lys Val Ile
            340                 345                 350

Glu Thr Pro Lys Ile Asn Tyr Asn Glu Lys Tyr Lys Trp Glu Phe Tyr
        355                 360                 365

Gln Val Lys Val Arg Thr Asp Glu Gly Gly Met Ile Glu Leu Arg Ile
370                 375                 380

Leu Thr Ser Glu Ser Glu Glu Lys Arg Gln Lys Lys Leu Lys Glu Leu
385                 390                 395                 400

Ala Lys Arg Ala Arg Glu Glu Glu Asn Tyr Ser Glu Lys Lys Lys Gln
                405                 410                 415

Trp Ala Ile Tyr Tyr Glu Leu Asp Glu Leu Phe Asp Asn Met Ala Tyr
            420                 425                 430

Ala Tyr Ala Leu Thr Cys His Lys Ala Gln Gly Ser Ser Ile Asp Asn
        435                 440                 445

Val Phe Leu Leu Val Ser Asp Met His Tyr Cys Arg Asp Lys Thr Lys
465                 470                 475                 480

Met Ile Tyr Thr Gly Leu Thr Arg Ala Lys Lys Cys Cys Tyr Val Gly
                485                 490                 495

<210> SEQ ID NO 11
<211> LENGTH: 421
<212> TYPE: PRT
<213> ORGANISM: Salinibacter ruber

<400> SEQUENCE: 11

Met Ser Thr Phe Ala Asp Ala Pro Phe Thr Glu Asp Gln Glu Glu Ala
1               5                   10                  15

Tyr Asp His Val Tyr Asp Arg Leu Ala Gln Gly Glu Arg Phe Thr Gly
            20                  25                  30

-continued

```
Leu Arg Gly Tyr Ala Gly Thr Gly Lys Thr Tyr Leu Val Ser Arg Leu
             35                  40                  45

Val Glu Gln Leu Leu Asp Glu Asp Cys Thr Val Thr Val Cys Ala Pro
 50                  55                  60

Thr His Lys Ala Val Gln Val Leu Ser Asp Glu Leu Gly Asp Ala Pro
 65                  70                  75                  80

Val Gln Met Gln Thr Leu His Ser Phe Leu Gly Leu Arg Leu Gln Pro
                 85                  90                  95

Lys Gln Asp Gly Glu Tyr Glu Leu Val Ala Glu Glu Arg Asn Phe
            100                 105                 110

Ala Glu Gly Val Val Ile Val Asp Glu Ala Ser Met Ile Gly Arg Glu
            115                 120                 125

Glu Trp Ser His Ile Gln Asp Ala Pro Phe Trp Val Gln Trp Leu Phe
        130                 135                 140

Val Gly Asp Pro Ala Gln Leu Pro Pro Val Asn Glu Asp Pro Ser Pro
145                 150                 155                 160

Ala Leu Asp Val Pro Gly Pro Thr Leu Glu Thr Ile His Arg Gln Ala
                165                 170                 175

Ala Asp Asn Pro Ile Leu Glu Leu Ala Thr Lys Ile Arg Thr Gly Ala
            180                 185                 190

Asp Gly Arg Phe Gly Ser Thr Phe Glu Asp Gly Lys Gly Val Ala Val
        195                 200                 205

Thr Arg Asn Arg Glu Glu Phe Leu Asp Ser Ile Leu Arg Ala Phe Asp
210                 215                 220

Ala Asp Ala Phe Ala Glu Asp Ala Thr His Ala Arg Val Leu Ala Tyr
225                 230                 235                 240

Arg Asn Lys Thr Val Arg Arg Tyr Asn Arg Glu Ile Arg Ala Glu Arg
                245                 250                 255

Tyr Gly Ala Asp Ala Asp Arg Phe Val Glu Gly Glu Trp Leu Val Gly
            260                 265                 270

Thr Glu Thr Trp Tyr Tyr Asp Gly Val Gln Arg Leu Thr Asn Ser Glu
        275                 280                 285

Glu Val Arg Val Lys Lys Ala Gln Val Glu Thr Phe Glu Ala Asp Asp
290                 295                 300

Gln Ser Glu Trp Thr Val Trp Glu Leu Lys Ile Arg Thr Pro Gly Arg
305                 310                 315                 320

Gly Leu Thr Arg Thr Ile His Val Leu His Glu Glu Arg Glu Arg
                325                 330                 335

Tyr Glu Asn Ala Leu Glu Arg Arg Gly Lys Ala Glu Asp Asp Pro
            340                 345                 350

Ser Lys Trp Asp Arg Phe Phe Glu Leu Arg Glu Arg Phe Ala Arg Val
355                 360                 365

Asp Tyr Ala Tyr Ala Thr Thr Val His Arg Ala Gln Gly Ser Thr Tyr
370                 375                 380

Asp Thr Val Phe Val Asp His Arg Asp Leu Arg Val Cys Arg Gly Glu
385                 390                 395                 400

Glu Arg Gly Ala Leu Leu Tyr Val Ala Val Thr Arg Pro Ser Arg Arg
                405                 410                 415

Leu Ala Leu Leu Val
            420

<210> SEQ ID NO 12
<211> LENGTH: 500
<212> TYPE: PRT
```

<213> ORGANISM: Sulfurimonas gotlandica GD1

<400> SEQUENCE: 12

Met Lys Ile Leu Asn Lys Glu Thr Tyr Lys Leu Ser Leu His Gln Glu
1               5                   10                  15

Glu Val Phe Thr Gln Ile Val Ser Gln Leu Asp Thr Lys Val Ser Ser
            20                  25                  30

Ile Leu Lys Ser Thr Asn Ile Glu Asp Tyr Leu Leu Ser Leu Thr Gly
        35                  40                  45

Pro Ala Gly Thr Gly Lys Thr Phe Leu Thr Thr Gln Ile Ala Lys Tyr
    50                  55                  60

Leu Val Glu Lys Arg Lys Glu Ser Glu Tyr Pro Met Ser Ser Asp Phe
65                  70                  75                  80

Asp Phe Thr Ile Thr Ala Pro Thr His Lys Ala Val Gly Val Leu Ser
                85                  90                  95

Lys Leu Leu Arg Glu Asn Asn Ile Gln Ser Ser Cys Lys Thr Ile His
            100                 105                 110

Ser Phe Leu Gly Ile Lys Pro Phe Ile Asp Tyr Thr Thr Gly Glu Glu
        115                 120                 125

Lys Phe Val Val Asp Lys Thr Asn Lys Arg Lys Asp Arg Thr Ser Ile
130                 135                 140

Leu Ile Val Asp Glu Ser Ser Met Ile Gly Asn Thr Leu Tyr Glu Tyr
145                 150                 155                 160

Ile Leu Glu Ala Ile Glu Asp Lys Arg Val Asn Val Val Leu Phe Ile
                165                 170                 175

Gly Asp Pro Tyr Gln Leu Leu Pro Ile Glu Asn Ser Lys Asn Glu Ile
            180                 185                 190

Tyr Asp Leu Pro Asn Arg Phe Phe Leu Ser Glu Val Val Arg Gln Ala
        195                 200                 205

Glu Asn Ser Tyr Ile Ile Arg Val Ala Thr Lys Leu Arg Glu Arg Ile
210                 215                 220

Lys Asn Gln Asp Phe Ile Ser Leu Gln Gln Phe Phe Gln Glu Asn Met
225                 230                 235                 240

Glu Asp Glu Ile Thr Phe Phe His Asn Lys Glu Ala Phe Leu Glu Asp
                245                 250                 255

Phe Tyr Lys Glu Glu Glu Trp Tyr Lys Glu Asn Lys Ile Leu Ala Thr
            260                 265                 270

Tyr Lys Asn Lys Asp Val Asp Ala Phe Asn Lys Ile Ile Arg Asn Lys
        275                 280                 285

Phe Trp Glu Gln Lys Gly Asn Thr Thr Pro Ser Thr Leu Leu Ala Gly
290                 295                 300

Asp Met Ile Arg Phe Lys Asp Ala Tyr Thr Val Gly Asp Ile Thr Ile
305                 310                 315                 320

Tyr His Asn Gly Gln Glu Leu Gln Leu Gly Ser Thr Glu Val Lys Tyr
                325                 330                 335

His Asp Ser Leu His Ile Glu Tyr Trp Glu Cys Lys Ser Ile Tyr Ala
            340                 345                 350

Leu Glu Gln Gln Val Phe Arg Val Val Asn Pro Asp Ser Glu Ala Val
        355                 360                 365

Phe Asn Gln Lys Leu Gln Ser Leu Ala Thr Lys Ala Lys Gln Ala Lys
370                 375                 380

Phe Pro Asp Asn Lys Lys Leu Trp Lys Leu Tyr Tyr Glu Thr Arg Asn
385                 390                 395                 400

```
Met Phe Ala Asn Val Gln Tyr Ile His Ala Ser Thr Ile His Lys Leu
                405                 410                 415

Gln Gly Ser Thr Tyr Asp Val Ser Tyr Ile Asp Ile Phe Ser Leu Val
            420                 425                 430

His Asn His Tyr Met Ser Asp Glu Glu Lys Tyr Arg Leu Leu Tyr Val
            435                 440                 445

Ala Ile Thr Arg Ala Ser Lys Asp Ile Lys Ile Phe Met Ser Ala Phe
450                 455                 460

Asp Arg Thr Ser Asp Glu Lys Val Ile Ile Asn Asn Gln Asn Ser Glu
465                 470                 475                 480

Thr Met Asn Thr Leu Lys Gln Leu His Asp Ile Asp Ile Ile Leu Lys
            485                 490                 495

Asp Leu Asp Leu
            500

<210> SEQ ID NO 13
<211> LENGTH: 450
<212> TYPE: PRT
<213> ORGANISM: Vibrio phage henriette 12B8

<400> SEQUENCE: 13

Met Ala Asp Phe Glu Leu Thr Leu Gly Gln Lys Thr Val Leu Gly Glu
1               5                   10                  15

Val Ile Ser Thr Ile Leu Lys Pro Val Asn Leu Asn Asp Thr Ser Arg
            20                  25                  30

Phe His Thr Met His Gly Pro Ala Gly Ser Gly Lys Thr Thr Val Leu
            35                  40                  45

Gln Arg Ile Ile Ser Gln Ile Pro Ala Tyr Lys Thr Ile Gly Phe Cys
50                  55                  60

Ser Pro Thr His Lys Ser Val Lys Val Ile Arg Arg Met Ala Arg Glu
65                  70                  75                  80

Ala Gly Ile Ser His Arg Val Asp Ile Arg Thr Ile His Ser Ala Leu
                85                  90                  95

Gly Leu Val Met Lys Pro Val Arg Gly Asp Glu Val Leu Val Lys Glu
            100                 105                 110

Pro Phe Ala Glu Glu Arg Ile Tyr Asp Val Leu Ile Ile Asp Glu Ala
            115                 120                 125

Gly Met Leu Asn Asp Glu Leu Ile Met Tyr Ile Leu Glu Ser Gln Ser
130                 135                 140

Ser Lys Val Ile Phe Val Gly Asp Met Cys Gln Ile Gly Pro Ile Gln
145                 150                 155                 160

Ser Asn Leu Pro Glu Glu Asp Gly Tyr Thr Pro Thr Ser Thr Asp Asp
            165                 170                 175

Val Ser Lys Val Phe Thr Glu Val Glu Met Met Ser Ala Leu Thr Glu
            180                 185                 190

Val Val Arg Gln Ala Glu Gly Ser Pro Ile Ile Gln Leu Ala Thr Glu
            195                 200                 205

Phe Arg Leu Ala Gln Asp Asp Ile Tyr Ala Asp Leu Pro Arg Ile Val
            210                 215                 220

Thr Asn Thr Thr Pro Asp Gly Asn Gly Ile Ile Thr Met Pro Asn Gly
225                 230                 235                 240

Asn Trp Val Asp Ser Ala Val Ala Arg Phe Gln Ser Asp Gln Phe Lys
                245                 250                 255

Glu Asp Pro Asp His Cys Arg Ile Val Cys Tyr Thr Asn Ala Met Val
            260                 265                 270
```

```
Asp Leu Cys Asn Asp Leu Val Arg Lys Arg Leu Phe Gly Ala Asp Val
            275                 280                 285

Pro Glu Trp Leu Glu Asp Glu Ile Leu Val Ala Gln Glu Met Gly Ser
290                 295                 300

Thr Trp Asn Asn Ala Asp Glu Leu Arg Ile Val Ser Ile Asp Asp His
305                 310                 315                 320

Phe Asp Gln Gln Tyr Glu Val Pro Cys Trp Arg Met Gln Leu Glu Ser
                325                 330                 335

Val Glu Asp His Lys Leu His Asn Ala Leu Val Val Lys Gly Asp Tyr
                340                 345                 350

Ile Glu Asp Phe Lys Phe Arg Leu Asn Ala Ile Ala Glu Arg Ala Asn
            355                 360                 365

Thr Asp Lys Asn Met Ser Gly Met His Trp Lys Glu Phe Trp Gly Met
370                 375                 380

Arg Lys Lys Phe Asn Thr Phe Lys Asn Val Tyr Ala Gly Thr Ala His
385                 390                 395                 400

Lys Ser Gln Gly Ser Thr Phe Asp Tyr Thr Tyr Val Phe Thr Pro Asp
                405                 410                 415

Phe Tyr Lys Phe Gly Ala Thr Met Thr Ile Lys Arg Leu Leu Tyr Thr
            420                 425                 430

Ala Ile Thr Arg Ser Arg Tyr Thr Thr Tyr Phe Ala Met Asn Thr Gly
            435                 440                 445

Ala Gln
    450

<210> SEQ ID NO 14
<211> LENGTH: 421
<212> TYPE: PRT
<213> ORGANISM: Vibrio phage phi-pp2

<400> SEQUENCE: 14

Met Gly Leu Thr Asn Cys Gln Gln Gly Ala Met Asp Ala Phe Leu Glu
1               5                   10                  15

Ser Asp Gly His Met Thr Ile Ser Gly Pro Ala Gly Ser Gly Lys Thr
            20                  25                  30

Phe Leu Met Lys Ser Ile Leu Glu Ala Leu Glu Ser Lys Gly Lys Asn
        35                  40                  45

Val Thr Met Val Thr Pro Thr His Gln Ala Lys Asn Val Leu His Lys
50                  55                  60

Ala Thr Gly Gln Glu Val Ser Thr Ile His Ser Leu Leu Lys Ile His
65                  70                  75                  80

Pro Asp Thr Tyr Glu Asp Gln Lys His Phe Thr Gln Ser Gly Glu Val
                85                  90                  95

Glu Gly Leu Asp Glu Ile Asp Val Leu Val Glu Glu Ala Ser Met
            100                 105                 110

Val Asp Glu Glu Leu Phe Gln Ile Thr Gly Arg Thr Met Pro Arg Lys
        115                 120                 125

Cys Arg Ile Leu Ala Val Gly Asp Lys Tyr Gln Leu Gln Pro Val Lys
130                 135                 140

His Asp Pro Gly Val Ile Ser Pro Phe Thr Lys Phe Thr Thr Phe
145                 150                 155                 160

Glu Met Asn Glu Val Val Arg Gln Ala Lys Asp Asn Pro Leu Ile Gln
                165                 170                 175

Val Ala Thr Glu Val Arg Asn Gly Gln Trp Leu Arg Thr Asn Trp Ser
```

```
            180                 185                 190
Lys Glu Arg Arg Gln Gly Val Leu His Val Pro Asn Val Asn Lys Met
        195                 200                 205
Leu Asp Thr Tyr Leu Ser Lys Val Asn Ser Pro Glu Asp Leu Leu Asp
        210                 215                 220
Tyr Arg Ile Leu Ala Tyr Thr Asn Asp Cys Val Asp Thr Phe Asn Gly
225                 230                 235                 240
Ile Ile Arg Glu His Val Tyr Asn Thr Ser Glu Pro Phe Ile Pro Gly
                245                 250                 255
Glu Tyr Leu Val Thr Gln Met Pro Val Met Val Ser Asn Gly Lys Tyr
            260                 265                 270
Pro Val Cys Val Ile Glu Asn Gly Glu Val Val Lys Ile Leu Asp Val
        275                 280                 285
Arg Gln Lys Thr Ile Asp Gly Met Leu Pro Lys Val Asp Asn Glu Ala
        290                 295                 300
Phe Asp Val Ala Val Leu Thr Val Glu Lys Glu Asp Gly Asn Val Tyr
305                 310                 315                 320
Glu Phe Thr Val Leu Trp Asp Asp Leu Gln Lys Glu Arg Phe Ala Arg
                325                 330                 335
Tyr Leu Ser Val Ala Ala Gly Thr Tyr Lys Ser Met Arg Gly Asn Thr
            340                 345                 350
Lys Arg Tyr Trp Arg Ala Phe Trp Gly Leu Lys Glu Gln Met Ile Glu
        355                 360                 365
Thr Lys Ser Leu Gly Ala Ser Thr Val His Lys Ser Gln Gly Thr Thr
        370                 375                 380
Val Lys Gly Val Cys Leu Tyr Thr Gln Asp Met Gly Tyr Ala Glu Pro
385                 390                 395                 400
Glu Ile Leu Gln Gln Leu Val Tyr Val Gly Leu Thr Arg Pro Thr Asp
                405                 410                 415
Trp Ala Leu Tyr Asn
            420

<210> SEQ ID NO 15
<211> LENGTH: 434
<212> TYPE: PRT
<213> ORGANISM: Aeromonas phage 65

<400> SEQUENCE: 15

Met Ser Glu Ser Glu Ile Thr Leu Thr Pro Ser Gln Asn Met Ala Val
1               5                   10                  15
Asn Glu Val Lys Asn Gly Thr Gly His Ile Thr Ile Ser Gly Pro Pro
                20                  25                  30
Gly Ser Gly Lys Thr Phe Leu Val Lys Tyr Leu Ile Lys Met Leu Gly
            35                  40                  45
Asp Glu Leu Gly Thr Val Leu Ala Ala Pro Thr His Gln Ala Lys Ile
        50                  55                  60
Val Leu Thr Glu Met Ser Gly Ile Glu Ala Cys Thr Ile His Ser Leu
65                  70                  75                  80
Met Lys Ile His Pro Glu Thr Leu Glu Asp Ile Gln Ile Phe Asp Gln
                85                  90                  95
Ser Lys Leu Pro Asp Leu Ser Asn Ile Arg Tyr Leu Ile Val Glu Glu
            100                 105                 110
Ala Ser Met His Ser Lys Thr Leu Phe Lys Ile Thr Met Lys Ser Ile
        115                 120                 125
```

-continued

Pro Pro Thr Cys Arg Ile Ile Ala Ile Gly Asp Lys Asp Gln Ile Gln
        130                 135                 140

Pro Glu Glu His Ala Gln Gly Glu Leu Ser Pro Tyr Phe Thr Asp Pro
145                 150                 155                 160

Arg Phe Ser Gln Ile Arg Leu Thr Asp Ile Met Arg Gln Ser Leu Asp
                165                 170                 175

Asn Pro Ile Ile Gln Val Ala Thr Lys Ile Arg Glu Gly Gly Trp Ile
            180                 185                 190

Glu Pro Asn Trp Asn Arg Asp Thr Lys Thr Gly Val Tyr Lys Val Ser
        195                 200                 205

Gly Ile Thr Asp Leu Val Asn Ser Tyr Leu Arg Ala Val Lys Thr Pro
210                 215                 220

Glu Asp Leu Thr Lys Tyr Arg Phe Leu Ala Tyr Thr Asn Lys Val Val
225                 230                 235                 240

Asn Lys Val Asn Ser Ile Val Arg Glu His Val Tyr Lys Thr Lys Leu
                245                 250                 255

Pro Phe Ile Glu Gly Glu Lys Ile Val Leu Gln Glu Pro Val Met Val
            260                 265                 270

Glu His Glu Asp Asp Thr Ile Glu Thr Ile Phe Thr Asn Gly Glu Val
        275                 280                 285

Val Thr Ile Asn Glu Ile Glu Val Phe Asp Arg Thr Ile Arg Ile Asp
290                 295                 300

Gly Ser Pro Glu Phe Lys Val Asn Ala Ala Lys Leu Ser Val Ser Ser
305                 310                 315                 320

Asp Tyr Ser Gly Ile Glu His Asp Phe Cys Val Leu Tyr Gly Ser Glu
                325                 330                 335

Ser Arg Leu Glu Phe Glu Tyr Gln Leu Ser Glu Ser Ala Gly Asn Ile
            340                 345                 350

Lys Gln Met Gly Lys Gly Gly Asn Gln Arg Ser Ala Trp Lys Ser Phe
        355                 360                 365

Trp Ala Ala Lys Lys Met Phe Ile Glu Thr Lys Ser Leu Gly Ala Ser
370                 375                 380

Thr Ile His Lys Ser Gln Gly Ser Thr Val Lys Gly Val Trp Leu Ala
385                 390                 395                 400

Leu His Asp Ile His Tyr Ala Asp Glu Glu Leu Lys Gln Gln Leu Val
                405                 410                 415

Tyr Val Gly Val Thr Arg Pro Thr Asp Phe Cys Leu Tyr Phe Asp Gly
            420                 425                 430

Thr Lys

<210> SEQ ID NO 16
<211> LENGTH: 420
<212> TYPE: PRT
<213> ORGANISM: Aeromonas phage CC2

<400> SEQUENCE: 16

Met Ala Val Asp Ala Val Gln Ser Gly Thr Gly His Ile Thr Ile Ser
1               5                   10                  15

Gly Pro Pro Gly Ser Gly Lys Thr Phe Leu Val Lys Tyr Ile Ile Lys
            20                  25                  30

Met Leu Gly Asp Glu Leu Gly Thr Val Leu Ala Ala Pro Thr His Gln
        35                  40                  45

Ala Lys Ile Val Leu Thr Glu Met Ser Gly Ile Glu Ala Cys Thr Ile
50                  55                  60

-continued

His Ser Leu Met Lys Ile His Pro Glu Thr Leu Glu Asp Ile Gln Ile
 65                  70                  75                  80

Phe Asp Gln Ser Lys Met Pro Asp Leu Ser Thr Val Arg Tyr Leu Ile
             85                  90                  95

Ile Glu Glu Ala Ser Met His Ser Lys Ala Leu Phe Asn Ile Thr Met
            100                 105                 110

Lys Ser Ile Pro Pro Thr Cys Arg Ile Ala Ile Gly Asp Lys Asp
        115                 120                 125

Gln Ile Gln Pro Val Asp His Ala Pro Gly Glu Leu Ser Pro Tyr Phe
    130                 135                 140

Thr Asp Ser Arg Phe Thr Gln Ile Arg Met Thr Asp Ile Met Arg Gln
145                 150                 155                 160

Ser Leu Asp Asn Pro Ile Ile Gln Val Ala Thr Thr Ile Arg Glu Gly
                165                 170                 175

Gly Trp Ile Tyr Gln Asn Trp Asn Lys Glu Lys Ser Gly Val Tyr
            180                 185                 190

Lys Val Lys Ser Ile Thr Asp Leu Ile Asn Ser Tyr Leu Arg Val Val
        195                 200                 205

Lys Thr Pro Glu Asp Leu Thr Lys Tyr Arg Phe Leu Ala Phe Thr Asn
    210                 215                 220

Lys Val Asp Lys Val Asn Ser Ile Val Arg Lys His Val Tyr Lys
225                 230                 235                 240

Thr Asp Leu Pro Phe Ile Glu Gly Lys Leu Val Leu Gln Glu Pro
                245                 250                 255

Val Met Val Glu Tyr Asp Asp Thr Ile Glu Thr Ile Phe Thr Asn
            260                 265                 270

Gly Glu Val Val Thr Val Asp Glu Ile Glu Val Ser Asp Met Asn Ile
        275                 280                 285

Arg Ile Asp Gly Ser Pro Ala Phe Ser Ile Ser Val Ala Lys Leu Lys
    290                 295                 300

Val Thr Ser Asp Phe Ser Gly Val Thr His Asp Ile Met Ser Val Tyr
305                 310                 315                 320

Gly Glu Asp Ser Lys Ala Glu Phe Asn Tyr Gln Leu Ser Glu Ala Ala
                325                 330                 335

Ala Val Ile Lys Gln Met Gln Arg Gly Gln Thr Lys Ala Ala Trp Ala
            340                 345                 350

Ser Phe Trp Asp Ala Lys Lys Thr Phe Thr Glu Thr Lys Ser Leu Gly
        355                 360                 365

Ala Cys Thr Ile His Lys Ser Gln Gly Ser Thr Val Lys Gly Val Trp
    370                 375                 380

Leu Gly Leu His Asp Ile Ser Tyr Ala Asp Thr Asp Leu Gln Gln
385                 390                 395                 400

Leu Val Tyr Val Gly Val Thr Arg Pro Thr Asp Phe Cys Leu Tyr Phe
                405                 410                 415

Asp Gly Ser Lys
            420

<210> SEQ ID NO 17
<211> LENGTH: 443
<212> TYPE: PRT
<213> ORGANISM: Cronobacter phage vB CsaM GAP161

<400> SEQUENCE: 17

Met Ser Glu Leu Thr Phe Asp Asp Leu Ser Asp Asp Gln Lys Ser Ala
1               5                   10                  15

-continued

```
His Asp Arg Val Ile His Asn Ile Gln Asn Ala Ile His Thr Thr Ile
         20                  25                  30

Thr Gly Gly Pro Gly Val Gly Lys Thr Thr Leu Val Lys Phe Val Phe
         35                  40                  45

Asn Thr Leu Lys Gly Leu Gly Ile Ser Gly Ile Trp Leu Thr Ala Pro
 50                  55                  60

Thr His Gln Ala Lys Asn Val Leu Ala Ala Thr Gly Met Asp Ala
 65                  70                  75                  80

Thr Thr Ile His Ser Ala Leu Lys Ile Ser Pro Val Thr Asn Glu Glu
                 85                  90                  95

Leu Arg Val Phe Glu Gln Gln Lys Gly Lys Lys Ala Pro Asp Leu Ser
                100                 105                 110

Thr Cys Arg Val Phe Val Val Glu Glu Val Ser Met Val Asp Met Asp
                115                 120                 125

Leu Phe Arg Ile Ile Arg Arg Ser Ile Pro Ser Asn Ala Val Ile Leu
 130                 135                 140

Gly Leu Gly Asp Lys Asp Gln Ile Arg Pro Val Asn Ala Asp Gly Arg
 145                 150                 155                 160

Val Glu Leu Ser Pro Phe Phe Asp Glu Glu Ile Phe Asp Val Ile Arg
                 165                 170                 175

Met Asp Lys Ile Met Arg Gln Ala Glu Gly Asn Pro Ile Ile Gln Val
                180                 185                 190

Ser Arg Ala Val Arg Asp Gly Lys Met Leu Lys Pro Met Ser Val Gly
                195                 200                 205

Asp Leu Gly Val Phe Gln His Ala Asn Ala Val Asp Phe Leu Arg Gln
                210                 215                 220

Tyr Phe Arg Arg Val Lys Thr Pro Asp Asp Leu Ile Glu Asn Arg Met
225                 230                 235                 240

Phe Ala Tyr Thr Asn Asp Asn Val Asp Lys Leu Asn Ala Thr Ile Arg
                245                 250                 255

Lys His Leu Tyr Lys Thr Thr Glu Pro Phe Ile Leu Asp Glu Val Ile
                260                 265                 270

Val Met Gln Glu Pro Leu Val Gln Glu Met Arg Leu Asn Gly Gln Ile
                275                 280                 285

Phe Thr Glu Ile Val Tyr Asn Asn Asn Glu Lys Ile Arg Val Leu Glu
                290                 295                 300

Ile Ile Pro Arg Arg Glu Val Ile Lys Ala Glu Lys Cys Asp Glu Lys
305                 310                 315                 320

Ile Glu Ile Glu Phe Tyr Leu Leu Lys Thr Val Ser Leu Glu Glu Glu
                325                 330                 335

Thr Glu Ala Gln Ile Gln Val Val Asp Pro Val Met Lys Asp Arg
                340                 345                 350

Leu Gly Asn Tyr Leu Ala Tyr Val Ala Ser Thr Tyr Lys Arg Ile Lys
                355                 360                 365

Gln Gln Thr Gly Tyr Lys Ala Pro Trp His Ser Phe Trp Ala Ile Lys
                370                 375                 380

Asn Lys Phe Gln Asp Val Lys Pro Leu Pro Val Cys Thr Tyr His Lys
385                 390                 395                 400

Ser Gln Gly Ser Thr Tyr Asp His Ala Tyr Met Tyr Thr Arg Asp Ala
                405                 410                 415

Tyr Ala Phe Ala Asp Tyr Asp Leu Cys Lys Gln Leu Ile Tyr Val Gly
                420                 425                 430
```

Val Thr Arg Ala Arg Tyr Thr Val Asp Tyr Val
            435                 440

<210> SEQ ID NO 18
<211> LENGTH: 442
<212> TYPE: PRT
<213> ORGANISM: Klebsiella phage KP15

<400> SEQUENCE: 18

Met Ser Glu Leu Thr Phe Asp Asp Leu Ser Glu Asp Gln Lys Asn Ala
1               5                   10                  15

His Asp Arg Val Ile Lys Asn Ile Arg Asn Lys Ile His Thr Thr Ile
            20                  25                  30

Thr Gly Gly Pro Gly Val Gly Lys Thr Thr Leu Val Lys Phe Val Phe
            35                  40                  45

Glu Thr Leu Lys Lys Leu Gly Ile Ser Gly Ile Trp Leu Thr Ala Pro
    50                  55                  60

Thr His Gln Ala Lys Asn Val Leu Ser Glu Ala Val Gly Met Asp Ala
65                  70                  75                  80

Thr Thr Ile His Ser Ala Leu Lys Ile Ser Pro Val Thr Asn Glu Glu
                85                  90                  95

Leu Arg Val Phe Glu Gln Gln Lys Gly Lys Lys Ala Ala Asp Leu Ser
            100                 105                 110

Glu Cys Arg Val Phe Val Glu Glu Val Ser Met Val Asp Lys Glu
            115                 120                 125

Leu Phe Arg Ile Ile Lys Arg Thr Ile Pro Ser Cys Ala Val Ile Leu
    130                 135                 140

Gly Leu Gly Asp Lys Asp Gln Ile Arg Pro Val Asn Thr Glu Gly Ile
145                 150                 155                 160

Thr Glu Leu Ser Pro Phe Phe Asp Glu Glu Ile Phe Asp Val Ile Arg
                165                 170                 175

Met Asp Lys Ile Met Arg Gln Ala Glu Gly Asn Pro Ile Ile Gln Val
            180                 185                 190

Ser Arg Ala Ile Arg Asp Gly Lys Pro Leu Met Pro Leu Met Asn Gly
            195                 200                 205

Glu Leu Gly Val Met Lys His Glu Asn Ala Ser Asp Phe Leu Arg Arg
210                 215                 220

Tyr Phe Ser Arg Val Lys Thr Pro Asp Leu Asn Asn Asn Arg Met
225                 230                 235                 240

Phe Ala Tyr Thr Asn Ala Asn Val Asp Lys Leu Asn Ala Val Ile Arg
                245                 250                 255

Lys His Leu Tyr Lys Thr Asp Gln Pro Phe Ile Val Gly Glu Val Val
            260                 265                 270

Val Met Gln Glu Pro Leu Val Thr Glu Gly Arg Val Asn Gly Val Ser
            275                 280                 285

Phe Val Glu Val Ile Tyr Asn Asn Asn Glu Gln Ile Lys Ile Leu Glu
    290                 295                 300

Ile Ile Pro Arg Ser Asp Thr Ile Lys Ala Asp Arg Cys Asp Pro Val
305                 310                 315                 320

Gln Ile Asp Tyr Phe Leu Met Lys Thr Glu Ser Met Phe Glu Asp Thr
                325                 330                 335

Lys Ala Asp Ile Gln Val Ile Ala Asp Pro Val Met Gln Glu Arg Leu
            340                 345                 350

Gly Asp Tyr Leu Asn Tyr Val Ala Phe Gln Tyr Lys Lys Met Lys Gln
            355                 360                 365

Glu Thr Gly Tyr Lys Ala Pro Trp Tyr Ser Phe Trp Gln Ile Lys Asn
        370                 375                 380

Lys Phe Gln Thr Val Lys Ala Leu Pro Val Cys Thr Tyr His Lys Gly
385                 390                 395                 400

Gln Gly Ser Thr Tyr Asp His Ser Tyr Met Tyr Thr Arg Asp Ala Tyr
                405                 410                 415

Ala Tyr Ala Asp Tyr Glu Leu Cys Lys Gln Leu Leu Tyr Val Gly Thr
                420                 425                 430

Thr Arg Ala Arg Phe Thr Val Asp Tyr Val
                435                 440

<210> SEQ ID NO 19
<211> LENGTH: 438
<212> TYPE: PRT
<213> ORGANISM: Stenotrophomonas phage IME13

<400> SEQUENCE: 19

Met Val Thr Tyr Asp Asp Leu Thr Val Gly Gln Lys Asp Ala Ile Glu
1               5                   10                  15

Lys Ala Leu Gln Ala Met Arg Thr Lys Arg His Ile Thr Ile Arg Gly
                20                  25                  30

Pro Ala Gly Ser Gly Lys Thr Thr Met Thr Arg Phe Leu Leu Glu Arg
            35                  40                  45

Leu Phe Gln Thr Gly Gln Gln Gly Ile Val Leu Thr Ala Pro Thr His
        50                  55                  60

Gln Ala Lys Lys Glu Leu Ser Lys His Ala Leu Arg Lys Ser Tyr Thr
65                  70                  75                  80

Ile Gln Ser Val Leu Lys Ile Asn Pro Ser Thr Leu Glu Glu Asn Gln
                85                  90                  95

Ile Phe Glu Gln Lys Gly Thr Pro Asp Phe Ser Lys Thr Arg Val Leu
            100                 105                 110

Ile Cys Asp Glu Val Ser Phe Tyr Thr Arg Lys Leu Phe Asp Ile Leu
        115                 120                 125

Met Arg Asn Val Pro Ser His Cys Val Val Ile Gly Ile Gly Asp Lys
130                 135                 140

Ala Gln Ile Arg Gly Val Ser Glu Asp Asp Thr His Glu Leu Ser Pro
145                 150                 155                 160

Phe Phe Thr Asp Asn Arg Phe Glu Gln Val Glu Leu Thr Glu Val Lys
                165                 170                 175

Arg His Gln Gly Pro Ile Ile Glu Val Ala Thr Asp Ile Arg Asn Gly
            180                 185                 190

Lys Trp Ile Tyr Glu Lys Leu Asp Asp Ser Gly Asn Gly Val Lys Gln
        195                 200                 205

Phe His Thr Val Lys Asp Phe Leu Ser Lys Tyr Phe Glu Arg Thr Lys
    210                 215                 220

Thr Pro Asn Asp Leu Leu Glu Asn Arg Ile Met Ala Tyr Thr Asn Asn
225                 230                 235                 240

Ser Val Asp Lys Leu Asn Ser Val Ile Arg Lys Gln Leu Tyr Gly Ala
                245                 250                 255

Asn Ala Ala Pro Phe Leu Pro Asp Glu Ile Leu Val Met Gln Glu Pro
            260                 265                 270

Leu Met Phe Asp Ile Asp Ile Gly Gly Gln Thr Leu Lys Glu Val Ile
        275                 280                 285

Phe Asn Asn Gly Gln Asn Val Arg Val Ile Asn Val Lys Pro Ser Arg

```
        290                 295                 300
Lys Thr Leu Lys Ala Lys Gly Val Gly Glu Ile Glu Val Glu Cys Thr
305                 310                 315                 320

Met Leu Glu Cys Glu Ser Tyr Glu Glu Asp Glu Asp Tyr Arg Arg
                325                 330                 335

Ala Trp Phe Thr Val Val His Asp Gln Asn Thr Gln Tyr Ala Ile Asn
                340                 345                 350

Glu Phe Leu Ser Ile Ile Ala Glu Lys Tyr Arg Ser Arg Glu Val Phe
                355                 360                 365

Pro Asn Trp Lys Asp Phe Trp Ala Ile Arg Asn Thr Phe Val Lys Val
                370                 375                 380

Arg Pro Leu Gly Ala Met Thr Phe His Lys Ser Gln Gly Ser Thr Phe
385                 390                 395                 400

Asp Asn Ala Tyr Leu Phe Thr Pro Cys Leu His Gln Tyr Cys Arg Asp
                405                 410                 415

Pro Asp Val Ala Gln Glu Leu Ile Tyr Val Gly Asn Thr Arg Ala Arg
                420                 425                 430

Lys Asn Val Cys Phe Val
                435

<210> SEQ ID NO 20
<211> LENGTH: 442
<212> TYPE: PRT
<213> ORGANISM: Acinetobacter phage Ac42

<400> SEQUENCE: 20

Met Asn Phe Glu Asp Leu Thr Glu Gly Gln Lys Asn Ala Tyr Thr Ala
1               5                   10                  15

Ala Ile Lys Ala Ile Glu Thr Val Pro Ser Ser Ala Glu Lys Arg
                20                  25                  30

His Leu Thr Ile Asn Gly Pro Ala Gly Thr Gly Lys Thr Thr Leu Thr
                35                  40                  45

Lys Phe Leu Ile Ala Glu Leu Ile Arg Arg Gly Glu Arg Gly Val Tyr
    50                  55                  60

Leu Ala Ala Pro Thr His Gln Ala Lys Lys Val Leu Ser Gln His Ala
65                  70                  75                  80

Gly Met Glu Ala Ser Thr Ile His Ser Leu Leu Lys Ile Asn Pro Thr
                85                  90                  95

Thr Tyr Glu Asp Ser Thr Thr Phe Glu Gln Lys Asp Val Pro Asp Met
                100                 105                 110

Ser Glu Cys Arg Val Leu Ile Cys Asp Glu Ala Ser Met Tyr Asp Leu
                115                 120                 125

Lys Leu Phe Gln Ile Leu Met Ser Ser Ile Pro Leu Cys Cys Thr Val
    130                 135                 140

Ile Ala Leu Gly Asp Ile Ala Gln Ile Arg Pro Val Glu Pro Gly Ala
145                 150                 155                 160

Phe Glu Gly Gln Val Ser Pro Phe Phe Thr Tyr Glu Lys Phe Glu Gln
                165                 170                 175

Val Ser Leu Thr Glu Val Met Arg Ser Asn Ala Pro Ile Ile Asp Val
                180                 185                 190

Ala Thr Ser Ile Arg Thr Gly Asn Trp Ile Tyr Glu Asn Val Ile Asp
                195                 200                 205

Gly Ala Gly Val His Asn Leu Thr Ser Glu Arg Ser Val Lys Ser Phe
                210                 215                 220
```

Met Glu Lys Tyr Phe Ser Ile Val Lys Thr Pro Glu Asp Leu Phe Glu
225                 230                 235                 240

Asn Arg Leu Leu Ala Phe Thr Asn Lys Ser Val Asp Asp Leu Asn Lys
            245                 250                 255

Ile Val Arg Lys Ile Tyr Asn Thr Leu Glu Pro Phe Ile Asp Gly
        260                 265                 270

Glu Val Leu Val Met Gln Pro Leu Ile Lys Ser Tyr Thr Tyr Glu
        275                 280                 285

Gly Lys Lys Val Ser Glu Ile Val Phe Asn Asn Gly Glu Met Val Lys
        290                 295                 300

Val Leu Cys Cys Ser Gln Thr Ser Asp Glu Ile Ser Val Arg Gly Cys
305                 310                 315                 320

Ser Thr Lys Tyr Met Val Arg Tyr Trp Gln Leu Asp Leu Gln Ser Leu
                325                 330                 335

Asp Asp Pro Asp Leu Thr Gly Ser Ile Asn Val Ile Val Asp Glu Ala
            340                 345                 350

Glu Ile Asn Lys Leu Asn Leu Val Leu Gly Lys Ser Ala Glu Gln Phe
        355                 360                 365

Lys Ser Gly Ala Val Lys Ala Ala Trp Ala Asp Trp Trp Lys Leu Lys
370                 375                 380

Arg Asn Phe His Lys Val Lys Ala Leu Pro Cys Ser Thr Ile His Lys
385                 390                 395                 400

Ser Gln Gly Thr Ser Val Asp Asn Val Phe Leu Tyr Thr Pro Cys Ile
                405                 410                 415

His Lys Ala Asp Ser Gln Leu Ala Gln Gln Leu Leu Tyr Val Gly Ala
            420                 425                 430

Thr Arg Ala Arg His Asn Val Tyr Tyr Ile
            435                 440

<210> SEQ ID NO 21
<211> LENGTH: 442
<212> TYPE: PRT
<213> ORGANISM: Shigella phage SP18

<400> SEQUENCE: 21

Met Ile Lys Phe Glu Asp Leu Asn Thr Gly Gln Lys Glu Ala Phe Asp
1               5                   10                  15

Tyr Ile Thr Glu Ala Ile Gln Arg Arg Ser Gly Glu Cys Ile Thr Leu
            20                  25                  30

Asn Gly Pro Ala Gly Thr Gly Lys Thr Thr Leu Thr Lys Phe Val Ile
        35                  40                  45

Asp His Leu Val Arg Asn Gly Val Met Gly Ile Val Leu Ala Ala Pro
    50                  55                  60

Thr His Gln Ala Lys Lys Val Leu Ser Lys Leu Ser Gly Gln Thr Ala
65                  70                  75                  80

Asn Thr Ile His Ser Ile Leu Lys Ile Asn Pro Thr Thr Tyr Glu Asp
                85                  90                  95

Gln Asn Ile Phe Glu Gln Arg Glu Met Pro Asp Met Ser Lys Cys Asn
            100                 105                 110

Val Leu Val Cys Asp Glu Ala Ser Met Tyr Asp Gly Ser Leu Phe Lys
        115                 120                 125

Ile Ile Cys Asn Ser Val Pro Glu Trp Cys Thr Ile Leu Gly Ile Gly
    130                 135                 140

Asp Met His Gln Leu Gln Pro Val Asp Pro Gly Ser Thr Gln Gln Lys
145                 150                 155                 160

```
Ile Ser Pro Phe Phe Thr His Pro Lys Phe Lys Gln Ile His Leu Thr
                165                 170                 175

Glu Val Met Arg Ser Asn Ala Pro Ile Ile Glu Val Ala Thr Glu Ile
            180                 185                 190

Arg Asn Gly Gly Trp Phe Arg Asp Cys Met Tyr Asp Gly His Gly Val
        195                 200                 205

Gln Gly Phe Thr Ser Gln Thr Ala Leu Lys Asp Phe Met Val Asn Tyr
    210                 215                 220

Phe Gly Ile Val Lys Asp Ala Asp Met Leu Met Glu Asn Arg Met Tyr
225                 230                 235                 240

Ala Tyr Thr Asn Lys Ser Val Glu Lys Leu Asn Asn Ile Ile Arg Arg
                245                 250                 255

Lys Leu Tyr Glu Thr Asp Lys Ala Phe Leu Pro Tyr Glu Val Leu Val
            260                 265                 270

Met Gln Glu Pro His Met Lys Glu Leu Glu Phe Glu Gly Lys Lys Phe
        275                 280                 285

Ser Glu Thr Ile Phe Asn Asn Gly Gln Leu Val Arg Ile Lys Asp Cys
    290                 295                 300

Lys Tyr Thr Ser Thr Ile Leu Arg Cys Lys Gly Glu Ser His Gln Leu
305                 310                 315                 320

Val Ile Asn Tyr Trp Asp Leu Glu Val Glu Ser Ile Asp Glu Asp Glu
                325                 330                 335

Glu Tyr Gln Val Asp Arg Ile Lys Val Leu Pro Glu Asp Gln Gln Pro
            340                 345                 350

Lys Phe Gln Ala Tyr Leu Ala Lys Val Ala Asp Thr Tyr Lys Gln Met
        355                 360                 365

Lys Ala Ala Gly Lys Arg Pro Glu Trp Lys Asp Phe Trp Lys Ala Arg
    370                 375                 380

Arg Thr Phe Leu Lys Val Arg Ala Leu Pro Val Ser Thr Ile His Lys
385                 390                 395                 400

Ala Gln Gly Val Ser Val Asp Lys Ala Phe Ile Tyr Thr Pro Cys Ile
                405                 410                 415

His Met Ala Glu Ala Ser Leu Ala Ser Gln Leu Ala Tyr Val Gly Ile
            420                 425                 430

Thr Arg Ala Arg Tyr Asp Ala Tyr Tyr Val
        435                 440

<210> SEQ ID NO 22
<211> LENGTH: 439
<212> TYPE: PRT
<213> ORGANISM: Yersinia phage phiR1-RT

<400> SEQUENCE: 22

Met Ile Thr Tyr Asp Asp Leu Thr Asp Gly Gln Lys Ser Ala Phe Asp
1               5                   10                  15

Asn Thr Met Glu Ala Ile Lys Asn Lys Lys Gly His Ile Thr Ile Asn
            20                  25                  30

Gly Pro Ala Gly Thr Gly Lys Thr Thr Leu Thr Lys Phe Ile Ile Asp
        35                  40                  45

His Leu Ile Lys Thr Gly Glu Ala Gly Ile Ile Leu Cys Ala Pro Thr
    50                  55                  60

His Gln Ala Lys Lys Val Leu Ser Lys Leu Ser Gly Met Asp Ala Ser
65                  70                  75                  80

Thr Ile His Ser Val Leu Lys Ile Asn Pro Thr Thr Tyr Glu Glu Asn
```

```
                85                  90                  95
Gln Ile Phe Glu Gln Arg Glu Val Pro Asp Leu Ala Ala Cys Arg Val
            100                 105                 110

Leu Ile Cys Asp Glu Ala Ser Phe Tyr Asp Arg Lys Leu Phe Gly Ile
            115                 120                 125

Ile Leu Ala Thr Val Pro Ser Trp Cys Thr Val Ile Ala Leu Gly Asp
            130                 135                 140

Lys Asp Gln Leu Arg Pro Val Thr Pro Gly Glu Ser Glu Gln Gln Leu
145                 150                 155                 160

Ser Pro Phe Phe Ser His Ala Lys Phe Lys Gln Val His Leu Thr Glu
                165                 170                 175

Ile Lys Arg Ser Asn Gly Pro Ile Ile Gln Val Ala Thr Asp Ile Arg
                180                 185                 190

Asn Gly Gly Trp Leu Ser Glu Asn Ile Val Asp Gly Glu Gly Val His
                195                 200                 205

Ala Phe Asn Ser Asn Thr Ala Leu Lys Asp Phe Met Ile Arg Tyr Phe
            210                 215                 220

Asp Val Val Lys Thr Ala Asp Asp Leu Ile Glu Ser Arg Met Leu Ala
225                 230                 235                 240

Tyr Thr Asn Lys Ser Val Asp Lys Leu Asn Gly Ile Ile Arg Arg Lys
                245                 250                 255

Leu Tyr Glu Thr Asp Lys Pro Phe Ile Asn Gly Glu Val Leu Val Met
                260                 265                 270

Gln Glu Pro Leu Met Lys Glu Leu Glu Phe Asp Gly Lys Lys Phe His
                275                 280                 285

Glu Ile Val Phe Asn Asn Gly Gln Leu Val Lys Ile Leu Tyr Ala Ser
            290                 295                 300

Glu Thr Ser Thr Phe Ile Ser Ala Arg Asn Val Pro Gly Glu Tyr Met
305                 310                 315                 320

Ile Arg Tyr Trp Asn Leu Glu Val Glu Thr Ala Asp Ser Asp Asp Asp
                325                 330                 335

Tyr Ala Thr Ser Gln Ile Gln Val Ile Cys Asp Pro Ala Glu Met Thr
                340                 345                 350

Lys Phe Gln Met Phe Leu Ala Lys Thr Ala Asp Thr Tyr Lys Asn Ser
                355                 360                 365

Gly Val Lys Ala Tyr Trp Lys Asp Phe Trp Ser Val Lys Asn Lys Phe
            370                 375                 380

Lys Lys Val Lys Ala Leu Pro Val Ser Thr Ile His Lys Ser Gln Gly
385                 390                 395                 400

Cys Thr Val Asn Asn Thr Phe Leu Tyr Thr Pro Cys Ile His Met Ala
                405                 410                 415

Asp Ala Gln Leu Ala Lys Gln Leu Leu Tyr Val Gly Ala Thr Arg Ala
                420                 425                 430

Arg Thr Asn Leu Tyr Tyr Ile
            435

<210> SEQ ID NO 23
<211> LENGTH: 441
<212> TYPE: PRT
<213> ORGANISM: Salmonella phage S16

<400> SEQUENCE: 23

Met Ile Thr Phe Glu Gln Leu Thr Ser Gly Gln Lys Leu Ala Phe Asp
1               5                   10                  15
```

Glu Thr Ile Arg Ala Ile Lys Glu Lys Lys Asn His Val Thr Ile Asn
            20                  25                  30

Gly Pro Ala Gly Thr Gly Lys Thr Thr Leu Thr Lys Phe Ile Met Glu
        35                  40                  45

His Leu Val Ser Thr Gly Glu Thr Gly Ile Ile Leu Thr Ala Pro Thr
 50                  55                  60

His Ala Ala Lys Lys Val Leu Thr Lys Leu Ser Gly Met Glu Ala Asn
65                  70                  75                  80

Thr Ile His Lys Ile Leu Lys Ile Asn Pro Thr Thr Tyr Glu Glu Ser
                85                  90                  95

Met Leu Phe Glu Gln Lys Glu Val Pro Asp Leu Ala Ser Cys Arg Val
            100                 105                 110

Leu Ile Cys Asp Glu Ala Ser Met Trp Asp Arg Lys Leu Phe Lys Ile
        115                 120                 125

Leu Met Ala Ser Ile Pro Lys Trp Cys Thr Ile Val Ala Ile Gly Asp
130                 135                 140

Val Ala Gln Ile Arg Pro Val Asp Pro Gly Glu Thr Glu Ala His Ile
145                 150                 155                 160

Ser Pro Phe Phe Ile His Lys Asp Phe Lys Gln Leu Asn Leu Thr Glu
                165                 170                 175

Val Met Arg Ser Asn Ala Pro Ile Ile Asp Val Ala Thr Asp Ile Arg
            180                 185                 190

Asn Gly Ser Trp Ile Tyr Glu Lys Thr Val Asp Gly His Gly Val His
        195                 200                 205

Gly Phe Thr Ser Thr Thr Ala Leu Lys Asp Phe Met Met Gln Tyr Phe
210                 215                 220

Ser Ile Val Lys Ser Pro Glu Asp Leu Phe Glu Asn Arg Met Leu Ala
225                 230                 235                 240

Phe Thr Asn Lys Ser Val Asp Lys Leu Asn Ser Ile Ile Arg Arg Arg
                245                 250                 255

Leu Tyr Gln Thr Glu Glu Ala Phe Val Val Gly Glu Val Ile Val Met
            260                 265                 270

Gln Glu Pro Leu Met Arg Glu Leu Val Phe Glu Gly Lys Lys Phe His
        275                 280                 285

Glu Thr Leu Phe Thr Asn Gly Gln Tyr Val Arg Ile Leu Ser Ala Asp
290                 295                 300

Tyr Thr Ser Ser Phe Leu Gly Ala Lys Gly Val Ser Gly Glu His Leu
305                 310                 315                 320

Ile Arg His Trp Val Leu Asp Val Glu Thr Tyr Asp Asp Glu Glu Tyr
                325                 330                 335

Ala Arg Glu Lys Ile Asn Val Ile Ser Asp Glu Gln Glu Met Asn Lys
            340                 345                 350

Phe Gln Phe Phe Leu Ala Lys Thr Ala Asp Thr Tyr Lys Asn Trp Asn
        355                 360                 365

Lys Gly Gly Lys Ala Pro Trp Ser Glu Phe Trp Asp Ala Lys Arg Lys
370                 375                 380

Phe His Lys Val Lys Ala Leu Pro Cys Ser Thr Phe His Lys Ala Gln
385                 390                 395                 400

Gly Ile Ser Val Asp Ser Ser Phe Ile Tyr Thr Pro Cys Ile His Val
                405                 410                 415

Ser Ser Asp Asn Lys Phe Lys Leu Glu Leu Leu Tyr Val Gly Ala Thr
            420                 425                 430

Arg Gly Arg His Asp Val Phe Phe Val

```
                435                 440

<210> SEQ ID NO 24
<211> LENGTH: 65
<212> TYPE: PRT
<213> ORGANISM: Artificial Sequence
<220> FEATURE:
<223> OTHER INFORMATION: preferred HhH domain

<400> SEQUENCE: 24

Gly Thr Gly Ser Gly Ala Trp Lys Glu Trp Leu Glu Arg Lys Val Gly
1               5                   10                  15

Glu Gly Arg Ala Arg Arg Leu Ile Glu Tyr Phe Gly Ser Ala Gly Glu
            20                  25                  30

Val Gly Lys Leu Val Glu Asn Ala Glu Val Ser Lys Leu Leu Glu Val
        35                  40                  45

Pro Gly Ile Gly Asp Glu Ala Val Ala Arg Leu Val Pro Gly Gly Ser
    50                  55                  60

Ser
65

<210> SEQ ID NO 25
<211> LENGTH: 299
<212> TYPE: PRT
<213> ORGANISM: Bacteriophage RB69

<400> SEQUENCE: 25

Met Phe Lys Arg Lys Ser Thr Ala Asp Leu Ala Ala Gln Met Ala Lys
1               5                   10                  15

Leu Asn Gly Asn Lys Gly Phe Ser Ser Glu Asp Lys Gly Glu Trp Lys
            20                  25                  30

Leu Lys Leu Asp Ala Ser Gly Asn Gly Gln Ala Val Ile Arg Phe Leu
        35                  40                  45

Pro Ala Lys Thr Asp Asp Ala Leu Pro Phe Ala Ile Leu Val Asn His
    50                  55                  60

Gly Phe Lys Lys Asn Gly Lys Trp Tyr Ile Glu Thr Cys Ser Ser Thr
65                  70                  75                  80

His Gly Asp Tyr Asp Ser Cys Pro Val Cys Gln Tyr Ile Ser Lys Asn
                85                  90                  95

Asp Leu Tyr Asn Thr Asn Lys Thr Glu Tyr Ser Gln Leu Lys Arg Lys
            100                 105                 110

Thr Ser Tyr Trp Ala Asn Ile Leu Val Val Lys Asp Pro Gln Ala Pro
        115                 120                 125

Asp Asn Glu Gly Lys Val Phe Lys Tyr Arg Phe Gly Lys Lys Ile Trp
    130                 135                 140

Asp Lys Ile Asn Ala Met Ile Ala Val Asp Thr Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
            180                 185                 190

Asn Gln Ser Ala Ile Pro Asn Ile Asp Asp Glu Ser Phe Gln Lys Glu
        195                 200                 205

Leu Phe Glu Gln Met Val Asp Leu Ser Glu Met Thr Ser Lys Asp Lys
    210                 215                 220

Phe Lys Ser Phe Glu Glu Leu Asn Thr Lys Phe Asn Gln Val Leu Gly
225                 230                 235                 240
```

```
Thr Ala Ala Leu Gly Gly Ala Ala Ala Ala Ser Val Ala Asp
                245                 250                 255

Lys Val Ala Ser Asp Leu Asp Asp Phe Asp Lys Asp Met Glu Ala Phe
            260                 265                 270

Ser Ser Ala Lys Thr Glu Asp Asp Phe Met Ser Ser Ser Ser Asp
            275                 280                 285

Asp Gly Asp Leu Asp Asp Leu Leu Ala Gly Leu
        290                 295
```

<210> SEQ ID NO 26
<211> LENGTH: 232
<212> TYPE: PRT
<213> ORGANISM: Bacteriophage T7

<400> SEQUENCE: 26

```
Met Ala Lys Lys Ile Phe Thr Ser Ala Leu Gly Thr Ala Glu Pro Tyr
1               5                   10                  15

Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

Ala Arg Gly Lys Lys Pro Leu Lys Pro Tyr Glu Gly Asp Met Pro Phe
                85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Glu Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Glu Glu Ser Glu
    210                 215                 220

Glu Ala Asp Glu Asp Gly Asp Phe
225                 230
```

<210> SEQ ID NO 27
<211> LENGTH: 324
<212> TYPE: PRT
<213> ORGANISM: Herpes virus 1

<400> SEQUENCE: 27

```
Met Asp Ser Pro Gly Gly Val Ala Pro Ala Ser Pro Val Glu Asp Ala
1               5                   10                  15

Ser Asp Ala Ser Leu Gly Gln Pro Glu Glu Gly Ala Pro Cys Gln Val
            20                  25                  30
```

Val Leu Gln Gly Ala Glu Leu Asn Gly Ile Leu Gln Ala Phe Ala Pro
            35                  40                  45

Leu Arg Thr Ser Leu Leu Asp Ser Leu Leu Val Met Gly Asp Arg Gly
 50                  55                  60

Ile Leu Ile His Asn Thr Ile Phe Gly Glu Gln Val Phe Leu Pro Leu
 65                  70                  75                  80

Glu His Ser Gln Phe Ser Arg Tyr Arg Trp Arg Gly Pro Thr Ala Ala
                 85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
            115                 120                 125

Gln Ala Pro Phe Arg Thr Leu Val Gln Arg Ile Trp Thr Thr Thr Ser
130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
            180                 185                 190

Ala Asp Ser Ala Thr Pro Thr Thr Phe Glu Leu Gly Val Asn Gly Lys
            195                 200                 205

Phe Ser Val Phe Thr Thr Ser Thr Cys Val Thr Phe Ala Ala Arg Glu
210                 215                 220

Glu Gly Val Ser Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
                245                 250                 255

Gly Glu Asn Thr His Arg Thr Phe Ser Val Val Val Asp Asp Cys Ser
            260                 265                 270

Met Arg Ala Val Leu Arg Arg Leu Gln Val Gly Gly Thr Leu Lys
            275                 280                 285

Phe Phe Leu Thr Thr Pro Val Pro Ser Leu Cys Val Thr Ala Thr Gly
            290                 295                 300

Pro Asn Ala Val Ser Ala Val Phe Leu Leu Lys Pro Gln Lys His His
305                 310                 315                 320

His His His His

<210> SEQ ID NO 28
<211> LENGTH: 251
<212> TYPE: PRT
<213> ORGANISM: Artificial Sequence
<220> FEATURE:
<223> OTHER INFORMATION: subunit 1 of PCNA

<400> SEQUENCE: 28

Met Phe Lys Ile Val Tyr Pro Asn Ala Lys Asp Phe Phe Ser Phe Ile
1               5                   10                  15

Asn Ser Ile Thr Asn Val Thr Asp Ser Ile Ile Leu Asn Phe Thr Glu
            20                  25                  30

Asp Gly Ile Phe Ser Arg His Leu Thr Glu Asp Lys Val Leu Met Ala
            35                  40                  45

Ile Met Arg Ile Pro Lys Asp Val Leu Ser Glu Tyr Ser Ile Asp Ser
 50                  55                  60

```
Pro Thr Ser Val Lys Leu Asp Val Ser Ser Val Lys Lys Ile Leu Ser
 65                  70                  75                  80

Lys Ala Ser Ser Lys Lys Ala Thr Ile Glu Leu Thr Glu Thr Asp Ser
                 85                  90                  95

Gly Leu Lys Ile Ile Ile Arg Asp Glu Lys Ser Gly Ala Lys Ser Thr
            100                 105                 110

Ile Tyr Ile Lys Ala Glu Lys Gly Gln Val Glu Gln Leu Thr Glu Pro
        115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Glu Met Arg Ile Ser
145                 150                 155                 160

Thr Glu Glu Asp Lys Ile Lys Ile Glu Ala Gly Glu Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
        195                 200                 205

Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
225                 230                 235                 240

Met Ile Phe Trp Ile Ala Pro Arg Leu Leu Glu
                245                 250

<210> SEQ ID NO 29
<211> LENGTH: 245
<212> TYPE: PRT
<213> ORGANISM: Artificial Sequence
<220> FEATURE:
<223> OTHER INFORMATION: subunit 2 of PCNA

<400> SEQUENCE: 29

Met Lys Ala Lys Val Ile Asp Ala Val Ser Phe Ser Tyr Ile Leu Arg
 1               5                  10                  15

Thr Val Gly Asp Phe Leu Ser Glu Ala Asn Phe Ile Val Thr Lys Glu
                20                  25                  30

Gly Ile Arg Val Ser Gly Ile Asp Pro Ser Arg Val Val Phe Leu Asp
            35                  40                  45

Ile Phe Leu Pro Ser Ser Tyr Phe Glu Gly Phe Glu Val Ser Gln Glu
        50                  55                  60

Lys Glu Ile Ile Gly Phe Lys Leu Glu Asp Val Asn Asp Ile Leu Lys
 65                  70                  75                  80

Arg Val Leu Lys Asp Asp Thr Leu Ile Leu Ser Ser Asn Glu Ser Lys
                 85                  90                  95

Leu Thr Leu Thr Phe Asp Gly Glu Phe Thr Arg Ser Phe Glu Leu Pro
            100                 105                 110

Leu Ile Gln Val Glu Ser Thr Gln Pro Ser Val Asn Leu Glu Phe
        115                 120                 125

Pro Phe Lys Ala Gln Leu Leu Thr Ile Thr Phe Ala Asp Ile Ile Asp
    130                 135                 140

Glu Leu Ser Asp Leu Gly Glu Val Leu Asn Ile His Ser Lys Glu Asn
145                 150                 155                 160

Lys Leu Tyr Phe Glu Val Ile Gly Asp Leu Ser Thr Ala Lys Val Glu
                165                 170                 175
```

```
Leu Ser Thr Asp Asn Gly Thr Leu Leu Glu Ala Ser Gly Ala Asp Val
            180                 185                 190

Ser Ser Ser Tyr Gly Met Glu Tyr Val Ala Asn Thr Thr Lys Met Arg
            195                 200                 205

Arg Ala Ser Asp Ser Met Glu Leu Tyr Phe Gly Ser Gln Ile Pro Leu
            210                 215                 220

Lys Leu Arg Phe Lys Leu Pro Gln Glu Gly Tyr Gly Asp Phe Tyr Ile
225                 230                 235                 240

Ala Pro Arg Ala Asp
                245

<210> SEQ ID NO 30
<211> LENGTH: 246
<212> TYPE: PRT
<213> ORGANISM: Artificial Sequence
<220> FEATURE:
<223> OTHER INFORMATION: sununit 3 of PCNA

<400> SEQUENCE: 30

Met Lys Val Val Tyr Asp Asp Val Arg Val Leu Lys Asp Ile Ile Gln
1               5                   10                  15

Ala Leu Ala Arg Leu Val Asp Glu Ala Val Leu Lys Phe Lys Gln Asp
            20                  25                  30

Ser Val Glu Leu Val Ala Leu Asp Arg Ala His Ile Ser Leu Ile Ser
            35                  40                  45

Val Asn Leu Pro Arg Glu Met Phe Lys Glu Tyr Asp Val Asn Asp Glu
        50                  55                  60

Phe Lys Phe Gly Phe Asn Thr Gln Tyr Leu Met Lys Ile Leu Lys Val
65                  70                  75                  80

Ala Lys Arg Lys Glu Ala Ile Glu Ile Ala Ser Glu Ser Pro Asp Ser
                85                  90                  95

Val Ile Ile Asn Ile Ile Gly Ser Thr Asn Arg Glu Phe Asn Val Arg
            100                 105                 110

Asn Leu Glu Val Ser Glu Gln Glu Ile Pro Glu Ile Asn Leu Gln Phe
            115                 120                 125

Asp Ile Ser Ala Thr Ile Ser Ser Asp Gly Phe Lys Ser Ala Ile Ser
        130                 135                 140

Glu Val Ser Thr Val Thr Asp Asn Val Val Glu Gly His Glu Asp
145                 150                 155                 160

Arg Ile Leu Ile Lys Ala Glu Gly Glu Ser Glu Val Glu Val Glu Phe
                165                 170                 175

Ser Lys Asp Thr Gly Gly Leu Gln Asp Leu Glu Phe Ser Lys Glu Ser
            180                 185                 190

Lys Asn Ser Tyr Ser Ala Glu Tyr Leu Asp Asp Val Leu Ser Leu Thr
            195                 200                 205

Lys Leu Ser Asp Tyr Val Lys Ile Ser Phe Gly Asn Gln Lys Pro Leu
        210                 215                 220

Gln Leu Phe Phe Asn Met Glu Gly Gly Gly Lys Val Thr Tyr Leu Leu
225                 230                 235                 240

Ala Pro Lys Val Leu Glu
                245

<210> SEQ ID NO 31
<211> LENGTH: 608
<212> TYPE: PRT
<213> ORGANISM: Bacillus subtilis phage phi29
```

<400> SEQUENCE: 31

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415
```

```
Gly Glu Glu Glu Thr Lys Asp Pro Val Tyr Thr Pro Met Gly Val Phe
            420                 425                 430

Ile Thr Ala Trp Ala Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Ser
            580                 585                 590

Gly Gly Gly Ser Gly Gly Ser Ala Trp Ser His Pro Gln Phe Glu Lys
            595                 600                 605

<210> SEQ ID NO 32
<211> LENGTH: 318
<212> TYPE: PRT
<213> ORGANISM: Herpes virus 1

<400> SEQUENCE: 32

Thr Asp Ser Pro Gly Gly Val Ala Pro Ala Ser Pro Val Glu Asp Ala
1               5                   10                  15

Ser Asp Ala Ser Leu Gly Gln Pro Glu Glu Gly Ala Pro Cys Gln Val
            20                  25                  30

Val Leu Gln Gly Ala Glu Leu Asn Gly Ile Leu Gln Ala Phe Ala Pro
        35                  40                  45

Leu Arg Thr Ser Leu Leu Asp Ser Leu Leu Val Met Gly Asp Arg Gly
50                  55                  60

Ile Leu Ile His Asn Thr Ile Phe Gly Glu Gln Val Phe Leu Pro Leu
65                  70                  75                  80

Glu His Ser Gln Phe Ser Arg Tyr Arg Trp Arg Gly Pro Thr Ala Ala
                85                  90                  95

Phe Leu Ser Leu Val Asp Gln Lys Arg Ser Leu Leu Ser Val Phe Arg
            100                 105                 110

Ala Asn Gln Tyr Pro Asp Leu Arg Arg Val Glu Leu Ala Ile Thr Gly
        115                 120                 125

Gln Ala Pro Phe Arg Thr Leu Val Gln Arg Ile Trp Thr Thr Thr Ser
    130                 135                 140

Asp Gly Glu Ala Val Glu Leu Ala Ser Glu Thr Leu Met Lys Arg Glu
145                 150                 155                 160

Leu Thr Ser Phe Val Val Leu Val Pro Gln Gly Thr Pro Asp Val Gln
                165                 170                 175

Leu Arg Leu Thr Arg Pro Gln Leu Thr Lys Val Leu Asn Ala Thr Gly
```

```
                180              185                 190
Ala Asp Ser Ala Thr Pro Thr Thr Phe Glu Leu Gly Val Asn Gly Lys
            195                 200                 205

Phe Ser Val Phe Thr Thr Ser Thr Cys Val Thr Phe Ala Ala Arg Glu
        210                 215                 220

Glu Gly Val Ser Ser Ser Thr Ser Thr Gln Val Gln Ile Leu Ser Asn
225                 230                 235                 240

Ala Leu Thr Lys Ala Gly Gln Ala Ala Asn Ala Lys Thr Val Tyr
            245                 250                 255

Gly Glu Asn Thr His Arg Thr Phe Ser Val Val Asp Asp Cys Ser
            260                 265                 270

Met Arg Ala Val Leu Arg Arg Leu Gln Val Gly Gly Thr Leu Lys
        275                 280                 285

Phe Phe Leu Thr Thr Pro Val Pro Ser Leu Cys Val Thr Ala Thr Gly
        290                 295                 300

Pro Asn Ala Val Ser Ala Val Phe Leu Leu Lys Pro Gln Lys
305                 310                 315

<210> SEQ ID NO 33
<211> LENGTH: 233
<212> TYPE: PRT
<213> ORGANISM: Bacteriophage RB69

<400> SEQUENCE: 33

Lys Gly Phe Ser Ser Glu Asp Lys Gly Glu Trp Lys Leu Lys Leu Asp
1               5                   10                  15

Ala Ser Gly Asn Gly Gln Ala Val Ile Arg Phe Leu Pro Ala Lys Thr
            20                  25                  30

Asp Asp Ala Leu Pro Phe Ala Ile Leu Val Asn His Gly Phe Lys Lys
        35                  40                  45

Asn Gly Lys Trp Tyr Ile Glu Thr Cys Ser Ser Thr His Gly Asp Tyr
    50                  55                  60

Asp Ser Cys Pro Val Cys Gln Tyr Ile Ser Lys Asn Asp Leu Tyr Asn
65                  70                  75                  80

Thr Asn Lys Thr Glu Tyr Ser Gln Leu Lys Arg Lys Thr Ser Tyr Trp
                85                  90                  95

Ala Asn Ile Leu Val Val Lys Asp Pro Gln Ala Pro Asp Asn Glu Gly
            100                 105                 110

Lys Val Phe Lys Tyr Arg Phe Gly Lys Lys Ile Trp Asp Lys Ile Asn
        115                 120                 125

Ala Met Ile Ala Val Asp Thr Glu Met Gly Glu Thr Pro Val Asp Val
    130                 135                 140

Thr Cys Pro Trp Glu Gly Ala Asn Phe Val Leu Lys Val Lys Gln Val
145                 150                 155                 160

Ser Gly Phe Ser Asn Tyr Asp Glu Ser Lys Phe Leu Asn Gln Ser Ala
                165                 170                 175

Ile Pro Asn Ile Asp Asp Glu Ser Phe Gln Lys Glu Leu Phe Glu Gln
            180                 185                 190

Met Val Asp Leu Ser Glu Met Thr Ser Lys Asp Lys Phe Lys Ser Phe
        195                 200                 205

Glu Glu Leu Asn Thr Lys Phe Asn Gln Val Leu Gly Thr Ala Ala Leu
    210                 215                 220

Gly Gly Ala Ala Ala Ala Ala Ser
225                 230
```

<210> SEQ ID NO 34
<211> LENGTH: 210
<212> TYPE: PRT
<213> ORGANISM: Bacteriophage T7

<400> SEQUENCE: 34

```
Ala Lys Lys Ile Phe Thr Ser Ala Leu Gly Thr Ala Glu Pro Tyr Ala
1               5                   10                  15

Tyr Ile Ala Lys Pro Asp Tyr Gly Asn Glu Glu Arg Gly Phe Gly Asn
            20                  25                  30

Pro Arg Gly Val Tyr Lys Val Asp Leu Thr Ile Pro Asn Lys Asp Pro
        35                  40                  45

Arg Cys Gln Arg Met Val Asp Glu Ile Val Lys Cys His Glu Glu Ala
    50                  55                  60

Tyr Ala Ala Ala Val Glu Glu Tyr Glu Ala Asn Pro Pro Ala Val Ala
65                  70                  75                  80

Arg Gly Lys Lys Pro Leu Lys Pro Tyr Glu Gly Asp Met Pro Phe Phe
                85                  90                  95

Asp Asn Gly Asp Gly Thr Thr Thr Phe Lys Phe Lys Cys Tyr Ala Ser
            100                 105                 110

Phe Gln Asp Lys Lys Thr Lys Glu Thr Lys His Ile Asn Leu Val Val
        115                 120                 125

Val Asp Ser Lys Gly Lys Lys Met Glu Asp Val Pro Ile Ile Gly Gly
    130                 135                 140

Gly Ser Lys Leu Lys Val Lys Tyr Ser Leu Val Pro Tyr Lys Trp Asn
145                 150                 155                 160

Thr Ala Val Gly Ala Ser Val Lys Leu Gln Leu Glu Ser Val Met Leu
                165                 170                 175

Val Glu Leu Ala Thr Phe Gly Gly Gly Glu Asp Asp Trp Ala Asp Glu
            180                 185                 190

Val Glu Glu Asn Gly Tyr Val Ala Ser Gly Ser Ala Lys Ala Ser Lys
        195                 200                 205

Pro Arg
    210
```

<210> SEQ ID NO 35
<211> LENGTH: 99
<212> TYPE: PRT
<213> ORGANISM: Halorubrum lacusprofundi

<400> SEQUENCE: 35

```
Ser Gly Glu Glu Leu Leu Asp Leu Ala Gly Val Arg Asn Val Gly Arg
1               5                   10                  15

Lys Arg Ala Arg Arg Leu Phe Glu Ala Gly Ile Glu Thr Arg Ala Asp
            20                  25                  30

Leu Arg Glu Ala Asp Lys Ala Val Val Leu Gly Ala Leu Arg Gly Arg
        35                  40                  45

Glu Arg Thr Ala Glu Arg Ile Leu Glu His Ala Gly Arg Glu Asp Pro
    50                  55                  60

Ser Met Asp Asp Val Arg Pro Asp Lys Ser Ala Ser Ala Ala Ala Thr
65                  70                  75                  80

Ala Gly Ser Ala Ser Asp Glu Asp Gly Glu Gly Gln Ala Ser Leu Gly
                85                  90                  95

Asp Phe Arg
```

```
<210> SEQ ID NO 36
<211> LENGTH: 102
<212> TYPE: PRT
<213> ORGANISM: Haloferax volcanii

<400> SEQUENCE: 36

Ser Gly Glu Glu Leu Leu Asp Leu Ala Gly Val Arg Gly Val Gly Arg
1               5                   10                  15

Lys Arg Ala Arg Arg Leu Phe Glu Ala Gly Val Glu Thr Arg Ala Asp
            20                  25                  30

Leu Arg Glu Ala Asp Lys Pro Arg Val Leu Ala Ala Leu Arg Gly Arg
        35                  40                  45

Arg Lys Thr Ala Glu Asn Ile Leu Glu Ala Ala Gly Arg Lys Asp Pro
    50                  55                  60

Ser Met Asp Ala Val Asp Glu Asp Asp Ala Pro Asp Asp Ala Val Pro
65                  70                  75                  80

Asp Asp Ala Gly Phe Glu Thr Ala Lys Glu Arg Ala Asp Gln Gln Ala
                85                  90                  95

Ser Leu Gly Asp Phe Glu
            100

<210> SEQ ID NO 37
<211> LENGTH: 55
<212> TYPE: PRT
<213> ORGANISM: Artificial Sequence
<220> FEATURE:
<223> OTHER INFORMATION: (HhH)2 domain

<400> SEQUENCE: 37

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro
    50                  55

<210> SEQ ID NO 38
<211> LENGTH: 107
<212> TYPE: PRT
<213> ORGANISM: Artificial Sequence
<220> FEATURE:
<223> OTHER INFORMATION: (HhH)2-(HhH)2 domain

<400> SEQUENCE: 38

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu Glu Val Pro Gly Ile Gly Asp Glu
        35                  40                  45

Ala Val Ala Arg Leu Val Pro Gly Tyr Lys Thr Leu Arg Asp Ala Gly
    50                  55                  60

Leu Thr Pro Ala Glu Ala Glu Arg Val Leu Lys Arg Tyr Gly Ser Val
65                  70                  75                  80

Ser Lys Val Gln Glu Gly Ala Thr Pro Asp Glu Leu Arg Glu Leu Gly
                85                  90                  95

Leu Gly Asp Ala Lys Ile Ala Arg Ile Leu Gly
            100                 105
```

-continued

<210> SEQ ID NO 39
<211> LENGTH: 132
<212> TYPE: PRT
<213> ORGANISM: Homo sapiens

<400> SEQUENCE: 39

Glu Ser Glu Thr Thr Thr Ser Leu Val Leu Glu Arg Ser Leu Asn Arg
1               5                   10                  15

Val His Leu Leu Gly Arg Val Gly Gln Asp Pro Val Leu Arg Gln Val
            20                  25                  30

Glu Gly Lys Asn Pro Val Thr Ile Phe Ser Leu Ala Thr Asn Glu Met
        35                  40                  45

Trp Arg Ser Gly Asp Ser Glu Val Tyr Gln Leu Gly Asp Val Ser Gln
50                  55                  60

Lys Thr Thr Trp His Arg Ile Ser Val Phe Arg Pro Gly Leu Arg Asp
65                  70                  75                  80

Val Ala Tyr Gln Tyr Val Lys Lys Gly Ser Arg Ile Tyr Leu Glu Gly
                85                  90                  95

Lys Ile Asp Tyr Gly Glu Tyr Met Asp Lys Asn Asn Val Arg Arg Gln
            100                 105                 110

Ala Thr Thr Ile Ile Ala Asp Asn Ile Ile Phe Leu Ser Asp Gln Thr
        115                 120                 125

Lys Glu Lys Glu
    130

<210> SEQ ID NO 40
<211> LENGTH: 123
<212> TYPE: PRT
<213> ORGANISM: Bacillus subtilis phage phi29

<400> SEQUENCE: 40

Glu Asn Thr Asn Ile Val Lys Ala Thr Phe Asp Thr Glu Thr Leu Glu
1               5                   10                  15

Gly Gln Ile Lys Ile Phe Asn Ala Gln Thr Gly Gly Gly Gln Ser Phe
            20                  25                  30

Lys Asn Leu Pro Asp Gly Thr Ile Ile Glu Ala Asn Ala Ile Ala Gln
        35                  40                  45

Tyr Lys Gln Val Ser Asp Thr Tyr Gly Asp Ala Lys Glu Glu Thr Val
50                  55                  60

Thr Thr Ile Phe Ala Ala Asp Gly Ser Leu Tyr Ser Ala Ile Ser Lys
65                  70                  75                  80

Thr Val Ala Glu Ala Ala Ser Asp Leu Ile Asp Leu Val Thr Arg His
                85                  90                  95

Lys Leu Glu Thr Phe Lys Val Lys Val Val Gln Gly Thr Ser Ser Lys
            100                 105                 110

Gly Asn Val Phe Phe Ser Leu Gln Leu Ser Leu
        115                 120

<210> SEQ ID NO 41
<211> LENGTH: 177
<212> TYPE: PRT
<213> ORGANISM: Escherichia coli

<400> SEQUENCE: 41

Ala Ser Arg Gly Val Asn Lys Val Ile Leu Val Gly Asn Leu Gly Gln
1               5                   10                  15

```
Asp Pro Glu Val Arg Tyr Met Pro Asn Gly Gly Ala Val Ala Asn Ile
         20                  25                  30

Thr Leu Ala Thr Ser Glu Ser Trp Arg Asp Lys Ala Thr Gly Glu Met
             35                  40                  45

Lys Glu Gln Thr Glu Trp His Arg Val Val Leu Phe Gly Lys Leu Ala
 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
                 85                  90                  95

Tyr Thr Thr Glu Val Val Asn Val Gly Gly Thr Met Gln Met Leu
                100                 105                 110

Gly Gly Arg Gln Gly Gly Ala Pro Ala Gly Gly Asn Ile Gly Gly
             115                 120                 125

Gly Gln Pro Gln Gly Gly Trp Gly Gln Pro Gln Pro Gln Gly Gly
         130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Ile Pro
                165                 170                 175

Phe

<210> SEQ ID NO 42
<211> LENGTH: 301
<212> TYPE: PRT
<213> ORGANISM: Enterobacteria phage T4

<400> SEQUENCE: 42

Met Phe Lys Arg Lys Ser Thr Ala Glu Leu Ala Ala Gln Met Ala Lys
  1               5                  10                  15

Leu Asn Gly Asn Lys Gly Phe Ser Ser Glu Asp Lys Gly Glu Trp Lys
             20                  25                  30

Leu Lys Leu Asp Asn Ala Gly Asn Gly Gln Ala Val Ile Arg Phe Leu
         35                  40                  45

Pro Ser Lys Asn Asp Glu Gln Ala Pro Phe Ala Ile Leu Val Asn His
 50                  55                  60

Gly Phe Lys Lys Asn Gly Lys Trp Tyr Ile Glu Thr Cys Ser Ser Thr
 65                  70                  75                  80

His Gly Asp Tyr Asp Ser Cys Pro Val Cys Gln Tyr Ile Ser Lys Asn
                 85                  90                  95

Asp Leu Tyr Asn Thr Asp Asn Lys Glu Tyr Ser Leu Val Lys Arg Lys
                100                 105                 110

Thr Ser Tyr Trp Ala Asn Ile Leu Val Val Lys Asp Pro Ala Ala Pro
             115                 120                 125

Glu Asn Glu Gly Lys Val Phe Lys Tyr Arg Phe Gly Lys Lys Ile Trp
         130                 135                 140

Asp Lys Ile Asn Ala Met Ile Ala Val Asp Val Glu Met Gly Glu Thr
145                 150                 155                 160

Pro Val Asp Val Thr Cys Pro Trp Glu Gly Ala Asn Phe Val Leu Lys
                165                 170                 175

Val Lys Gln Val Ser Gly Phe Ser Asn Tyr Asp Glu Ser Lys Phe Leu
                180                 185                 190

Asn Gln Ser Ala Ile Pro Asn Ile Asp Asp Glu Ser Phe Gln Lys Glu
             195                 200                 205
```

```
Leu Phe Glu Gln Met Val Asp Leu Ser Glu Met Thr Ser Lys Asp Lys
    210                 215                 220
Phe Lys Ser Phe Glu Glu Leu Asn Thr Lys Phe Gly Gln Val Met Gly
225                 230                 235                 240
Thr Ala Val Met Gly Gly Ala Ala Ala Thr Ala Ala Lys Lys Ala Asp
                245                 250                 255
Lys Val Ala Asp Asp Leu Asp Ala Phe Asn Val Asp Asp Phe Asn Thr
            260                 265                 270
Lys Thr Glu Asp Asp Phe Met Ser Ser Ser Ser Gly Ser Ser Ser Ser
        275                 280                 285
Ala Asp Asp Thr Asp Leu Asp Asp Leu Leu Asn Asp Leu
        290                 295                 300

<210> SEQ ID NO 43
<211> LENGTH: 177
<212> TYPE: PRT
<213> ORGANISM: Artificial Sequence
<220> FEATURE:
<223> OTHER INFORMATION: EcoSSB-CterAla

<400> SEQUENCE: 43

Ala Ser Arg Gly Val Asn Lys Val Ile Leu Val Gly Asn Leu Gly Gln
1               5                   10                  15
Asp Pro Glu Val Arg Tyr Met Pro Asn Gly Gly Ala Val Ala Asn Ile
            20                  25                  30
Thr Leu Ala Thr Ser Glu Ser Trp Arg Asp Lys Ala Thr Gly Glu Met
        35                  40                  45
Lys Glu Gln Thr Glu Trp His Arg Val Val Leu Phe Gly Lys Leu Ala
    50                  55                  60
Glu Val Ala Ser Glu Tyr Leu Arg Lys Gly Ser Gln Val Tyr Ile Glu
65                  70                  75                  80
Gly Gln Leu Arg Thr Arg Lys Trp Thr Asp Gln Ser Gly Gln Asp Arg
                85                  90                  95
Tyr Thr Thr Glu Val Val Val Asn Val Gly Gly Thr Met Gln Met Leu
            100                 105                 110
Gly Gly Arg Gln Gly Gly Gly Ala Pro Ala Gly Gly Asn Ile Gly Gly
        115                 120                 125
Gly Gln Pro Gln Gly Gly Trp Gly Gln Pro Gln Pro Gln Gly Gly
    130                 135                 140
Asn Gln Phe Ser Gly Gly Ala Gln Ser Arg Pro Gln Gln Ser Ala Pro
145                 150                 155                 160
Ala Ala Pro Ser Asn Glu Pro Pro Met Ala Phe Ala Ala Ile Pro
                165                 170                 175
Phe

<210> SEQ ID NO 44
<211> LENGTH: 177
<212> TYPE: PRT
<213> ORGANISM: Artificial Sequence
<220> FEATURE:
<223> OTHER INFORMATION: EcoSSB-CterNGGN

<400> SEQUENCE: 44

Ala Ser Arg Gly Val Asn Lys Val Ile Leu Val Gly Asn Leu Gly Gln
1               5                   10                  15
Asp Pro Glu Val Arg Tyr Met Pro Asn Gly Gly Ala Val Ala Asn Ile
            20                  25                  30
```

```
Thr Leu Ala Thr Ser Glu Ser Trp Arg Asp Lys Ala Thr Gly Glu Met
         35                  40                  45

Lys Glu Gln Thr Glu Trp His Arg Val Val Leu Phe Gly Lys Leu Ala
 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
                 85                  90                  95

Tyr Thr Thr Glu Val Val Val Asn Val Gly Gly Thr Met Gln Met Leu
                100                 105                 110

Gly Gly Arg Gln Gly Gly Gly Ala Pro Ala Gly Gly Asn Ile Gly Gly
                115                 120                 125

Gly Gln Pro Gln Gly Gly Trp Gly Gln Pro Gln Gln Pro Gln Gly Gly
            130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asn Phe Gly Gly Asn Ile Pro
                165                 170                 175

Phe

<210> SEQ ID NO 45
<211> LENGTH: 152
<212> TYPE: PRT
<213> ORGANISM: Artificial Sequence
<220> FEATURE:
<223> OTHER INFORMATION: EcoSSB-Q152del

<400> SEQUENCE: 45

Ala Ser Arg Gly Val Asn Lys Val Ile Leu Val Gly Asn Leu Gly Gln
1               5                  10                  15

Asp Pro Glu Val Arg Tyr Met Pro Asn Gly Gly Ala Val Ala Asn Ile
                 20                  25                  30

Thr Leu Ala Thr Ser Glu Ser Trp Arg Asp Lys Ala Thr Gly Glu Met
         35                  40                  45

Lys Glu Gln Thr Glu Trp His Arg Val Val Leu Phe Gly Lys Leu Ala
 50                  55                  60

Glu Val Ala Ser Glu Tyr Leu Arg Lys Gly Ser Gln Val Tyr Ile Glu
 65                  70                  75                  80

Gly Gln Leu Arg Thr Arg Lys Trp Thr Asp Gln Ser Gly Gln Asp Arg
                 85                  90                  95

Tyr Thr Thr Glu Val Val Val Asn Val Gly Gly Thr Met Gln Met Leu
                100                 105                 110

Gly Gly Arg Gln Gly Gly Gly Ala Pro Ala Gly Gly Asn Ile Gly Gly
                115                 120                 125

Gly Gln Pro Gln Gly Gly Trp Gly Gln Pro Gln Gln Pro Gln Gly Gly
            130                 135                 140

Asn Gln Phe Ser Gly Gly Ala Gln
145                 150

<210> SEQ ID NO 46
<211> LENGTH: 117
<212> TYPE: PRT
<213> ORGANISM: Artificial Sequence
<220> FEATURE:
<223> OTHER INFORMATION: EcoSSB-G117del

<400> SEQUENCE: 46
```

```
Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
            35                  40                  45

Lys Glu Gln Thr Glu Trp His Arg Val Val Leu Phe Gly Lys Leu Ala
50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly
        115
```

<210> SEQ ID NO 47
<211> LENGTH: 984
<212> TYPE: PRT
<213> ORGANISM: Methanopyrus kandleri

<400> SEQUENCE: 47

```
Met Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30

Val Leu Ala Thr Arg Tyr Leu Met Glu Arg Ser Ser Ser Ala Lys Asn
            35                  40                  45

Asp Glu Glu Leu Leu Glu Leu His Gln Asn Phe Ile Leu Leu Thr Gly
50                  55                  60

Ser Tyr Ala Cys Ser Ile Asp Pro Thr Glu Asp Arg Tyr Gln Asn Val
65                  70                  75                  80

Ile Val Arg Gly Val Asn Phe Asp Glu Arg Val Gln Arg Leu Ser Thr
                85                  90                  95

Gly Gly Ser Pro Ala Arg Tyr Ala Ile Val Tyr Arg Arg Gly Trp Arg
            100                 105                 110

Ala Ile Ala Lys Ala Leu Asp Ile Asp Glu Glu Asp Val Pro Ala Ile
            115                 120                 125

Glu Val Arg Ala Val Lys Arg Asn Pro Leu Gln Pro Ala Leu Tyr Arg
            130                 135                 140

Ile Leu Val Arg Tyr Gly Arg Val Asp Leu Met Pro Val Thr Val Asp
145                 150                 155                 160

Glu Val Pro Pro Glu Met Ala Gly Glu Phe Glu Arg Leu Ile Glu Arg
                165                 170                 175

Tyr Asp Val Pro Ile Asp Glu Lys Glu Glu Arg Ile Leu Glu Ile Leu
            180                 185                 190

Arg Glu Asn Pro Trp Thr Pro His Asp Glu Ile Ala Arg Arg Leu Gly
            195                 200                 205

Leu Ser Val Ser Glu Val Gly Glu Lys Asp Pro Glu Ser Ser Gly
            210                 215                 220

Ile Tyr Ser Leu Trp Ser Arg Val Val Asn Ile Glu Tyr Asp Glu
225                 230                 235                 240

Arg Thr Ala Lys Arg His Val Lys Arg Arg Asp Arg Leu Leu Glu Glu
```

```
                245                 250                 255
Leu Tyr Glu His Leu Glu Glu Leu Ser Glu Arg Tyr Leu Arg His Pro
            260                 265                 270
Leu Thr Arg Arg Trp Ile Val Glu His Lys Arg Asp Ile Met Arg Arg
            275                 280                 285
Tyr Leu Glu Gln Arg Ile Val Glu Cys Ala Leu Lys Leu Gln Asp Arg
            290                 295                 300
Tyr Gly Ile Arg Glu Asp Val Ala Leu Cys Leu Ala Arg Ala Phe Asp
305                 310                 315                 320
Gly Ser Ile Ser Met Ile Ala Thr Thr Pro Tyr Arg Thr Leu Lys Asp
                325                 330                 335
Val Cys Pro Asp Leu Thr Leu Glu Glu Ala Lys Ser Val Asn Arg Thr
            340                 345                 350
Leu Ala Thr Leu Ile Asp Glu His Gly Leu Ser Pro Asp Ala Ala Asp
            355                 360                 365
Glu Leu Ile Glu His Phe Glu Ser Ile Ala Gly Ile Leu Ala Thr Asp
            370                 375                 380
Leu Glu Glu Ile Glu Arg Met Tyr Glu Glu Gly Arg Leu Ser Glu Glu
385                 390                 395                 400
Ala Tyr Arg Ala Ala Val Glu Ile Gln Leu Ala Glu Leu Thr Lys Lys
                405                 410                 415
Glu Gly Val Gly Arg Lys Thr Ala Glu Arg Leu Leu Arg Ala Phe Gly
            420                 425                 430
Asn Pro Glu Arg Val Lys Gln Leu Ala Arg Glu Phe Glu Ile Glu Lys
            435                 440                 445
Leu Ala Ser Val Glu Gly Val Gly Glu Arg Val Leu Arg Ser Leu Val
450                 455                 460
Pro Gly Tyr Ala Ser Leu Ile Ser Ile Arg Gly Ile Asp Arg Glu Arg
465                 470                 475                 480
Ala Glu Arg Leu Leu Lys Lys Tyr Gly Gly Tyr Ser Lys Val Arg Glu
                485                 490                 495
Ala Gly Val Glu Glu Leu Arg Glu Asp Gly Leu Thr Asp Ala Gln Ile
            500                 505                 510
Arg Glu Leu Lys Gly Leu Lys Thr Leu Glu Ser Ile Val Gly Asp Leu
            515                 520                 525
Glu Lys Ala Asp Glu Leu Lys Arg Lys Tyr Gly Ser Ala Ser Ala Val
            530                 535                 540
Arg Arg Leu Pro Val Glu Glu Leu Arg Glu Leu Gly Phe Ser Asp Asp
545                 550                 555                 560
Glu Ile Ala Glu Ile Lys Gly Ile Pro Lys Lys Leu Arg Glu Ala Phe
                565                 570                 575
Asp Leu Glu Thr Ala Ala Glu Leu Tyr Glu Arg Tyr Gly Ser Leu Lys
            580                 585                 590
Glu Ile Gly Arg Arg Leu Ser Tyr Asp Asp Leu Leu Glu Leu Gly Ala
            595                 600                 605
Thr Pro Lys Ala Ala Ala Glu Ile Lys Gly Pro Glu Phe Lys Phe Leu
            610                 615                 620
Leu Asn Ile Glu Gly Val Gly Pro Lys Leu Ala Glu Arg Ile Leu Glu
625                 630                 635                 640
Ala Val Asp Tyr Asp Leu Glu Arg Leu Ala Ser Leu Asn Pro Glu Glu
                645                 650                 655
Leu Ala Glu Lys Val Glu Gly Leu Gly Glu Glu Leu Ala Glu Arg Val
            660                 665                 670
```

Val Tyr Ala Ala Arg Glu Arg Val Glu Ser Arg Arg Lys Ser Gly Arg
            675                 680                 685

Gln Glu Arg Ser Glu Glu Glu Trp Lys Glu Trp Leu Glu Arg Lys Val
        690                 695                 700

Gly Glu Gly Arg Ala Arg Arg Leu Ile Glu Tyr Phe Gly Ser Ala Gly
705                 710                 715                 720

Glu Val Gly Lys Leu Val Glu Asn Ala Glu Val Ser Lys Leu Leu Glu
                725                 730                 735

Val Pro Gly Ile Gly Asp Glu Ala Val Ala Arg Leu Val Pro Gly Tyr
            740                 745                 750

Lys Thr Leu Arg Asp Ala Gly Leu Thr Pro Ala Glu Ala Glu Arg Val
        755                 760                 765

Leu Lys Arg Tyr Gly Ser Val Ser Lys Val Gln Glu Gly Ala Thr Pro
    770                 775                 780

Asp Glu Leu Arg Glu Leu Gly Leu Gly Asp Ala Lys Ile Ala Arg Ile
785                 790                 795                 800

Leu Gly Leu Arg Ser Leu Val Asn Lys Arg Leu Asp Val Asp Thr Ala
                805                 810                 815

Tyr Glu Leu Lys Arg Arg Tyr Gly Ser Val Ser Ala Val Arg Lys Ala
            820                 825                 830

Pro Val Lys Glu Leu Arg Glu Leu Gly Leu Ser Asp Arg Lys Ile Ala
        835                 840                 845

Arg Ile Lys Gly Ile Pro Glu Thr Met Leu Gln Val Arg Gly Met Ser
    850                 855                 860

Val Glu Lys Ala Glu Arg Leu Leu Glu Arg Phe Asp Thr Trp Thr Lys
865                 870                 875                 880

Val Lys Glu Ala Pro Val Ser Glu Leu Val Arg Val Pro Gly Val Gly
                885                 890                 895

Leu Ser Leu Val Lys Glu Ile Lys Ala Gln Val Asp Pro Ala Trp Lys
            900                 905                 910

Ala Leu Leu Asp Val Lys Gly Val Ser Pro Glu Leu Ala Asp Arg Leu
        915                 920                 925

Val Glu Glu Leu Gly Ser Pro Tyr Arg Val Leu Thr Ala Lys Lys Ser
    930                 935                 940

Asp Leu Met Arg Val Glu Arg Val Gly Pro Lys Leu Ala Glu Arg Ile
945                 950                 955                 960

Arg Ala Ala Gly Lys Arg Tyr Val Glu Arg Arg Ser Arg Glu
                965                 970                 975

Arg Ile Arg Arg Lys Leu Arg Gly
            980

<210> SEQ ID NO 48
<211> LENGTH: 299
<212> TYPE: PRT
<213> ORGANISM: Methanopyrus kandleri

<400> SEQUENCE: 48

Ser Gly Arg Gln Glu Arg Ser Glu Glu Glu Trp Lys Glu Trp Leu Glu
1               5                   10                  15

Arg Lys Val Gly Glu Gly Arg Ala Arg Arg Leu Ile Glu Tyr Phe Gly
            20                  25                  30

Ser Ala Gly Glu Val Gly Lys Leu Val Glu Asn Ala Glu Val Ser Lys
        35                  40                  45

Leu Leu Glu Val Pro Gly Ile Gly Asp Glu Ala Val Ala Arg Leu Val

```
            50                  55                  60
Pro Gly Tyr Lys Thr Leu Arg Asp Ala Gly Leu Thr Pro Ala Glu Ala
 65                  70                  75                  80

Glu Arg Val Leu Lys Arg Tyr Gly Ser Val Ser Lys Val Gln Glu Gly
                 85                  90                  95

Ala Thr Pro Asp Glu Leu Arg Glu Leu Gly Leu Gly Asp Ala Lys Ile
            100                 105                 110

Ala Arg Ile Leu Gly Leu Arg Ser Leu Val Asn Lys Arg Leu Asp Val
        115                 120                 125

Asp Thr Ala Tyr Glu Leu Lys Arg Arg Tyr Gly Ser Val Ser Ala Val
    130                 135                 140

Arg Lys Ala Pro Val Lys Glu Leu Arg Glu Leu Gly Leu Ser Asp Arg
145                 150                 155                 160

Lys Ile Ala Arg Ile Lys Gly Ile Pro Glu Thr Met Leu Gln Val Arg
                165                 170                 175

Gly Met Ser Val Glu Lys Ala Glu Arg Leu Leu Glu Arg Phe Asp Thr
            180                 185                 190

Trp Thr Lys Val Lys Glu Ala Pro Val Ser Glu Leu Val Arg Val Pro
        195                 200                 205

Gly Val Gly Leu Ser Leu Val Lys Glu Ile Lys Ala Gln Val Asp Pro
    210                 215                 220

Ala Trp Lys Ala Leu Leu Asp Val Lys Gly Val Ser Pro Glu Leu Ala
225                 230                 235                 240

Asp Arg Leu Val Glu Glu Leu Gly Ser Pro Tyr Arg Val Leu Thr Ala
                245                 250                 255

Lys Lys Ser Asp Leu Met Arg Val Glu Arg Val Gly Pro Lys Leu Ala
            260                 265                 270

Glu Arg Ile Arg Ala Ala Gly Lys Arg Tyr Val Glu Arg Arg Ser
        275                 280                 285

Arg Arg Glu Arg Ile Arg Lys Leu Arg Gly
    290                 295

<210> SEQ ID NO 49
<211> LENGTH: 853
<212> TYPE: PRT
<213> ORGANISM: Escherichia coli

<400> SEQUENCE: 49

Met Ser Ala Ile Glu Asn Phe Asp Ala His Thr Pro Met Met Gln Gln
 1               5                  10                  15

Tyr Leu Arg Leu Lys Ala Gln His Pro Glu Ile Leu Leu Phe Tyr Arg
                20                  25                  30

Met Gly Asp Phe Tyr Glu Leu Phe Tyr Asp Asp Ala Lys Arg Ala Ser
            35                  40                  45

Gln Leu Leu Asp Ile Ser Leu Thr Lys Arg Gly Ala Ser Ala Gly Glu
        50                  55                  60

Pro Ile Pro Met Ala Gly Ile Pro Tyr His Ala Val Glu Asn Tyr Leu
 65                  70                  75                  80

Ala Lys Leu Val Asn Gln Gly Glu Ser Val Ala Ile Cys Glu Gln Ile
                 85                  90                  95

Gly Asp Pro Ala Thr Ser Lys Gly Pro Val Glu Arg Lys Val Val Arg
            100                 105                 110

Ile Val Thr Pro Gly Thr Ile Ser Asp Glu Ala Leu Leu Gln Glu Arg
        115                 120                 125
```

-continued

```
Gln Asp Asn Leu Leu Ala Ala Ile Trp Gln Asp Ser Lys Gly Phe Gly
    130                 135                 140
Tyr Ala Thr Leu Asp Ile Ser Ser Gly Arg Phe Arg Leu Ser Glu Pro
145                 150                 155                 160
Ala Asp Arg Glu Thr Met Ala Ala Glu Leu Gln Arg Thr Asn Pro Ala
                165                 170                 175
Glu Leu Leu Tyr Ala Glu Asp Phe Ala Glu Met Ser Leu Ile Glu Gly
            180                 185                 190
Arg Arg Gly Leu Arg Arg Pro Leu Trp Glu Phe Glu Ile Asp Thr
        195                 200                 205
Ala Arg Gln Gln Leu Asn Leu Gln Phe Gly Thr Arg Asp Leu Val Gly
    210                 215                 220
Phe Gly Val Glu Asn Ala Pro Arg Gly Leu Cys Ala Ala Gly Cys Leu
225                 230                 235                 240
Leu Gln Tyr Ala Lys Asp Thr Gln Arg Thr Thr Leu Pro His Ile Arg
                245                 250                 255
Ser Ile Thr Met Glu Arg Glu Gln Asp Ser Ile Ile Met Asp Ala Ala
            260                 265                 270
Thr Arg Arg Asn Leu Glu Ile Thr Gln Asn Leu Ala Gly Gly Ala Glu
        275                 280                 285
Asn Thr Leu Ala Ser Val Leu Asp Cys Thr Val Thr Pro Met Gly Ser
    290                 295                 300
Arg Met Leu Lys Arg Trp Leu His Met Pro Val Arg Asp Thr Arg Val
305                 310                 315                 320
Leu Leu Glu Arg Gln Gln Thr Ile Gly Ala Leu Gln Asp Phe Thr Ala
                325                 330                 335
Gly Leu Gln Pro Val Leu Arg Gln Val Gly Asp Leu Glu Arg Ile Leu
            340                 345                 350
Ala Arg Leu Ala Leu Arg Thr Ala Arg Pro Arg Asp Leu Ala Arg Met
        355                 360                 365
Arg His Ala Phe Gln Gln Leu Pro Glu Leu Arg Ala Gln Leu Glu Thr
    370                 375                 380
Val Asp Ser Ala Pro Val Gln Ala Leu Arg Glu Lys Met Gly Glu Phe
385                 390                 395                 400
Ala Glu Leu Arg Asp Leu Leu Glu Arg Ala Ile Ile Asp Thr Pro Pro
                405                 410                 415
Val Leu Val Arg Asp Gly Gly Val Ile Ala Ser Gly Tyr Asn Glu Glu
            420                 425                 430
Leu Asp Glu Trp Arg Ala Leu Ala Asp Gly Ala Thr Asp Tyr Leu Glu
        435                 440                 445
Arg Leu Glu Val Arg Glu Arg Glu Arg Thr Gly Leu Asp Thr Leu Lys
    450                 455                 460
Val Gly Phe Asn Ala Val His Gly Tyr Tyr Ile Gln Ile Ser Arg Gly
465                 470                 475                 480
Gln Ser His Leu Ala Pro Ile Asn Tyr Met Arg Arg Gln Thr Leu Lys
                485                 490                 495
Asn Ala Glu Arg Tyr Ile Ile Pro Glu Leu Lys Glu Tyr Glu Asp Lys
            500                 505                 510
Val Leu Thr Ser Lys Gly Lys Ala Leu Ala Leu Glu Lys Gln Leu Tyr
        515                 520                 525
Glu Glu Leu Phe Asp Leu Leu Leu Pro His Leu Glu Ala Leu Gln Gln
    530                 535                 540
Ser Ala Ser Ala Leu Ala Glu Leu Asp Val Leu Val Asn Leu Ala Glu
```

```
                545                 550                 555                 560
Arg Ala Tyr Thr Leu Asn Tyr Thr Cys Pro Thr Phe Ile Asp Lys Pro
                565                 570                 575

Gly Ile Arg Ile Thr Glu Gly Arg His Pro Val Val Glu Gln Val Leu
                580                 585                 590

Asn Glu Pro Phe Ile Ala Asn Pro Leu Asn Leu Ser Pro Gln Arg Arg
                595                 600                 605

Met Leu Ile Ile Thr Gly Pro Asn Met Gly Gly Lys Ser Thr Tyr Met
610                 615                 620

Arg Gln Thr Ala Leu Ile Ala Leu Met Ala Tyr Ile Gly Ser Tyr Val
625                 630                 635                 640

Pro Ala Gln Lys Val Glu Ile Gly Pro Ile Asp Arg Ile Phe Thr Arg
                645                 650                 655

Val Gly Ala Ala Asp Asp Leu Ala Ser Gly Arg Ser Thr Phe Met Val
                660                 665                 670

Glu Met Thr Glu Thr Ala Asn Ile Leu His Asn Ala Thr Glu Tyr Ser
                675                 680                 685

Leu Val Leu Met Asp Glu Ile Gly Arg Gly Thr Ser Thr Tyr Asp Gly
                690                 695                 700

Leu Ser Leu Ala Trp Ala Cys Ala Glu Asn Leu Ala Asn Lys Ile Lys
705                 710                 715                 720

Ala Leu Thr Leu Phe Ala Thr His Tyr Phe Glu Leu Thr Gln Leu Pro
                725                 730                 735

Glu Lys Met Glu Gly Val Ala Asn Val His Leu Asp Ala Leu Glu His
                740                 745                 750

Gly Asp Thr Ile Ala Phe Met His Ser Val Gln Asp Gly Ala Ala Ser
                755                 760                 765

Lys Ser Tyr Gly Leu Ala Val Ala Ala Leu Ala Gly Val Pro Lys Glu
                770                 775                 780

Val Ile Lys Arg Ala Arg Gln Lys Leu Arg Glu Leu Glu Ser Ile Ser
785                 790                 795                 800

Pro Asn Ala Ala Ala Thr Gln Val Asp Gly Thr Gln Met Ser Leu Leu
                805                 810                 815

Ser Val Pro Glu Glu Thr Ser Pro Ala Val Glu Ala Leu Glu Asn Leu
                820                 825                 830

Asp Pro Asp Ser Leu Thr Pro Arg Gln Ala Leu Glu Trp Ile Tyr Arg
                835                 840                 845

Leu Lys Ser Leu Val
            850

<210> SEQ ID NO 50
<211> LENGTH: 64
<212> TYPE: PRT
<213> ORGANISM: Sulfolobus solfataricus

<400> SEQUENCE: 50

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60
```

<210> SEQ ID NO 51
<211> LENGTH: 99
<212> TYPE: PRT
<213> ORGANISM: Sulfolobus solfataricus P2

<400> SEQUENCE: 51

```
Glu Lys Met Ser Ser Gly Thr Pro Thr Pro Ser Asn Val Val Leu Ile
 1               5                  10                  15

Gly Lys Lys Pro Val Met Asn Tyr Val Leu Ala Ala Leu Thr Leu Leu
            20                  25                  30

Asn Gln Gly Val Ser Glu Ile Val Lys Ala Arg Gly Arg Ala Ile
        35                  40                  45

Ser Lys Ala Val Asp Thr Val Glu Ile Val Arg Asn Arg Phe Leu Pro
50                  55                  60

Asp Lys Ile Glu Ile Lys Glu Ile Arg Val Gly Ser Gln Val Val Thr
65                  70                  75                  80

Ser Gln Asp Gly Arg Gln Ser Arg Val Ser Thr Ile Glu Ile Ala Ile
                85                  90                  95

Arg Lys Lys
```

<210> SEQ ID NO 52
<211> LENGTH: 88
<212> TYPE: PRT
<213> ORGANISM: Sulfolobus solfataricus P2

<400> SEQUENCE: 52

```
Thr Glu Lys Leu Asn Glu Ile Val Val Arg Lys Thr Lys Asn Val Glu
 1               5                  10                  15

Asp His Val Leu Asp Val Ile Val Leu Phe Asn Gln Gly Ile Asp Glu
            20                  25                  30

Val Ile Leu Lys Gly Thr Gly Arg Glu Ile Ser Lys Ala Val Asp Val
        35                  40                  45

Tyr Asn Ser Leu Lys Asp Arg Leu Gly Asp Gly Val Gln Leu Val Asn
50                  55                  60

Val Gln Thr Gly Ser Glu Val Arg Asp Arg Arg Ile Ser Tyr Ile
65                  70                  75                  80

Leu Leu Arg Leu Lys Arg Val Tyr
                85
```

<210> SEQ ID NO 53
<211> LENGTH: 107
<212> TYPE: PRT
<213> ORGANISM: Escherichia coli

<400> SEQUENCE: 53

```
Ala Gln Gln Ser Pro Tyr Ser Ala Ala Met Ala Glu Gln Arg His Gln
 1               5                  10                  15

Glu Trp Leu Arg Phe Val Asp Leu Leu Lys Asn Ala Tyr Gln Asn Asp
            20                  25                  30

Leu His Leu Pro Leu Leu Asn Leu Met Leu Thr Pro Asp Glu Arg Glu
        35                  40                  45

Ala Leu Gly Thr Arg Val Arg Ile Val Glu Glu Leu Leu Arg Gly Glu
50                  55                  60

Met Ser Gln Arg Glu Leu Lys Asn Glu Leu Gly Ala Gly Ile Ala Thr
65                  70                  75                  80

Ile Thr Arg Gly Ser Asn Ser Leu Lys Ala Ala Pro Val Glu Leu Arg
                85                  90                  95
```

Gln Trp Leu Glu Glu Val Leu Leu Lys Ser Asp
            100                 105

<210> SEQ ID NO 54
<211> LENGTH: 237
<212> TYPE: PRT
<213> ORGANISM: Enterobacteria phage lambda

<400> SEQUENCE: 54

Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 55
<211> LENGTH: 60
<212> TYPE: PRT
<213> ORGANISM: Crenarchaea

<400> SEQUENCE: 55

Met Ser Ser Gly Lys Lys Pro Val Lys Val Lys Thr Pro Ala Gly Lys
1               5                   10                  15

Glu Ala Glu Leu Val Pro Glu Lys Val Trp Ala Leu Ala Pro Lys Gly
            20                  25                  30

Arg Lys Gly Val Lys Ile Gly Leu Phe Lys Asp Pro Glu Thr Gly Lys
        35                  40                  45

Tyr Phe Arg His Lys Leu Pro Asp Asp Tyr Pro Ile
    50                  55                  60

<210> SEQ ID NO 56

<211> LENGTH: 136
<212> TYPE: PRT
<213> ORGANISM: Homo sapiens

<400> SEQUENCE: 56

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 57
<211> LENGTH: 89
<212> TYPE: PRT
<213> ORGANISM: Enterobacteria phage T4

<400> SEQUENCE: 57

Met Ala Lys Lys Glu Met Val Glu Phe Asp Glu Ala Ile His Gly Glu
1               5                   10                  15

Asp Leu Ala Lys Phe Ile Lys Glu Ala Ser Asp His Lys Leu Lys Ile
            20                  25                  30

Ser Gly Tyr Asn Glu Leu Ile Lys Asp Ile Arg Ile Arg Ala Lys Asp
        35                  40                  45

Glu Leu Gly Val Asp Gly Lys Met Phe Asn Arg Leu Leu Ala Leu Tyr
50                  55                  60

His Lys Asp Asn Arg Asp Val Phe Glu Ala Glu Thr Glu Glu Val Val
65                  70                  75                  80

Glu Leu Tyr Asp Thr Val Phe Ser Lys
                85

<210> SEQ ID NO 58
<211> LENGTH: 339
<212> TYPE: PRT
<213> ORGANISM: Homo sapiens

<400> SEQUENCE: 58

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
    130                 135                 140

Gln Leu Pro Ile Asp Arg Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Arg Leu Ala
                245                 250                 255

Asp Glu Phe Gly Val Ala Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 59
<211> LENGTH: 375
<212> TYPE: PRT
<213> ORGANISM: Citromicrobium bathyomarinum JL354

<400> SEQUENCE: 59

Met Lys Ala Thr Ile Glu Arg Ala Thr Leu Leu Arg Cys Leu Ser His
1               5                   10                  15

Val Gln Ser Val Val Glu Arg Arg Asn Thr Ile Pro Ile Leu Ser Asn
            20                  25                  30

Val Leu Ile Asp Ala Asp Ala Gly Gly Val Lys Val Met Ala Thr
        35                  40                  45

Asp Leu Asp Leu Gln Val Val Glu Thr Met Thr Ala Ala Ser Val Glu
    50                  55                  60

Ser Ala Gly Ala Ile Thr Val Ser Ala His Leu Leu Phe Asp Ile Ala
65                  70                  75                  80

Arg Lys Leu Pro Asp Gly Ser Gln Val Ser Leu Glu Thr Ala Asp Asn
                85                  90                  95

```
Arg Met Val Val Lys Ala Gly Arg Ser Arg Phe Gln Leu Pro Thr Leu
            100                 105                 110

Pro Arg Asp Asp Phe Pro Val Ile Val Glu Gly Glu Leu Pro Thr Ser
        115                 120                 125

Phe Glu Leu Pro Ala Arg Glu Leu Ala Glu Met Ile Asp Arg Thr Arg
    130                 135                 140

Phe Ala Ile Ser Thr Glu Glu Thr Arg Tyr Tyr Leu Asn Gly Ile Phe
145                 150                 155                 160

Leu His Val Ser Asp Glu Ala Arg Pro Val Leu Lys Ala Ala Ala Thr
                165                 170                 175

Asp Gly His Arg Leu Ala Arg Tyr Thr Leu Asp Arg Pro Glu Gly Ala
            180                 185                 190

Glu Gly Met Pro Asp Val Ile Val Pro Arg Lys Ala Val Gly Glu Leu
        195                 200                 205

Arg Lys Leu Leu Glu Glu Ala Leu Asp Ser Asn Val Gln Ile Asp Leu
    210                 215                 220

Ser Ala Ser Lys Ile Arg Phe Ala Leu Gly Gly Glu Gly Gly Val Val
225                 230                 235                 240

Leu Thr Ser Lys Leu Ile Asp Gly Thr Phe Pro Asp Tyr Ser Arg Val
                245                 250                 255

Ile Pro Thr Gly Asn Asp Lys Leu Leu Arg Leu Asp Pro Lys Ala Phe
            260                 265                 270

Phe Gln Gly Val Asp Arg Val Ala Thr Ile Ala Thr Glu Lys Thr Arg
        275                 280                 285

Ala Val Lys Met Gly Leu Asp Glu Asp Lys Val Thr Leu Ser Val Thr
    290                 295                 300

Ser Pro Asp Asn Gly Thr Ala Ala Glu Glu Ile Ala Ala Glu Tyr Lys
305                 310                 315                 320

Ala Glu Gly Phe Glu Ile Gly Phe Asn Ala Asn Tyr Leu Lys Asp Ile
                325                 330                 335

Leu Gly Gln Ile Asp Ser Asp Thr Val Glu Leu His Leu Ala Asp Ala
            340                 345                 350

Gly Ala Pro Thr Leu Ile Arg Arg Asp Glu Asn Ser Pro Ala Leu Tyr
        355                 360                 365

Val Leu Met Pro Met Arg Val
    370                 375

<210> SEQ ID NO 60
<211> LENGTH: 50
<212> TYPE: DNA
<213> ORGANISM: Artificial sequence
<220> FEATURE:
<223> OTHER INFORMATION: Synthetic Polynucleotide

<400> SEQUENCE: 60
tttttttttt tttttttttt tttttttttt tttttttttt tttttttttt              50

<210> SEQ ID NO 61
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 61
ggttgtttct gttggtgctg atattgc                                        27
```

<210> SEQ ID NO 62
<211> LENGTH: 97138
<212> TYPE: DNA
<213> ORGANISM: Artificial Sequence
<220> FEATURE:
<223> OTHER INFORMATION: Synthetic Polynucleotide

<400> SEQUENCE: 62

| | | | | | |
|---|---|---|---|---|---|
| gctccactaa | agggccgatt | gacgggcggc | gacctcgcgg | gttttcgcta | tttatgaaaa | 60
| ttttccggtt | taaggcgttt | ccgttcttct | tcgtcataac | ttaatgtttt | tatttaaaat | 120
| accctctgaa | agaaaggaa | acgacaggtg | ctgaaagcga | ggcttttttgg | cctctgtcgt | 180
| ttcctttctc | tgttttttgtc | cgtggaatga | acaatgaaag | tcaacaaaaa | gcagctggct | 240
| gacattttcg | gtgcgagtat | ccgtaccatt | cagaactggc | aggaacaggg | aatgcccgtt | 300
| ctgcgaggcg | gtggcaaggg | taatgagtg | ctttatgact | ctgccgccgt | cataaaatgg | 360
| tatgccgaaa | gggatgctga | aattgagaac | gaaaagctgc | gccgggaggt | tgaagaactg | 420
| cggcaggcca | gcgaggcaga | tctccagcca | ggaactattg | agtacgaacg | ccatcgactt | 480
| acgcgtgcgc | aggccgacgc | acaggaactg | aagaatgcca | gagactccgc | tgaagtggtg | 540
| gaaaccgcat | tctgtacttt | cgtgctgtcg | cggatcgcag | gtgaaattgc | cagtattctc | 600
| gacgggctcc | ccctgtcggt | gcagcggcgt | tttccggaac | tggaaaaccg | acatgttgat | 660
| ttcctgaaac | gggatatcat | caaagccatg | aacaaagcag | ccgcgctgga | tgaactgata | 720
| ccggggttgc | tgagtgaata | tatcgaacag | tcaggttaac | aggctgcggc | attttgtccg | 780
| cgccgggctt | cgctcactgt | tcaggccgga | gccacagacc | gccgttgaat | gggcggatgc | 840
| taattactat | ctcccgaaag | aatccgcata | ccaggaaggg | cgctgggaaa | cactgcccttt | 900
| tcagcgggcc | atcatgaatg | cgatgggcag | cgactacatc | cgtgaggtga | atgtggtgaa | 960
| gtctgcccgt | gtcggttatt | ccaaaatgct | gctgggtgtt | tatgcctact | ttatagagca | 1020
| taagcagcgc | aacacccta | tctggttgcc | gacggatggt | gatgccgaga | ctttatgaa | 1080
| aacccacgtt | gagccgacta | ttcgtgatat | tccgtcgctg | ctggcgctgg | ccccgtggta | 1140
| tggcaaaaag | caccgggata | acacgctcac | catgaagcgt | ttcactaatg | ggcgtggctt | 1200
| ctggtgcctg | ggcggtaaag | cggcaaaaaa | ctaccgtgaa | aagtcggtgg | atgtggcggg | 1260
| ttatgatgaa | cttgctgctt | ttgatgatga | tattgaacag | gaaggctctc | cgacgttcct | 1320
| gggtgacaag | cgtattgaag | gctcggtctg | gccaaagtcc | atccgtggct | ccacgccaaa | 1380
| agtgagaggc | acctgtcaga | ttgagcgtgc | agccagtgaa | tccccgcatt | ttatgcgttt | 1440
| tcatgttgcc | tgcccgcatt | gcggggagga | gcagtatctt | aaatttggcg | acaaagagac | 1500
| gccgtttggc | ctcaaatgga | cgccggatga | cccctccagc | gtgttttatc | tctgcgagca | 1560
| taatgcctgc | gtcatccgcc | agcaggagct | ggacttact | gatgcccgtt | atatctgcga | 1620
| aaagaccggg | atctggaccc | gtgatggcat | tctctggttt | tcgtcatccg | gtgaagagat | 1680
| tgagccacct | gacagtgtga | cctttcacat | ctggacagcg | tacagcccgt | tcaccacctg | 1740
| ggtgcagatt | gtcaaagact | ggatgaaaac | gaaagggat | acgggaaaac | gtaaaaccttt | 1800
| cgtaaacacc | acgctcggtg | agacgtggga | ggcgaaaatt | ggcgaacgtc | cggatgctga | 1860
| agtgatggca | gagcggaaag | agcattattc | agcgcccgtt | cctgaccgtg | tggcttacct | 1920
| gaccgccggt | atcgactccc | agctggaccg | ctacgaaatg | cgcgtatggg | gatggggcc | 1980
| gggtgaggaa | agctggctga | ttgaccggca | gattattatg | ggccgccacg | acgatgaaca | 2040
| gacgctgctg | cgtgtggatg | aggccatcaa | taaaacctat | acccgccgga | atggtgcaga | 2100

```
aatgtcgata tcccgtatct gctgggatac tggcgggatt gacccgacca ttgtgtatga    2160
acgctcgaaa aaacatgggc tgttccgggt gatccccatt aaaggggcat ccgtctacgg    2220
aaagccggtg gccagcatgc cacgtaagcg aaacaaaaac ggggtttacc ttaccgaaat    2280
cggtacggat accgcgaaag agcagattta taaccgcttc acactgacgc cggaagggga    2340
tgaaccgctt cccggtgccg ttcacttccc gaataacccg gatattttg atctgaccga    2400 agcgcagcag ctgactgctg aagagcaggt cgaaaaatgg gtggatgcca ggaaaaaaat    2460
actgtgggac agcaaaaagc gacgcaatga ggcactcgac tgcttcgttt atgcgctggc    2520
ggcgctgcgc atcagtattt cccgctggca gctggatctc agtgcgctgc tggcgagcct    2580
gcaggaagag gatggtgcag caaccaacaa gaaaacactg gcagattacg cccgtgcctt    2640
atccggagag gatgaatgac gcgacaggaa gaacttgccg ctgcccgtgc ggcactgcat    2700
gacctgatga caggtaaacg ggtggcaaca gtacagaaag acggacgaag ggtggagttt    2760
acggccactt ccgtgtctga cctgaaaaaa tatattgcag agctggaagt gcagaccggc    2820
atgacacagc gacgcagggg acctgcagga ttttatgtat gaaaacgccc accattccca    2880
cccttctggg gccggacggc atgacatcgc tgcgcgaata tgccggttat cacggcggtg    2940
gcagcggatt tggagggcag ttgcggtcgt ggaacccacc gagtgaaagt gtggatgcag    3000
ccctgttgcc caactttacc cgtggcaatg cccgcgcaga cgatctggta cgcaataacg    3060
gctatgccgc caacgccatc cagctgcatc aggatcatat cgtcgggtct ttttccggc    3120 tcagtcatcg cccaagctgg cgctatctgg gcatcgggga ggaagaagcc cgtgccttt    3180 cccgcgaggt tgaagcggca tggaaagagt ttgccgagga tgactgctgc tgcattgacg    3240
ttgagcgaaa acgcacgttt accatgatga ttcgggaagg tgtggccatg cacgccttta    3300
acggtgaact gttcgttcag gccacctggg ataccagttc gtcgcggctt ttccggacac    3360
agttccggat ggtcagcccg aagcgcatca gcaaccccgaa caataccggc gacagccgga    3420
actgccgtgc cggtgtgcag attaatgaca gcggtgcggc gctgggatat tacgtcagcg    3480
aggacgggta tcctggctgg atgccgcaga atggacatg gataccccgt gagttacccg    3540
gcgggcgcgc ctcgttcatt cacgtttttg aacccgtgga ggacgggcag actcgcggtg    3600
caaatgtgtt ttacagcgtg atggagcaga tgaagatgct cgacacgctg cagaacacgc    3660
agctgcagag cgccattgtg aaggcgatgt atgccgccac cattgagagt gagctggata    3720
cgcagtcagc gatggatttt attctgggcg cgaacagtca ggagcagcgg gaaaggctga    3780
ccggctggat tggtgaaatt gccgcgtatt acgccgcagc gccggtccgg ctgggaggcg    3840
caaaagtacc gcacctgatg ccgggtgact cactgaacct gcagacggct caggatacgg    3900
ataacgctac ctccgtgttt gagcagtcac tgctgcggta tcgctgcc gggctggtg    3960 tctcgtatga gcagctttcc cggaattacg cccagatgag ctactccacg gcacgggcca    4020
gtgcgaacga tcgtgggcg tactttatgg ggcggcgaaa attcgtcgca tcccgtcagg    4080
cgagccagat gtttctgtgc tggctggaag aggccatcgt tcgccgcgtg gtgacgttac    4140
cttcaaaagc gcgcttcagt tttcaggaag cccgcagtgc ctggggaac tgcgactgga    4200 taggctccgg tcgtatggcc atcgatggtc tgaaagaagt tcaggaagcg gtgatgctga    4260
tagaagccgg actgagtacc tacgagaaag agtgcgcaaa acgcggtgac gactatcagg    4320 aaattttgc ccagcaggtc cgtgaaacga tggagcgccg tgcagccggt cttaaaccgc    4380
ccgcctgggg ggctgcagca tttgaatccg ggctgcgaca tcaacagag gaggagaaga    4440 gtgacagcag agctgcgtaa tctcccgcat attgccagca tggcctttaa tgagccgctg    4500
```

```
atgcttgaac cgcctatgc gcgggttttc ttttgtgcgc ttgcaggcca gcttgggatc   4560
agcagcctga cggatgcggt gtccggcgac agcctgactg cccaggaggc actcgcgacg   4620
ctggcattat ccggtgatga tgacggacca cgacaggccc gcagttatca ggtcatgaac   4680
ggcatcgccg tgctgccggt gtccggcacg ctggtcagcc ggacgcgggc gctgcagccg   4740
tactcgggga tgaccggtta caacggcatt atcgcccgtc tgcaacaggc tgccagcgat   4800
ccgatggtgg acggcattct gctcgatatg gacacgcccg cgggatggt ggcggggca   4860 tttgactgcg ctgacatcat cgcccgtgtg cgtgacataa aaccggtatg ggcgcttgcc   4920
aacgacatga actgcagtgc aggtcagttg cttgccagtg ccgcctcccg gcgtctggtc   4980
acgcagaccg cccggacagg ctccatcggc gtcatgatgg ctcacagtaa ttacggtgct   5040
gcgctggaga aacagggtgt ggaaatcacg ctgatttaca gcggcagcca taaggtggat   5100
ggcaacccct acagccatct tccggatgac gtccgggaga cactgcagtc ccggatggac   5160
gcaacccgcc agatgtttgc gcagaaggtg tcggcatata ccggcctgtc cgtgcaggtt   5220
gtgctggata ccgaggctgc agtgtacagc ggtcaggagg ccattgatgc cggactggct   5280
gatgaacttg ttaacagcac cgatgcgatc accgtcatgc gtgatgcact ggatgcacgt   5340
aaatcccgtc tctcaggagg gcgaatgacc aaagagactc aatcaacaac tgtttcagcc   5400
actgcttcgc aggctgacgt tactgacgtg gtgccagcga cggagggcga gaacgccagc   5460
gcggcgcagc cggacgtgaa cgcgcagatc accgcagcgg ttgcggcaga aacagccgc   5520 attatgggga tcctcaactg tgaggaggct cacggacgcg aagaacaggc acgcgtgctg   5580
gcagaaaccc ccggtatgac cgtgaaaacg gcccgccgca ttctggccgc agcaccacag   5640
agtgcacagg cgcgcagtga cactgcgctg gatcgtctga tgcaggggc accggcaccg   5700 ctggctgcag gtaacccggc atctgatgcc gttaacgatt tgctgaacac accagtgtaa   5760
gggatgttta tgacgagcaa agaaaccttt acccattacc agccgcaggg caacagtgac   5820
ccggctcata ccgcaaccgc gcccggcgga ttgagtgcga aagcgcctgc aatgaccccg   5880
ctgatgctgg acacctccag ccgtaagctg gttgcgtggg atggcaccac cgacggtgct   5940
gccgttggca ttcttgcggt tgctgctgac cagaccagca ccacgctgac gttctacaag   6000
tccggcacgt tccgttatga ggatgtgctc tggccggagg ctgccagcga cgagacgaaa   6060
aaacggaccg cgtttgccgg aacggcaatc agcatcgttt aactttaccc ttcatcacta   6120
aaggccgcct gtgcggcttt ttttacggga tttttttatg tcgatgtaca caaccgccca   6180
actgctggcg gcaaatgagc agaaatttaa gtttgatccg ctgtttctgc gtctcttttt   6240
ccgtgagagc tatcccttca ccacggagaa agtctatctc tcacaaattc cgggactggt   6300
aaacatggcc ctgtacgttt cgccgattgt ttccggtgag gttatccgtt ccgtggcgg   6360 ctccacctct gaatttacgc cgggatatgt caagccgaag catgaagtga atccgcagat   6420 gacccctgcgt cgcctgccgg atgaagatcc gcagaatctg gcggacccgg cttaccgccg   6480
ccgtcgcatc atcatgcaga acatgcgtga cgaagagctg gccattgctc aggtcgaaga   6540
gatgcaggca gtttctgccg tgcttaaggg caaatacacc atgaccggtg aagccttcga   6600
tccggttgag gtggatatgg gccgcagtga ggagaataac atcacgcagt ccggcggcac   6660
ggagtggagc aagcgtgaca agtccacgta tgacccgacc gacgatatcg aagcctacgc   6720
gctgaacgcc agcggtgtgg tgaatatcat cgtgttcgat ccgaaaggct gggcgctgtt   6780
ccgttccttc aaagccgtca aggagaagct ggataccgt cgtggctcta attccgagct   6840
```

-continued

```
ggagacagcg gtgaaagacc tgggcaaagc ggtgtcctat aagggatgt atggcgatgt     6900
ggccatcgtc gtgtattccg gacagtacgt ggaaaacggc gtcaaaaaga acttcctgcc     6960
ggacaacacg atggtgctgg ggaacactca ggcacgcggt ctgcgcacct atggctgcat     7020
tcaggatgcg gacgcacagc gcgaaggcat aacgcctct gcccgttacc cgaaaaactg     7080
ggtgaccacc ggcgatccgg cgcgtgagtt caccatgatt cagtcagcac cgctgatgct     7140
gctggctgac cctgatgagt tcgtgtccgt acaactggcg taatcatggc ccttcggggc     7200
cattgtttct ctgtggagga gtccatgacg aaagatgaac tgattgcccg tctccgctcg     7260
ctgggtgaac aactgaaccg tgatgtcagc ctgacgggga cgaaagaaga actggcgctc     7320
cgtgtggcag agctgaaaga ggagcttgat gacacggatg aaactgccgg tcaggacacc     7380
cctctcagcc gggaaaatgt gctgaccgga catgaaaatg aggtgggatc agcgcagccg     7440
gataccgtga ttctggatac gtctgaactg gtcacggtcg tggcactggt gaagctgcat     7500
actgatgcac ttcacgccac gcgggatgaa cctgtggcat ttgtgctgcc gggaacggcg     7560
tttcgtgtct ctgccggtgt ggcagccgaa atgacagagc gcggcctggc cagaatgcaa     7620
taacgggagg cgctgtggct gatttcgata acctgttcga tgctgccatt gcccgcgccg     7680
atgaaacgat acgcgggtac atgggaacgt cagccaccat tacatccggt gagcagtcag     7740
gtgcggtgat acgtggtgtt tttgatgacc ctgaaaatat cagctatgcc ggacagggcg     7800
tgcgcgttga aggctccagc ccgtccctgt ttgtccggac tgatgaggtg cggcagctgc     7860
ggcgtggaga cacgctgacc atcggtgagg aaaatttctg ggtagatcgg gtttcgccgg     7920
atgatggcgg aagttgtcat ctctggcttg acggggcgt accgcctgcc gttaaccgtc     7980
gccgctgaaa ggggatgta tggccataaa aggtcttgag caggccgttg aaaacctcag     8040
ccgtatcagc aaaacggcgg tgcctggtgc cgccgcaatg ccattaacc gcgttgcttc     8100
atccgcgata tcgcagtcgg cgtcacaggt tgcccgtgag acaaaggtac gccggaaact     8160
ggtaaaggaa agggccaggc tgaaaagggc cacggtcaaa atccgcagg ccagaatcaa     8220
agttaaccgg ggggatttgc ccgtaatcaa gctgggtaat gcgcgggttg tcctttcgcg     8280
ccgcaggcgt cgtaaaaagg ggcagcgttc atccctgaaa ggtggcggca gcgtgcttgt     8340
ggtgggtaac cgtcgtattc ccggcgcgtt tattcagcaa ctgaaaaatg gccggtggca     8400
tgtcatgcag cgtgtggctg ggaaaaaccg ttaccccatt gatgtggtga aaatcccgat     8460
ggcggtgccg ctgaccacgg cgtttaaaca aaatattgag cggatacggc gtgaacgtct     8520
tccgaaagag ctgggctatg cgctgcagca tcaactgagg atggtaataa agcgatgaaa     8580
catactgaac tccgtgcagc cgtactggat gcactggaga agcatgacac cggggcgacg     8640
tttttttgatg gtcgccccgc tgttttttgat gaggcggatt ttccggcagt tgccgtttat     8700
ctcaccggcg ctgaatacac gggcgaagag ctggacagcg ataccgtggca ggcggagctg     8760
catatcgaag ttttcctgcc tgctcaggtg ccggattcag agctggatgc gtggatggag     8820
tcccggattt atccggtgat gagcgatatc ccggcactgt cagatttgat caccagtatg     8880
gtggccagcg gctatgacta ccggcgcgac gatgatgcgg gcttgtggag ttcagccgat     8940
ctgacttatg tcattaccta tgaaatgtga ggacgctatg cctgtaccaa atcctacaat     9000
gccggtgaaa ggtgccggga ccaccctgtg ggtttataag gggagcggtg acccttacgc     9060
gaatccgctt tcagacgttg actggtcgcg tctggcaaaa gttaaagacc tgacgcccgg     9120
cgaactgacc gctgagtcct atgacgacag ctatctcgat gatgaagatg cagactggac     9180
tgcgaccggg caggggcaga aatctgccgg agataccagc ttcacgctgg cgtggatgcc     9240
```

```
cggagagcag gggcagcagg cgctgctggc gtggtttaat gaaggcgata cccgtgccta   9300
taaaatccgc ttcccgaacg gcacggtcga tgtgttccgt ggctgggtca gcagtatcgg   9360
taaggcggtg acggcgaagg aagtgatcac ccgcacggtg aaagtcacca atgtgggacg   9420
tccgtcgatg gcagaagatc gcagcacggt aacagcggca accggcatga ccgtgacgcc   9480
tgccagcacc tcggtggtga aagggcagag caccacgctg accgtggcct tccagccgga   9540
gggcgtaacc gacaagagct ttcgtgcggt gtctgcggat aaaacaaaag ccaccgtgtc   9600
ggtcagtggt atgaccatca ccgtgaacgg cgttgctgca ggcaaggtca acattccggt   9660
tgtatccggt aatggtgagt ttgctgcggt tgcagaaatt accgtcaccg ccagttaatc   9720
cggagagtca gcgatgttcc tgaaaaccga atcatttgaa cataacggtg tgaccgtcac   9780
gctttctgaa ctgtcagccc tgcagcgcat tgagcatctc gccctgatga acggcaggc   9840 agaacaggcg gagtcagaca gcaaccggaa gtttactgtg gaagacgcca tcagaaccgg   9900
cgcgtttctg gtggcgatgt ccctgtggca taaccatccg cagaagacgc agatgccgtc   9960
catgaatgaa gccgttaaac agattgagca ggaagtgctt accacctggc ccacggaggc  10020
aatttctcat gctgaaaacg tggtgtaccg gctgtctggt atgtatgagt ttgtggtgaa  10080
taatgcccct gaacagacag aggacgccgg gcccgcagag cctgtttctg cgggaaagtg  10140
ttcgacggtg agctgagttt tgccctgaaa ctggcgcgtg agatggggcg acccgactgg  10200
cgtgccatgc ttgccgggat gtcatccacg gagtatgccg actggcaccg cttttacagt  10260
acccattatt ttcatgatgt tctgctggat atgcactttt ccgggctgac gtacaccgtg  10320
ctcagcctgt ttttcagcga tccggatatg catccgctgg atttcagtct gctgaaccgg  10380
cgcgaggctg acgaagagcc tgaagatgat gtgctgatgc agaaagcggc agggcttgcc  10440
ggaggtgtcc gctttggccc ggacgggaat gaagttatcc ccgcttcccc ggatgtggcg  10500
gacatgacgg aggatgacgt aatgctgatg acagtatcag aagggatcgc aggaggagtc  10560
cggtatggct gaaccggtag gcgatctggt cgttgatttg agtctggatg cggccagatt  10620
tgacgagcag atggcagag tcaggcgtca ttttctggt acggaaagtg atgcgaaaaa  10680
aacagcggca gtcgttgaac agtcgctgag ccgacaggcg ctggctgcac agaaagcggg  10740
gatttccgtc gggcagtata aagccgccat gcgtatgctg cctgcacagt tcaccgacgt  10800
ggccacgcag cttgcaggcg ggcaaagtcc gtggctgatc ctgctgcaac aggggggca  10860 ggtgaaggac tccttcggcg ggatgatccc catgttcagg gggcttgccg gtgcgatcac  10920
cctgccgatg gtggggggcca cctcgctggc ggtggcgacc ggtgcgctgg cgtatgcctg  10980
gtatcagggc aactcaaccc tgtccgattt caacaaaacg ctggtccttt ccggcaatca  11040
ggcgggactg acggcagatc gtatgctggt cctgtccaga gccgggcagg cggcagggct  11100
gacgtttaac cagaccagcg agtcactcag cgcactggtt aaggcggggg taagcggtga  11160
ggctcagatt gcgtccatca gccagagtgt ggcgcgtttc tcctctgcat ccggcgtgga  11220
ggtggacaag gtcgctgaag ccttcgggaa gctgaccaca gacccgacgt cggggctgac  11280
ggcgatggct cgccagttcc ataacgtgtc ggcggagcag attgcgtatg ttgctcagtt  11340
gcagcgttcc ggcgatgaag ccggggcatt gcaggcggcg aacgaggccg caacgaaagg  11400
gtttgatgac cagacccgcc gcctgaaaga aacatgggc acgctggaga cctgggcaga  11460
caggactgcg cgggcattca aatccatgtg ggatgcggtg ctggatattg gtcgtcctga  11520
taccgcgcag gagatgctga ttaaggcaga ggctgcgtat aagaaagcag acgacatctg  11580
```

```
gaatctgcgc aaggatgatt attttgttaa cgatgaagcg cgggcgcgtt actgggatga    11640
tcgtgaaaag gcccgtcttg cgcttgaagc cgcccgaaag aaggctgagc agcagactca    11700
acaggacaaa aatgcgcagc agcagagcga taccgaagcg tcacggctga aatataccga    11760
agaggcgcag aaggcttacg aacggctgca gacgccgctg gagaaatata ccgcccgtca    11820
ggaagaactg aacaaggcac tgaaagacgg gaaaatcctg caggcggatt acaacacgct    11880
gatggcggcg gcgaaaaagg attatgaagc gacgctgaaa aagccgaaac agtccagcgt    11940
gaaggtgtct gcgggcgatc gtcaggaaga cagtgctcat gctgccctgc tgacgcttca    12000
ggcagaactc cggacgctgg agaagcatgc cggagcaaat gagaaaatca gccagcagcg    12060
ccgggatttg tggaaggcgg agagtcagtt cgcggtactg gaggaggcgg cgcaacgtcg    12120
ccagctgtct gcacaggaga aatccctgct ggcgcataaa gatgagacgc tggagtacaa    12180
acgccagctg gctgcacttg cgacaaggt tacgtatcag gagcgcctga acgcgctggc    12240
gcagcaggcg gataaattcg cacagcagca acgggcaaaa cgggccgcca ttgatgcgaa    12300
aagccggggg ctgactgacc ggcaggcaga acggaagcc acggaacagc gcctgaagga    12360
acagtatggc gataatccgc tggcgctgaa taacgtcatg tcagagcaga aaaagacctg    12420
ggcggctgaa gaccagcttc gcgggaactg gatggcaggc ctgaagtccg gctggagtga    12480
gtgggaagag agcgccacgg acagtatgtc gcaggtaaaa agtgcagcca cgcagacctt    12540
tgatggtatt gcacagaata tggcggcgat gctgaccggc agtgagcaga actggcgcag    12600
cttcacccgt tccgtgctgt ccatgatgac agaaattctg cttaagcagg caatggtggg    12660
gattgtcgga agtatcggca gcgccattgg cggggctgtt ggtggcggcg catccgcgtc    12720
aggcggtaca gccattcagg ccgctgcggc gaaattccat tttgcaaccg gaggatttac    12780
gggaaccggc ggcaaatatg agccagcggg gattgttcac cgtggtgagt ttgtcttcac    12840
gaaggaggca accagccgga ttggcgtggg gaatctttac cggctgatgc gcggctatgc    12900
caccggcggt tatgtcggta cacccgggcag catggcagac agccggtcgc aggcgtccgg    12960
gacgtttgag cagaataacc atgtggtgat taacaacgac ggcacgaacg gcagataggg    13020
tccggctgct ctgaaggcgg tgtatgacat ggcccgcaag ggtgcccgtg atgaaattca    13080
gacacagatg cgtgatggtg gcctgttctc cggaggtgga cgatgaagac cttccgctgg    13140
aaagtgaaac ccgtatggga tgtggcttcg gtcccttctg taagaaaggt gcgctttggt    13200
gatggctatt ctcagcgagc gcctgccggg ctgaatgcca acctgaaaac gtacagcgtg    13260
acgctttctg tccccgtga ggaggccacg gtactggagt cgtttctgga agagcacggg    13320
ggctggaaat cctttctgtg gacgccgcct tatgagtggc ggcagataaa ggtgacctgc    13380
gcaaaatggt cgtcgcgggt cagtatgctg cgtgttgagt tcagcgcaga gtttgaacag    13440
gtggtgaact gatgcaggat atccggcagg aaacactgaa tgaatgcacc cgtgcggagc    13500
agtcggccag cgtggtgctc tgggaaatcg acctgacaga ggtcggtgga gaacgttatt    13560
ttttctgtaa tgagcagaac gaaaaaggtg agccggtcac ctggcagggg cgacagtatc    13620
agccgtatcc cattcagggg agcggttttg aactgaatgg caaaggcacc agtacgcgcc    13680
ccacgctgac ggtttctaac ctgtacggta tggtcaccgg gatggcggaa gatatgcaga    13740
gtctggtcgg cggaacggtg gtccggcgta aggtttacgc ccgttttctg gatgcggtga    13800
acttcgtcaa cggaaacagt tacgccgatc cggagcagga ggtgatcagc cgctggcgca    13860
ttgagcagtg cagcgaactg agcgcggtga gtgcctcctt tgtactgtcc acgccgacgg    13920
aaacggatgg cgctgttttt ccgggacgta tcatgctggc caacacctgc acctggacct    13980
```

```
atcgcggtga cgagtgcggt tatagcggtc cggctgtcgc ggatgaatat gaccagccaa    14040
cgtccgatat cacgaaggat aaatgcagca aatgcctgag cggttgtaag ttccgcaata    14100
acgtcggcaa ctttggcggc ttcctttcca ttaacaaact ttcgcagtaa atcccatgac    14160
acagacagaa tcagcgattc tggcgcacgc ccggcgatgt cgccagcgg agtcgtgcgg     14220
cttcgtggta agcacgccgg agggggaaag atatttcccc tgcgtgaata tctccggtga    14280
gccgaggct atttccgtat gtcgccggaa gactggctgc aggcagaaat gcagggtgag     14340
attgtggcgc tggtccacag ccaccccggt ggtctgccct ggctgagtga ggccgaccgg    14400
cggctgcagg tgcagagtga tttgccgtgg tggctggtct gccgggggac gattcataag    14460
ttccgctgtg tgccgcatct caccgggcgg cgctttgagc acggtgtgac ggactgttac    14520
acactgttcc gggatgctta tcatctggcg gggattgaga tgccggactt tcatcgtgag    14580
gatgactggt ggcgtaacgg ccagaatctc tatctggata atctggaggc gacggggctg    14640
tatcaggtgc cgttgtcagc ggcacagccg ggcgatgtgc tgctgtgctg ttttggttca    14700
tcagtgccga atcacgccgc aatttactgc ggcgacggcg agctgctgca ccatattcct    14760
gaacaactga gcaaacgaga gaggtacacc gacaaatggc agcgacgcac acactccctc    14820
tggcgtcacc gggcatggcg cgcatctgcc tttacgggga tttacaacga tttggtcgcc    14880
gcatcgacct tcgtgtgaaa acggggctg aagccatccg ggcactggcc acacagctcc     14940
cggcgtttcg tcagaaactg agcgacggct ggtatcaggt acggattgcc gggcgggacg    15000
tcagcacgtc cgggttaacg gcgcagttac atgagactct gcctgatggc gctgtaattc    15060
atattgttcc cagagtcgcc ggggccaagt caggtggcgt attccagatt gtcctggggg    15120
ctgccgccat tgccggatca ttctttaccg ccggagccac ccttgcagca tgggggcag     15180
ccattggggc cggtggtatg accggcatcc tgttttctct cggtgccagt atggtgctcg    15240
gtggtgtggc gcagatgctg gcaccgaaag ccagaactcc ccgtatacag acaacggata    15300
acggtaagca gaacacctat ttctcctcac tggataacat ggttgcccag ggcaatgttc    15360
tgcctgttct gtacggggaa atgcgcgtgg ggtcacgcgt ggtttctcag gagatcagca    15420
cggcagacga aggggacggt ggtcaggttg tggtgattgg tcgctgatgc aaaatgtttt    15480
atgtgaaacc gcctgcgggc ggttttgtca tttatggagc gtgaggaatg ggtaaaggaa    15540
gcagtaaggg gcatacccg cgcgaagcga aggacaacct gaagtccacg cagttgctga     15600
gtgtgatcga tgccatcagc gaagggccga ttgaaggtcc ggtggatggc ttaaaaagcg    15660
tgctgctgaa cagtacgccg gtgctggaca ctgaggggaa taccaacata tccggtgtca    15720
cggtggtgtt ccgggctggt gagcaggagc agactccgcc ggagggattt gaatcctccg    15780
gctccgagac ggtgctgggt acggaagtga aatatgacac gccgatcacc cgcaccatta    15840
cgtctgcaaa catcgaccgt ctgcgcttta ccttcggtgt acaggcactg gtggaaacca    15900
cctcaaaggg tgacaggaat ccgtcggaag tccgcctgct ggttcagata caacgtaacg    15960
gtggctgggt gacggaaaaa gacatcacca ttaagggcaa aaccacctcg cagtatctgg    16020
cctcggtggt gatgggtaac ctgccgccgc gcccgtttaa tatccggatg cgcaggatga    16080
cgccggacag caccacagac cagctgcaga acaaaacgct ctggtcgtca tacactgaaa    16140
tcatcgatgt gaaacagtgc tacccgaaca cggcactggt cggcgtgcag gtggactcgg    16200
agcagttcgg cagccagcag gtgagccgta attatcatct gcgcgggcgt attctgcagg    16260
tgccgtcgaa ctataaccccg cagacgcggc aatacagcgg tatctgggac ggaacgttta    16320
```

```
aaccggcata cagcaacaac atggcctggt gtctgtggga tatgctgacc catccgcgct   16380
acggcatggg gaaacgtctt ggtgcggcgg atgtggataa atgggcgctg tatgtcatcg   16440
gccagtactg cgaccagtca gtgccggacg gctttggcgg cacggagccg cgcatcacct   16500
gtaatgcgta cctgaccaca cagcgtaagg cgtgggatgt gctcagcgat ttctgctcgg   16560
cgatgcgctg tatgccggta tggaacgggc agacgctgac gttcgtgcag gaccgaccgt   16620
cggataagac gtggacctat aaccgcagta atgtggtgat gccggatgat ggcgcgccgt   16680
tccgctacag cttcagcgcc ctgaaggacc gccataatgc cgttgaggtg aactggattg   16740
acccgaacaa cggctgggag acggcgacag agcttgttga agatacgcag gccattgccc   16800
gttacggtcg taatgttacg aagatggatg cctttggctg taccagccgg gggcaggcac   16860
accgcgccgg gctgtggctg attaaaacag aactgctgga aacgcagacc gtggatttca   16920
gcgtcggcgc agaagggctt cgccatgtac cgggcgatgt tattgaaatc tgcgatgatg   16980
actatgccgg tatcagcacc ggtggtcgtg tgctggcggt gaacagccag acccggacgc   17040
tgacgctcga ccgtgaaatc acgctgccat cctccggtac cgcgctgata agcctggttg   17100
acggaagtgg caatccggtc agcgtggagg ttcagtccgt caccgacggc gtgaaggtaa   17160
aagtgagccg tgttcctgac ggtgttgctg aatacagcgc atgggagctg aagctgccga   17220
cgctgcgcca gcgactgttc cgctgcgtga gtatccgtga gaacgacgac ggcacgtatg   17280
ccatcaccgc cgtgcagcat gtgccggaaa aagaggccat cgtggataac ggggcgcact   17340
ttgacggcga acagagtggc acggtgaatg gtgtcacgcc gccagcggtg cagcacctga   17400
ccgcagaagt cactgcagac agcgggggaat atcaggtgct ggcgcgatgg gacacaccga   17460
aggtggtgaa gggcgtgagt ttcctgctcc gtctgaccgt aacagcggac gacggcagtg   17520
agcggctggt cagcacggcc cggacgacgg aaaccacata ccgcttcacg caactggcgc   17580
tggggaacta caggctgaca gtccgggcgg taaatgcgtg ggggcagcag ggcgatccgg   17640
cgtcggtatc gttccggatt gccgcaccgg cagcaccgtc gaggattgag ctgacgccgg   17700
gctattttca gataaccgcc acgccgcatc ttgccgttta tgacccgacg gtacagtttg   17760
agttctggtt ctcggaaaag cagattgcgg atatcagaca ggttgaaacc agcacgcgtt   17820
atcttggtac ggcgctgtac tggatagccg ccagtatcaa tatcaaaccg ggccatgatt   17880
attactttta tatccgcagt gtgaacaccg ttggcaaatc ggcattcgtg gaggccgtcg   17940
gtcgggcgag cgatgatgcg gaaggttacc tggattttt caaaggcaag ataaccgaat   18000
cccatctcgg caaggagctg ctggaaaaag tcgagctgac ggaggataac gccagcagac   18060
tggaggagtt ttcgaaagag tggaaggatg ccagtgataa gtggaatgcc atgtgggctg   18120
tcaaaattga gcagaccaaa gacggcaaac attatgtcgc gggtattggc ctcagcatgg   18180
aggacacgga ggaaggcaaa ctgagccagt ttctggttgc cgccaatcgt atcgcattta   18240
ttgacccggc aaacgggaat gaaacgccga tgtttgtggc gcaggcaac cagatattca   18300 tgaacgacgt gttcctgaag cgcctgacgg cccccaccat taccagcggc ggcaatcctc   18360
cggccttttc cctgacaccg gacggaaagc tgaccgctaa aaatgcggat atcagtggca   18420
gtgtgaatgc gaactccggg acgctcagta atgtgacgat agctgaaaac tgtacgataa   18480
acggtacgct gagggcggaa aaaatcgtcg gggacattgt aaaggcggcg agcgcggctt   18540
ttccgcgcca gcgtgaaagc agtgtggact ggccgtcagg tacccgtact gtcaccgtga   18600
ccgatgacca tccttttgat cgccagatag tggtgcttcc gctgacgttt cgcggaagta   18660
agcgtactgt cagcggcagg acaacgtatt cgatgtgtta tctgaaagta ctgatgaacg   18720
```

```
gtgcggtgat ttatgatggc gcggcgaacg aggcggtaca ggtgttctcc cgtattgttg   18780
acatgccagc gggtcgggga aacgtgatcc tgacgttcac gcttacgtcc acacggcatt   18840
cggcagatat tccgccgtat acgtttgcca gcgatgtgca ggttatggtg attaagaaac   18900
aggcgctggg catcagcgtg gtctgagtgt gttacagagg ttcgtccggg aacgggcgtt   18960
ttattataaa acagtgagag gtgaacgatg cgtaatgtgt gtattgccgt tgctgtcttt   19020
gccgcacttg cggtgacagt cactccggcc cgtgcgaagg tggacatgg tacgtttacg    19080 gtgggctatt ttcaagtgaa accgggtaca ttgccgtcgt tgtcgggcgg ggataccggt   19140
gtgagtcatc tgaaagggat taacgtgaag taccgttatg agctgacgga cagtgtgggg   19200
gtgatggctt ccctggggtt cgccgcgtcg aaaaagagca gcacagtgat gaccggggag   19260
gatacgtttc actatgagag cctgcgtgga cgttatgtga gcgtgatggc cggaccggtt   19320
ttacaaatca gtaagcaggt cagtgcgtac gccatggccg gagtggctca cagtcggtgg   19380
tccggcagta caatggatta ccgtaagacg gaaatcactc ccgggtatat gaaagagacg   19440
accactgcca gggacgaaag tgcaatgcgg catacctcag tggcgtggag tgcaggtata   19500
cagattaatc cggcagcgtc cgtcgttgtt gatattgctt atgaaggctc cggcagtggc   19560
gactggcgta ctgacggatt catcgttggg gtcggttata aattctgatt agccaggtaa   19620
cacagtgtta tgacagcccg ccggaaccgg tgggcttttt tgtggggtga atatggcagt   19680
aaagatttca ggagtcctga agacggcac aggaaaaccg gtacagaact gcaccattca     19740
gctgaaagcc agacgtaaca gcaccacggt ggtggtgaac acggtgggct cagagaatcc   19800
ggatgaagcc gggcgttaca gcatggatgt ggagtacggt cagtacagtg tcatcctgca   19860
ggttgacggt tttccaccat cgcacgccgg gaccatcacc gtgtatgaag attcacaacc   19920
ggggacgctg aatgattttc tctgtgccat gacggaggat gatgcccggc cggaggtgct   19980
gcgtcgtctt gaactgatgg tggaagaggt ggcgcgtaac gcgtccgtgg tggcacagag   20040
tacggcagac gcgaagaaat cagccggcga tgccagtgca tcagctgctc aggtcgcggc   20100
ccttgtgact gatgcaactg actcagcacg cgccgccagc acgtccgccg gacaggctgc   20160
atcgtcagct caggaagcgt cctccggcgc agaagcggca tcagcaaagg ccactgaagc   20220
ggaaaaaagt gccgcagccg cagagtcctc aaaaaacgcg gcggccacca gtgccggtgc   20280
ggcgaaaacg tcagaaacga atgctgcagc gtcacaacaa tcagccgcca cgtctgcctc   20340
caccgcggcc acgaaagcgt cagaggccgc cacttcagca cgagatgcgg tggcctcaaa   20400
agaggcagca aaatcatcag aaacgaacgc atcatcaagt gccggtcgtg cagcttcctc   20460
ggcaacggcg gcagaaaatt ctgccagggc ggcaaaaacg tccgagacga atgccaggtc   20520
atctgaaaca gcagcggaac ggagcgcctc tgccgcggca gacgcaaaaa cagcggcggc   20580
ggggagtgcg tcaacggcat ccacgaaggc gacagaggct gcgggaagtg cggtatcagc   20640
atcgcagagc aaaagtgcgg cagaagcggc ggcaatacgt gcaaaaaatt cggcaaaacg   20700
tgcagaagat atagcttcag ctgtcgcgct tgaggatgcg gacacaacga gaaagggggat  20760 agtgcagctc agcagtgcaa ccaacagcac gtctgaaacg cttgctgcaa cgccaaaggc   20820
ggttaaggtg gtaatggatg aaacgaacag aaaagcccac tggacagtcc ggcactgacc   20880
ggaacgccaa cagcaccaac cgcgctcagg ggaacaaaca atacccagat tgcgaacacc   20940
gcttttgtac tggccgcgat tgcagatgtt atcgacgcgt cacctgacgc actgaatacg   21000
ctgaatgaac tggccgcagc gctcgggaat gatccagatt ttgctaccac catgactaac   21060
```

```
gcgcttgcgg gtaaacaacc gaagaatgcg acactgacgg cgctggcagg gctttccacg   21120
gcgaaaaata aattaccgta ttttgcggaa aatgatgccg ccagcctgac tgaactgact   21180
caggttggca gggatattct ggcaaaaaat tccgttgcag atgttcttga ataccttggg   21240
gccggtgaga attcggcctt tccggcaggt gcgccgatcc cgtggccatc agatatcgtt   21300
ccgtctggct acgtcctgat gcaggggcag gcgtttgaca aatcagccta cccaaaactt   21360
gctgtcgcgt atccatcggg tgtgcttcct gatatgcgag gctggacaat caaggggaaa   21420
cccgccagcg gtcgtgctgt attgtctcag gaacaggatg gaattaagtc gcacacccac   21480
agtgccagtg catccggtac ggatttgggg acgaaaacca tcgtcgtt tgattacggg     21540 acgaaaacaa caggcagttt cgattacggc accaaatcga cgaataacac gggggctcat   21600
gctcacagtc tgagcggttc aacaggggcc gcgggtgctc atgcccacac aagtggttta   21660
aggatgaaca gttctggctg gagtcagtat ggaacagcaa ccattacagg aagtttatcc   21720
acagttaaag gaaccagcac acagggtatt gcttatttat cgaaaacgga cagtcagggc   21780
agccacagtc actcattgtc cggtacagcc gtgagtgccg gtgcacatgc gcatacagtt   21840
ggtattggtg cgcaccagca tccggttgtt atcggtgctc atgcccattc tttcagtatt   21900
ggttcacacg gacacaccat caccgttaac gctgcgggta acgcgaaaaa caccgtcaaa   21960
aacattgcat ttaactatat tgtgaggctt gcataatggc attcagaatg agtgaacaac   22020
cacggaccat aaaaatttat aatctgctgg ccggaactaa tgaatttatt ggtgaaggtg   22080
acgcatatat tccgcctcat accggtctgc ctgcaaacag taccgatatt gcaccgccag   22140
atattccggc tggctttgtg gctgttttca acagtgatga ggcatcgtgg catctcgttg   22200
aagaccatcg gggtaaaacc gtctatgacg tggcttccgg cgacgcgtta tttatttctg   22260
aactcggtcc gttaccggaa aattttacct ggttatcgcc gggagggaa tatcagaagt    22320 ggaacggcac agcctgggtg aaggatacgg aagcagaaaa actgttccgg atccgggagg   22380
cggaagaaac aaaaaaaagc ctgatgcagg tagccagtga gcatattgcg ccgcttcagg   22440
atgctgcaga tctggaaatt gcaacgaagg aagaaacctc gttgctggaa gcctggaaga   22500
agtatcgggt gttgctgaac cgtgttgata catcaactgc acctgatatt gagtggcctg   22560
ctgtccctgt tatggagtaa tcgttttgtg atatgccgca gaaacgttgt atgaaataac   22620
gttctgcggt tagttagtat attgtaaagc tgagtattgg tttatttggc gattattatc   22680
ttcaggagaa taatggaagt tctatgactc aattgttcat agtgtttaca tcaccgccaa   22740
ttgcttttaa gactgaacgc atgaaatatg gttttcgtc atgttttgag tctgctgttg    22800
atatttctaa agtcggtttt ttttcttcgt tttctctaac tattttccat gaaatacatt   22860
tttgattatt atttgaatca attccaatta cctgaagtct ttcatctata attggcattg   22920
tatgtattgg tttattggag tagatgcttg cttttctgag ccatagctct gatatccaaa   22980
tgaagccata ggcatttgtt attttggctc tgtcagctgc ataacgccaa aaaatatatt   23040
tatctgcttg atcttcaaat gttgtattga ttaaatcaat tggatggaat tgtttatcat   23100
aaaaaattaa tgtttgaatg tgataaccgt cctttaaaaa agtcgtttct gcaagcttgg   23160
ctgtatagtc aactaactct tctgtcgaag tgatattttt aggcttatct accagtttta   23220
gacgctcttt aatatcttca ggaattattt tattgtcata ttgtatcatg ctaaatgaca   23280
atttgcttat ggagtaatct tttaatttta aataagttat tctcctggct tcatcaaata   23340
aagagtcgaa tgatgttggc gaaatcacat cgtcacccat tggattgttt atttgtatgc   23400
caagagagtt acagcagtta tacattctgc catagattat agctaaggca tgtaataatt   23460
```

```
cgtaatctttt tagcgtatta gcgacccatc gtctttctga tttaataata gatgattcag   23520
ttaaatatga aggtaatttc ttttgtgcaa gtctgactaa cttttttata ccaatgttta   23580
acatactttc atttgtaata aactcaatgt catttcttc aatgtaagat gaaataagag   23640
tagcctttgc ctcgctatac atttctaaat cgccttgttt ttctatcgta ttgcgagaat   23700
ttttagccca agccattaat ggatcatttt tccatttttc aataacatta ttgttatacc   23760
aaatgtcata tcctataatc tggttttttgt tttttttgaat aataaatgtt actgttcttg   23820
cggtttggag gaattgattc aaattcaagc gaaataattc agggtcaaaa tatgtatcaa   23880
tgcagcattt gagcaagtgc gataaatctt taagtcttct ttcccatggt ttttttagtca   23940 taaaactctc cattttgata ggttgcatgc tagatgctga tatattttag aggtgataaa   24000
attaactgct taactgtcaa tgtaatacaa gttgtttgat ctttgcaatg attcttatca   24060 gaaccatat agtaaattag ttacacagga aattttttaat attattatta tcattcatta   24120
tgtattaaaa ttagagttgt ggcttggctc tgctaacacg ttgctcatag gagatatggt   24180
agagccgcag acacgtcgta tgcaggaacg tgctgcggct ggctggtgaa cttccgatag   24240
tgcgggtgtt gaatgatttc cagttgctac cgattttaca tatttttttgc atgagagaat   24300 ttgtaccacc tcccaccgac catctatgac tgtacgccac tgtccctagg actgctatgt   24360
gccggagcgg acattacaaa cgtccttctc ggtgcatgcc actgttgcca atgacctgcc   24420
taggaattgg ttagcaagtt actaccggat tttgtaaaaa cagccctcct catataaaaa   24480
gtattcgttc acttccgata agcgtcgtaa ttttctatct ttcatcatat tctagatccc   24540
tctgaaaaaa tcttccgagt ttgctaggca ctgatacata actcttttcc aataatttggg   24600 gaagtcattc aaatctataa taggtttcag atttgcttca ataaattctg actgtagctg   24660
ctgaaacgtt gcggttgaac tatatttcct tataacttttt acgaaagagt ttctttgagt   24720
aatcacttca ctcaagtgct tccctgcctc caaacgatac ctgttagcaa tatttaatag   24780
cttgaaatga tgaagagctc tgtgtttgtc ttcctgcctc cagttcgccg ggcattcaac   24840 ataaaactg atagcacccg gagttccgga aacgaaattt gcatataccc attgctcacg   24900
aaaaaaaatg tccttgtcga tatagggatg aatcgcttgg tgtacctcat ctactgcgaa   24960 aacttgaccct ttctctccca tattgcagtc gcggcacgat ggaactaaat taataggcat   25020
caccgaaaat tcaggataat gtgcaatagg aagaaaatga tctatatttt ttgtctgtcc   25080
tatatcacca caaatggac attttttcacc tgatgaaaca agcatgtcat cgtaatatgt   25140
tctagcgggt ttgtttttat ctcggagatt attttcataa agcttttcta atttaacctt   25200
tgtcaggtta ccaactacta aggttgtagg ctcaagaggg tgtgtcctgt cgtaggtaaa   25260
taactgacct gtcgagctta atattctata ttgttgttct ttctgcaaaa agtggggaa   25320 gtgagtaatg aaattatttc taacatttat ctgcatcata ccttccgagc atttattaag   25380
catttcgcta taagttctcg ctggaagagg tagttttttc attgtacttt accttcatct   25440
ctgttcatta tcatcgcttt taaaacggtt cgaccttcta atcctatctg accattataa   25500 tttttttagaa tggtttcata agaaagctct gaatcaacgg actgcgataa taagtggtgg   25560
tatccagaat ttgtcacttc aagtaaaaac acctcacgag ttaaaacacc taagttctca   25620
ccgaatgtct caatatccgg acggataata tttattgctt ctcttgaccg taggactttc   25680
cacatgcagg attttggaac ctcttgcagt actactgggg aatgagttgc aattattgct   25740
acaccattgc gtgcatcgag taagtcgctt aatgttcgta aaaaagcaga gagcaaaggt   25800
```

```
ggatgcagat gaacctctgg ttcatcgaat aaaactaatg acttttcgcc aacgacatct   25860
actaatcttg tgatagtaaa taaaacaatt gcatgtccag agctcattcg aagcagatat   25920
ttctggatat tgtcataaaa caatttagtg aatttatcat cgtccacttg aatctgtggt   25980
tcattacgtc ttaactcttc atatttagaa atgaggctga tgagttccat atttgaaaag   26040
ttttcatcac tacttagttt tttgatagct tcaagccaga gttgtctttt tctatctact   26100
ctcatacaac caataaatgc tgaaatgaat tctaagcgga gatcgcctag tgattttaaa   26160
ctattgctgg cagcattctt gagtccaata taaaagtatt gtgtacctttt gctgggtca   26220 ggttgttctt taggaggagt aaaaggatca aatgcactaa acgaaactga acaagcgat    26280 cgaaaatatc cctttgggat tcttgactcg ataagtctat tattttcaga gaaaaaatat   26340
tcattgtttt ctgggttggt gattgcacca atcattccat tcaaaattgt tgttttacca   26400
cacccattcc gcccgataaa agcatgaatg ttcgtgctgg gcatagaatt aaccgtcacc   26460 tcaaaggta tagttaaatc actgaatccg ggagcacttt ttctattaaa tgaaagtgg    26520 aaatctgaca attctggcaa accatttaac acacgtgcga actgtccatg aatttctgaa   26580
agagttaccc ctctaagtaa tgaggtgtta aggacgcttt cattttcaat gtcggctaat   26640
cgatttggcc atactactaa atcctgaata gctttaagaa ggttatgttt aaaaccatcg   26700
cttaatttgc tgagattaac atagtagtca atgctttcac ctaaggaaaa aaacatttca   26760
gggagttgac tgaatttttt atctattaat gaataagtgc ttacttcttc tttttgacct   26820
acaaaaccaa ttttaacatt tccgatatcg cattttcac catgctcatc aaagacagta    26880
agataaaaca ttgtaacaaa ggaatagtca ttccaaccat ctgctcgtag gaatgcctta   26940 ttttttcta ctgcaggaat atacccgcct ctttcaataa cactaaactc caacatatag    27000
taacccttaa ttttattaaa ataaccgcaa tttatttggc ggcaacacag gatctctctt   27060
ttaagttact ctctattaca tacgttttcc atctaaaaat tagtagtatt gaacttaacg   27120
gggcatcgta ttgtagtttt ccatatttag ctttctgctt cctttggat aacccactgt    27180 tattcatgtt gcatggtgca ctgtttatac caacgatata gtctattaat gcatatatag   27240
tatcgccgaa cgattagctc ttcaggcttc tgaagaagcg tttcaagtac taataagccg   27300
atagatagcc acggacttcg tagccatttt tcataagtgt taacttccgc tcctcgctca   27360
taacagacat tcactacagt tatggcggaa aggtatgcat gctgggtgtg gggaagtcgt   27420
gaaagaaaag aagtcagctg cgtcgtttga catcactgct atcttcttac tggttatgca   27480
ggtcgtagtg ggtggcacac aaagctttgc actggattgc gaggctttgt gcttctctgg   27540
agtgcgacag gtttgatgac aaaaaattag cgcaagaaga caaaaatcac cttgcgctaa   27600
tgctctgtta caggtcacta ataccatcta agtagttgat tcatagtgac tgcatatgtt   27660
gtgttttaca gtattatgta gtctgttttt tatgcaaaat ctaatttaat atattgatat   27720
ttatatcatt ttacgtttct cgttcagctt ttttatacta agttggcatt ataaaaaagc   27780
attgcttatc aatttgttgc aacgaacagg tcactatcag tcaaaataaa atcattattt   27840
gatttcaatt ttgtcccact ccctgcctct gtcatcacga tactgtgatg ccatggtgtc   27900
cgacttatgc ccgagaagat gttgagcaaa cttatcgctt atctgcttct catagagtct   27960
tgcagacaaa ctgcgcaact cgtgaaaggt aggcggatcc ccttcgaagg aaagacctga   28020
tgcttttcgt gcgcgcataa aataccttga tactgtgccg gatgaaagcg gttcgcgacg   28080
agtagatgca attatggttt ctccgccaag aatctctttg catttatcaa gtgtttcctt   28140
cattgatatt ccgagagcat caatatgcaa tgctgttggg atggcaattt ttacgcctgt   28200
```

```
tttgctttgc tcgacataaa gatatccatc tacgatatca gaccacttca tttcgcataa    28260
atcaccaact cgttgcccgg taacaacagc cagttccatt gcaagtctga gccaacatgg    28320
tgatgattct gctgcttgat aaattttcag gtattcgtca gccgtaagtc ttgatctcct    28380
tacctctgat tttgctgcgc gagtggcagc gacatggttt gttgttatat ggccttcagc    28440
tattgcctct cggaatgcat cgctcagtgt tgatctgatt aacttggctg acgccgcctt    28500
gccctcgtct atgtatccat tgagcattgc cgcaatttct tttgtggtga tgtcttcaag    28560
tggagcatca ggcagacccc tccttattgc tttaattttg ctcatgtaat ttatgagtgt    28620
cttctgcttg attcctctgc tggccaggat tttttcgtag cgatcaagcc atgaatgtaa    28680
cgtaacggaa ttatcactgt tgattctcgc tgtcagaggc ttgtgtttgt gtcctgaaaa    28740
taactcaatg ttggcctgta tagcttcagt gattgcgatt cgcctgtctc tgcctaatcc    28800
aaactcttta cccgtccttg ggtccctgta gcagtaatat ccattgtttc ttatataaag    28860
gttaggggt aaatcccggc gctcatgact tcgccttctt cccatttctg atcctcttca    28920
aaaggccacc tgttactggt cgatttaagt caacctttac cgctgattcg tggaacagat    28980
actctcttcc atccttaacc ggaggtggga atatcctgca ttcccgaacc catcgacgaa    29040
ctgtttcaag gcttcttgga cgtcgctggc gtgcgttcca ctcctgaagt gtcaagtaca    29100
tcgcaaagtc tccgcaatta cacgcaagaa aaaccgcca tcaggcggct tggtgttctt    29160
tcagttcttc aattcgaata ttggttacgt ctgcatgtgc tatctgcgcc catatcatcc    29220
agtggtcgta gcagtcgttg atgttctccg cttcgataac tctgttgaat ggctctccat    29280
tccattctcc tgtgactcgg aagtgcattt atcatctcca taaaacaaaa cccgccgtag    29340
cgagttcaga taaataaat ccccgcgagt gcgaggattg ttatgtaata ttgggtttaa    29400
tcatctatat gttttgtaca gagagggcaa gtatcgtttc caccgtactc gtgataataa    29460
ttttgcacgg tatcagtcat ttctcgcaca ttgcagaatg gggatttgtc ttcattagac    29520
ttataaacct tcatggaata tttgtatgcc gactctatat ctataccttc atctacataa    29580
acaccttcgt gatgtctgca tggagacaag acaccggatc tgcacaacat tgataacgcc    29640
caatctttt gctcagactc taactcattg atactcattt ataaactcct tgcaatgtat    29700
gtcgtttcag ctaaacggta tcagcaatgt ttatgtaaag aaacagtaag ataatactca    29760
acccgatgtt tgagtacggt catcatctga cactacagac tctggcatcg ctgtgaagac    29820
gacgcgaaat tcagcatttt cacaagcgtt atcttttaca aaaccgatct cactctcctt    29880
tgatgcgaat gccagcgtca gacatcatat gcagatactc acctgcatcc tgaacccatt    29940
gacctccaac cccgtaatag cgatgcgtaa tgatgtcgat agttactaac gggtcttgtt    30000
cgattaactg ccgcagaaac tcttccaggt caccagtgca gtgcttgata acaggagtct    30060
tcccaggatg gcgaacaaca agaaactggt ttccgtcttc acggacttcg ttgctttcca    30120
gtttagcaat acgcttactc ccatccgaga taacaccttc gtaatactca cgctgctcgt    30180
tgagttttga ttttgctgtt tcaagctcaa cacgcagttt ccctactgtt agcgcaatat    30240
cctcgttctc ctggtcgcgg cgtttgatgt attgctggtt tctttcccgt tcatccagca    30300
gttccagcac aatcgatggt gttaccaatt catggaaaag gtctgcgtca atcccccagt    30360
cgtcatgcat tgcctgctct gccgcttcac gcagtgcctg agagttaatt tcgctcactt    30420
cgaacctctc tgtttactga taagttccag atcctcctgg caacttgcac aagtccgaca    30480
accctgaacg accaggcgtc ttcgttcatc tatcggatcg ccacactcac aacaatgagt    30540
```

```
ggcagatata gcctggtggt tcaggcggcg catttttatt gctgtgttgc gctgtaattc   30600
ttctatttct gatgctgaat caatgatgtc tgccatcttt cattaatccc tgaactgttg   30660
gttaatacgc ttgagggtga atgcgaataa taaaaaagga gcctgtagct ccctgatgat   30720
tttgcttttc atgttcatcg ttccttaaag acgccgttta acatgccgat tgccaggctt   30780
aaatgagtcg gtgtgaatcc catcagcgtt accgtttcgc ggtgcttctt cagtacgcta   30840
cggcaaatgt catcgacgtt tttatccgga aactgctgtc tggcttttt tgatttcaga   30900
attagcctga cgggcaatgc tgcgaagggc gttttcctgc tgaggtgtca ttgaacaagt   30960
cccatgtcgg caagcataag cacacagaat atgaagcccg ctgccagaaa aatgcattcc   31020
gtggttgtca tacctggttt ctctcatctg cttctgcttt cgccaccatc atttccagct   31080
tttgtgaaag ggatgcggct aacgtatgaa attcttcgtc tgtttctact ggtattggca   31140
caaacctgat tccaatttga gcaaggctat gtgccatctc gatactcgtt cttaactcaa   31200
cagaagatgc tttgtgcata cagcccctcg tttattattt atctcctcag ccagccgctg   31260
tgctttcagt ggatttcgga taacagaaag gccgggaaat acccagcctc gctttgtaac   31320
ggagtagacg aaagtgattg cgcctacccg gatattatcg tgaggatgcg tcatcgccat   31380
tgctccccaa atacaaaacc aatttcagcc agtgcctcgt ccattttttc gatgaactcc   31440
ggcacgatct cgtcaaaact cgccatgtac ttttcatccc gctcaatcac gacataatgc   31500
aggccttcac gcttcatacg cgggtcatag ttggcaaagt accaggcatt ttttcgcgtc   31560
acccacatgc tgtactgcac ctgggccatg taagctgact ttatggcctc gaaaccaccg   31620
agccggaact tcatgaaatc ccgggaggta acgggcatt tcagttcaag gccgttgccg   31680
tcactgcata aaccatcggg agagcaggcg gtacgcatac tttcgtcgcg atagatgatc   31740
ggggattcag taacattcac gccggaagtg aattcaaaca gggttctggc gtcgttctcg   31800
tactgttttc cccaggccag tgctttagcg ttaacttccg gagccacacc ggtgcaaacc   31860
tcagcaagca gggtgtggaa gtaggacatt ttcatgtcag gccacttctt tccggagcgg   31920
ggttttgcta tcacgttgtg aacttctgaa gcggtgatga cgccgagccg taatttgtgc   31980
cacgcatcat cccctgttc gacagctctc acatcgatcc cggtacgctg caggataatg   32040
tccggtgtca tgctgccacc ttctgctctg cggctttctg tttcaggaat ccaagagctt   32100
ttactgcttc ggcctgtgtc agttctgacg atgcacgaat gtcgcggcga atatctgggg   32160
aacagagcgg caataagtcg tcatcccatg ttttatccag ggcgatcagc agagtgttaa   32220
tctcctgcat ggtttcatcg ttaaccgag tgatgtcgcg ttccggctga cgttctgcag   32280
tgtatgcagt attttcgaca atgcgctcgg cttcatcctt gtcatagata ccagcaaatc   32340
cgaaggccag acgggcacac tgaatcatgg ctttatgacg taacatccgt ttgggatgcg   32400
actgccacgg ccccgtgatt tctctgcctt cgcgagtttt gaatggttcg cggcggcatt   32460
catccatcca ttcggtaacg cagatcggat gattacggtc cttgcggtaa atccggcatg   32520
tacaggattc attgtcctgc tcaaagtcca tgccatcaaa ctgctggttt tcattgatga   32580
tgcgggacca gccatcaacg cccaccaccg gaacgatgcc attctgctta tcaggaaagg   32640
cgtaaatttc tttcgtccac ggattaaggc cgtactggtt ggcaacgatc agtaatgcga   32700
tgaactgcgc atcgctggca tcacctttaa atgccgtctg gcgaagagtg gtgatcagtt   32760
cctgtgggtc gacagaatcc atgccgacac gttcagccag cttcccagcc agcgttgcga   32820
gtgcagtact cattcgtttt atacctctga atcaatatca acctggtggt gagcaatggt   32880
ttcaaccatg taccggatgt gttctgccat gcgctcctga aactcaacat cgtcatcaaa   32940
```

```
cgcacgggta atggattttt tgctggcccc gtggcgttgc aaatgatcga tgcatagcga    33000
ttcaaacagg tgctggggca ggccttttc catgtcgtct gccagttctg cctctttctc     33060
ttcacgggcg agctgctggt agtgacgcgc ccagctctga gcctcaagac gatcctgaat    33120
gtaataagcg ttcatggctg aactcctgaa atagctgtga aaatatcgcc cgcgaaatgc    33180
cgggctgatt aggaaaacag gaaaggggt tagtgaatgc ttttgcttga tctcagtttc     33240
agtattaata tccattttt ataagcgtcg acggcttcac gaaacatctt ttcatcgcca     33300
ataaaagtgg cgatagtgaa tttagtctgg atagccataa gtgtttgatc cattctttgg    33360
gactcctggc tgattaagta tgtcgataag gcgtttccat ccgtcacgta atttacgggt    33420
gattcgttca agtaaagatt cggaagggca gccagcaaca ggccaccctg caatggcata    33480
ttgcatggtg tgctccttat ttatacataa cgaaaaacgc ctcgagtgaa gcgttattgg    33540
tatgcggtaa aaccgcactc aggcggcctt gatagtcata tcatctgaat caaatattcc    33600
tgatgtatcg atatcggtaa ttcttattcc ttcgctacca tccattggag gccatccttc    33660
ctgaccattt ccatcattcc agtcgaactc acacacaaca ccatatgcat ttaagtcgct    33720
tgaaattgct ataagcagag catgttgcgc cagcatgatt aatacagcat ttaatacaga    33780
gccgtgttta ttgagtcggt attcagagtc tgaccagaaa ttattaatct ggtgaagttt    33840
ttcctctgtc attcgtcat ggtcgattc aatttctatt gatgctttcc agtcgtaatc      33900
aatgatgtat ttttgatgt tgacatctg ttcatatcct cacagataaa aaatcgccct      33960
cacactggag ggcaaagaag atttccaata atcagaacaa gtcggctcct gtttagttac    34020
gagcgacatt gctccgtgta ttcactcgtt ggaatgaata cacagtgcag tgtttattct    34080
gttatttatg ccaaaaataa aggccactat caggcagctt tgttgttctg tttaccaagt    34140
tctctggcaa tcattgccgt cgttcgtatt gcccatttat cgacatattt cccatcttcc    34200
attacaggaa acatttcttc aggcttaacc atgcattccg attgcagctt gcatccattg    34260
catcgcttga attgtccaca ccattgattt ttatcaatag tcgtagtcat acggatagtc    34320
ctggtattgt tccatcacat cctgaggatg ctcttcgaac tcttcaaatt cttcttccat    34380
atatcacctt aaatagtgga ttgcggtagt aaagattgtg cctgtctttt aaccacatca    34440
ggctcggtgg ttctcgtgta cccctacagc gagaaatcgg ataaactatt acaaccccta    34500
cagtttgatg agtatagaaa tggatccact cgttattctc ggacgagtgt tcagtaatga    34560
acctctggag agaaccatgt atatgatcgt tatctgggtt ggacttctgc ttttaagccc    34620
agataactgg cctgaatatg ttaatgagag aatcggtatt cctcatgtgt ggcatgtttt    34680
cgtctttgct cttgcatttt cgctagcaat taatgtgcat cgattatcag ctattgccag    34740
cgccagatat aagcgattta agctaagaaa acgcattaag atgcaaaacg ataaagtgcg    34800
atcagtaatt caaaacctta cagaagagca atctatggtt ttgtgcgcag cccttaatga    34860
aggcaggaag tatgtggtta catcaaaaca attcccatac attagtgagt tgattgagct    34920
tggtgtgttg aacaaaactt tttcccgatg gaatggaaag catatattat tcccctattga   34980 ggatatttac tggactgaat tagttgccag ctatgatcca tataatattg agataaagcc    35040
aaggccaata tctaagtaac tagataagag gaatcgattt tcccttaatt ttctggcgtc    35100
cactgcatgt tatgccgcgt tcgccaggct tgctgtacca tgtgcgctga ttcttgcgct    35160
caatacgttg caggttgctt tcaatctgtt tgtggtattc agccagcact gtaaggtcta    35220
tcggatttag tgcgctttct actcgtgatt tcggtttgcg attcagcgag agaatagggc    35280
```

```
ggttaactgg ttttgcgctt acccccaacca acaggggatt tgctgctttc cattgagcct   35340
gtttctctgc gcgacgttcg cggcggcgtg tttgtgcatc catctggatt ctcctgtcag   35400
ttagctttgg tggtgtgtgg cagttgtagt cctgaacgaa aacccccgc  gattggcaca   35460
ttggcagcta atccggaatc gcacttacgg ccaatgcttc gtttcgtatc acacacccca   35520
aagccttctg ctttgaatgc tgcccttctt cagggcttaa ttttttaagag cgtcaccttc   35580
atggtggtca gtgcgtcctg ctgatgtgct cagtatcacc gccagtggta tttatgtcaa   35640
caccgccaga gataaatttat caccgcagat ggttatctgt atgtttttta tatgaattta   35700
tttttttgcag gggggcattg tttggtaggt gagagatctg aattgctatg tttagtgagt   35760
tgtatctatt tattttttcaa taaatacaat tggttatgtg ttttgggggc gatcgtgagg   35820
caaagaaaac ccggcgctga ggccgggtta ttcttgttct ctggtcaaat tatatagttg   35880
gaaaacaagg atgcatatat gaatgaacga tgcagaggca atgccgatgg cgatagtggg   35940
tatcatgtag ccgcttatgc tggaaagaag caataacccg cagaaaaaca aagctccaag   36000
ctcaacaaaa ctaagggcat agacaataac taccgatgtc atatacccat actctctaat   36060
cttggccagt cggcgcgttc tgcttccgat tagaaacgtc aaggcagcaa tcaggattgc   36120
aatcatggtt cctgcatatg atgacaatgt cgccccaaga ccatctctat gagctgaaaa   36180
agaaacacca ggaatgtagt ggcggaaaag gagatagcaa atgcttacga taacgtaagg   36240
aattattact atgtaaacac caggcatgat tctgttccgc ataattactc ctgataatta   36300
atccttaact ttgcccacct gccttttaaa acattccagt atatcacttt tcattcttgc   36360
gtagcaatat gccatctctt cagctatctc agcattggtg accttgttca gaggcgctga   36420
gagatggcct ttttctgata gataatgttc tgttaaaata tctccggcct catctttgc   36480
ccgcaggcta atgtctgaaa attgaggtga cgggttaaaa ataatatcct tggcaacctt   36540
ttttatatcc cttttaaatt ttggcttaat gactatatcc aatgagtcaa aaagctcccc   36600
ttcaatatct gttgccccta agacctttaa tatatcgcca aatacaggta gcttggcttc   36660
taccttcacc gttgttcggc cgatgaaatg catatgcata acatcgtctt tggtggttcc   36720
cctcatcagt ggctctatct gaacgcgctc tccactgctt aatgacattc ctttcccgat   36780
taaaaaatct gtcagatcgg atgtggtcgg cccgaaaaca gttctggcaa aaccaatggt   36840
gtcgccttca acaaacaaaa aagatgggaa tcccaatgat tcgtcatctg cgaggctgtt   36900
cttaatatct tcaactgaag ctttagagcg atttatcttc tgaaccagac tcttgtcatt   36960
tgttttggta aagagaaaag ttttttccatc gattttatga atatacaaat aattggagcc   37020
aacctgcagg tgatgattat cagccagcag agaattaagg aaaacagaca ggtttattga   37080
gcgcttatct ttccctttat ttttgctgcg gtaagtcgca taaaaaccat tcttcataat   37140
tcaatccatt tactatgtta tgttctgagg ggagtgaaaa ttcccctaat tcgatgaaga   37200
ttcttgctca attgttatca gctatgcgcc gaccagaaca ccttgccgat cagccaaacg   37260
tctcttcagg ccactgacta gcgataactt tccccacaac ggaacaactc tcattgcatg   37320
ggatcattgg gtactgtggg tttagtggtt gtaaaacac  ctgaccgcta tccctgatca   37380
gtttcttgaa ggtaaactca tcaccccccaa gtctggctat gcagaaatca cctggctcaa   37440
cagcctgctc agggtcaacg agaattaaca ttccgtcagg aaagcttggc ttggagcctg   37500
ttggtgcggt catggaatta ccttcaacct caagccagaa tgcagaatca ctggcttttt   37560
tggttgtgct tacccatctc tccgcatcac ctttggtaaa ggttctaagc ttaggtgaga   37620
acatccctgc ctgaacatga gaaaaaacag ggtactcata ctcacttcta agtgacggct   37680
```

```
gcatactaac cgcttcatac atctcgtaga tttctctggc gattgaaggg ctaaattctt    37740
caacgctaac tttgagaatt tttgtaagca atgcggcgtt ataagcattt aatgcattga    37800
tgccattaaa taaagcacca acgcctgact gccccatccc catcttgtct gcgacagatt    37860
cctgggataa gccaagttca ttttctttt tttcataaat tgctttaagg cgacgtgcgt    37920
cctcaagctg ctcttgtgtt aatggtttct ttttgtgct catacgttaa atctatcacc    37980
gcaagggata aatatctaac accgtgcgtg ttgactattt tacctctggc ggtgataatg    38040
gttgcatgta ctaaggaggt tgtatggaac aacgcataac cctgaaagat tatgcaatgc    38100
gctttgggca aaccaagaca gctaaagatc tcggcgtata tcaaagcgcg atcaacaagg    38160
ccattcatgc aggccgaaag atttttttaa ctataaacgc tgatggaagc gtttatgcgg    38220
aagaggtaaa gccctttccg agtaacaaaa aacaacagc ataaataacc ccgctcttac    38280
acattccagc cctgaaaaag ggcatcaaat taaccacac ctatggtgta tgcatttatt    38340
tgcatacatt caatcaattg ttatctaagg aaatacttac atatggttcg tgcaaacaaa    38400
cgcaacgagg ctctacgaat cgagagtgcg ttgcttaaca aaatcgcaat gcttggaact    38460
gagaagacag cggaagctgt gggcgttgat aagtcgcaga tcagcaggtg gaagagggac    38520
tggattccaa agttctcaat gctgcttgct gttcttgaat gggggggtcgt tgacgacgac    38580 atggctcgat tggcgcgaca agttgctgcg attctcacca ataaaaaacg cccggcggca    38640
accgagcgtt ctgaacaaat ccagatggag ttctgaggtc attactggat ctatcaacag    38700
gagtcattat gacaaataca gcaaaaatac tcaacttcgg cagaggtaac tttgccggac    38760
aggagcgtaa tgtggcagat ctcgatgatg gttacgccag actatcaaat atgctgcttg    38820
aggcttattc gggcgcagat ctgaccaagc gacagtttaa agtgctgctt gccattctgc    38880
gtaaaaccta tgggtggaat aaaccaatgg acagaatcac cgattctcaa cttagcgaga    38940
ttacaaagtt acctgtcaaa cggtgcaatg aagccaagtt agaactcgtc agaatgaata    39000
ttatcaagca gcaaggcggc atgttttggac caaataaaaa catctcagaa tggtgcatcc    39060
ctcaaaacga gggaaaatcc cctaaaacga gggataaaac atccctcaaa ttgggggatt    39120
gctatccctc aaaacagggg gacacaaaag acactattac aaaagaaaaa agaaaagatt    39180
attcgtcaga gaattctggc gaatcctctg accagccaga aaacgacctt tctgtggtga    39240
aaccggatgc tgcaattcag agcggcagca agtgggggac agcagaagac ctgaccgccg    39300
cagagtggat gtttgacatg gtgaagacta tcgcaccatc agccagaaaa ccgaattttg    39360
ctgggtgggc taacgatatc cgcctgatgc gtgaacgtga cggacgtaac caccgcgaca    39420
tgtgtgtgct gttccgctgg gcatgccagg acaacttctg gtccggtaac gtgctgagcc    39480
cggccaaact ccgcgataag tggacccaac tcgaaatcaa ccgtaacaag caacaggcag    39540
gcgtgacagc cagcaaacca aaactcgacc tgacaaacac agactggatt tacggggtgg    39600
atctatgaaa aacatcgccg cacagatggt taactttgac cgtgagcaga tgcgtcggat    39660
cgccaacaac atgccggaac agtacgacga aaagccgcag gtacagcagg tagcgcagat    39720
catcaacggt gtgttcagcc agttactggc aactttcccg cgcagcctgg ctaaccgtga    39780
ccagaacgaa gtgaacgaaa tccgtcgcca gtgggttctg gcttttcggg aaaacggat    39840 caccacgatg gaacaggtta acgcaggaat gcgcgtagcc cgtcggcaga atcgaccatt    39900
tctgccatca cccgggcagt tgttgcatg tgtgccgggaa gaagcatccg ttaccgccgg    39960
actgccaaac gtcagcgagc tggttgatat ggtttacgag tattgccgga agcgaggcct    40020
```

```
gtatccggat gcggagtctt atccgtggaa atcaaacgcg cactactggc tggttaccaa    40080
cctgtatcag aacatgcggg ccaatgcgct tactgatgcg gaattacgcc gtaaggccgc    40140
agatgagctt gtccatatga ctgcgagaat taaccgtggt gaggcgatcc ctgaaccagt    40200
aaaacaactt cctgtcatgg gcggtagacc tctaaatcgt gcacaggctc tggcgaagat    40260
cgcagaaatc aaagctaagt tcggactgaa aggagcaagt gtatgacggg caaagaggca    40320
attattcatt acctggggac gcataatagc ttctgtgcgc cggacgttgc cgcgctaaca    40380
ggcgcaacag taaccagcat aaatcaggcc gcggctaaaa tggcacgggc aggtcttctg    40440
gttatcgaag gtaaggtctg gcgaacggtg tattaccggt ttgctaccag ggaagaacgg    40500
gaaggaaaga tgagcacgaa cctggttttt aaggagtgtc gccagagtgc cgcgatgaaa    40560
cgggtattgg cggtatatgg agttaaaaga tgaccatcta cattactgag ctaataacag    40620
gcctgctggt aatcgcaggc ctttttattt gggggagagg gaagtcatga aaaaactaac    40680
ctttgaaatt cgatctccag cacatcagca aaacgctatt cacgcagtac agcaaatcct    40740
tccagaccca accaaaccaa tcgtagtaac cattcaggaa cgcaaccgca gcttagacca    40800
aaacaggaag ctatgggcct gcttaggtga cgtctctcgt caggttgaat ggcatggtcg    40860
ctggctggat gcagaaagct ggaagtgtgt gtttaccgca gcattaaagc agcaggatgt    40920
tgttcctaac cttgccggga atggctttgt ggtaataggc cagtcaacca gcaggatgcg    40980
tgtaggcgaa tttgcggagc tattagagct tatacaggca ttcggtacag agcgtggcgt    41040
taagtggtca gacgaagcga gactggctct ggagtggaaa gcgagatggg gagacagggc    41100
tgcatgataa atgtcgttag tttctccggt ggcaggacgt cagcatattt gctctggcta    41160
atggagcaaa agcgacgggc aggtaaagac gtgcattacg ttttcatgga tacaggttgt    41220
gaacatccaa tgcatatatcg gtttgtcagg aagttgtga agttctggga tataccgctc    41280
accgtattgc aggttgatat caacccggag cttggacagc caaatggtta tacggtatgg    41340
gaaccaaagg atattcagac gcgaatgcct gttctgaagc catttatcga tatggtaaag    41400
aaatatggca ctccatacgt cggcggcgcg ttctgcactg acagattaaa actcgttccc    41460
ttcaccaaat actgtgatga ccatttcggg cgagggaatt acaccacgtg gattggcatc    41520
agagctgatg aaccgaagcg gctaaagcca aagcctggaa tcagatatct tgctgaactg    41580
tcagactttg agaaggaaga tatcctcgca tggtggaagc aacaaccatt cgatttgcaa    41640
ataccggaac atctcggtaa ctgcatattc tgcattaaaa aatcaacgca aaaaatcgga    41700
cttgcctgca aagatgagga gggattgcag cgtgttttta atgaggtcat cacgggatcc    41760
catgtgcgtg acggacatcg ggaaacgcca aaggagatta tgtaccgagg aagaatgtcg    41820
ctggacggta tcgcgaaaat gtattcagaa aatgattatc aagccctgta tcaggacatg    41880
gtacgagcta aaagattcga taccggctct tgttctgagt catgcgaaat atttggaggg    41940
cagcttgatt tcgacttcgg gagggaagct gcatgatgcg atgttatcgg tgcggtaat     42000 gcaaagaaga taaccgcttc cgaccaaatc aaccttactg gaatcgatgg tgtctccggt    42060
gtgaaagaac accaacaggg gtgttaccac taccgcagga aaaggaggac gtgtggcgag    42120
acagcgacga agtatcaccg acataatctg cgaaaactgc aaataccttc caacgaaacg    42180
caccagaaat aaacccaagc caatcccaaa agaatctgac gtaaaaacct tcaactacac    42240
ggctcacctg tgggatatcc ggtggctaag acgtcgtgcg aggaaaacaa ggtgattgac    42300
caaaatcgaa gttacgaaca agaaagcgtc gagcgagctt taacgtgcgc taactgcggt    42360
cagaagctgc atgtgctgga agttcacgtg tgtgagcact gctgcgcaga actgatgagc    42420
```

```
gatccgaata gctcgatgca cgaggaagaa gatgatggct aaaccagcgc gaagacgatg    42480
taaaaacgat gaatgccggg aatggtttca ccctgcattc gctaatcagt ggtggtgctc    42540
tccagagtgt ggaaccaaga tagcactcga acgacgaagt aaagaacgcg aaaaagcgga    42600
aaaagcagca gagaagaaac gacgacgaga ggagcagaaa cagaaagata aacttaagat    42660
tcgaaaactc gccttaaagc cccgcagtta ctggattaaa caagcccaac aagccgtaaa    42720
cgccttcatc agagaaagag accgcgactt accatgtatc tcgtgcggaa cgctcacgtc    42780
tgctcagtgg gatgccggac attaccggac aactgctgcg gcacctcaac tccgatttaa    42840
tgaacgcaat attcacaagc aatgcgtggt gtgcaaccag cacaaaagcg aaatctcgt     42900 tccgtatcgc gtcgaactga ttagccgcat cgggcaggaa gcagtagacg aaatcgaatc    42960
aaaccataac cgccatcgct ggactatcga agagtgcaag gcgatcaagg cagagtacca    43020
acagaaactc aaagacctgc gaaatagcag aagtgaggcc gcatgacgtt ctcagtaaaa    43080
accattccag acatgctcgt tgaaacatac ggaaatcaga cagaagtagc acgcagactg    43140
aaatgtagtc gcggtacggt cagaaaatac gttgatgata agacgggaa aatgcacgcc     43200 atcgtcaacg acgttctcat ggttcatcgc ggatggagtg aaagagatgc gctattacga    43260
aaaaattgat ggcagcaaat accgaaatat ttgggtagtt ggcgatctgc acggatgcta    43320
cacgaacctg atgaacaaac tggatacgat tggattcgac aacaaaaaag acctgcttat    43380
ctcggtgggc gatttggttg atcgtggtgc agagaacgtt gaatgcctgg aattaatcac    43440
attcccctgg ttcagagctg tacgtggaaa ccatgagcaa atgatgattg atggcttatc    43500
agagcgtgga aacgttaatc actggctgct taatggcggt ggctggttct ttaatctcga    43560
ttacgacaaa gaaattctgg ctaaagctct tgcccataaa gcagatgaac ttccgttaat    43620
catcgaactg gtgagcaaag ataaaaaata tgttatctgc cacgccgatt atcccttga     43680 cgaatacgag tttggaaagc cagttgatca tcagcaggta atctggaacc gcgaacgaat    43740
cagcaactca caaaacggga tcgtgaaaga aatcaaaggc gcggacacgt tcatctttgg    43800
tcatacgcca gcagtgaaac cactcaagtt tgccaaccaa atgtatatcg ataccggcgc    43860
agtgttctgc ggaaacctaa cattgattca ggtacaggga gaaggcgcat gagactcgaa    43920
agcgtagcta aatttcattc gccaaaaagc ccgatgatga gcgactcacc acgggccacg    43980
gcttctgact ctctttccgg tactgatgtg atggctgcta tggggatggc gcaatcacaa    44040
gccggattcg gtatggctgc attctgcggt aagcacgaac tcagccagaa cgacaaacaa    44100
aaggctatca actatctgat gcaatttgca cacaaggtat cggggaaata ccgtggtgtg    44160
gcaaagcttg aaggaaatac taaggcaaag gtactgcaag tgctcgcaac attcgcttat    44220
gcggattatt gccgtagtgc cgcgacgccg ggggcaagat gcagagattg ccatggtaca    44280
ggccgtgcgg ttgatattgc caaaacagag ctgtggggga gagttgtcga gaaagagtgc    44340
ggaagatgca aaggcgtcgg ctattcaagg atgccagcaa gcgcagcata tcgcgctgtg    44400
acgatgctaa tcccaaacct tacccaaccc acctggtcac gcactgttaa gccgctgtat    44460
gacgctctgg tggtgcaatg ccacaaagaa gagtcaatcg cagacaacat tttgaatgcg    44520
gtcacacgtt agcagcatga ttgccacgga tgcaacata ttaacggcat gatattgact     44580
tattgaataa aattgggtaa atttgactca acgatgggtt aattcgctcg ttgtggtagt    44640
gagatgaaaa gaggcggcgc ttactaccga ttccgcctag ttggtcactt cgacgtatcg    44700
tctggaactc caaccatcgc aggcagagag gtctgcaaaa tgcaatcccg aaacagttcg    44760
```

-continued

```
caggtaatag ttagagcctg cataacggtt tcgggatttt ttatatctgc acaacaggta   44820
agagcattga gtcgataatc gtgaagagtc ggcgagcctg gttagccagt gctctttccg   44880
ttgtgctgaa ttaagcgaat accggaagca gaaccggatc accaaatgcg tacaggcgtc   44940
atcgccgccc agcaacagca caacccaaac tgagccgtag ccactgtctg tcctgaattc   45000
attagtaata gttacgctgc ggccttttac acatgacctt cgtgaaagcg ggtggcagga   45060
ggtcgcgcta acaacctcct gccgttttgc ccgtgcatat cggtcacgaa caaatctgat   45120
tactaaacac agtagcctgg atttgttcta tcagtaatcg accttattcc taattaaata   45180
gagcaaatcc ccttattggg ggtaagacat gaagatgcca gaaaaacatg acctgttggc   45240
cgccattctc gcggcaaagg aacaaggcat cggggcaatc cttgcgtttg caatggcgta   45300
ccttcgcggc agatataatg gcggtgcgtt tacaaaaaca gtaatcgacg caacgatgtg   45360
cgccattatc gcctagttca ttcgtgacct tctcgacttc gccggactaa gtagcaatct   45420
cgcttatata acgagcgtgt ttatcggcta catcggtact gactcgattg gttcgcttat   45480
caaacgcttc gctgctaaaa aagccggagt agaagatggt agaaatcaat aatcaacgta   45540
aggcgttcct cgatatgctg gcgtggtcgg agggaactga taacggacgt cagaaaacca   45600
gaaatcatgg ttatgacgtc attgtaggcg gagagctatt tactgattac tccgatcacc   45660
ctcgcaaact tgtcacgcta aacccaaaac tcaaatcaac aggcgccgga cgctaccagc   45720
ttctttcccg ttggtgggat gcctaccgca agcagcttgg cctgaaagac ttctctccga   45780
aaagtcagga cgctgtggca ttgcagcaga ttaaggagcg tggcgcttta cctatgattg   45840
atcgtggtga tatccgtcag gcaatcgacc gttgcagcaa tatctgggct tcactgccgg   45900
gcgctggtta tggtcagttc gagcataagg ctgacagcct gattgcaaaa ttcaaagaag   45960
cgggcggaac ggtcagagag attgatgtat gagcagagtc accgcgatta tctccgctct   46020
ggttatctgc atcatcgtct gcctgtcatg ggctgttaat cattaccgtg ataacgccat   46080
tacctacaaa gcccagcgcg acaaaaatgc cagagaactg aagctggcga acgcggcaat   46140
tactgacatg cagatgcgtc agcgtgatgt tgctgcgctc gatgcaaaat acacgaagga   46200
gttagctgat gctaaagctg aaaatgatgc tctgcgtgat gatgttgccg ctggtcgtcg   46260
tcggttgcac atcaaagcag tctgtcagtc agtgcgtgaa gccaccaccg cctccggcgt   46320
ggataatgca gcctcccccc gactggcaga caccgctgaa cgggattatt tcaccctcag   46380
agagaggctg atcactatgc aaaaacaact ggaaggaacc cagaagtata ttaatgagca   46440
gtgcagatag agttgcccat atcgatgggc aactcatgca attattgtga gcaatacaca   46500
cgcgcttcca gcggagtata aatgcctaaa gtaataaaac cgagcaatcc atttacgaat   46560
gtttgctggg tttctgtttt aacaacattt tctgcgccgc cacaaatttt ggctgcatcg   46620
acagttttct tctgcccaat tccagaaacg aagaaatgat gggtgatggt ttcctttggt   46680
gctactgctg ccggtttgtt ttgaacagta acgtctgtt gagcacatcc tgtaataagc   46740
agggccagcg cagtagcgag tagcattttt ttcatggtgt tattcccgat gcttttgaa   46800
gttcgcagaa tcgtatgtgt agaaaattaa acaaacccta acaatgagt tgaaatttca   46860
tattgttaat atttattaat gtatgtcagg tgcgatgaat cgtcattgta ttcccggatt   46920
aactatgtcc acagccctga cggggaactt ctctgcggga gtgtccggga ataattaaaa   46980
cgatgcacac agggtttagc gcgtacacgt attgcattat gccaacgccc cggtgctgac   47040
acggaagaaa ccggacgtta tgattagcg tggaaagatt tgtgtagtgt tctgaatgct   47100
ctcagtaaat agtaatgaat tatcaaaggt atagtaatat cttttatgtt catggatatt   47160
```

```
tgtaacccat cggaaaactc ctgctttagc aagattttcc ctgtattgct gaaatgtgat  47220
ttctcttgat ttcaacctat cataggacgt ttctataaga tgcgtgtttc ttgagaattt  47280
aacatttaca accttttaa gtccttttat taacacggtg ttatcgtttt ctaacacgat   47340
gtgaatatta tctgtggcta gatagtaaat ataatgtgag acgttgtgac gttttagttc  47400
agaataaaac aattcacagt ctaaatcttt tcgcacttga tcgaatattt ctttaaaaat  47460
ggcaacctga gccattggta aaaccttcca tgtgatacga gggcgcgtag tttgcattat  47520 cgttttatc gtttcaatct ggtctgacct ccttgtgttt tgttgatgat ttatgtcaaa   47580
tattaggaat gttttcactt aatagtattg gttgcgtaac aaagtgcggt cctgctggca  47640
ttctggaggg aaatacaacc gacagatgta tgtaaggcca acgtgctcaa atcttcatac  47700
agaaagattt gaagtaatat tttaaccgct agatgaagag caagcgcatg gagcgacaaa  47760
atgaataaag aacaatctgc tgatgatccc tccgtggatc tgattcgtgt aaaaaatatg  47820
cttaatagca ccatttctat gagttaccct gatgttgtaa ttgcatgtat agaacataag  47880
gtgtctctgg aagcattcag agcaattgag gcagcgttgg tgaagcacga taataatatg  47940
aaggattatt ccctggtggt tgactgatca ccataactgc taatcattca aactatttag  48000
tctgtgacag agccaacacg cagtctgtca ctgtcaggaa agtggtaaaa ctgcaactca  48060
attactgcaa tgccctcgta attaagtgaa tttacaatat cgtcctgttc ggagggaaga  48120
acgcgggatg ttcattcttc atcacttta attgatgtat atgctctctt ttctgacgtt   48180
agtctccgac ggcaggcttc aatgacccag gctgagaaat tcccggaccc ttttgctca   48240 agagcgatgt taatttgttc aatcatttgg ttaggaaagc ggatgttgcg ggttgttgtt  48300
ctgcgggttc tgttcttcgt tgacatgagg ttgccccgta ttcagtgtcg ctgatttgta  48360
ttgtctgaag ttgtttttac gttaagttga tgcagatcaa ttaatacgat acctgcgtca  48420
taattgatta tttgacgtgg tttgatggcc tccacgcacg ttgtgatatg tagatgataa  48480
tcattatcac tttacgggtc cttttccggtg atccgacagg ttacggggcg gcgacctcgt  48540
tctgtttatg tttcttgttt gttagccttt tggctaacaa acaagaaaca taaacagaac  48600
gcgtaacctg tcggatcacc ggaaaggacc cgtaaagtga taatgattat catctacata  48660
tcacaacgtg cgtggaggcc atcaaaccac gtcaaataat caattatgac gcaggtatcg  48720
tattaattga tctgcatcaa cttaacgtaa aaacaacttc agacaataca aatcagcgac  48780
actgaatacg gggcaacctc atgtcaacga agaacagaac ccgcagaaca acaacccgca  48840
acatccgctt tcctaaccaa atgattgaac aaattaacat cgctcttgag caaaaagggt  48900
ccgggaattt ctcagcctgg gtcattgaag cctgccgtcg gagactaacg tcagaaaga   48960 gagcatatac atcaattaaa agtgatgaag aatgaacatc ccgcgttctt ccctccgaac  49020
aggacgatat tgtaaattca cttaattacg agggcattgc agtaattgag ttgcagtttt  49080
accactttcc tgacagtgac agactgcgtg ttggctctgt cacagactaa atagtttgaa  49140
tgattagcag ttatggtgat cagtcaacca ccagggaata atccttcata ttattatcgt  49200
gcttcaccaa cgctgcctca attgctctga atgcttccag agacacctta tgttctatac  49260
atgcaattac aacatcaggg taactcatag aaatggtgct attaagcata ttttttacac  49320
gaatcagatc cacggaggga tcatcagcag attgttcttt attcattttg tcgctccatg  49380
cgcttgctct tcatctagcg gttaaaatat tacttcaaat cttctgtat gaagatttga   49440 gcacgttggc cttacataca tctgtcggtt gtatttccct ccagaatgcc agcaggaccg  49500
```

```
cactttgtta cgcaaccaat actattaagt gaaacattc ctaatatttg acataaatca    49560
tcaacaaaac acaaggaggt cagaccagat tgaaacgata aaaacgataa tgcaaactac    49620
gcgccctcgt atcacatgga aggttttacc aatggctcag gttgccattt ttaaagaaat    49680
attcgatcaa gtgcgaaaag atttagactg tgaattgttt tattctgaac taaaacgtca    49740
caacgtctca cattatattt actatctagc cacagataat attcacatcg tgttagaaaa    49800
cgataacacc gtgttaataa aaggacttaa aaaggttgta aatgttaaat tctcaagaaa    49860
cacgcatctt atagaaacgt cctatgatag gttgaaatca agagaaatca catttcagca    49920
atacagggaa aatcttgcta aagcaggagt tttccgatgg gttacaaata tccatgaaca    49980
taaaagatat tactatacct ttgataattc attactattt actgagagca ttcagaacac    50040
tacacaaatc tttccacgct aaatcataac gtccggtttc ttccgtgtca gcaccggggc    50100
gttggcataa tgcaatacgt gtacgcgcta accctgtgt gcatcgtttt aattattccc     50160
ggacactccc gcagagaagt tccccgtcag ggctgtggac atagttaatc cgggaataca    50220
atgacgattc atcgcacctg acatacatta ataatatta caatatgaa atttcaactc      50280
attgtttagg gtttgtttaa ttttctacac atacgattct gcgaacttca aaaagcatcg    50340
ggataacac catgaaaaaa atgctactcg ctactgcgct ggccctgctt attacaggat     50400
gtgctcaaca gacgtttact gttcaaaaca aacggcagc agtagcacca aaggaaacca     50460
tcacccatca tttcttcgtt tctggaattg ggcagaagaa aactgtcgat gcagccaaaa    50520
tttgtggcgg cgcagaaaat gttgttaaaa cagaaaccca gcaaacattc gtaaatggat    50580
tgctcggttt tattacttta ggcatttata ctccgctgga agcgcgtgtg tattgctcac    50640
aataattgca tgagttgccc atcgatatgg gcaactctat ctgcactgct cattaatata    50700
cttctggtt ccttccagtt gtttttgcat agtgatcagc ctctctctga gggtgaaata    50760
atcccgttca gcggtgtctg ccagtcgggg ggaggctgca ttatccacgc cggaggcggt    50820
ggtggcttca cgcactgact gacagactgc tttgatgtgc aaccgacgac gaccagcggc    50880
aacatcatca cgcagagcat cattttcagc tttagcatca gctaactcct tcgtgtattt    50940
tgcatcgagc gcagcaacat cacgctgacg catctgcatg tcagtaattg ccgcgttcgc    51000
cagcttcagt tctctggcat tttttgtcgcg ctgggctttg taggtaatgg cgttatcacg    51060
gtaatgatta acagcccatg acaggcagac gatgatgcag ataaccagag cggagataat    51120
cgcggtgact ctgctcatac atcaatctct ctgaccgttc cgcccgcttc tttgaatttt    51180
gcaatcaggc tgtcagcctt atgctcgaac tgaccataac cagcgcccgg cagtgaagcc    51240
cagatattgc tgcaacggtc gattgcctga cggatatcac cacgatcaat cataggtaaa    51300
gcgccacgct ccttaatctg ctgcaatgcc acagcgtcct gacttttcgg agagaagtct    51360
ttcaggccaa gctgcttgcg gtaggcatcc caccaacggg aaagaagctg gtagcgtccg    51420
gcgcctgttg atttgagttt tgggtttagc gtgacaagtt tgcgagggtg atcggagtaa    51480
tcagtaaata gctctccgcc tacaatgacg tcataaccat gatttctggt tttctgacgt    51540
ccgttatcag ttccctccga ccacgccagc atatcgagga acgccttacg ttgattattg    51600
atttctacca tcttctactc cggctttttt agcagcgaag cgtttgataa gcgaaccaat    51660
cgagtcagta ccgatgtagc cgataaacac gctcgttata aagcgagat tgctacttag     51720
tccggcgaag tcgagaaggt cacgaatgaa ctaggcgata atggcgcaca tcgttgcgtc    51780
gattactgtt tttgtaaacg caccgccatt atatctgccg cgaaggtacg ccattgcaaa    51840
cgcaaggatt gccccgatgc cttgttcctt tgccgcgaga atggcggcca acaggtcatg    51900
```

```
tttttctggc atcttcatgt cttaccccca ataaggggat ttgctctatt taattaggaa   51960
taaggtcgat tactgataga acaaatccag gctactgtgt ttagtaatca gatttgttcg   52020
tgaccgatat gcacgggcaa aacggcagga ggttgttagc gcgacctcct gccacccgct   52080
ttcacgaagg tcatgtgtaa aaggccgcag cgtaactatt actaatgaat tcaggacaga   52140
cagtggctac ggctcagttt gggttgtgct gttgctgggc ggcgatgacg cctgtacgca   52200
tttggtgatc cggttctgct tccggtattc gcttaattca gcacaacgga aagagcactg   52260
gctaaccagg ctcgccgact cttcacgatt atcgactcaa tgctcttacc tgttgtgcag   52320
atataaaaaa tcccgaaacc gttatgcagg ctctaactat tacctgcgaa ctgtttcggg   52380
attgcatttt gcagacctct ctgcctgcga tggttggagt tccagacgat acgtcgaagt   52440
gaccaactag gcggaatcgg tagtaagcgc cgcctctttt catctcacta ccacaacgag   52500
cgaattaacc catcgttgag tcaaatttac ccaattttat tcaataagtc aatatcatgc   52560
cgttaatatg ttgccatccg tggcaatcat gctgctaacg tgtgaccgca ttcaaaatgt   52620
tgtctgcgat tgactcttct ttgtggcatt gcaccaccag agcgtcatac agcggcttaa   52680
cagtgcgtga ccaggtgggt tgggtaaggt ttgggattag catcgtcaca gcgcgatatg   52740
ctgcgcttgc tggcatcctt gaatagccga cgcctttgca tcttccgcac tctttctcga   52800
caactctccc ccacagctct gttttggcaa tatcaaccgc acggcctgta ccatggcaat   52860
ctctgcatct tgccccggc gtcgcggcac tacggcaata atccgcataa gcgaatgttg    52920
cgagcacttg cagtaccttt gccttagtat ttccttcaag cttttgccaca ccacggtatt   52980 tccccgatac cttgtgtgca aattgcatca gatagttgat agccttttgt ttgtcgttct   53040
ggctgagttc gtgcttaccg cagaatgcag ccataccgaa tccggcttgt gattgcgcca   53100
tccccatagc agccatcaca tcagtaccgg aaagagagtc agaagccgtg gcccgtggtg   53160
agtcgctcat catcgggctt tttggcgaat gaaatttagc tacgctttcg agtctcatgc   53220
gccttctccc tgtacctgaa tcaatgttag gtttccgcag aacactgcgc cggtatcgat   53280
atacatttgg ttggcaaact tgagtggttt cactgctggc gtatgaccaa agatgaacgt   53340
gtccgcgcct ttgatttctt tcacgatccc gttttgtgag ttgctgattc gttcgcggtt   53400
ccagattacc tgctgatgat caactggctt tccaaactcg tattcgtcaa agggataatc   53460
ggcgtggcag ataacatatt ttttatcttt gctcaccagt tcgatgatta acggaagttc   53520
atctgcttta tgggcaagag ctttagccag aatttctttg tcgtaatcga gattaaagaa   53580
ccagccaccg ccattaagca gccagtgatt aacgtttcca cgctctgata agccatcaat   53640
catcatttgc tcatggtttc cacgtacagc tctgaaccag gggaatgtga ttaattccag   53700
gcattcaacg ttctctgcac cacgatcaac caaatcgccc accgagataa gcaggtcttt   53760
tttgttgtcg aatccaatcg tatccagttt gttcatcagg ttcgtgtagc atccgtgcag   53820
atcgccaact acccaaatat ttcggtattt gctgccatca ttttttcgt aatagccat    53880 ctctttcact ccatccgcga tgaaccatga gaacgtcgtt gacgatggcg tgcattttcc   53940
cgtctttatc atcaacgtat tttctgaccg taccgcgact acatttcagt ctgcgtgcta   54000
cttctgtctg atttccgtat gtttcaacga gcatgtctgg aatggttttt actgagaacg   54060
tcatgcggcc tcacttctgc tatttcgcag gtctttgagt ttctgttggt actctgcctt   54120
gatcgccttg cactcttcga tagtccacgc atggcggtta tggtttgatt cgatttcgtc   54180
tactgcttcc tgcccgatgc ggctaatcag ttcgacgcga tacggaacga gatttccgct   54240
```

```
tttgtgctgg ttgcacacca cgcattgctt gtgaatattg cgttcattaa atcggagttg    54300
aggtgccgca gcagttgtcc ggtaatgtcc ggcatcccac tgagcagacg tgagcgttcc    54360
gcacgagata catggtaagt cgcggtctct ttctctgatg aaggcgttta cggcttgttg    54420
ggcttgttta atccagtaac tgcggggctt aaggcgagt tttcgaatct aagtttatc     54480 tttctgtttc tgctcctctc gtcgtcgttt cttctctgct gcttttccg cttttcgcg     54540 ttctttactt cgtcgttcga gtgctatctt ggttccacac tctggagagc accaccactg    54600
attagcgaat gcagggtgaa accattcccg gcattcatcg ttttacatc gtcttcgcgc     54660 tggtttagcc atcatcttct tcctcgtgca tcgagctatt cggatcgctc atcagttctg    54720
cgcagcagtg ctcacacacg tgaacttcca gcacatgcag cttctgaccg cagttagcgc    54780
acgttaaagc tcgctcgacg ctttcttgtt cgtaacttcg attttggtca atcaccttgt    54840
tttcctcgca cgacgtctta gccaccggat atcccacagg tgagccgtgt agttgaaggt    54900
ttttacgtca gattcttttg ggattggctt gggtttattt ctggtgcgtt tcgttggaag    54960
gtatttgcag ttttcgcaga ttatgtcggt gatacttcgt cgctgtctcg ccacacgtcc    55020
tccttttcct gcggtagtgg taacacccct gttggtgttc tttcacaccg gagacaccat    55080
cgattccagt aaggttgatt tggtcggaag cggttatctt ctttgcattc accgcaccga    55140
taacatcgca tcatgcagct tccctcccga agtcgaaatc aagctgccct ccaaatattt    55200
cgcatgactc agaacaagag ccggtatcga atcttttagc tcgtaccatg tcctgataca    55260
gggcttgata atcattttct gaatacattt tcgcgatacc gtccagcgac attcttcctc    55320
ggtacataat ctcctttggc gtttcccgat gtccgtcacg cacatgggat cccgtgatga    55380
cctcattaaa aacacgctgc aatccctcct catctttgca ggcaagtccg attttttgcg    55440 ttgattttt aatgcagaat atgcagttac cgagatgttc cggtatttgc aaatcgaatg     55500
gttgttgctt ccaccatgcg aggatatctt ccttctcaaa gtctgacagt tcagcaagat    55560
atctgattcc aggctttggc tttagccgct tcggttcatc agctctgatg ccaatccacg    55620
tggtgtaatt ccctcgcccg aaatggtcat cacagtattt ggtgaaggga acgagtttta    55680
atctgtcagt gcagaacgcg ccgccgacgt atggagtgcc atatttcttt accatatcga    55740
taaatggctt cagaacaggc attcgcgtct gaatatcctt tggttcccat accgtataac    55800
catttggctg tccaagctcc gggttgatat caacctgcaa tacggtgagc ggtatatccc    55860
agaacttcac aacttccctg acaaaccgat atgtcattgg atgttcacaa cctgtatcca    55920
tgaaaacgta atgcacgtct ttacctgccc gtcgcttttg ctccattagc cagagcaaat    55980
atgctgacgt cctgccaccg gagaaactaa cgacatttat catgcagccc tgtctcccca    56040
tctcgctttc cactccagag ccagtctcgc ttcgtctgac cacttaacgc cacgctctgt    56100
accgaatgcc tgtataagct ctaatagctc cgcaaattcg cctacacgca tcctgctggt    56160
tgactggcct attaccacaa agccattccc ggcaaggtta ggaacaacat cctgctgctt    56220
taatgctgcg gtaaacacac acttccagct ttctgcatcc agccagcgac catgccattc    56280
aacctgacga gagacgtcac ctaagcaggc ccatagcttc ctgttttggt ctaagctgcg    56340
gttgcgttcc tgaatggtta ctacgattgg tttggtggg tctggaagga tttgctgtac     56400
tgcgtgaata gcgttttgct gatgtgctgg agatcgaatt tcaaaggtta gttttttcat    56460
gacttccctc tcccccaaat aaaaaggcct gcgattacca gcaggcctgt tattagctca    56520
gtaatgtaga tggtcatctt ttaactccat ataccgccaa tacccgtttc atcgcggcac    56580
tctggcgaca ctccttaaaa accaggttcg tgctcatctt tccttcccgt tcttccctgg    56640
```

```
tagcaaaccg gtaatacacc gttcgccaga ccttaccttc gataaccaga agacctgccc    56700
gtgccatttt agccgcggcc tgatttatgc tggttactgt tgcgcctgtt agcgcggcaa    56760
cgtccggcgc acagaagcta ttatgcgtcc ccaggtaatg aataattgcc tctttgcccg    56820
tcatacactt gctcctttca gtccgaactt agctttgatt tctgcgatct tcgccagagc    56880
ctgtgcacga tttagaggtc taccgcccat gacaggaagt tgttttactg gttcagggat    56940
cgcctcacca cggttaattc tcgcagtcat atggacaagc tcatctgcgg ccttacggcg    57000
taattccgca tcagtaagcg cattggcccg catgttctga tacaggttgg taaccagcca    57060
gtagtgcgcg tttgatttcc acggataaga ctccgcatcc ggatacaggc ctcgcttccg    57120
gcaatactcg taaaccatat caaccagctc gctgacgttt ggcagtccgg cggtaacgga    57180
tgcttcttcc cggcaccatg caacaaactg cccgggtgat ggcagaaatg gtcgattctg    57240
ccgacgggct acgcgcattc ctgcgttaac ctgttccatc gtggtgatcc cgttttcccg    57300
aaaagccaga acccactggc gacggatttc gttcacttcg ttctggtcac ggttagccag    57360
gctcgccggg aaagttgcca gtaactggct gaacacaccg ttgatgatct gcgctacctg    57420
ctgtacctgc ggcttttcgt cgtactgttc cggcatgttg ttggcgatcc gacgcatctg    57480
ctcacggtca agttaaccta tctgtgcggc gatgtttttc atagatccac cccgtaaatc    57540
cagtctgtgt ttgtcaggtc gagttttggt ttgctggctg tcacgcctgc ctgttgcttg    57600
ttacggttga tttcgagttg ggtccactta tcgcggagtt tggccgggct cagcacgtta    57660
ccggaccaga agttgtcctg gcatgcccag cggaacagca cacacatgtc gcggtggtta    57720
cgtccgtcac gttcacgcat caggcggata tcgttagccc acccagcaaa attcggtttt    57780
ctggctgatg gtgcgatagt cttcaccatg tcaaacatcc actctgcggc ggtcaggtct    57840
tctgctgtcc cccacttgct gccgctctga attgcagcat ccggtttcac cacagaaagg    57900
tcgttttctg gctggtcaga ggattcgcca gaattctctg acgaataatc ttttctttt    57960 tcttttgtaa tagtgtcttt tgtgtccccc tgttttgagg gatagcaatc ccccaatttg    58020
agggatgttt tatccctcgt tttagggggat tttccctcgt tttgagggat gcaccattct    58080
gagatgtttt tatttggtcc aaacatgccg ccttgctgct tgataatatt cattctgacg    58140
agttctaact tggcttcatt gcaccgtttg acaggtaact ttgtaatctc gctaagttga    58200
gaatcggtga ttctgtccat tggtttattc cacccatagg ttttacgcag aatggcaagc    58260
agcactttaa actgtcgctt ggtcagatct gcgcccgaat aagcctcaag cagcatattt    58320
gatagtctgc cgtaaccatc atcgagatct gccacattac gctcctgtcc ggcaaagtta    58380
cctctgccga agttgagtat ttttgctgta tttgtcataa tgactcctgt tgatagatcc    58440
agtaatgacc tcagaactcc atctggattt gttcagaacg ctcggttgcc gccgggcgtt    58500
ttttattggt gagaatcgca gcaacttgtc gcgccaatcg agccatgtcg tcgtcaacga    58560
ccccccattc aagaacagca agcagcattg agaactttgg aatccagtcc ctcttccacc    58620
tgctgatctg cgacttatca acgcccacag cttccgctgt cttctcagtt ccaagcattg    58680
cgattttgtt aagcaacgca ctctcgattc gtagagcctc gttgcgtttg tttgcacgaa    58740
ccatatgtaa gtatttcctt agataacaat tgattgaatg tatgcaaata aatgcataca    58800
ccataggtgt ggtttaattt gatgcccttt tcagggctg aatgtgtaa gagcggggtt    58860 atttatgctg ttgttttttt gttactcggg aagggcttta cctcttccgc ataaacgctt    58920
ccatcagcgt ttatagttaa aaaaatcttt cggcctgcat gaatggcctt gttgatcgcg    58980
```

```
ctttgatata cgccgagatc tttagctgtc ttggtttgcc caaagcgcat tgcataatct    59040
ttcagggtta tgcgttgttc catacaacct ccttagtaca tgcaaccatt atcaccgcca    59100
gaggtaaaat agtcaacacg cacggtgtta gatatttatc ccttgcggtg atagatttaa    59160
cgtatgagca caaaaagaa  accattaaca caagagcagc ttgaggacgc acgtcgcctt    59220
aaagcaattt atgaaaaaaa gaaaatgaa  cttggcttat cccaggaatc tgtcgcagac    59280
aagatgggga tggggcagtc aggcgttggt gctttattta atggcatcaa tgcattaaat    59340
gcttataacg ccgcattgct tacaaaaatt ctcaaagtta gcgttgaaga atttagccct    59400
tcaatcgcca gagaaatcta cgagatgtat gaagcggtta gtatgcagcc gtcacttaga    59460
agtgagtatg agtaccctgt tttttctcat gttcaggcag ggatgttctc acctaagctt    59520
agaaccttta ccaaaggtga tgcggagaga tgggtaagca caaccaaaaa agccagtgat    59580
tctgcattct ggcttgaggt tgaaggtaat tccatgaccg caccaacagg ctccaagcca    59640
agctttcctg acggaatgtt aattctcgtt gaccctgagc aggctgttga gccaggtgat    59700
ttctgcatag ccagacttgg gggtgatgag tttaccttca agaaactgat cagggatagc    59760
ggtcaggtgt ttttacaacc actaaaccca cagtacccaa tgatcccatg caatgagagt    59820
tgttccgttg tggggaaagt tatcgctagt cagtggcctg aagagacgtt tggctgatcg    59880
gcaaggtgtt ctggtcggcg catagctgat aacaattgag caagaatctt catcgaatta    59940
ggggaatttt cactcccctc agaacataac atagtaaatg gattgaatta tgaagaatgg    60000
tttttatgcg acttaccgca gcaaaaataa agggaaagat aagcgctcaa taaacctgtc    60060
tgttttcctt aattctctgc tggctgataa tcatcacctg caggttggct ccaattattt    60120
gtatattcat aaaatcgatg gaaaaacttt tctctttacc aaaacaaatg acaagagtct    60180
ggttcagaag ataaatcgct ctaaagcttc agttgaagat attaagaaca gcctcgagaa    60240
tgacgaatca ttgggattcc catctttttt gtttgttgaa ggcgacacca ttggttttgc    60300
cagaactgtt tcgggccga  ccacatccga tctgacagat ttttaatcg  ggaaaggaat    60360 gtcattaagc agtggagagc gcgttcagat agagccactg atgaggggaa ccaccaaaga    60420
cgatgttatg catatgcatt tcatcggccg aacaacggtg aaggtagaag ccaagctacc    60480
tgtatttggc gatatattaa aggtcttagg ggcaacagat attgaagggg agcttttga    60540 ctcattggat atagtcatta agccaaaatt taaaagggat ataaaaaagg ttgccaagga    60600 tattatttt  aacccgtcac ctcaattttc agacattagc ctgcgggcaa aagatgaggc    60660
cggagatatt ttaacagaac attatctatc agaaaaaggc catctctcag cgcctctgaa    60720
caaggtcacc aatgctgaga tagctgaaga gatggcatat tgctacgcaa gaatgaaaag    60780
tgatatactg gaatgtttta aaaggcaggt gggcaaagtt aaggattaat tatcaggagt    60840
aattatgcgg aacagaatca tgcctggtgt ttacatagta ataattcctt acgttatcgt    60900
aagcatttgc tatctccttt tccgccacta cattcctggt gtttcttttt cagctcatag    60960
agatggtctt ggggcgacat tgtcatcata tgcaggaacc atgattgcaa tcctgattgc    61020
tgccttgacg tttctaatcg gaagcagaac gcgccgactg gccaagatta gagagtatgg    61080
gtatatgaca tcgtagtta  ttgtctatgc ccttagtttt gttgagcttg gagctttgtt    61140
tttctgcggg ttattgcttc tttccagcat aagcggctac atgatacccca ctatcgccat    61200 cggcattgcc tctgcatcgt tcattcatat atgcatcctt gttttccaac tatataattt    61260
gaccagagaa caagaataac ccggcctcag cgccgggttt tctttgcctc acgatcgccc    61320
ccaaaacaca taaccaattg tatttattga aaaataaata gatacaactc actaaacata    61380
```

```
gcaattcaga tctctcacct accaaacaat gccccctgc aaaaaataaa ttcatataaa    61440
aaacatacag ataaccatct gcggtgataa attatctctg gcggtgttga cataaatacc   61500
actggcggtg atactgagca catcagcagg acgcactgac caccatgaag gtgacgctct   61560 taaaattaa gccctgaaga agggcagcat tcaaagcaga aggctttggg gtgtgtgata    61620
cgaaacgaag cattggccgt aagtgcgatt ccggattagc tgccaatgtg ccaatcgcgg   61680
ggggttttcg ttcaggacta caactgccac acaccaccaa agctaactga caggagaatc   61740
cagatggatg cacaaacacg ccgccgcgaa cgtcgcgcag agaaacaggc tcaatggaaa   61800
gcagcaaatc ccctgttggt tggggtaagc gcaaaaccag ttaaccgccc tattctctcg   61860
ctgaatcgca aaccgaaatc acgagtagaa agcgcactaa atccgataga ccttacagtg   61920
ctggctgaat accacaaaca gattgaaagc aacctgcaac gtattgagcg caagaatcag   61980
cgcacatggt acagcaagcc tggcgaacgc ggcataacat gcagtggacg ccagaaaatt   62040
aagggaaaat cgattcctct tatctagtta cttagatatt ggccttggct ttatctcaat   62100
attatatgga tcatagctgg caactaattc agtccagtaa atatcctcaa tagggaataa   62160
tatatgcttt ccattccatc gggaaaaagt tttgttcaac acaccaagct caatcaactc   62220
actaatgtat gggaattgtt ttgatgtaac cacatacttc ctgccttcat taagggctgc   62280
gcacaaaacc atagattgct cttctgtaag gttttgaatt actgatcgca ctttatcgtt   62340
ttgcatctta atgcgttttc ttagcttaaa tcgcttatat ctggcgctgg caatagctga   62400
taatcgatgc acattaattg ctagcgaaaa tgcaagagca aagacgaaaa catgccacac   62460
atgaggaata ccgattctct cattaacata ttcaggccag ttatctgggc ttaaaagcag   62520
aagtccaacc cagataacga tcatatacat ggttctctcc agaggttcat tactgaacac   62580
tcgtccgaga ataacgagtg gatccatttc tatactcatc aaactgtagg ggttgtaata   62640
gtttatccga tttctcgctg taggggtaca cgagaaccac cgagcctgat gtggttaaaa   62700
gacaggcaca atctttacta ccgcaatcca ctatttaagg tgatatatgg aagaagaatt   62760
tgaagagttc gaagagcatc ctcaggatgt gatggaacaa taccaggact atccgtatga   62820
ctacgactat tgataaaaat caatggtgtg gacaattcaa gcgatgcaat ggatgcaagc   62880
tgcaatcgga atgcatggtt aagcctgaag aaatgtttcc tgtaatggaa gatgggaaat   62940
atgtcgataa atgggcaata cgaacgacgg caatgattgc cagagaactt ggtaaacaga   63000
acaacaaagc tgcctgatag tggccttttat ttttggcata aataacagaa taaacactgc   63060
actgtgtatt cattccaacg agtgaataca cggagcaatg tcgctcgtaa ctaaacagga   63120
gccgacttgt tctgattatt ggaaatcttc tttgccctcc agtgtgaggg cgattttta   63180 tctgtgagga tatgaacaga tgtcaaacat caaaaaatac atcattgatt acgactgaa    63240 agcatcaata gaaattgaaa tcgaccatga cgtaatgaca gaggaaaaac ttcaccagat   63300
taataatttc tggtcagact ctgaataccg actcaataaa cacggctctg tattaaatgc   63360
tgtattaatc atgctggcgc aacatgctct gcttatagca atttcaagcg acttaaatgc   63420
atatggtgtt gtgtgtgagt tcgactggaa tgatggaaat ggtcaggaag datggcctcc   63480
aatggatggt agcgaaggaa taagaattac cgatatcgat acatcaggaa tatttgattc   63540
agatgatatg actatcaagg ccgcctgagt gcggttttac cgcataccaa taacgcttca   63600
ctcgaggcgt ttttcgttat gtataaataa ggagcacacc atgcaatatg ccattgcagg   63660
gtggcctgtt gctggctgcc cttccgaatc tttacttgaa cgaatcaccc gtaaattacg   63720
```

```
tgacggatgg aaacgcctta tcgacatact taatcagcca ggagtcccaa agaatggatc    63780
aaacacttat ggctatccag actaaattca ctatcgccac ttttattggc gatgaaaaga    63840
tgtttcgtga agccgtcgac gcttataaaa aatggatatt aatactgaaa ctgagatcaa    63900
gcaaaagcat tcactaaccc cctttcctgt tttcctaatc agcccggcat ttcgcgggcg    63960
atattttcac agctatttca ggagttcagc catgaacgct tattacattc aggatcgtct    64020
tgaggctcag agctgggcgc gtcactacca gcagctcgcc cgtgaagaga aagaggcaga    64080
actggcagac gacatggaaa aaggcctgcc ccagcacctg tttgaatcgc tatgcatcga    64140
tcatttgcaa cgccacgggg ccagcaaaaa atccattacc cgtgcgtttg atgacgatgt    64200
tgagtttcag gagcgcatgg cagaacacat ccggtacatg gttgaaacca ttgctcacca    64260
ccaggttgat attgattcag aggtataaaa cgaatgagta ctgcactcgc aacgctggct    64320
gggaagctgg ctgaacgtgt cggcatggat tctgtcgacc cacaggaact gatcaccact    64380
cttcgccaga cggcatttaa aggtgatgcc agcgatgcgc agttcatcgc attactgatc    64440
gttgccaacc agtacggcct taatccgtgg acgaaagaaa tttacgcctt tcctgataag    64500
cagaatggca tcgttccggt ggtgggcgtt gatggctggt cccgcatcat caatgaaaac    64560
cagcagtttg atggcatgga cttt gagcag gacaatgaat cctgtacatg ccggatttac    64620
cgcaaggacc gtaatcatcc gatctgcgtt accgaatgga tggatgaatg ccgccgcgaa    64680
ccattcaaaa ctcgcgaagg cagagaaatc acggggccgt ggcagtcgca tcccaaacgg    64740
atgttacgtc ataaagccat gattcagtgt gcccgtctgg ccttcggatt tgctggtatc    64800
tatgacaagg atgaagccga gcgcattgtc gaaaatactg catacactgc agaacgtcag    64860
ccggaacgcg acatcactcc ggttaacgat gaaaccatgc aggagattaa cactctgctg    64920
atcgccctgg ataaaacatg ggatgacgac ttattgccgc tctgttccca gatatttcgc    64980
cgcgacattc gtgcatcgtc agaactgaca caggccgaag cagtaaaagc tcttggattc    65040
ctgaaacaga aagccgcaga gcagaaggtg gcagcatgac accggacatt atcctgcagc    65100
gtaccgggat cgatgtgaga gctgtcgaac aggggga tga tgcgtggcac aaattacggc    65160
tcggcgtcat caccgcttca gaagttcaca acgtgatagc aaaacccgc tccggaaaga    65220 agtggcctga catgaaaatg tcctacttcc acaccctgct tgctgaggtt tgcaccggtg    65280
tggctccgga agttaacgct aaagcactgg cctggggaaa acagtacgag aacgacgcca    65340
gaaccctgtt tgaattcact tccggcgtga atgttactga atccccgatc atctatcgcg    65400
acgaaagtat gcgtaccgcc tgctctcccg atggtttatg cagtgacggc aacggccttg    65460
aactgaaatg cccgtttacc tcccgggatt tcatgaagtt ccggctcggt ggtttcgagg    65520
ccataaagtc agcttacatg gcccaggtgc agtacagcat gtgggtgacg cgaaaaaatg    65580
cctggtactt tgccaactat gacccgcgta tgaagcgtga aggcctgcat tatgtcgtga    65640
ttgagcggga tgaaaagtac atggcgagtt ttgacgagat cgtgccggag ttcatcgaaa    65700
aaatggacga ggcactggct gaaattggtt ttgtatttgg ggagcaatgg cgatgacgca    65760
tcctcacgat aatatccggg taggcgcaat cactttcgtc tactccgtta caaagcgagg    65820 ctgggtatt cccggccttt ctgttatccg aaatccactg aaagcacagc ggctggctga    65880
ggagataaat aataaacgag gggctgtatg cacaaagcat cttctgttga gttaagaacg    65940
agtatcgaga tggcacatag ccttgctcaa attggaatca ggtttgtgcc aataccagta    66000
gaaacagaca aagaatttca tacgttagcc gcatcccttt cacaaaagct ggaaatgatg    66060
gtggcgaaag cagaagcaga tgagagaaac caggtatgac aaccacggaa tgcattttc    66120
```

```
tggcagcggg cttcatattc tgtgtgctta tgcttgccga catgggactt gttcaatgac    66180
acctcagcag gaaaacgccc ttcgcagcat gcccgtcag gctaattctg aaatcaaaaa    66240
aagccagaca gcagtttccg gataaaaacg tcgatgacat ttgccgtagc gtactgaaga    66300
agcaccgcga aacggtaacg ctgatgggat tcacaccgac tcatttaagc ctggcaatcg    66360
gcatgttaaa cggcgtcttt aaggaacgat gaacatgaaa agcaaaatca tcagggagct    66420
acaggctcct tttttattat tcgcattcac cctcaagcgt attaaccaac agttcaggga    66480
ttaatgaaag atggcagaca tcattgattc agcatcagaa atagaagaat tacagcgcaa    66540
cacagcaata aaaatgcgcc gcctgaacca ccaggctata tctgccactc attgttgtga    66600
gtgtggcgat ccgatagatg aacgaagacg cctggtcgtt cagggttgtc ggacttgtgc    66660
aagttgccag gaggatctgg aacttatcag taaacagaga ggttcgaagt gagcgaaatt    66720
aactctcagg cactgcgtga agcggcagag caggcaatgc atgacgactg gggatttgac    66780
gcagaccttt tccatgaatt ggtaacacca tcgattgtgc tggaactgct ggatgaacgg    66840
gaaagaaacc agcaatacat caaacgccgc gaccaggaga acgaggatat tgcgctaaca    66900
gtagggaaac tgcgtgttga gcttgaaaca gcaaaatcaa aactcaacga gcagcgtgag    66960
tattacgaag gtgttatctc ggatgggagt aagcgtattg ctaaactgga aagcaacgaa    67020
gtccgtgaag acgaaaacca gtttcttgtt gttcgccatc ctgggaagac tcctgttatc    67080
aagcactgca ctggtgacct ggaagagttt ctgcggcagt taatcgaaca agacccgtta    67140
gtaactatcg acatcattac gcatcgctat tacggggttg gaggtcaatg ggttcaggat    67200
gcaggtgagt atctgcatat gatgtctgac gctggcattc gcatcaaagg agagtgagat    67260 cggtttttgta aaagataacg cttgtgaaaa tgctgaattt cgcgtcgtct tcacagcgat    67320
gccagagtct gtagtgtcag atgatgaccg tactcaaaca tcgggttgag tattatctta    67380
ctgtttcttt acataaacat tgctgatacc gtttagctga aacgacatac attgcaagga    67440
gtttataaat gagtatcaat gagttagagt ctgagcaaaa agattgggcg ttatcaatgt    67500
tgtgcagatc cggtgtcttg tctccatgca gacatcacga aggtgtttat gtagatgaag    67560
gtatagatat agagtcggca tacaaatatt ccatgaaggt ttataagtct aatgaagaca    67620
aatccccatt ctgcaatgtg cgagaaatga ctgataccgt gcaaaattat tatcacgagt    67680
acggtggaaa cgatacttgc cctctctgta caaaacatat agatgattaa acccaatatt    67740
acataacaat cctcgcactc gcggggattt attttatctg aactcgctac ggcgggtttt    67800
gttttatgga gatgataaat gcacttccga gtcacaggag aatggaatgg agagccattc    67860
aacagagtta tcgaagcgga gaacatcaac gactgctacg accactggat gatatgggcg    67920
cagatagcac atgcagacgt aaccaatatt cgaattgaag aactgaaaga acaccaagcc    67980
gcctgatggc ggttttttct tgcgtgtaat tgcggagact ttgcgatgta cttgacactt    68040
caggagtgga acgcacgcca gcgacgtcca agaagccttg aaacagttcg tcgatgggtt    68100
cgggaatgca ggatattccc acctccggtt aaggatggaa gagagtatct gttccacgaa    68160
tcagcggtaa aggttgactt aaatcgacca gtaacaggtg gccttttgaa gaggatcaga    68220
aatgggaaga aggcgaagtc atgagcgccg ggatttaccc cctaaccttt atataagaaa    68280
caatggatat tactgctaca gggacccaag gacgggtaaa gagtttggat taggcagaga    68340
caggcgaatc gcaatcactg aagctataca ggccaacatt gagttatttt caggacacaa    68400
acacaagcct ctgacagcga gaatcaacag tgataattcc gttacgttac attcatggct    68460
```

```
tgatcgctac gaaaaaatcc tggccagcag aggaatcaag cagaagacac tcataaatta    68520
catgagcaaa attaaagcaa taaggagggg tctgcctgat gctccacttg aagacatcac    68580
cacaaaagaa attgcggcaa tgctcaatgg atacatagac gagggcaagg cggcgtcagc    68640
caagttaatc agatcaacac tgagcgatgc attccgagag gcaatagctg aaggccatat    68700
aacaacaaac catgtcgctg ccactcgcgc agcaaaatca gaggtaagga gatcaagact    68760
tacggctgac gaatacctga aaatttatca agcagcagaa tcatcaccat gttggctcag    68820
acttgcaatg gaactggctg ttgttaccgg gcaacgagtt ggtgatttat gcgaaatgaa    68880
gtggtctgat atcgtagatg gatatcttta tgtcgagcaa agcaaaacag gcgtaaaaat    68940
tgccatccca acagcattgc atattgatgc tctcggaata tcaatgaagg aaacacttga    69000
taaatgcaaa gagattcttg gcggagaaac cataattgca tctactcgtc gcgaaccgct    69060
ttcatccggc acagtatcaa ggtattttat gcgcgcacga aaagcatcag gtctttcctt    69120
cgaaggggat ccgcctacct ttcacgagtt gcgcagtttg tctgcaagac tctatgagaa    69180
gcagataagc gataagtttg ctcaacatct tctcgggcat aagtcggaca ccatggcatc    69240
acagtatcgt gatgacagag gcagggagtg ggacaaaatt gaaatcaaat aatgatttta    69300
ttttgactga tagtgacctg ttcgttgcaa caaattgata agcaatgctt ttttataatg    69360
ccaacttagt ataaaaagc tgaacgagaa acgtaaaatg atataaatat caatatatta    69420
aattagattt tgcataaaaa acagactaca taatactgta aaacacaaca tatgcagtca    69480
ctatgaatca actacttaga tggtattagt gacctgtaac agagcattag cgcaaggtga    69540
tttttgtctt cttgcgctaa tttttttgtca tcaaacctgt cgcactccag agaagcacaa    69600
agcctcgcaa tccagtgcaa agctttgtgt gccacccact acgacctgca taaccagtaa    69660
gaagatagca gtgatgtcaa acgacgcagc tgacttcttt tctttcacga cttccccaca    69720
cccagcatgc ataccttttcc gccataactg tagtgaatgt ctgttatgag cgaggagcgg    69780
aagttaacac ttatgaaaaa tggctacgaa gtccgtggct atctatcggc ttattagtac    69840
ttgaaacgct tcttcagaag cctgaagagc taatcgttcg gcgatactat atatgcatta    69900
atagactata tcgttggtat aaacagtgca ccatgcaaca tgaataacag tgggttatcc    69960
aaaaggaagc agaaagctaa atatggaaaa ctacaatacg atgccccgtt aagttcaata    70020
ctactaattt ttagatggaa aacgtatgta ataggagagta acttaaaaga gagatcctgt    70080
gttgccgcca ataaaattgc ggttatttta ataaaattaa gggttactat atgttggagt    70140
ttagtgttat tgaaagaggc gggtatattc ctgcagtaga aaaaaataag gcattcctac    70200
gagcagatgg ttgaatgac tattcctttg ttacaatgtt ttatcttact gtctttgatg    70260
agcatggtga aaaatgcgat atcggaaatg ttaaaattgg ttttgtaggt caaaagaag    70320 aagtaagcac ttattcatta atagataaaa aattcagtca actccctgaa atgttttttt    70380
ccttaggtga aagcattgac tactatgtta atctcagcaa attaagcgat ggttttaaac    70440
ataaccttct taaagctatt caggatttag tagtatggcc aaatcgatta gccgacattg    70500
aaaatgaaag cgtccttaac acctcattac ttagaggggt aactctttca gaaattcatg    70560
gacagttcgc acgtgtgtta aatggttttgc cagaattgtc agatttccac ttttcattta    70620
atagaaaaag tgctcccgga ttcagtgatt taactatacc ttttgaggtg acggttaatt    70680
ctatgcccag cacgaacatt catgcttttta tcgggcggaa tgggtgtggt aaaacaacaa    70740
ttttgaatgg aatgattggt gcaatcacca acccagaaaa caatgaatat ttttctctg    70800 aaaataatag acttatcgag tcaagaatcc caaagggata ttttcgatcg cttgtttcag    70860
```

```
tttcgtttag tgcatttgat ccttttactc ctcctaaaga acaacctgac ccagcaaaag   70920
gtacacaata cttttatatt ggactcaaga atgctgccag caatagttta aaatcactag   70980
gcgatctccg cttagaattc atttcagcat ttattggttg tatgagagta datagaaaaa   71040
gacaactctg gcttgaagct atcaaaaaac taagtagtga tgaaaactt tcaaatatgg    71100 aactcatcag cctcatttct aaatatgaag agttaagacg taatgaacca cagattcaag   71160
tggacgatga taaattcact aaattgtttt atgacaatat ccagaaatat ctgcttcgaa   71220
tgagctctgg acatgcaatt gttttattta ctatcacaag attagtagat gtcgttggcg   71280
aaaagtcatt agttttattc gatgaaccag aggttcatct gcatccacct ttgctctctg   71340
cttttttacg aacattaagc gacttactcg atgcacgcaa tggtgtagca ataattgcaa   71400
ctcattcccc agtagtactg caagaggttc caaaatcctg catgtggaaa gtcctacggt   71460
caagagaagc aataaatatt atccgtccgg atattgagac attcggtgag aacttaggtg   71520
ttttaactcg tgaggtgttt ttacttgaag tgacaaattc tggataccac cacttattat   71580
cgcagtccgt tgattcagag ctttcttatg aaaccattct aaaaaattat aatggtcaga   71640
taggattaga aggtcgaacc gttttaaaag cgatgataat gaacagagat gaaggtaaag   71700
tacaatgaaa aaactacctc ttccagcgag aacttatagc gaaatgctta ataaatgctc   71760
ggaaggtatg atgcagataa atgttagaaa taatttcatt actcacttcc ccacttttt    71820 gcagaaagaa caacaatata gaatattaag ctcgacaggt cagttattta cctacgacag   71880
gacacaccct cttgagccta caaccttagt agttggtaac ctgacaaagg ttaaattaga   71940
aaagctttat gaaaataatc tccgagataa aaacaaaccc gctagaacat attacgatga   72000
catgcttgtt tcatcaggtg aaaaatgtcc attttgtggt gatataggac agacaaaaaa   72060
tatagatcat tttcttccta ttgcacatta tcctgaattt tcggtgatgc ctattaattt   72120
agttccatcg tgccgcgact gcaatatggg agagaaggt caagtttttcg cagtagatga   72180 ggtacaccaa gcgattcatc cctatatcga caaggacatt tttttttcgtg agcaatgggt   72240 atatgcaaat ttcgttttccg gaactccggg tgctatcagt ttttatgttg aatgcccggc   72300
gaactggagg caggaagaca acacagagc tcttcatcat ttcaagctat taaatattgc   72360
taacaggtat cgtttggagg cagggaagca cttgagtgaa gtgattactc aaagaaactc   72420
tttcgtaaaa gttataagga aatatagttc aaccgcaacg tttcagcagc tacagtcaga   72480
atttattgaa gcaaatctga aacctattat agatttgaat gacttcccca attattggaa   72540
aagagttatg tatcagtgcc tagcaaactc ggaagatttt ttcagaggga tctagaatat   72600
gatgaaagat agaaaattac gacgcttatc ggaagtgaac gaatacttt tatatgagga    72660 gggctgtttt tacaaaatcc ggtagtaact tgctaaccaa ttcctaggca ggtcattggc   72720
aacagtggca tgcaccgaga aggacgtttg taatgtccgc tccggcacat agcagtccta   72780
gggacagtgg cgtacagtca tagatggtcg gtgggaggtg gtacaaattc tctcatgcaa   72840
aaaatatgta aaatcggtag caactggaaa tcattcaaca cccgcactat cggaagttca   72900
ccagccagcc gcagcacgtt cctgcatacg acgtgtctgc ggctctacca tatctcctat   72960
gagcaacgtg ttagcagagc caagccacaa ctctaatttt aatacataat gaatgataat   73020
aataatatta aaaatttcct gtgtaactaa tttactatat ggtttctgat aagaatcatt   73080
gcaaagatca aacaacttgt attacattga cagttaagca gttaatttta tcacctctaa   73140
aatatatcag catctagcat gcaacctatc aaaatggaga gttttatgac taaaaaacca   73200
```

```
tgggaaagaa gacttaaaga tttatcgcac ttgctcaaat gctgcattga tacatatttt    73260
gaccctgaat tatttcgctt gaatttgaat caattcctcc aaaccgcaag aacagtaaca    73320
tttattattc aaaaaaacaa aaaccagatt ataggatatg acatttggta taacaataat    73380
gttattgaaa aatggaaaaa tgatccatta atggcttggg ctaaaaattc tcgcaatacg    73440
atagaaaaac aaggcgattt agaaatgtat agcgaggcaa aggctactct tatttcatct    73500
tacattgaag aaaatgacat tgagtttatt acaaatgaaa gtatgttaaa cattggtata    73560
aaaaagttag tcagacttgc acaaaagaaa ttaccttcat atttaactga atcatctatt    73620
attaaatcag aaagacgatg ggtcgctaat acgctaaaag attacgaatt attacatgcc    73680
ttagctataa tctatggcag aatgtataac tgctgtaact ctcttggcat acaaataaac    73740
aatccaatgg gtgacgatgt gatttcgcca acatcattcg actctttatt tgatgaagcc    73800
aggagaataa cttatttaaa attaaaagat tactccataa gcaaattgtc atttagcatg    73860
atacaatatg acaataaaat aattcctgaa gatattaaag agcgtctaaa actggtagat    73920
aagcctaaaa atatcacttc gacagaagag ttagttgact atacagccaa gcttgcgaaa    73980 acgactttt taaaggacgg ttatcacatt caaacattaa tttttatga taaacaattc    74040 catccaattg atttaatcaa tacaaacattt gaagatcaag cagataaata tatttttgg     74100 cgttatgcag ctgacagagc caaaataaca aatgcctatg gcttcatttg gatatcagag    74160
ctatggctca gaaaagcaag catctactcc aataaaccaa tacatacaat gccaattata    74220
gatgaaagac ttcaggtaat tggaattgat tcaaataata atcaaaaatg tatttcatgg    74280
aaaatagtta gagaaaacga agaaaaaaaa ccgactttag aaatatcaac agcagactca    74340
aaacatgacg aaaaaccata tttcatgcgt tcagtcttaa aagcaattgg cggtgatgta    74400
aacactatga caattgagt catagaactt ccattattct cctgaagata ataatcgcca    74460
aataaaccaa tactcagctt tacaatatac taactaaccg cagaacgtta tttcatacaa    74520
cgtttctgcg gcatatcaca aaacgattac tccataacag ggacagcagg ccactcaata    74580
tcaggtgcag ttgatgtatc aacacggttc agcaacaccc gatacttctt ccaggcttcc    74640
agcaacgagg tttcttcctt cgttgcaatt tccagatctg cagcatcctg aagcggcgca    74700
atatgctcac tggctacctg catcaggctt ttttttgttt cttccgcctc ccggatccgg    74760
aacagttttt ctgcttccgt atccttcacc caggctgtgc cgttccactt ctgatattcc    74820
cctcccggcg ataaccaggt aaaattttcc ggtaacggac cgagttcaga aataaataac    74880
gcgtcgccgg aagccacgtc atagacggtt ttaccccgat ggtcttcaac gagatgccac    74940
gatgcctcat cactgttgaa aacagccaca aagccagccg gaatatctgg cggtgcaata    75000
tcggtactgt ttgcaggcag accggtatga ggcggaatat atgcgtcacc ttcaccaata    75060
aattcattag ttccggccag cagattataa attttatgg tccgtggttg ttcactcatt     75120
ctgaatgcca ttatgcaagc ctcacaatat agttaaatgc aatgttttg acggtgtttt     75180 ccgcgttacc cgcagcgtta acggtgatgg tgtgtccgtg tgaaccaata ctgaaagaat    75240
gggcatgagc accgataaca accggatgct ggtgcgcacc aataccaact gtatgcgcat    75300
gtgcaccggc actcacggct gtaccggaca atgagtgact gtggctgccc tgactgtccg    75360
ttttcgataa ataagcaata ccctgtgtgc tggttccttt aactgtggat aaacttcctg    75420
taatggttgc tgttccatac tgactccagc cagaactgtt catccttaaa ccacttgtgt    75480
gggcatgagc acccgcggcc cctgttgaac cgctcagact gtgagcatga gccccgtgt     75540 tattcgtcga tttggtgccg taatcgaaac tgcctgttgt tttcgtcccg taatcaaacg    75600
```

```
acgatgtggt tttcgtcccc aaatccgtac cggatgcact ggcactgtgg gtgtgcgact   75660
taattccatc ctgttcctga gacaatacag cacgaccgct ggcgggtttc cccttgattg   75720
tccagcctcg catatcagga agcacacccg atggatacgc gacagcaagt tttgggtagg   75780
ctgatttgtc aaacgcctgc ccctgcatca ggacgtagcc agacggaacg atatctgatg   75840
gccacgggat cggcgcacct gccggaaagg ccgaattctc accggcccca aggtattcaa   75900
gaacatctgc aacggaattt tttgccagaa tatccctgcc aacctgagtc agttcagtca   75960
ggctggcggc atcattttcc gcaaaatacg gtaatttatt tttcgccgtg gaaagccctg   76020
ccagcgccgt cagtgtcgca ttcttcggtt gtttacccgc aagcgcgtta gtcatggtgg   76080
tagcaaaatc tggatcattc ccgagcgctg cggccagttc attcagcgta ttcagtgcgt   76140
caggtgacgg gtcgataaca tctgcaatcg cggccagtac aaaagcggtg ttcgcaatct   76200
gggtattgtt tgttcccctg agcgcggttg gtgctgttgg cgttccggtc agtgccggac   76260
tgtccagtgg gcttttctgt tcgtttcatc cattaccacc ttaaccgcct ttggcgttgc   76320
agcaagcgtt tcagacgtgc tgttggttgc actgctgagc tgcactatcc cctttctcgt   76380
tgtgtccgca tcctcaagcg cgacagctga agctatatct tctgcacgtt ttgccgaatt   76440
ttttgcacgt attgccgccg cttctgccgc acttttgctc tgcgatgctg ataccgcact   76500
tcccgcagcc tctgtcgcct tcgtggatgc cgttgacgca ctccccgccg ccgctgtttt   76560
tgcgtctgcc gcggcagagg cgctccgttc cgctgctgtt tcagatgacc tggcattcgt   76620
ctcggacgtt tttgccgccc tggcagaatt ttctgccgcc gttgccgagg aagctgcacg   76680
accggcactt gatgatgcgt tcgtttctga tgattttgct gcctcttttg aggccaccgc   76740
atctcgtgct gaagtggcgg cctctgacgc tttcgtggcc gcggtggagg cagacgtggc   76800
ggctgattgt tgtgacgctg cagcattcgt ttctgacgtt ttcgccgcac cggcactggt   76860
ggccgccgcg ttttttgagg actctgcggc tgcggcactt ttttccgctt cagtggcctt   76920
tgctgatgcc gcttctgcgc cggaggacgc ttcctgagct gacgatgcag cctgtccggc   76980
ggacgtgctg gcgcgcgtg ctgagtcagt tgcatcagtc acaagggccg cgacctgagc   77040
agctgatgca ctggcatcgc cggctgattt cttcgcgtct gccgtactct gtgccaccac   77100
ggacgcgtta cgcgccacct cttccaccat cagttcaaga cgacgcagca cctccggccg   77160
ggcatcatcc tccgtcatgg cacagagaaa atcattcagc gtccccggtt gtgaatcttc   77220
atacacggtg atggtcccgg cgtgcgatgg tggaaaaccg tcaacctgca ggatgacact   77280
gtactgaccg tactccacat ccatgctgta acgcccggct tcatccggat tctctgagcc   77340
caccgtgttc accaccaccg tggtgctgtt acgtctggct ttcagctgaa tggtgcagtt   77400
ctgtaccggt tttcctgtgc cgtctttcag gactcctgaa atctttactg ccatattcac   77460
cccacaaaaa agcccaccgg ttccggcggg ctgtcataac actgtgttac ctggctaatc   77520
agaatttata accgaccccaa acgatgaatc cgtcagtacg ccagtcgcca ctgccggagc   77580
cttcataagc aatatcaaca cgacggacg ctgccggatt aatctgtata cctgcactcc   77640
acgccactga ggtatgccgc attgcacttt cgtccctggc agtggtcgtc tctttcatat   77700
acccgggagt gatttccgtc ttacggtaat ccattgtact gccggaccac cgactgtgag   77760
ccactccggc catggcgtac gcactgacct gcttactgat ttgtaaaacc ggtccggcca   77820
tcacgctcac ataacgtcca cgcaggctct catagtgaaa cgtatcctcc ccggtcatca   77880
ctgtgctgct cttttttcgac gcggcgaacc ccagggaagc catcaccccc acactgtccg   77940
```

```
tcagctcata acggtacttc acgttaatcc ctttcagatg actcacaccg gtatccccgc    78000
ccgacaacga cggcaatgta cccggtttca cttgaaaata gcccaccgta aacgtaccat    78060
gtccaccttc cgcacgggcc ggagtgactg tcaccgcaag tgcggcaaag acagcaacgg    78120
caatacacac attacgcatc gttcacctct cactgtttta taataaaacg cccgttcccg    78180
gacgaacctc tgtaacacac tcagaccacg ctgatgccca gcgcctgttt cttaatcacc    78240
ataacctgca catcgctggc aaacgtatac ggcggaatat ctgccgaatg ccgtgtggac    78300
gtaagcgtga acgtcaggat cacgtttccc cgacccgctg gcatgtcaac aatacgggag    78360
aacacctgta ccgcctcgtt cgccgcgcca tcataaatca ccgcaccgtt catcagtact    78420
ttcagataac acatcgaata cgttgtcctg ccgctgacag tacgcttact tccgcgaaac    78480
gtcagcggaa gcaccactat ctggcgatca aaaggatggt catcggtcac ggtgacagta    78540
cgggtacctg acggccagtc cacactgctt tcacgctggc gcggaaaagc cgcgctcgcc    78600
gcctttacaa tgtccccgac gattttttcc gccctcagcg taccgtttat cgtacagttt    78660
tcagctatcg tcacattact gagcgtcccg gagttcgcat tcacactgcc actgatatcc    78720
gcatttttag cggtcagctt tccgtccggt gtcaggaaa aggccggagg attgccgccg    78780
ctggtaatgg tggggccgt caggcgcttc aggaacacgg cgttcatgaa tatctggttg    78840
ccctgcgcca caaacatcgg cgtttcattc ccgtttgccg ggtcaataaa tgcgatacga    78900
ttggcggcaa ccagaaactg gctcagtttg ccttcctccg tgtcctccat gctgaggcca    78960
atacccgcga cataatgttt gccgtctttg gtctgctcaa ttttgacagc ccacatggca    79020
ttccacttat cactggcatc cttccactct ttcgaaaact cctccagtct gctggcgtta    79080
tcctccgtca gctcgacttt ttccagcagc tccttgccga gatgggattc ggttatcttg    79140
cctttgaaaa aatccaggta accttccgca tcatcgctcg cccgaccgac ggcctccacg    79200
aatgccgatt tgccaacggt gttcacactg cggatataaa agtaataatc atggcccggt    79260
ttgatattga tactggcggc tatccagtac agcgccgtac caagataacg cgtgctggtt    79320
tcaacctgtc tgatatccgc aatctgcttt tccgagaacc agaactcaaa ctgtaccgtc    79380
gggtcataaa cggcaagatg cggcgtggcg gttatctgaa aatagcccgg cgtcagctca    79440
atcctcgacg gtgctgccgg tgcggcaatc cggaacgata ccgacgccgg atcgccctgc    79500
tgcccccacg catttaccgc ccggactgtc agcctgtagt tccccagcgc cagttgcgtg    79560
aagcggtatg tggtttccgt cgtccgggcc gtgctgacca gccgctcact gccgtcgtcc    79620
gctgttacgg tcagacggag caggaaactc acgcccttca ccaccttcgg tgtgtcccat    79680
cgcgccagca cctgatattc cccgctgtct gcagtgactt ctgcggtcag gtgctgcacc    79740
gctggcggcg tgacaccatt caccgtgcca ctctgttcgc cgtcaaagtg cgccccgtta    79800
tccacgatgg cctcttttc cggcacatgc tgcacggcgg tgatggcata cgtgccgtcg    79860
tcgttctcac ggatactcac gcagcggaac agtcgctggc gcagcgtcgg cagcttcagc    79920
tcccatacgc tgtattcagc aacaccgtca ggaacacggc tcacttttac cttcacgccg    79980
tcggtgacgg actgaaccct cacgctgacc ggattgccac ttccgtcaac caggcttatc    80040
agcgcggtac cggaggatgg cagcgtgatt tcacggtcga gcgtcagcgt ccgggtctgg    80100
ctgttcaccg ccagcacacg accaccggtg ctgataccgg catagtcatc atcgcagatt    80160
tcaataacat cgcccggtac atggcgaagc ccttctgcgc cgacgctgaa atccacggtc    80220
tgcgtttcca gcagttctgt tttaatcagc cacagcccgg cgcggtgtgc ctgccccgg    80280 ctggtacagc caaaggcatc catcttcgta acattacgac cgtaacgggc aatggcctgc    80340
```

```
gtatcttcaa caagctctgt cgccgtctcc cagccgttgt tcgggtcaat ccagttcacc    80400
tcaacggcat tatggcggtc cttcagggcg ctgaagctgt agcggaacgg cgcgccatca    80460
tccggcatca ccacattact gcggttatag gtccacgtct tatccgacgg tcggtcctgc    80520
acgaacgtca gcgtctgccc gttccatacc ggcatacagc gcatcgccga gcagaaatcg    80580
ctgagcacat cccacgcctt acgctgtgtg gtcaggtacg cattacaggt gatgcgcggc    80640
tccgtgccgc caaagccgtc cggcactgac tggtcgcagt actggccgat gacatacagc    80700
gcccatttat ccacatccgc cgcaccaaga cgtttcccca tgccgtagcg cggatgggtc    80760
agcatatccc acagacacca ggccatgttg ttgctgtatg ccggtttaaa cgttccgtcc    80820
cagataccgc tgtattgccg cgtctgcggg ttatagttcg acggcacctg cagaatacgc    80880
ccgcgcagat gataattacg gctcacctgc tggctgccga actgctccga gtccacctgc    80940
acgccgacca gtgccgtgtt cgggtagcac tgtttcacat cgatgatttc agtgtatgac    81000
gaccagagcg ttttgttctg cagctggtct gtggtgctgt ccggcgtcat cctgcgcatc    81060
cggatattaa acgggcgcgg cggcaggtta cccatcacca ccgaggccag atactgcgag    81120
gtggttttgc ccttaatggt gatgtctttt tccgtcaccc agccaccgtt acgttgtatc    81180
tgaaccagca ggcggacttc cgacggattc ctgtcaccct ttgaggtggt ttccaccagt    81240
gcctgtacac cgaaggtaaa gcgcagacgg tcgatgtttg cagacgtaat ggtgcgggtg    81300
atcggcgtgt catatttcac ttccgtaccc agcaccgtct cggagccgga ggattcaaat    81360
ccctccggcg gagtctgctc ctgctcacca gccggaaaca ccaccgtgac accggatatg    81420
ttggtattcc cctcagtgtc cagcaccggc gtactgttca gcagcacgct tttaagcca    81480
tccaccggac cttcaatcgg cccttcgctg atggcatcga tcacactcag caactgcgtg    81540
gacttcaggt tgtccttcgc ttcgcgcggg gtatgcccct tactgcttcc tttacccatt    81600
cctcacgctc cataaatgac aaaaccgccc gcaggcggtt tcatataaaa cattttgcat    81660
cagcgaccaa tcaccacaac ctgaccaccg tccccttcgt ctgccgtgct gatctcctga    81720
gaaaccacgc gtgaccccac gcgcatttcc ccgtacagaa caggcagaac attgccctgg    81780
gcaaccatgt tatccagtga ggagaaatag gtgttctgct taccgttatc cgttgtctgt    81840
atacggggag ttctggcttt cggtgccagc atctgcgcca caccaccgag caccatactg    81900
gcaccgagag aaaacaggat gccggtcata ccaccggccc caatggctgc cccccatgct    81960
gcaagggtgg ctccggcggt aaagaatgat ccggcaatgg cggcagcccc caggacaatc    82020
tggaatacgc cacctgactt ggcccccggcg actctgggaa caatatgaat tacagcgcca    82080
tcaggcagag tctcatgtaa ctgcgccgtt aacccggacg tgctgacgtc ccgcccggca    82140
atccgtacct gataccagcc gtcgctcagt ttctgacgaa acgccgggag ctgtgtggcc    82200
agtgcccgga tggcttcagc ccccgttttc acacgaaggt cgatgcggcg accaaatcgt    82260
tgtaaatccc cgtaaaggca gatgcgcgcc atgcccggtg acgccagagg gagtgtgtgc    82320
gtcgctgcca tttgtcggtg tacctctctc gtttgctcag ttgttcagga atatggtgca    82380
gcagctcgcc gtcgccgcag taaattgcgg cgtgattcgg cactgatgaa ccaaaacagc    82440
acagcagcac atcgcccggc tgtgccgctg acaacggcac ctgatacagc cccgtcgcct    82500
ccagattatc cagatagaga ttctggccgt tacgccacca gtcatcctca cgatgaaagt    82560
ccggcatctc aatccccgcc agatgataag catcccggaa cagtgtgtaa cagtccgtca    82620
caccgtgctc aaagcgccgc ccggtgagat gcggcacaca gcggaactta tgaatcgtcc    82680
```

```
cccggcagac cagccaccac ggcaaatcac tctgcacctg cagccgccgg tcggcctcac   82740
tcagccaggg cagaccaccg gggtggctgt ggaccagcgc cacaatctca ccctgcattt   82800
ctgcctgcag ccagtcttcc ggcgacatac ggaaatagcc tccggctcac cggagatatt   82860
cacgcagggg aaatatcttt ccccctccgg cgtgcttacc acgaagccgc acgactccgc   82920
tggcgcacat cgccgggcgt gcgccagaat cgctgattct gtctgtgtca tgggatttac   82980
tgcgaaagtt tgttaatgga aaggaagccg ccaaagttgc cgacgttatt gcggaactta   83040
caaccgctca ggcatttgct gcatttatcc ttcgtgatat cggacgttgg ctggtcatat   83100
tcatccgcga cagccggacc gctataaccg cactcgtcac cgcgataggt ccaggtgcag   83160
gtgttggcca gcatgatacg tcccggaaaa acagcgccat ccgtttccgt cggcgtggac   83220
agtacaaagg aggcactcac cgcgctcagt tcgctgcact gctcaatgcg ccagcggctg   83280
atcacctcct gctccggatc ggcgtaactg tttccgttga cgaagttcac cgcatccaga   83340
aaacgggcgt aaaccttacg ccggaccacc gttccgccga ccagactctg catatcttcc   83400
gccatcccgg tgaccatacc gtacaggtta gaaaccgtca gcgtgggggcg cgtactggtg   83460 cctttgccat tcagttcaaa accgctcccc tgaatgggat acggctgata ctgtcgcccc   83520
tgccaggtga ccggctcacc tttttcgttc tgctcattac agaaaaaata acgttctcca   83580
ccgacctctg tcaggtcgat ttcccagagc accacgctgg ccgactgctc cgcacgggtg   83640
cattcattca gtgtttcctg ccggatatcc tgcatcagtt caccacctgt tcaaactctg   83700
cgctgaactc aacacgcagc atactgaccc gcgacgacca ttttgcgcag gtcacccttta   83760 tctgccgcca ctcataaggc ggcgtccaca gaaaggattt ccagccccg tgctcttcca   83820 gaaacgactc cagtaccgtg gcctcctcac ggggacaga aagcgtcacg ctgtacgttt   83880
tcaggttggc attcagcccg gcaggcgctc gctgagaata gccatcacca aagcgcacct   83940
ttcttacaga agggaccgaa gccacatcca taccgggttt cactttccag cggaaggtct   84000
tcatcgtcca cctccggaga acaggccacc atcacgcatc tgtgtctgaa tttcatcacg   84060
ggcacccttg cgggccatgt catacaccgc cttcagagca gccggaccta tctgcccgtt   84120
cgtgccgtcg ttgttaatca ccacatggtt attctgctca aacgtcccgg acgcctgcga   84180
ccggctgtct gccatgctgc ccggtgtacc gacataaccg ccggtggcat agccgcgcat   84240
cagccggtaa agattcccca cgccaatccg gctggttgcc tccttcgtga agacaaactc   84300
accacggtga acaatccccg ctggctcata tttgccgccg gttcccgtaa atcctccggt   84360
tgcaaaatgg aatttcgccg cagcggcctg aatggctgta ccgcctgacg cggatgcgcc   84420
gccaccaaca gccccgccaa tggcgctgcc gatactcccg acaatcccca ccattgcctg   84480
cttaagcaga atttctgtca tcatggacag cacggaacgg gtgaagctgc gccagttctg   84540
ctcactgccg gtcagcatcg ccgccatatt ctgtgcaata ccatcaaagg tctgcgtggc   84600 tgcactttt acctgcgaca tactgtccgt ggcgctctct tcccactcac tccagccgga   84660
cttcaggcct gccatccagt tcccgcgaag ctggtcttca gccgcccagg tcttttttctg   84720 ctctgacatg acgttattca gcgccagcgg attatcgcca tactgttcct tcaggcgctg   84780
ttccgtggct tcccgttctg cctgccggtc agtcagcccc cggcttttcg catcaatggc   84840
ggcccgtttt gcccgttgct gctgtgcgaa tttatccgcc tgctgcgcca gcgcgttcag   84900
gcgctcctga tacgtaacct tgtcgccaag tgcagccagc tggcgtttgt actccagcgt   84960 ctcatctttta tgcgccagca gggatttctc ctgtgcagac agctggcgac gttgcgccgc   85020
ctcctccagt accgcgaact gactctccgc cttccacaaa tcccggcgct gctggctgat   85080
```

```
tttctcattt gctccggcat gcttctccag cgtccggagt tctgcctgaa gcgtcagcag      85140
ggcagcatga gcactgtctt cctgacgatc gcccgcagac accttcacgc tggactgttt      85200 cggcttttc agcgtcgctt cataatcctt tttcgccgcc gccatcagcg tgttgtaatc       85260
cgcctgcagg attttcccgt ctttcagtgc cttgttcagt tcttcctgac gggcggtata      85320
tttctccagc ggcgtctgca gccgttcgta agccttctgc gcctcttcgg tatatttcag     85380
ccgtgacgct tcggtatcgc tctgctgctg cgcattttg tcctgttgag tctgctgctc      85440
agccttcttt cgggcggctt caagcgcaag acgggccttt tcacgatcat cccagtaacg     85500
cgcccgcgct tcatcgttaa caaaataatc atccttgcgc agattccaga tgtcgtctgc    85560
tttcttatac gcagcctctg ccttaatcag catctcctgc gcggtatcag gacgaccaat     85620
atccagcacc gcatcccaca tggatttgaa tgcccgcgca gtcctgtctg cccaggtctc    85680
cagcgtgccc atgttctctt tcaggcggcg ggtctggtca tcaaacccctt tcgttgcggc   85740 ctcgttcgcc gcctgcaatg ccccggcttc atcgccggaa cgctgcaact gagcaacata   85800
cgcaatctgc tccgccgaca cgttatggaa ctggcgagcc atcgccgtca gccccgacgt    85860
cgggtctgtg gtcagcttcc cgaaggcttc agcgaccttg tccacctcca cgccggatgc    85920
agaggagaaa cgcgccacac tctggctgat ggacgcaatc tgagcctcac cgcttacccc   85980
cgccttaacc agtgcgctga gtgactcgct ggtctggtta acgtcagcc ctgccgcctg     86040 cccggctctg gacaggacca gcatacgatc tgccgtcagt cccgcctgat gccggaaag   86100 gaccagcgtt ttgttgaaat cggacagggt tgagttgccc tgataccagg catacgccag   86160
cgcaccggtc gccaccgcca gcgaggtggc ccccaccatc ggcagggtga tcgcaccggc     86220 aagcccctg aacatgggga tcatcccgcc gaaggagtcc ttcacctgcc ccccctgttg     86280
cagcaggatc agccacggac tttgcccgcc tgcaagctgc gtggccacgt cggtgaactg   86340
tgcaggcagc atacgcatgg cggctttata ctgcccgacg gaaatcccg ctttctgtgc    86400 agccagcgcc tgtcggctca gcgactgttc aacgactgcc gctgttttt tcgcatcact    86460 ttccgtacca gaaaaatgac gcctgactct ggccatctgc tcgtcaaatc tggccgcatc    86520
cagactcaaa tcaacgacca gatcgcctac cggttcagcc ataccggact cctcctgcga    86580
tcccttctga tactgtcatc agcattacgt catcctccgt catgtccgcc acatccgggg    86640
aagcggggat aacttcattc ccgtccgggc caaagcggac acctccggca gccctgccg    86700 ctttctgcat cagcacatca tcttcaggct cttcgtcagc ctcgcgccgg ttcagcagac   86760
tgaaatccag cggatgcata tccggatcgc tgaaaaacag gctgagcacg gtgtacgtca   86820
gcccggaaaa gtgcatatcc agcagaacat catgaaaata atgggtactg taaaagcggt    86880
gccagtcggc atactccgtg gatgacatcc cggcaagcat ggcacgccag tcgggtcgcc   86940
ccatctcacg cgccagtttc agggcaaaac tcagctcacc gtcgaacact ttcccgcaga    87000
aacaggctct gcgggcccgg cgtcctctgt ctgttcaggg gcattattca ccacaaactc    87060
atacatacca gacagccggt acaccacgtt ttcagcatga gaaattgcct ccgtgggcca    87120
ggtggtaagc acttcctgct caatctgttt aacggcttca ttcatggacg gcatctgcgt   87180
cttctgcgga tggttatgcc acagggacat cgccaccaga aacgcgccgg ttctgatggc    87240
gtcttccaca gtaaacttcc ggttgctgtc tgactccgcc tgttctgcct gccgtttcat   87300
cagggcgaga tgctcaatgc gctgcagggc tgacagttca gaaagcgtga cggtcacacc    87360
gttatgttca aatgattcgg ttttcaggaa catcgctgac tctccggatt aactggcggt     87420
```

```
gacggtaatt tctgcaaccg cagcaaactc accattaccg gatacaaccg gaatgttgac   87480
cttgcctgca gcaacgccgt tcacggtgat ggtcatacca ctgaccgaca cggtggcttt   87540
tgttttatcc gcagacaccg cacgaaagct cttgtcggtt acgccctccg gctggaaggc   87600
cacggtcagc gtggtgctct gcccttcac caccgaggtg ctggcaggcg tcacggtcat    87660
gccggttgcc gctgttaccg tgctgcgatc ttctgccatc gacggacgtc ccacattggt   87720
gactttcacc gtgcgggtga tcacttcctt cgccgtcacc gccttaccga tactgctgac   87780
ccagccacgg aacacatcga ccgtgccgtt cgggaagcgg atttttatagg cacgggtatc   87840 gccttcatta aaccacgcca gcagcgcctg ctgcccctgc tctccgggca tccacgccag   87900
cgtgaagctg gtatctccgg cagatttctg cccctgcccg gtcgcagtcc agtctgcatc   87960
ttcatcatcg agatagctgt cgtcatagga ctcagcggtc agttcgccgg gcgtcaggtc   88020
tttaactttt gccagacgcg accagtcaac gtctgaaagc ggattcgcgt aagggtcacc   88080 gctccccta taaacccaca gggtggtccc ggcacctttc accggcattg taggatttgg    88140
tacaggcata gcgtcctcac atttcatagg taatgacata agtcagatcg gctgaactcc   88200
acaagcccgc atcatcgtcg cgccggtagt catagccgct ggccaccata ctggtgatca   88260
aatctgacag tgccgggata tcgctcatca ccggataaat ccgggactcc atccacgcat   88320
ccagctctga atccggcacc tgagcaggca ggaaaacttc gatatgcagc tccgcctgcc   88380
aggtatcgct gtccagctct tcgcccgtgt attcagcgcc ggtgagataa acggcaactg   88440
ccggaaaatc cgcctcatca aaacagcgg ggcgaccatc aaaaaacgtc gccccggtgt    88500
catgcttctc cagtgcatcc agtacggctg cacggagttc agtatgtttc atcgctttat   88560
taccatcctc agttgatgct gcagcgcata gcccagctct ttcggaagac gttcacgccg   88620
tatccgctca atattttgtt taaacgccgt ggtcagcggc accgccatcg ggattttcac   88680
cacatcaatg gggtaacggt ttttcccagc cacacgctgc atgacatgcc accggccatt   88740
tttcagttgc tgaataaacg cgccgggaat acgacggtta cccaccacaa gcacgctgcc   88800
gccacctttc agggatgaac gctgccccctt tttacgacgc ctgcggcgcg aaaggacaac   88860
ccgcgcatta cccagcttga ttacgggcaa atcccccccgg ttaactttga ttctggcctg   88920 cggattttg accgtggccc ttttcagcct ggcccttttcc tttaccagtt ccggcgtac    88980 ctttgtctca cgggcaacct gtgacgccga ctgcgatatc gcggatgaag caacgcggtt   89040
aatggccatt gcggcggcac caggcaccgc cgttttgctg atacggctga ggttttcaac   89100
ggcctgctca agaccttta tggccataca tcccccttc agcggcgacg gttaacggca     89160
ggcggtacgc cccgtccaag ccagagatga caacttccgc catcatccgg cgaaacccga   89220
tctacccaga aattttcctc accgatggtc agcgtgtctc cacgccgcag ctgccgcacc   89280
tcatcagtcc ggacaaacag gacgggctg gagccttcaa cgcgcacgcc ctgtccggca    89340
tagctgatat tttcagggtc atcaaaaaca ccacgtatca ccgcacctga ctgctcaccg   89400
gatgtaatgg tggctgacgt tcccatgtac ccgcgtatcg tttcatcggc gcgggcaatg   89460
gcagcatcga acaggttatc gaaatcagcc acagcgcctc ccgttattgc attctggcca   89520
ggccgcgctc tgtcatttcg gctgccacac cggcagagac acgaaacgcc gttcccggca   89580
gcacaaatgc cacaggttca tccgcgtgg cgtgaagtgc atcagtatgc agcttcacca   89640
gtgccacgac cgtgaccagt tcagacgtat ccagaatcac ggtatccggc tgcgctgatc   89700
ccacctcatt ttcatgtccg gtcagcacat ttttcccggct gagaggggtg tcctgaccgg    89760
cagtttcatc cgtgtcatca agctcctctt tcagctctgc cacacggagc gccagttctt   89820
```

-continued

```
ctttcgtccc cgtcaggctg acatcacggt tcagttgttc acccagcgag cggagacggg   89880
caatcagttc atctttcgtc atggactcct ccacagagaa acaatgggcc cgaagggcca   89940
tgattacgcc agttgtacgg acacgaactc atcagggtca gccagcagca tcagcggtgc   90000
tgactgaatc atggtgaact cacgcgccgg atcgccggtg gtcacccagt ttttcgggta   90060
acgggcagag gcgttaatgc cttcgcgctg tgcgtccgca tcctgaatgc agccataggt   90120
gcgcagaccg cgtgcctgag tgttccccag caccatcgtg ttgtccggca ggaagttctt   90180
tttgacgccg ttttccacgt actgtccgga atacacgacg atggccacat cgccatacat   90240 cccctttatag gacaccgctt tgcccaggtc tttcaccgct gtctccagct cggaattaga   90300
gccacgacgg gtatccagct tctccttgac ggctttgaag gaacggaaca gcgcccagcc   90360
tttcggatcg aacacgatga tattcaccac accgctggcg ttcagcgcgt aggcttcgat   90420
atcgtcggtc gggtcatacg tggacttgtc acgcttgctc cactccgtgc cgccggactg   90480
cgtgatgtta ttctcctcac tgcggcccat atccacctca accggatcga aggcttcacc   90540
ggtcatggtg tatttgccct taagcacggc agaaactgcc tgcatctctt cgacctgagc   90600
aatggccagc tcttcgtcac gcatgttctg catgatgatg cgacggcggc ggtaagccgg   90660
gtccgccaga ttctgcggat cttcatccgg caggcgacgc agggtcatct gcggattcac   90720
ttcatgcttc ggcttgacat atcccggcgt aaattcagag gtggagccgc cacgggaacg   90780
gataacctca ccggaaacaa tcggcgaaac gtacagcgcc atgtttacca gtcccggaat   90840
ttgtgagaga tagactttct ccgtggtgaa gggatagctc tcacggaaaa agagacgcag   90900
aaacagcgga tcaaacttaa atttctgctc atttgccgcc agcagttggg cggttgtgta   90960
catcgacata aaaaaatccc gtaaaaaaag ccgcacaggc ggcctttagt gatgaagggt   91020
aaagttaaac gatgctgatt gccgttccgg caaacgcggt ccgttttttc gtctcgtcgc   91080
tggcagcctc cggccagagc acatcctcat aacggaacgt gccggacttg tagaacgtca   91140
gcgtggtgct ggtctggtca gcagcaaccg caagaatgcc aacggcagca ccgtcggtgg   91200
tgccatccca cgcaaccagc ttacggctgg aggtgtccag catcagcggg gtcattgcag   91260
gcgctttcgc actcaatccg ccgggcgcgg ttgcggtatg agccgggtca ctgttgccct   91320
gcggctggta atgggtaaag gtttcttttgc tcgtcataaa catcccttac actggtgtgt   91380
tcagcaaatc gttaacggca tcagatgccg ggttacctgc agccagcggt gccggtgccc   91440
cctgcatcag acgatccagc gcagtgtcac tgcgcgcctg tgcactctgt ggtgctgcgg   91500
ccagaatgcg gcgggccgtt ttcacggtca taccgggggt ttctgccagc acgcgtgcct   91560
gttcttcgcg tccgtgagcc tcctcacagt tgaggatccc cataatgcgg ctgttttctg   91620
ccgcaaccgc tgcggtgatc tgcgcgttca cgtccggctg cgccgcgctg gcgttctcgc   91680
cctccgtcgc tggcaccacg tcagtaacgt cagcctgcga agcagtggct gaaacagttg   91740
ttgattgagt ctctttggtc attcgcccte ctgagagacg ggatttacgt gcatccagtg   91800
catcacgcat gacggtgatc gcatcggtgc tgttaacaag ttcatcagcc agtccggcat   91860
caatggcctc ctgaccgctg tacactgcag cctcggtatc cagcacaacc tgcacggaca   91920
ggccggtata tgccgacacc ttctgcgcaa acatctggcg ggttgcgtcc atccgggact   91980
gcagtgtctc ccggacgtca tccggaagat ggctgtaggg gttgccatcc accttatggc   92040
tgccgctgta aatcagcgtg atttccacac cctgtttctc cagcgcagca ccgtaattac   92100
tgtgagccat catgacgccg atggagcctg tccgggcggt ctgcgtgacc agacgccggg   92160
```

-continued

```
aggcggcact ggcaagcaac tgacctgcac tgcagttcat gtcgttggca agcgcccata    92220
ccggttttat gtcacgcaca cgggcgatga tgtcagcgca gtcaaatgcc cccgccacca    92280
tcccgccggg cgtgtccata tcgagcagaa tgccgtccac catcggatcg ctggcagcct    92340
gttgcagacg ggcgataatg ccgttgtaac cggtcatccc cgagtacggc tgcagcgccc    92400
gcgtccggct gaccagcgtg ccggacaccg gcagcacggc gatgccgttc atgacctgat    92460
aactgcgggc ctgtcgtggt ccgtcatcat caccggataa tgccagcgtc gcgagtgcct    92520
cctgggcagt caggctgtcg ccggacaccg catccgtcag gctgctgatc ccaagctggc    92580
ctgcaagcgc acaaaagaaa acccgcgcat aggcgggttc aagcatcagc ggctcattaa    92640
aggccatgct ggcaatatgc gggagattac gcagctctgc tgtcactctt ctcctcctct    92700
gttgattgtc gcagcccgga ttcaaatgct gcagccgccc aggcgggcgg tttaagaccg    92760
gctgcacggc gctccatcgt ttcacggacc tgctgggcaa aaatttcctg atagtcgtca    92820
ccgcgttttg cgcactcttt ctcgtaggta ctcagtccgg cttctatcag catcaccgct    92880
tcctgaactt ctttcagacc atcgatggcc atacgaccgg agcctatcca gtcgcagttc    92940
ccccaggcac tgcgggcttc ctgaaaactg aagcgcgctt ttgaaggtaa cgtcaccacg    93000
cggcgaacga tggcctcttc cagccagcac agaaacatct ggctcgcctg acgggatgcg    93060
acgaattttc gccgcccat aaagtacgcc cacgactcgt tcgcactggc ccgtgccgtg     93120
gagtagctca tctgggcgta attccgggaa agctgctcat acgagacacc cagcccggca    93180
gcgatatacc gcagcagtga ctgctcaaac acggagtagc cgttatccgt atcctgagcc    93240
gtctgcaggt tcagtgagtc acccggcatc aggtgcggta cttttgcgcc tcccagccgg    93300
accggcgctg cggcgtaata cgcggcaatt tcaccaatcc agccggtcag cctttcccgc    93360
tgctcctgac tgttcgcgcc cagaataaaa tccatcgctg actgcgtatc cagctcactc    93420
tcaatggtgg cggcatacat cgccttcaca atggcgctct gcagctgcgt gttctgcagc    93480
gtgtcgagca tcttcatctg ctccatcacg ctgtaaaaca catttgcacc gcgagtctgc    93540
ccgtcctcca cgggttcaaa aacgtgaatg aacgaggcgc gcccgccggg taactcacgg    93600
ggtatccatg tccatttctg cggcatccag ccaggatacc cgtcctcgct gacgtaatat    93660
cccagcgccg caccgctgtc attaatctgc acaccggcac ggcagttccg gctgtcgccg    93720
gtattgttcg ggttgctgat gcgcttcggg ctgaccatcc ggaactgtgt ccggaaaagc    93780
cgcgacgaac tggtatccca ggtggcctga acgaacagtt caccgttaaa ggcgtgcatg    93840
gccacacctt cccgaatcat catggtaaac gtgcgttttc gctcaacgtc aatgcagcag    93900
cagtcatcct cggcaaactc tttccatgcc gcttcaacct cgcgggaaaa ggcacgggct    93960
tcttcctccc cgatgcccag atagcgccag cttgggcgat gactgagccg gaaaaaagac    94020
ccgacgatat gatcctgatg cagctggatg gcgttggcgg catagccgtt attgcgtacc    94080
agatcgtctg cgcgggcatt gccacgggta agttgggca acagggctgc atccacactt     94140
tcactcggtg ggttccacga ccgcaactgc cctccaaatc cgctgccacc gccgtgataa    94200
ccggcatatt cgcgcagcga tgtcatgccg tccggcccca gaagggtggg aatggtgggc    94260
gttttcatac ataaaatcct gcaggtcccc tgcgtcgctg tgtcatgccg gtctgcactt    94320
ccagctctgc aatatatttt ttcaggtcag acacggaagt ggccgtaaac tccacccttc    94380
gtccgtcttt ctgtactgtt gccaccgtt tacctgtcat caggtcatgc agtgccgcac     94440
gggcagcgga aagttcttcc tgtcgcgtca ttcatcctct ccggataagg cacgggcgta    94500
atctgccagt gttttcttgt tggttgctgc accatcctct tcctgcaggc tcgccagcag    94560
```

```
cgcactgaga tccagctgcc agcgggaaat actgatgcgc agcgccgcca gcgcataaac   94620
gaagcagtcg agtgcctcat tgcgtcgctt tttgctgtcc cacagtattt ttttcctgcc   94680
atccacccat ttttcgacct gctcttcagc agtcagctgc tgcgcttcgg tcagatcaaa   94740
aatatccggg ttattcggga agtgaacggc accgggaagc ggttcatccc cttccggcgt   94800
cagtgtgaag cggttataaa tctgctcttt cgcggtatcc gtaccgattt cggtaaggta   94860
aaccccgttt ttgtttcgct tacgtggcat gctggccacc ggcttccgt agacggatgc   94920 ccctttaatg gggatcaccc ggaacagccc atgttttttc gagcgttcat acacaatggt   94980
cgggtcaatc ccgccagtat cccagcagat acgggatatc gacatttctg caccattccg   95040
gcgggtatag gttttattga tggcctcatc cacacgcagc agcgtctgtt catcgtcgtg   95100
gcggcccata ataatctgcc ggtcaatcag ccagctttcc tcacccggcc cccatcccca   95160
tacgcgcatt tcgtagcggt ccagctggga gtcgataccg gcggtcaggt aagccacacg   95220
gtcaggaacg ggcgctgaat aatgctcttt ccgctctgcc atcacttcag catccggacg   95280
ttcgccaatt ttcgcctccc acgtctcacc gagcgtggtg tttacgaagg ttttacgttt   95340
tcccgtatcc cctttcgttt tcatccagtc tttgacaatc tgcacccagg tggtgaacgg   95400
gctgtacgct gtccagatgt gaaaggtcac actgtcaggt ggctcaatct cttcaccgga   95460
tgacgaaaac cagagaatgc catcacgggt ccagatcccg gtcttttcgc agatataacg   95520
ggcatcagta aagtccagct cctgctggcg gatgacgcag gcattatgct cgcagagata   95580
aaacacgctg gaggggtcat ccggcgtcca tttgaggcca aacggcgtct ctttgtcgcc   95640
aaatttaaga tactgctcct ccccgcaatg cgggcaggca acatgaaaac gcataaaatg   95700
cggggattca ctggctgcac gctcaatctg acaggtgcct ctcactttg gcgtggagcc   95760 acggatggac tttggccaga ccgagccttc aatacgcttg tcacccagga acgtcggaga   95820
gccttcctgt tcaatatcat catcaaaagc agcaagttca tcataaccccg ccacatccac   95880 cgacttttca cggtagtttt ttgccgcttt accgcccagg caccagaagc cacgcccatt   95940
agtgaaacgc ttcatggtga gcgtgttatc ccggtgcttt ttgccatacc acggggccag   96000
cgccagcagc gacggaatat cacgaatagt cggctcaacg tgggttttca taaagttctc   96060
ggcatcacca tccgtcggca accagataag ggtgttgcgc tgcttatgct ctataaagta   96120
ggcataaaca cccagcagca ttttggaata accgacacgg gcagacttca ccacattcac   96180
ctcacggatg tagtcgctgc ccatcgcatt catgatggcc cgctgaaagg gcagtgtttc   96240
ccagcgccct tcctggtatg cggattcttt cgggagatag taattagcat ccgcccattc   96300
aacggcggtc tgtggctccg gcctgaacag tgagcgaagc ccggcgcgga caaaatgccg   96360
cagcctgtta acctgactgt tcgatatatt cactcagcaa ccccggtatc agttcatcca   96420
gcgcggctgc tttgttcatg gctttgatga tatcccgttt caggaaatca acatgtcggt   96480
tttccagttc cggaaaacgc cgctgcaccg acaggggggag cccgtcgaga atactggcaa   96540
tttcacctgc gatccgcgac agcacgaaag tacagaatgc ggtttccacc acttcagcgg   96600
agtctctggc attcttcagt tcctgtgcgt cggcctgcgc acgcgtaagt cgatggcgtt   96660
cgtactcaat agttcctggc tggagatctg cctcgctggc ctgccgcagt tcttcaacct   96720
cccggcgcag cttttcgttc tcaatttcag catccctttc ggcataccat tttatgacgg   96780
cggcagagtc ataaagcacc tcattaccct tgccaccgcc tcgcagaacg ggcattcct   96840 gttcctgcca gttctgaatg gtacggatac tcgcaccgaa aatgtcagcc agctgctttt   96900
```

-continued

```
tgttgacttc cattgttcat tccacggaca aaaacagaga aaggaaacga cagaggccaa    96960
aaagcctcgc tttcagcacc tgtcgtttcc tttcttttca gagggtattt taaataaaaa    97020
cattaagtta tgacgaagaa gaacggaaac gccttaaacc ggaaaatttt cataaatagc    97080 gaaaaccgc gaggtcgccg cccaggtcgc cgcccgtcaa tcggccctt agtggagc       97138
```

<210> SEQ ID NO 63
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 63

```
gcaatatcag caccaacaga aacaacct                                           28
```

<210> SEQ ID NO 64
<211> LENGTH: 44
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (37)..(37)
<223> OTHER INFORMATION: Carboxyfluorescein (FAM) attached to T

<400> SEQUENCE: 64

```
tttttttttt tttttttttt tttttttttt tttttttttt tttt                         44
```

<210> SEQ ID NO 65
<211> LENGTH: 75
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (1)..(75)
<223> OTHER INFORMATION: Carboxyfluorescein (FAM) attached to one T in
      sequence

<400> SEQUENCE: 65

```
tttttttttt tttttttttt tttttttttt tttttttttt tttttttttt tttttttttt        60
tttttttttt ttttt                                                         75
```

<210> SEQ ID NO 66
<211> LENGTH: 970
<212> TYPE: PRT
<213> ORGANISM: Clostridium botulinum

<400> SEQUENCE: 66

```
Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
```

```
                    85                  90                  95
Asp Glu Arg Ile Ile Ala Ala Tyr Arg Glu Ala Val Val Glu Ala Leu
                100                 105                 110
His Trp Ala Glu Lys Asn Ala Ala Glu Thr Arg Val Val Glu Lys Gly
                115                 120                 125
Met Val Val Thr Gln Ala Thr Gly Asn Leu Ala Ile Gly Leu Phe Gln
                130                 135                 140
His Asp Thr Asn Arg Asn Gln Glu Pro Asn Leu His Phe His Ala Val
145                 150                 155                 160
Ile Ala Asn Val Thr Gln Gly Lys Asp Gly Lys Trp Arg Thr Leu Lys
                165                 170                 175
Asn Asp Arg Leu Trp Gln Leu Asn Thr Thr Leu Asn Ser Ile Ala Met
                180                 185                 190
Ala Arg Phe Arg Val Ala Val Glu Lys Leu Gly Tyr Glu Pro Gly Pro
                195                 200                 205
Val Leu Lys His Gly Asn Phe Glu Ala Arg Gly Ile Ser Arg Glu Gln
                210                 215                 220
Val Met Ala Phe Ser Thr Arg Arg Lys Glu Val Leu Glu Ala Arg Arg
225                 230                 235                 240
Gly Pro Gly Leu Asp Ala Gly Arg Ile Ala Ala Leu Asp Thr Arg Ala
                245                 250                 255
Ser Lys Glu Gly Ile Glu Asp Arg Ala Thr Leu Ser Lys Gln Trp Ser
                260                 265                 270
Glu Ala Ala Gln Ser Ile Gly Leu Asp Leu Lys Pro Leu Val Asp Arg
                275                 280                 285
Ala Arg Thr Lys Ala Leu Gly Gln Gly Met Glu Ala Thr Arg Ile Gly
                290                 295                 300
Ser Leu Val Glu Arg Gly Arg Ala Trp Leu Ser Arg Phe Ala Ala His
305                 310                 315                 320
Val Arg Gly Asp Pro Ala Asp Pro Leu Val Pro Pro Ser Val Leu Lys
                325                 330                 335
Gln Asp Arg Gln Thr Ile Ala Ala Ala Gln Ala Val Ala Ser Ala Val
                340                 345                 350
Arg His Leu Ser Gln Arg Glu Ala Ala Phe Glu Arg Thr Ala Leu Tyr
                355                 360                 365
Lys Ala Ala Leu Asp Phe Gly Leu Pro Thr Thr Ile Ala Asp Val Glu
                370                 375                 380
Lys Arg Thr Arg Ala Leu Val Arg Ser Gly Asp Leu Ile Ala Gly Lys
385                 390                 395                 400
Gly Glu His Lys Gly Trp Leu Ala Ser Arg Asp Ala Val Val Thr Glu
                405                 410                 415
Gln Arg Ile Leu Ser Glu Val Ala Ala Gly Lys Gly Asp Ser Ser Pro
                420                 425                 430
Ala Ile Thr Pro Gln Lys Ala Ala Ser Val Gln Ala Ala Ala Leu
                435                 440                 445
Thr Gly Gln Gly Phe Arg Leu Asn Glu Gly Gln Leu Ala Ala Ala Arg
                450                 455                 460
Leu Ile Leu Ile Ser Lys Asp Arg Thr Ile Ala Val Gln Gly Ile Ala
465                 470                 475                 480
Gly Ala Gly Lys Ser Ser Val Leu Lys Pro Val Ala Glu Val Leu Arg
                485                 490                 495
Asp Glu Gly His Pro Val Ile Gly Leu Ala Ile Gln Asn Thr Leu Val
                500                 505                 510
```

-continued

```
Gln Met Leu Glu Arg Asp Thr Gly Ile Gly Ser Gln Thr Leu Ala Arg
            515                 520                 525
Phe Leu Gly Gly Trp Asn Lys Leu Leu Asp Asp Pro Gly Asn Val Ala
        530                 535                 540
Leu Arg Ala Glu Ala Gln Ala Ser Leu Lys Asp His Val Leu Val Leu
545                 550                 555                 560
Asp Glu Ala Ser Met Val Ser Asn Glu Asp Lys Glu Lys Leu Val Arg
                565                 570                 575
Leu Ala Asn Leu Ala Gly Val His Arg Leu Val Leu Ile Gly Asp Arg
            580                 585                 590
Lys Gln Leu Gly Ala Val Asp Ala Gly Lys Pro Phe Ala Leu Leu Gln
        595                 600                 605
Arg Ala Gly Ile Ala Arg Ala Glu Met Ala Thr Asn Leu Arg Ala Arg
    610                 615                 620
Asp Pro Val Val Arg Glu Ala Gln Ala Ala Gln Ala Gly Asp Val
625                 630                 635                 640
Arg Lys Ala Leu Arg His Leu Lys Ser His Thr Val Glu Ala Arg Gly
                645                 650                 655
Asp Gly Ala Gln Val Ala Ala Glu Thr Trp Leu Ala Leu Asp Lys Glu
            660                 665                 670
Thr Arg Ala Arg Thr Ser Ile Tyr Ala Ser Gly Arg Ala Ile Arg Ser
        675                 680                 685
Ala Val Asn Ala Ala Val Gln Gln Gly Leu Leu Ala Ser Arg Glu Ile
    690                 695                 700
Gly Pro Ala Lys Met Lys Leu Glu Val Leu Asp Arg Val Asn Thr Thr
705                 710                 715                 720
Arg Glu Glu Leu Arg His Leu Pro Ala Tyr Arg Ala Gly Arg Val Leu
                725                 730                 735
Glu Val Ser Arg Lys Gln Gln Ala Leu Gly Leu Phe Ile Gly Glu Tyr
            740                 745                 750
Arg Val Ile Gly Gln Asp Arg Lys Gly Lys Leu Val Glu Val Glu Asp
        755                 760                 765
Lys Arg Gly Lys Arg Phe Arg Phe Asp Pro Ala Arg Ile Arg Ala Gly
    770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
        835                 840                 845
Asp Pro Met Leu Lys Arg Ile Asp Leu Ala Tyr Ala Leu Asn Val His
850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
            900                 905                 910
Gly Ala Ala Val Ala Arg Asn Lys Gly Glu Lys Ala Ser Ala Ile Glu
        915                 920                 925
```

```
Val Thr Gly Ser Val Lys Pro Thr Ala Thr Lys Gly Ser Gly Val Asp
        930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 67
<211> LENGTH: 46
<212> TYPE: DNA
<213> ORGANISM: Artificial sequence
<220> FEATURE:
<223> OTHER INFORMATION: Synthetic Polynucleotide

<400> SEQUENCE: 67
tttttttttt tttttttttt tttttttttt tttttttttt tttttt             46

<210> SEQ ID NO 68
<211> LENGTH: 1292
<212> TYPE: DNA
<213> ORGANISM: Artificial Sequence
<220> FEATURE:
<223> OTHER INFORMATION: Synthetic Polynucleotide

<400> SEQUENCE: 68
gccatcagat tgtgtttgtt agtcgctttt ttttttttgga attttttttt tggaattttt    60 ttttttgacgc tcagtaatgt gacgatagct gaaaactgta cgataaacgg tacgctgagg   120
gcggaaaaaa tcgtcgggga cattgtaaag gcggcgagcg cggcttttcc gcgccagcgt   180
gaaagcagtg tggactggcc gtcaggtacc cgtactgtca ccgtgaccga tgaccatcct   240
tttgatcgcc agatagtggt gcttccgctg acgtttcgcg gaagtaagcg tactgtcagc   300
ggcaggacaa cgtattcgat gtgttatctg aaagtactga tgaacggtgc ggtgatttat   360
gatggcgcgg cgaacgaggc ggtacaggtg ttctcccgta ttgttgacat gccagcgggt   420
cggggaaacg tgatcctgac gttcacgctt acgtccacac ggcattcggc agatattccg   480
ccgtatacgt ttgccagcga tgtgcaggtt atggtgatta agaaacaggc gctgggcatc   540
agcgtggtct gagtgtgttt ttttttttgga attttttttt tttttcatcg   600
tcgtgagtag tgaaccgtaa gctgcgttct gtttcggatg tatgaaaaca tacatccgaa   660
acagaacgca gcttacggtt cactactcac gacgatgaaa aaaaaaattc caaaaaaaaa   720
attccaaaaa aaaaacacac tcagaccacg ctgatgccca gcgcctgttt cttaatcacc   780
ataacctgca catcgctggc aaacgtatac ggcggaatat ctgccgaatg ccgtgtggac   840
gtaagcgtga acgtcaggat cacgtttccc cgacccgctg gcatgtcaac aatacgggag   900
aacacctgta ccgcctcgtt cgccgcgcca tcataaatca ccgcaccgtt catcagtact   960
ttcagataac acatcgaata cgttgtcctg ccgctgacag tacgcttact tccgcgaaac  1020
gtcagcggaa gcaccactat ctggcgatca aaaggatggt catcggtcac ggtgacagta  1080
cgggtacctg acggccagtc cacactgctt tcacgctggc gcggaaaagc cgcgctcgcc  1140
gcctttacaa tgtccccgac gatttttttcc gccctcagcg taccgtttat cgtacagttt  1200
tcagctatcg tcacattact gagcgtcaaa aaaaaaattc caaaaaaaaa attccaaaaa  1260
aaaaaagcga ctaacaaaca caatctgatg gc                                1292

<210> SEQ ID NO 69
<211> LENGTH: 7240
<212> TYPE: DNA
```

<213> ORGANISM: Artificial Sequence
<220> FEATURE:
<223> OTHER INFORMATION: Synthetic Polynucleotide

<400> SEQUENCE: 69

```
gccatcagat tgtgtttgtt agtcgctgcc atcagattgt gtttgttagt cgcttttttt      60
ttttggaatt ttttttttgg aattttttttt ttgcgctaac aacctcctgc cgttttgccc    120
gtgcatatcg gtcacgaaca aatctgatta ctaaacacag tagcctggat tgttctatc     180
agtaatcgac cttattccta attaaataga gcaaatcccc ttattggggg taagacatga    240
agatgccaga aaacatgac ctgttggccg ccattctcgc ggcaaaggaa caaggcatcg      300
gggcaatcct tgcgtttgca atggcgtacc ttcgcggcag atataatggc ggtgcgttta    360
caaaaacagt aatcgacgca acgatgtgcg ccattatcgc ctagttcatt cgtgaccttc    420
tcgacttcgc cggactaagt agcaatctcg cttatataac gagcgtgttt atcggctaca    480
tcggtactga ctcgattggt tcgcttatca aacgcttcgc tgctaaaaaa gccggagtag    540
aagatggtag aaatcaataa tcaacgtaag gcgttcctcg atatgctggc gtggtcggag    600
ggaactgata acggacgtca gaaaaccaga atcatggtt atgacgtcat tgtaggcgga    660
gagctattta ctgattactc cgatcaccct cgcaaacttg tcacgctaaa cccaaaactc    720
aaatcaacag gcgccggacg ctaccagctt cttttccgtt ggtgggatgc ctaccgcaag    780
cagcttggcc tgaaagactt ctctccgaaa agtcaggacg ctgtggcatt gcagcagatt    840
aaggagcgtg gcgctttacc tatgattgat cgtggtgata ccgtcaggc aatcgaccgt    900
tgcagcaata tctgggcttc actgccgggc gctggttatg gtcagttcga gcataaggct    960
gacagcctga ttgcaaaatt caaagaagcg ggcggaacgg tcagagagat tgatgtatga   1020
gcagagtcac cgcgattatc tccgctctgg ttatctgcat catcgtctgc ctgtcatggg   1080
ctgttaatca ttaccgtgat aacgccatta cctacaaagc ccagcgcgac aaaaatgcca   1140
gagaactgaa gctggcgaac gcggcaatta ctgacatgca gatgcgtcag cgtgatgttg   1200
ctgcgctcga tgcaaaatac acgaaggagt tagctgatgc taaagctgaa atgatgctc    1260
tgcgtgatga tgttgccgct ggtcgtcgtc ggttgcacat caaagcagtc tgtcagtcag   1320
tgcgtgaagc caccaccgcc tccggcgtgg ataatgcagc ctcccccga ctggcagaca   1380
ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
aataaaaccg agcaatccat ttacgaatgt ttgctgggtt tctgttttaa caacattttc   1620
tgcgccgcca caattttgg ctgcatcgac agttttcttc tgcccaattc cagaaacgaa   1680
gaaatgatgg gtgatggttt cctttggtgc tactgctgcc ggtttgtttt gaacagtaaa   1740
cgtctgttga gcacatcctg taataagcag ggccagcgca gtagcgagta gcatttttt    1800
catggtgtta ttcccgatgc ttttttgaagt tcgcagaatc gtatgtgtag aaaattaaac   1860
aaaccctaaa caatgagttg aaatttcata ttgttaatat ttattaatgt atgtcaggtg   1920
cgatgaatcg tcattgtatt cccggattaa ctatgtccac agccctgacg gggaacttct   1980
ctgcgggagt gtccgggaat aattaaaacg atgcacacag ggtttagcgc gtacacgtat   2040
tgcattatgc caacgccccg gtgctgacac ggaagaaacc ggacgttatg atttagcgtg   2100
gaaagatttg tgtagtgttc tgaatgctct cagtaaatag taatgaatta tcaaaggtat   2160
agtaatatct tttatgttca tggatatttg taacccatcg gaaaactcct gctttagcaa   2220
```

```
gattttccct gtattgctga aatgtgattt ctcttgattt caacctatca taggacgttt    2280
ctataagatg cgtgtttctt gagaatttaa catttacaac cttttttaagt cctttttatta   2340 acacggtgtt atcgttttct aacacgatgt gaatattatc tgtggctaga tagtaaatat    2400
aatgtgagac gttgtgacgt tttagttcag aataaaacaa ttcacagtct aaatcttttc    2460
gcacttgatc gaatatttct ttaaaaatgg caacctgagc cattggtaaa accttccatg    2520
tgatacgagg gcgcgtagtt tgcattatcg ttttttatcgt ttcaatctgg tctgacctcc    2580
ttgtgttttg ttgatgattt atgtcaaata ttaggaatgt tttcacttaa tagtattggt    2640
tgcgtaacaa agtgcggtcc tgctggcatt ctggagggaa atacaaccga cagatgtatg   2700
taaggccaac gtgctcaaat cttcatacag aaagatttga agtaatattt taaccgctag    2760
atgaagagca agcgcatgga gcgacaaaat gaataaagaa caatctgctg atgatccctc    2820
cgtggatctg attcgtgtaa aaaatatgct taatagcacc atttctatga gttaccctga    2880
tgttgtaatt gcatgtatag aacataaggt gtctctggaa gcattcagag caattggagc    2940
agcgttggtg aagcacgata ataatatgaa ggattattcc ctggtggttg actgatcacc    3000
ataactgcta atcattcaaa ctatttagtc tgtgacagag ccaacacgca gtctgtcact    3060
gtcaggaaag tggtaaaaact gcaactcaat tactgcaatg ccctcgtaat taagtgaatt    3120
tacaatatcg tcctgttcgg agggaagaac gcgggatgtt cattcttcat cactttttaat    3180 tgatgtatat gctctctttt ctgacgttag tctccgacgg caggcttcaa tgacccaggc   3240
tgagaaattc ccggacccttt tttgctcaag agcgatgtta atttgttcaa tcatttggtt   3300
aggaaagcgg atgttgcggg ttgttgttct gcgggttctg ttcttcgttg acatgaggtt    3360
gccccgtatt cagtgtcgct gatttgtatt gtctgaagtt gttttttacgt taagttgatg    3420 cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagcacg ttctgtttat    3600
gtttcttgtt tgttagcctt ttggctaaca aacaagaaac ataaacagaa cgtgcttacg    3660
gttcactact cacgacgatg ttttttttttgg tacctttttt ttcaccggaa aggacccgta   3720
aagtgataat gattatcatc tacatatcac aacgtgcgtg gaggccatca aaccacgtca    3780
aataatcaat tatgacgcag gtatcgtatt aattgatctg catcaactta acgtaaaaac    3840
aacttcagac aatacaaatc agcgacactg aatacggggc aacctcatgt caacgaagaa    3900
cagaacccgc agaacaacaa cccgcaacat ccgctttcct aaccaaatga ttgaacaaat    3960
taacatcgct cttgagcaaa aagggtccgg gaatttctca gcctgggtca ttgaagcctg    4020
ccgtcggaga ctaacgtcag aaaagagagc atatacatca attaaaagtg atgaagaatg    4080
aacatcccgc gttcttccct ccgaacagga cgatattgta aattcactta attacgaggg    4140
cattgcagta attgagttgc agttttacca ctttcctgac agtgacagac tgcgtgttgg    4200
ctctgtcaca gactaaatag tttgaatgat tagcagttat ggtgatcagt caaccaccag    4260
ggaataatcc ttcatattat tatcgtgctt caccaacgct gcctcaattg ctctgaatgc    4320
ttccagagac accttatgtt ctatacatgc aattacaaca tcagggtaac tcatagaaat    4380
ggtgctatta agcatatttt ttacacgaat cagatccacg gagggatcat cagcagattg    4440
ttctttattc attttgtcgc tccatgcgct tgctcttcat ctagcggtta aaatattact    4500
tcaaatcttt ctgtatgaag atttgagcac gttggcctta catacatctg tcggttgtat    4560
```

-continued

```
ttccctccag aatgccagca ggaccgcact ttgttacgca accaatacta ttaagtgaaa    4620
acattcctaa tatttgacat aaatcatcaa caaaacacaa ggaggtcaga ccagattgaa    4680
acgataaaaa cgataatgca aactacgcgc cctcgtatca catggaaggt tttaccaatg    4740
gctcaggttg ccattttttaa agaaatattc gatcaagtgc gaaaagattt agactgtgaa    4800
ttgtttatt ctgaactaaa acgtcacaac gtctcacatt atatttacta tctagccaca    4860
gataatattc acatcgtgtt agaaaacgat aacaccgtgt taataaaagg acttaaaaag    4920
gttgtaaatg ttaaattctc aagaaacacg catcttatag aaacgtccta tgataggttg    4980
aaatcaagag aaatcacatt tcagcaatac agggaaaatc ttgctaaagc aggagttttc    5040
cgatgggtta caaatatcca tgaacataaa agatattact ataccttga taattcatta    5100
ctatttactg agagcattca gaacactaca caaatctttc cacgctaaat cataacgtcc    5160
ggtttcttcc gtgtcagcac cggggcgttg gcataatgca atacgtgtac gcgctaaacc    5220
ctgtgtgcat cgtttttaatt attcccggac actcccgcag agaagttccc cgtcagggct    5280
gtggacatag ttaatccggg aatacaatga cgattcatcg cacctgacat acattaataa    5340
atattaacaa tatgaaattt caactcattg tttagggttt gtttaatttt ctacacatac    5400
gattctgcga acttcaaaaa gcatcgggaa taacaccatg aaaaaaatgc tactcgctac    5460
tgcgctggcc ctgcttatta caggatgtgc tcaacagacg tttactgttc aaaacaaacc    5520
ggcagcagta gcaccaaagg aaaccatcac ccatcatttc ttcgtttctg gaattgggca    5580
gaagaaaact gtcgatgcag ccaaaatttg tggcggcgca gaaaatgttg ttaaaacaga    5640
aacccagcaa acattcgtaa atggattgct cggttttatt actttaggca tttatactcc    5700
gctggaagcg cgtgtgtatt gctcacaata attgcatgag ttgcccatcg atatgggcaa    5760
ctctatctgc actgctcatt aatatacttc tgggttcctt ccagttgttt ttgcatagtg    5820
atcagcctct ctctgagggt gaaataatcc cgttcagcgg tgtctgccag tcgggggag    5880
gctgcattat ccacgccgga ggcggtggtg gcttcacgca ctgactgaca gactgctttg    5940
atgtgcaacc gacgacgacc agcggcaaca tcatcacgca gagcatcatt ttcagcttta    6000
gcatcagcta actccttcgt gtattttgca tcgagcgcag caacatcacg ctgacgcatc    6060
tgcatgtcag taattgccgc gttcgccagc ttcagttctc tggcattttt gtcgcgctgg    6120
gctttgtagg taatggcgtt atcacggtaa tgattaacag cccatgacag gcagacgatg    6180
atgcagataa ccagagcgga gataatcgcg gtgactctgc tcatacatca atctctctga    6240
ccgttccgcc cgcttctttg aattttgcaa tcaggctgtc agcctttatgc tcgaactgac    6300
cataaccagc gcccggcagt gaagcccaga tattgctgca acggtcgatt gcctgacgga    6360
tatcaccacg atcaatcata ggtaaagcgc cacgctcctt aatctgctgc aatgccacag    6420
cgtcctgact tttcggagag aagtctttca ggccaagctg cttgcggtag gcatcccacc    6480
aacgggaaag aagctggtag cgtccggcgc ctgttgattt gagttttggg tttagcgtga    6540
caagtttgcg agggtgatcg gagtaatcag taaatagctc tccgcctaca atgacgtcat    6600
aaccatgatt tctggttttc tgacgtccgt tatcagttcc ctccgaccac gccagcatat    6660
cgaggaacgc cttacgttga ttattgattt ctaccatctt ctactccggc ttttttagca    6720
gcgaagcgtt tgataagcga accaatcgag tcagtaccga tgtagccgat aaacacgctc    6780
gttatataag cgagattgct acttagtccg gcgaagtcga aaggtcacg aatgaactag    6840
gcgataatgg cgcacatcgt tgcgtcgatt actgttttg taaacgcacc gccattatat    6900
ctgccgcgaa ggtacgccat tgcaaacgca aggattgccc cgatgccttg ttcctttgcc    6960
```

```
gcgagaatgg cggccaacag gtcatgtttt tctggcatct tcatgtctta cccccaataa      7020 gggatttgc tctatttaat taggaataag gtcgattact gatagaacaa atccaggcta       7080
ctgtgtttag taatcagatt tgttcgtgac cgatatgcac gggcaaaacg gcaggaggtt      7140
gttagcgcaa aaaaaaatt ccaaaaaaaa aattccaaaa aaaaaagcg actaacaaac        7200 acaatctgat ggcagcgact aacaaacaca atctgatggc                           7240
```

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 70

```
tttttttttt tttttttttt                                                   20
```

<210> SEQ ID NO 71
<211> LENGTH: 7240
<212> TYPE: DNA
<213> ORGANISM: Artificial Sequence
<220> FEATURE:
<223> OTHER INFORMATION: Synthetic Polynucleotide

<400> SEQUENCE: 71

```
gccatcagat tgtgtttgtt agtcgctgcc atcagattgt gtttgttagt cgcttttttt        60
ttttggaatt ttttttttgg aattttttttt ttgcgctaac aacctcctgc cgttttgccc      120
gtgcatatcg gtcacgaaca atctgattga ctaaacacag tagcctggat tgttctatc       180 agtaatcgac cttattccta attaaataga gcaaatcccc ttattggggg taagacatga      240
agatgccaga aaaacatgac ctgttggccg ccattctcgc ggcaaaggaa caaggcatcg      300
gggcaatcct tgcgtttgca atggcgtacc ttcgcggcag atataatggc ggtgcgttta      360
caaaaacagt aatcgacgca acgatgtgcg ccattatcgc ctagttcatt cgtgaccttc      420
tcgacttcgc cggactaagt agcaatctcg cttatataac gagcgtgttt atcggctaca      480
tcggtactga ctcgattggt tcgcttatca aacgcttcgc tgctaaaaaa gccggagtag      540
aagatggtag aaatcaataa tcaacgtaag gcgttcctcg atatgctggc gtggtcggag      600
ggaactgata acggacgtca gaaaccaga atcatggtt atgacgtcat tgtaggcgga        660
gagctattta ctgattactc cgatcaccct cgcaaacttg tcacgctaaa cccaaaactc      720
aaatcaacag gcgccggacg ctaccagctt cttttcccgtt ggtgggatgc ctaccgcaag     780
cagcttggcc tgaaagactt ctctccgaaa agtcaggacg ctgtggcatt gcagcagatt      840
aaggagcgtg gcgctttacc tatgattgat cgtggtgata tccgtcaggc aatcgaccgt      900
tgcagcaata tctgggcttc actgccgggc gctggttatg gtcagttcga gcataaggct      960
gacagcctga ttgcaaaatt caagaagcg ggcggaacgg tcagagagat tgatgtgatga    1020 gcagagtcac cgcgattatc tccgctctgg ttatctgcat catcgtctgc ctgtcatggg    1080
ctgttaatca ttaccgtgat aacgccatta cctacaaagc ccagcgcgac aaaaatgcca    1140
gagaactgaa gctggcgaac gcggcaatta ctgacatgca gatgcgtcag cgtgatgttg    1200
ctgcgctcga tgcaaaatac acgaaggagt tagctgatgc taaagctgaa aatgatgctc    1260
tgcgtgatga tgttgccgct ggtcgtcgtc ggttgcacat caaagcagtc tgtcagtcag    1320
tgcgtgaagc caccaccgcc tccggcgtgg ataatgcagc ctcccccga ctggcagaca    1380
```

```
ccgctgaacg ggattatttc accctcagag agaggctgat cactatgcaa aaacaactgg    1440
aaggaaccca gaagtatatt aatgagcagt gcagatagag ttgcccatat cgatgggcaa    1500
ctcatgcaat tattgtgagc aatacacacg cgcttccagc ggagtataaa tgcctaaagt    1560
aataaaaccg agcaatccat ttacgaatgt ttgctgggtt tctgttttaa caacattttc    1620
tgcgccgcca caaattttgg ctgcatcgac agttttcttc tgcccaattc agaaacgaa     1680 gaaatgatgg gtgatggttt cctttggtgc tactgctgcc ggtttgtttt gaacagtaaa    1740
cgtctgttga gcacatcctg taataagcag ggccagcgca gtagcgagta gcatttttt     1800 catggtgtta ttcccgatgc ttttgaagt tcgcagaatc gtatgtgtag aaaattaaac     1860
aaaccctaaa caatgagttg aaatttcata ttgttaatat ttattaatgt atgtcaggtg    1920
cgatgaatcg tcattgtatt cccggattaa ctatgtccac agccctgacg gggaacttct    1980
ctgcgggagt gtccgggaat aattaaaacg atgcacacag ggtttagcgc gtacacgtat    2040
tgcattatgc caacgccccg gtgctgacac ggaagaaacc ggacgttatg atttagcgtg    2100
gaaagatttg tgtagtgttc tgaatgctct cagtaaaatag taatgaatta tcaaaggtat    2160
agtaatatct tttatgttca tggatatttg taacccatcg gaaaactcct gctttagcaa    2220
gattttccct gtattgctga aatgtgattt ctcttgattt caacctatca taggacgttt    2280
ctataagatg cgtgtttctt gagaatttaa catttacaac ctttttaagt cctttttatta   2340 acacggtgtt atcgttttct aacacgatgt gaatattatc tgtggctaga tagtaaatat    2400
aatgtgagac gttgtgacgt tttagttcag aataaaacaa ttcacagtct aaatcttttc    2460
gcacttgatc gaatatttct ttaaaaatgg caacctgagc cattggtaaa accttccatg    2520
tgatacgagg gcgcgtagtt tgcattatcg ttttttatcgt ttcaatctgg tctgacctcc    2580
ttgtgttttg ttgatgattt atgtcaaata ttaggaatgt tttcacttaa tagtattggt    2640
tgcgtaacaa agtgcggtcc tgctggcatt ctggagggaa atacaaccga cagatgtatg    2700
taaggccaac gtgctcaaat cttcatacag aaagatttga agtaatattt taaccgctag    2760
atgaagagca agcgcatgga gcgacaaaat gaataaagaa caatctgctg atgatccctc    2820
cgtggatctg attcgtgtaa aaaatatgct taatagcacc attctatga gttaccctga    2880 tgttgtaatt gcatgtatag aacataaggt gtctctggaa gcattcagag caattgaggc    2940
agcgttggtg aagcacgata ataatatgaa ggattattcc ctggtggttg actgatcacc    3000
ataactgcta atcattcaaa ctatttagtc tgtgacagag ccaacacgca gtctgtcact    3060
gtcaggaaag tggtaaaact gcaactcaat tactgcaatg ccctcgtaat taagtgaatt    3120
tacaatatcg tcctgttcgg agggaagaac gcgggatgtt cattcttcat cacttttaat    3180
tgatgtatat gctctctttt ctgacgttag tctccgacgg caggcttcaa tgacccaggc    3240
tgagaaattc ccggacccctt tttgctcaag agcgatgtta atttgttcaa tcatttggtt    3300
aggaaagcgg atgttgcggg ttgttgttct gcgggttctg ttcttcgttg acatgaggtt    3360
gccccgtatt cagtgtcgct gatttgtatt gtctgaagtt ttttttacgt taagttgatg    3420
cagatcaatt aatacgatac ctgcgtcata attgattatt tgacgtggtt tgatggcctc    3480
cacgcacgtt gtgatatgta gatgataatc attatcactt tacgggtcct ttccggtgaa    3540 aaaaaggta ccaaaaaaaa catcgtcgtg agtagtgaac cgtaagcacg ttctgtttat    3600
gtttcttgtt tgttagcctt ttggctaaca aacaagaaac ataaacagaa cgtgcttacg    3660
gttcactact cacgacgatg ttttttttgg tacctttttt ttcaccggaa aggaccgta    3720 aagtgataat gattatcatc tacatatcac aacgtgcgtg gaggccatca aaccacgtca    3780
```

```
aataatcaat tatgacgcag gtatcgtatt aattgatctg catcaactta acgtaaaaac   3840
aacttcagac aatacaaatc agcgacactg aatacggggc aacctcatgt caacgaagaa   3900
cagaacccgc agaacaacaa cccgcaacat ccgctttcct aaccaaatga ttgaacaaat   3960
taacatcgct cttgagcaaa aagggtccgg gaatttctca gcctgggtca ttgaagcctg   4020
ccgtcggaga ctaacgtcag aaaagagagc atatacatca attaaaagtg atgaagaatg   4080
aacatcccgc gttcttccct ccgaacagga cgatattgta aattcactta attacgaggg   4140
cattgcagta attgagttgc agttttacca cttcctgac agtgacagac tgcgtgttgg    4200
ctctgtcaca gactaaatag tttgaatgat tagcagttat ggtgatcagt caaccaccag   4260
ggaataatcc ttcatattat tatcgtgctt caccaacgct gcctcaattg ctctgaatgc   4320
ttccagagac accttatgtt ctatacatgc aattacaaca tcagggtaac tcatagaaat   4380
ggtgctatta agcatatttt ttacacgaat cagatccacg gagggatcat cagcagattg   4440
ttctttattc atttttgtcgc tccatgcgct tgctcttcat ctagcggtta aaatattact   4500
tcaaatcttt ctgtatgaag atttgagcac gttggcctta catacatctg tcggttgtat   4560
ttccctccag aatgccagca ggaccgcact ttgttacgca accaatacta ttaagtgaaa   4620
acattcctaa tatttgacat aaatcatcaa caaaacacaa ggaggtcaga ccagattgaa   4680
acgataaaaa cgataatgca aactacgcgc cctcgtatca catggaaggt tttaccaatg   4740
gctcaggttg ccattttaa agaaatattc gatcaagtgc gaaaagattt agactgtgaa    4800
ttgttttatt ctgaactaaa acgtcacaac gtctcacatt atatttacta tctagccaca   4860
gataatattc acatcgtgtt agaaaacgat aacaccgtgt aataaaagg acttaaaaag    4920 gttgtaaatg ttaaattctc aagaaacacg catcttatag aaacgtccta tgataggttg   4980
aaatcaagag aaatcacatt tcagcaatac agggaaaatc ttgctaaagc aggagttttc   5040
cgatgggtta caaatatcca tgaacataaa agatattact ataccttga taattcatta    5100 ctatttactg agagcattca gaacactaca caaatctttc cacgctaaat cataacgtcc   5160
ggtttcttcc gtgtcagcac cggggcgttg gcataatgca atacgtgtac gcgctaaacc   5220
ctgtgtgcat cgttttaatt attcccggac actcccgcag agaagttccc cgtcagggct   5280
gtggacatag ttaatccggg aatacaatga cgattcatcg cacctgacat acattaataa   5340
atattaacaa tatgaaattt caactcattg tttagggttt gtttaatttt ctacacatac   5400
gattctgcga acttcaaaaa gcatcgggaa taacaccatg aaaaaaatgc tactcgctac   5460
tgcgctggcc ctgcttatta caggatgtgc tcaacagacg tttactgttc aaaacaaacc   5520
ggcagcagta gcaccaaagg aaaccatcac ccatcatttc ttcgtttctg gaattgggca   5580
gaagaaaact gtcgatgcag ccaaaatttg tggcggcgca gaaaatgttg ttaaaacaga   5640
aacccagcaa acattcgtaa atggattgct cggttttatt actttaggca tttatactcc   5700
gctggaagcg cgtgtgtatt gctcacaata attgcatgag ttgcccatcg atatgggcaa   5760
ctctatctgc actgctcatt aatatacttc tgggttcctt ccagttgttt ttgcatagtg   5820
atcagcctct ctctgagggt gaaataatcc cgttcagcgg tgtctgccag tcgggggag    5880 gctgcattat ccacgccgga ggcggtggtg gcttcacgca ctgactgaca gactgctttg   5940
atgtgcaacc gacgacgacc agcggcaaca tcatcacgca gagcatcatt ttcagcttta   6000
gcatcagcta actccttcgt gtattttgca tcgagcgcag caacatcacg ctgacgcatc   6060
tgcatgtcag taattgccgc gttcgccagc ttcagttctc tggcattttt gtcgcgctgg   6120
```

```
gctttgtagg taatggcgtt atcacggtaa tgattaacag cccatgacag gcagacgatg    6180
atgcagataa ccagagcgga gataatcgcg gtgactctgc tcatacatca atctctctga    6240
ccgttccgcc cgcttctttg aattttgcaa tcaggctgtc agccttatgc tcgaactgac    6300
cataaccagc gcccggcagt gaagcccaga tattgctgca acggtcgatt gcctgacgga    6360
tatcaccacg atcaatcata ggtaaagcgc cacgctcctt aatctgctgc aatgccacag    6420
cgtcctgact tttcggagag aagtctttca ggccaagctg cttgcggtag gcatcccacc    6480
aacgggaaag aagctggtag cgtccggcgc ctgttgattt gagttttggg tttagcgtga    6540
caagtttgcg agggtgatcg gagtaatcag taaatagctc tccgcctaca atgacgtcat    6600
aaccatgatt tctggttttc tgacgtccgt tatcagttcc ctccgaccac gccagcatat    6660
cgaggaacgc cttacgttga ttattgattt ctaccatctt ctactccggc ttttttagca    6720
gcgaagcgtt tgataagcga accaatcgag tcagtaccga tgtagccgat aaacacgctc    6780
gttatataag cgagattgct acttagtccg gcgaagtcga gaaggtcacg aatgaactag    6840
gcgataatgg cgcacatcgt tgcgtcgatt actgtttttg taaacgcacc gccattatat    6900
ctgccgcgaa ggtacgccat tgcaaacgca aggattgccc cgatgccttg ttcctttgcc    6960
gcgagaatgg cggccaacag gtcatgtttt tctggcatct tcatgtctta cccccaataa    7020
ggggatttgc tctatttaat taggaataag gtcgattact gatagaacaa atccaggcta    7080
ctgtgtttag taatcagatt tgttcgtgac cgatatgcac gggcaaaacg gcaggaggtt    7140
gttagcgcaa aaaaaaaatt ccaaaaaaaa aattccaaaa aaaaaaagcg actaacaaac    7200
acaatctgat ggcagcgact aacaaacaca atctgatggc                         7240
```

<210> SEQ ID NO 72
<211> LENGTH: 3653
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3648)..(3648)
<223> OTHER INFORMATION: n is uridine

<400> SEQUENCE: 72

```
gccatcagat tgtgtttgtt agtcgctgcc atcagattgt gtttgttagt cgcttttttt      60
ttttggaatt ttttttttgg aattttttttt ttgcgctaac aacctcctgc cgttttgccc    120
gtgcatatcg gtcacgaaca aatctgatta ctaaacacag tagcctggat tgttctatc     180 agtaatcgac cttattccta attaaataga gcaaatcccc ttattggggg taagacatga    240
agatgccaga aaaacatgac ctgttggccg ccattctcgc ggcaaaggaa caaggcatcg    300
gggcaatcct tgcgtttgca atggcgtacc ttcgcggcag atataatggc ggtgcgttta    360
caaaaacagt aatcgacgca acgatgtgcg ccattatcgc ctagttcatt cgtgaccttc    420
tcgacttcgc cggactaagt agcaatctcg cttatataac gagcgtgttt atcggctaca    480
tcggtactga ctcgattggt tcgcttatca aacgcttcgc tgctaaaaaa gccggagtag    540
aagatggtag aaatcaataa tcaacgtaag gcgttcctcg atatgctggc gtggtcggag    600
ggaactgata acggacgtca gaaaaccaga atcatggtt atgacgtcat tgtaggcgga    660 gagctatttta ctgattactc cgatcaccct cgcaaacttg tcacgctaaa cccaaaactc    720
aaatcaacag gcgccggacg ctaccagctt cttttcccgtt ggtgggatgc ctaccgcaag    780
cagcttggcc tgaaagactt ctctccgaaa agtcaggacg ctgtggcatt gcagcagatt    840
```

```
aaggagcgtg gcgctttacc tatgattgat cgtggtgata tccgtcaggc aatcgaccgt    900
tgcagcaata tctgggcttc actgccgggc gctggttatg gtcagttcga gcataaggct    960
gacagcctga ttgcaaaatt caaagaagcg ggcggaacgg tcagagagat tgatgtatga   1020
gcagagtcac cgcgattatc tccgctctgg ttatctgcat catcgtctgc ctgtcatggg   1080
ctgttaatca ttaccgtgat aacgccatta cctacaaagc ccagcgcgac aaaaatgcca   1140
gagaactgaa gctggcgaac gcggcaatta ctgacatgca gatgcgtcag cgtgatgttg   1200
ctgcgctcga tgcaaaatac acgaaggagt tagctgatgc taaagctgaa atgatgctc    1260 tgcgtgatga tgttgccgct ggtcgtcgtc ggttgcacat caaagcagtc tgtcagtcag   1320
tgcgtgaagc caccaccgcc tccggcgtgg ataatgcagc ctcccccga ctggcagaca    1380 ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
aataaaaccg agcaatccat ttacgaatgt ttgctgggtt tctgttttaa caacattttc   1620
tgcgccgcca caaattttgg ctgcatcgac agttttcttc tgcccaattc cagaaacgaa   1680
gaaatgatgg gtgatggttt cctttggtgc tactgctgcc ggtttgtttt gaacagtaaa   1740
cgtctgttga gcacatcctg taataagcag ggccagcgca gtagcgagta gcattttttt   1800
catggtgtta ttcccgatgc ttttgaagt tcgcagaatc gtatgtgtag aaaattaaac    1860
aaaccctaaa caatgagttg aaatttcata ttgttaatat ttattaatgt atgtcaggtg   1920
cgatgaatcg tcattgtatt cccggattaa ctatgtccac agccctgacg gggaacttct   1980
ctgcgggagt gtccgggaat aattaaaacg atgcacacag ggtttagcgc gtacacgtat   2040
tgcattatgc caacgccccg gtgctgacac ggaagaaacc ggacgttatg atttagcgtg   2100
gaaagatttg tgtagtgttc tgaatgctct cagtaaatag taatgaatta tcaaaggtat   2160
agtaatatct tttatgttca tggatatttg taacccatcg gaaaactcct gctttagcaa   2220
gattttccct gtattgctga atgtgatttt ctcttgattt caacctatca taggacgttt   2280
ctataagatg cgtgtttctt gagaatttaa cattacaac cttttaagt cctttatta     2340 acacggtgtt atcgttttct aacacgatgt gaatattatc tgtggctaga tagtaaatat   2400
aatgtgagac gttgtgacgt tttagttcag aataaaacaa ttcacagtct aaatcttttc   2460
gcacttgatc gaatatttct ttaaaaatgg caacctgagc cattggtaaa accttccatg   2520
tgatacgagg gcgcgtagtt tgcattatcg tttttatcgt ttcaatctgg tctgacctcc   2580
ttgtgttttg ttgatgattt atgtcaaata ttaggaatgt tttcacttaa tagtattggt   2640
tgcgtaacaa agtgcggtcc tgctggcatt ctggagggaa atacaaccga cagatgtatg   2700
taaggccaac gtgctcaaat cttcatacag aaagatttga agtaatattt taaccgctag   2760
atgaagagca agcgcatgga gcgacaaaat gaataaagaa caatctgctg atgatccctc   2820
cgtggatctg attcgtgtaa aaaatatgct taatagcacc atttctatga gttaccctga   2880
tgttgtaatt gcatgtatag aacataaggt gtctctggaa gcattcagag caattgaggc   2940
agcgttggtg aagcacgata ataatatgaa ggattattcc ctggtggttg actgatcacc   3000
ataactgcta atcattcaaa ctatttagtc tgtgacagag ccaacacgca gtctgtcact   3060
gtcaggaaag tggtaaaact gcaactcaat tactgcaatg ccctcgtaat taagtgaatt   3120
tacaatatcg tcctgttcgg agggaagaac gcgggatgtt cattcttcat cacttttaat   3180
```

```
tgatgtatat gctctctttt ctgacgttag tctccgacgg caggcttcaa tgacccaggc    3240
tgagaaattc ccggacccct tttgctcaag agcgatgtta atttgttcaa tcatttggtt    3300
aggaaagcgg atgttgcggg ttgttgttct gcgggttctg ttcttcgttg acatgaggtt    3360
gccccgtatt cagtgtcgct gatttgtatt gtctgaagtt gtttttacgt taagttgatg    3420
cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagcagc gacggctgag    3600
aagttccact caagcctctg acactgattg acacggttta gtagaacntt ttt          3653
```

<210> SEQ ID NO 73
<211> LENGTH: 3643
<212> TYPE: DNA
<213> ORGANISM: Artificial Sequence
<220> FEATURE:
<223> OTHER INFORMATION: Synthetic Polynucleotide

<400> SEQUENCE: 73

```
cttctcaatg tgtacgtgtc ctctagaggc ttgagtggaa cttctcagcc gtcgctgctt      60
acggttcact actcacgacg atgttttttt tggtaccttt tttttcaccg gaaaggaccc     120
gtaaagtgat aatgattatc atctacatat cacaacgtgc gtggaggcca tcaaaccacg     180
tcaaataatc aattatgacg caggtatcgt attaattgat ctgcatcaac ttaacgtaaa     240
aacaacttca gacaatacaa atcagcgaca ctgaatacgg ggcaacctca tgtcaacgaa     300
gaacagaacc cgcagaacaa caacccgcaa catccgcttt cctaaccaaa tgattgaaca     360
aattaacatc gctcttgagc aaaaagggtc cgggaatttc tcagcctggg tcattgaagc     420
ctgccgtcgg agactaacgt cagaaaagag agcatataca tcaattaaaa gtgatgaaga     480
atgaacatcc cgcgttcttc cctccgaaca ggacgatatt gtaaattcac ttaattacga     540
gggcattgca gtaattgagt tgcagtttta ccactttcct gacagtgaca gactgcgtgt     600
tggctctgtc acagactaaa tagtttgaat gattagcagt tatggtgatc agtcaaccac     660
cagggaataa tccttcatat tattatcgtg cttcaccaac gctgcctcaa ttgctctgaa     720
tgcttccaga gacaccttat gttctataca tgcaattaca acatcagggt aactcataga     780
aatggtgcta ttaagcatat ttttacacg aatcagatcc acggagggat catcagcaga     840
ttgttcttta ttcattttgt cgctccatgc gcttgctctt catctagcgg ttaaaatatt     900
acttcaaatc tttctgtatg aagatttgag cacgttggcc ttacatacat ctgtcggttg     960
tatttccctc cagaatgcca gcaggaccgc actttgttac gcaaccaata ctattaagtg    1020
aaaacattcc taatatttga cataaatcat caacaaaaca caaggaggtc agaccagatt    1080
gaaacgataa aaacgataat gcaaactacg cgccctcgta tcacatggaa ggttttacca    1140
atggctcagg ttgccatttt taagaaaata ttcgatcaag tgcgaaaaga tttagactgt    1200
gaattgtttt attctgaact aaaacgtcac aacgtctcac attatattta ctatctagcc    1260
acagataata ttcacatcgt gttagaaaac gataacaccg tgttaataaa aggacttaaa    1320
aaggttgtaa atgttaaatt ctcaagaaac acgcatctta tagaaacgtc ctatgatagg    1380
ttgaaatcaa gagaaatcac atttcagcaa tacagggaaa atcttgctaa agcaggagtt    1440
ttccgatggg ttacaaatat ccatgaacat aaaagatatt actataacct tgataattca    1500
ttactattta ctgagagcat tcagaacact acacaaatct ttccacgcta aatcataacg    1560 tccggttttct tccgtgtcag caccggggcg ttggcataat gcaatacgtg tacgcgctaa    1620
```

```
accctgtgtg catcgtttta attattcccg cagactcccg cagagaagtt ccccgtcagg    1680
gctgtggaca tagttaatcc gggaatacaa tgacgattca tcgcacctga catacattaa    1740
taaatattaa caatatgaaa tttcaactca ttgtttaggg tttgtttaat tttctacaca    1800
tacgattctg cgaacttcaa aaagcatcgg gaataacacc atgaaaaaaa tgctactcgc    1860
tactgcgctg gccctgctta ttacaggatg tgctcaacag acgtttactg ttcaaaacaa    1920
accggcagca gtagcaccaa aggaaaccat cacccatcat ttcttcgttt ctggaattgg    1980
gcagaagaaa actgtcgatg cagccaaaat tgtggcggc gcagaaaatg ttgttaaaac     2040
agaaacccag caaacattcg taaatggatt gctcggtttt attactttag gcatttatac    2100
tccgctggaa gcgcgtgtgt attgctcaca ataattgcat gagttgccca tcgatatggg    2160
caactctatc tgcactgctc attaatatac ttctgggttc cttccagttg tttttgcata    2220
gtgatcagcc tctctctgag ggtgaaataa tcccgttcag cggtgtctgc cagtcggggg    2280
gaggctgcat tatccacgcc ggaggcggtg gtggcttcac gcactgactg acagactgct    2340
tgatgtgca accgacgacg accagcggca acatcatcac gcagagcatc attttcagct    2400
ttagcatcag ctaactcctt cgtgtatttt gcatcgagcg cagcaacatc acgctgacgc    2460
atctgcatgt cagtaattgc cgcgttcgcc agcttcagtt ctctggcatt tttgtcgcgc    2520
tgggctttgt aggtaatggc gttatcacgg taatgattaa cagcccatga caggcagacg    2580
atgatgcaga taaccagagc ggagataatc gcggtgactc tgctcataca tcaatctctc    2640
tgaccgttcc gcccgcttct ttgaattttg caatcaggct gtcagcctta tgctcgaact    2700
gaccataacc agcgcccggc agtgaagccc agatattgct gcaacggtcg attgcctgac    2760
ggatatcacc acgatcaatc ataggtaaag cgccacgctc cttaatctgc tgcaatgcca    2820
cagcgtcctg acttttcgga gagaagtctt tcaggccaag ctgcttgcgg taggcatccc    2880
accaacggga aagaagctgg tagcgtccgg cgcctgttga tttgagtttt gggtttagcg    2940
tgacaagttt gcgagggtga tcggagtaat cagtaaatag ctctccgcct acaatgacgt    3000
cataaccatg atttctggtt ttctgacgtc cgttatcagt tccctccgac cacgccagca    3060
tatcgaggaa cgccttacgt tgattattga tttctaccat cttctactcc ggcttttta    3120
gcagcgaagc gtttgataag cgaaccaatc gagtcagtac cgatgtagcc gataaacacg    3180
ctcgttatat aagcgagatt gctacttagt ccggcgaagt cgagaaggtc acgaatgaac    3240
taggcgataa tggcgcacat cgttgcgtcg attactgttt tgtaaacgc accgccatta    3300
tatctgccgc gaaggtacgc cattgcaaac gcaaggattg ccccgatgcc ttgttccttt    3360
gccgcgagaa tggcggccaa caggtcatgt ttttctggca tcttcatgtc ttaccccaa     3420
taagggatt tgctctattt aattaggaat aaggtcgatt actgatagaa caaatccagg     3480
ctactgtgtt tagtaatcag atttgttcgt gaccgatatg cacgggcaaa acggcaggag    3540
gttgttagcg caaaaaaaaa attccaaaaa aaaaattcca aaaaaaaaaa gcgactaaca    3600
aacacaatct gatggcagcg actaacaaac acaatctgat ggc                      3643
```

<210> SEQ ID NO 74
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 74

```
gcaatatcag caccaacaga acaaccttt gaggcgagcg gtcaa          45
```

```
<210> SEQ ID NO 75
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 75
ttgaccgctc gcctc                                          15
```

```
<210> SEQ ID NO 76
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 76
tttttttttt                                                10
```

```
<210> SEQ ID NO 77
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 77
ggttgtttct gttggtgctg atattgcact gagtgaccaa tcagctacgt ttttttttt    59
```

```
<210> SEQ ID NO 78
<211> LENGTH: 3636
<212> TYPE: DNA
<213> ORGANISM: Artificial Sequence
<220> FEATURE:
<223> OTHER INFORMATION: Synthetic Polynucleotide

<400> SEQUENCE: 78
ggttgtttct gttggtgctg atattgctgc catcagattg tgtttgttag tcgcttttt    60
tttttggaat ttttttttg gaatttttt tttgcgctaa caacctcctg ccgttttgcc   120
cgtgcatatc ggtcacgaac aaatctgatt actaaacaca gtagcctgga tttgttctat   180
cagtaatcga ccttattcct aattaaatag agcaaatccc cttattgggg gtaagacatg   240
aagatgccag aaaacatga cctgttggcc gccattctcg cggcaaagga acaaggcatc   300
ggggcaatcc ttgcgtttgc aatggcgtac cttcgcggca gatataatgg cggtgcgttt   360
acaaaaacag taatcgacgc aacgatgtgc gccattatcg cctagttcat tcgtgacctt   420
ctcgacttcg ccggactaag tagcaatctc gcttatataa cgagcgtgtt tatcggctac   480
atcggtactg actcgattgg ttcgcttatc aaacgcttcg ctgctaaaaa agccggagta   540
gaagatggta gaaatcaata atcaacgtaa ggcgttcctc gatatgctgg cgtggtcgga   600
gggaactgat aacggacgtc agaaaaccag aaatcatggt tatgacgtca ttgtaggcgg   660
agagctattt actgattact ccgatcaccc tcgcaaactt gtcacgctaa acccaaaact   720
caaatcaaca ggcgccggac gctaccagct tctttcccgt tggtgggatg cctaccgcaa   780
gcagcttggc ctgaaagact tctctccgaa aagtcaggac gctgtggcat tgcagcagat   840
taaggagcgt ggcgctttac ctatgattga tcgtggtgat atccgtcagg caatcgaccg   900
ttgcagcaat atctgggctt cactgccggg cgctggttat ggtcagttcg agcataaggc   960
```

```
tgacagcctg attgcaaaat tcaaagaagc gggcggaacg gtcagagaga ttgatgtatg    1020
agcagagtca ccgcgattat ctccgctctg gttatctgca tcatcgtctg cctgtcatgg    1080
gctgttaatc attaccgtga taacgccatt acctacaaag cccagcgcga caaaaatgcc    1140
agagaactga agctggcgaa cgcggcaatt actgacatgc agatgcgtca gcgtgatgtt    1200
gctgcgctcg atgcaaaata cacgaaggag ttagctgatg ctaaagctga aaatgatgct    1260
ctgcgtgatg atgttgccgc tggtcgtcgt cggttgcaca tcaaagcagt ctgtcagtca    1320
gtgcgtgaag ccaccaccgc ctccggcgtg gataatgcag cctcccccg actggcagac     1380 accgctgaac gggattattt caccctcaga gagaggctga tcactatgca aaacaactg     1440 gaaggaaccc agaagtatat taatgagcag tgcagataga gttgcccata tcgatgggca    1500
actcatgcaa ttattgtgag caatacacac gcgcttccag cggagtataa atgcctaaag    1560
taataaaacc gagcaatcca tttacgaatg tttgctgggt ttctgtttta caacattttt    1620
ctgcgccgcc acaaattttg gctgcatcga cagttttctt ctgcccaatt ccagaaacga    1680
agaaatgatg ggtgatggtt tcctttggtg ctactgctgc cggtttgttt tgaacagtaa    1740
acgtctgttg agcacatcct gtaataagca gggccagcgc agtagcgagt agcattttt    1800 tcatggtgtt attcccgatg cttttgaag ttcgcagaat cgtatgtgta gaaaattaaa     1860
caaaccctaa acaatgagtt gaaatttcat attgttaata tttattaatg tatgtcaggt    1920
gcgatgaatc gtcattgtat tcccggatta actatgtcca cagccctgac ggggaacttc    1980
tctgcgggag tgtccgggaa taattaaaac gatgcacaca gggtttagcg cgtacacgta    2040
ttgcattatg ccaacgcccc ggtgctgaca cggaagaaac cggacgttat gatttagcgt    2100
ggaaagattt gtgtagtgtt ctgaatgctc tcagtaaata gtaatgaatt atcaaaggta    2160
tagtaatatc ttttatgttc atggatattt gtaacccatc ggaaaactcc tgctttagca    2220
agattttccc tgtattgctg aaatgtgatt tctcttgatt tcaacctatc ataggacgtt    2280
tctataagat gcgtgtttct tgagaattta acatttacaa ccttttttaag tccttttatt    2340 aacacggtgt tatcgttttc taacacgatg tgaatattat ctgtggctag atagtaaata    2400
taatgtgaga cgttgtgacg ttttagttca gaataaaaca attcacagtc taaatctttt    2460
cgcacttgat cgaatatttc tttaaaaatg gcaacctgag ccattggtaa aaccttccat    2520
gtgatacgag ggcgcgtagt ttgcattatc gtttttatcg tttcaatctg gtctgacctc    2580
cttgtgtttt gttgatgatt tatgtcaaat attaggaatg ttttcactta atagtattgg    2640
ttgcgtaaca aagtgcggtc ctgctggcat tctggaggga aatacaaccg acagatgtat    2700
gtaaggccaa cgtgctcaaa tcttcataca gaaagatttg aagtaatatt ttaaccgcta    2760
gatgaagagc aagcgcatgg agcgacaaaa tgaataaaga acaatctgct gatgatccct    2820
ccgtggatct gattcgtgta aaaaatatgc ttaatagcac catttctatg agttaccctg    2880
atgttgtaat tgcatgtata gaacataagg tgtctctgga agcattcaga gcaattgagg    2940
cagcgttggt gaagcacgat aataatatga aggattattc cctggtggtt gactgatcac    3000
cataactgct aatcattcaa actatttagt ctgtgacaga gccaacacgc agtctgtcac    3060
tgtcaggaaa gtggtaaaac tgcaactcaa ttactgcaat gccctcgtaa ttaagtgaat    3120
ttacaatatc gtcctgttcg gagggaagaa cgcgggatgt tcattcttca tcactttaa    3180 ttgatgtata tgctctcttt tctgacgtta gtctccgacg gcaggcttca atgacccagg    3240
ctgagaaatt cccggaccct ttttgctcaa gagcgatgtt aatttgttca atcatttggt    3300
```

-continued

```
taggaaagcg gatgttgcgg gttgttgttc tgcgggttct gttcttcgtt gacatgaggt    3360
tgccccgtat tcagtgtcgc tgatttgtat tgtctgaagt tgtttttacg ttaagttgat    3420
gcagatcaat taatacgata cctgcgtcat aattgattat ttgacgtggt ttgatggcct    3480
ccacgcacgt tgtgatatgt agatgataat cattatcact ttacgggtcc tttccggtga    3540
aaaaaaaggt accaaaaaaa acatcgtcgt gagtagtgaa ccgtaagccg tcctgtcgct    3600
gtgtctcgga cactgattga cacggtttag tagagc                              3636

<210> SEQ ID NO 79
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 79 ttttttttt tttttttttt tttttttcg agacacagcg acaggacgtc ct              52

<210> SEQ ID NO 80
<211> LENGTH: 83
<212> TYPE: DNA
<213> ORGANISM: Artificial Sequence
<220> FEATURE:
<223> OTHER INFORMATION: Synthetic Polynucleotide

<400> SEQUENCE: 80
cgtagctgat tgaggtcact cagtgcaata tcagcaccaa cagaaacaac ctttgaggcg    60
agcggtcaag cgacgaggtg tcc                                            83
```

The invention claimed is:

1. A method of controlling the movement of a polynucleotide with respect to a transmembrane pore, comprising
contacting the polynucleotide with a DNA-dependent ATPase (Dda) helicase modified to comprise a first cysteine residue and/or a first non-natural amino acid that has been introduced into (i) the tower domain, (ii) the pin domain, or (iii) the 1A (RecA-like motor) domain, wherein the first cysteine residue and/or the first non-natural amino acid is connected to a second cysteine residue and/or second non-natural amino acid that has been introduced into (i) the tower domain, (ii) the pin domain, or (iii) the 1A (RecA-like motor) domain and wherein the helicase retains its ability to control the movement of a polynucleotide with respect to the transmembrane pore, and thereby controlling the movement of the polynucleotide, in order to form a complex; and
contacting a transmembrane pore with the complex.

2. The method of claim 1 further comprising taking one or more measurements as the polynucleotide moves with respect to the pore wherein the measurements are indicative of one or more characteristics of the target polynucleotide and thereby characterising the target polynucleotide.

3. The method according to claim 2, wherein
the one or more characteristics of the target polynucleotide are measured by electrical measurement and/or optical measurement, wherein the electrical measurement is a current measurement, an impedance measurement, a tunnelling measurement or a field effect transistor (FET) measurement.

4. The method according to claim 1, wherein:
(A) the transmembrane pore is a transmembrane protein pore derived from a hemolysin, leukocidin, *Mycobacterium smegmatis* porin A (MspA), MspB, MspC, MspD, outer membrane porin F (OmpF), outer membrane porin G (OmpG), outer membrane phospholipase A, *Neisseria* autotransporter lipoprotein (NalP) or WZA transmembrane protein pore; or
(B) the transmembrane pore is:
(a) formed of eight identical subunits as shown in SEQ ID NO: 2 or (b) a variant thereof in which one or more of the eight subunits has at least 50% homology to SEQ ID NO: 2 based on amino acid identity over the entire sequence and retains pore activity; or
(c) α-hemolysin formed of seven identical subunits as shown in SEQ ID NO: 4 or (d) a variant thereof in which one or more of the seven subunits has at least 50% homology to SEQ ID NO: 4 based on amino acid identity over the entire sequence and retains pore activity; or
(C) the transmembrane pore is a solid state pore.

5. The method of claim 1, wherein the complex comprises an additional polynucleotide binding moiety, wherein:
the Dda helicase is attached to the additional polynucleotide binding moiety.

* * * * *